(12) United States Patent
Lee et al.

(10) Patent No.: US 9,871,208 B2
(45) Date of Patent: *Jan. 16, 2018

(54) CONDENSED CYCLIC COMPOUND AND ORGANIC LIGHT-EMITTING DEVICE INCLUDING THE SAME

(71) Applicant: SAMSUNG DISPLAY CO., LTD., Yongin, Gyeonggi-Do (KR)

(72) Inventors: Eunyoung Lee, Yongin (KR); Jino Lim, Yongin (KR); Youngkook Kim, Yongin (KR); Junha Park, Yongin (KR); Eunjae Jeong, Yongin (KR); Seokhwan Hwang, Yongin (KR)

(73) Assignee: SAMSUNG DISPLAY CO., LTD., Yongin, Gyeonggi-Do (KR)

( * ) Notice: Subject to any disclaimer, the term of this patent is extended or adjusted under 35 U.S.C. 154(b) by 295 days.

This patent is subject to a terminal disclaimer.

(21) Appl. No.: 14/631,181

(22) Filed: Feb. 25, 2015

(65) Prior Publication Data
US 2015/0243908 A1 Aug. 27, 2015

(30) Foreign Application Priority Data

Feb. 26, 2014 (KR) .................. 10-2014-0022880
Aug. 13, 2014 (KR) .................. 10-2014-0105428
Feb. 5, 2015 (KR) .................. 10-2015-0018132

(51) Int. Cl.
*H01L 51/00* (2006.01)
*C07D 401/10* (2006.01)
(Continued)

(52) U.S. Cl.
CPC ........ *H01L 51/0072* (2013.01); *C07D 221/18* (2013.01); *C07D 401/04* (2013.01); *C07D 401/10* (2013.01); *C07D 405/10* (2013.01); *C07F 9/5765* (2013.01); *C07F 9/65583* (2013.01); *C07F 9/65683* (2013.01); *H01L 51/0054* (2013.01); *H01L 51/0058* (2013.01);
(Continued)

(58) Field of Classification Search
None
See application file for complete search history.

(56) References Cited

U.S. PATENT DOCUMENTS 5,645,948 A 7/1997 Shi et al.
6,465,115 B2 10/2002 Shi et al.
(Continued)

FOREIGN PATENT DOCUMENTS

JP 10-17860 A 1/1998
JP 11-87067 A 3/1999
(Continued)

OTHER PUBLICATIONS

Zheng et al. "Synthesis, Structures, and Optical Properties of Aza[4]helicenes" European Journal of Organic Chemistry, 2013, 3059-3066.*

(Continued)

*Primary Examiner* — Robert S Loewe
(74) *Attorney, Agent, or Firm* — Lee & Morse, P.C.

(57) ABSTRACT

A condensed cyclic compound and an organic light-emitting device including the condensed cyclic compound, the condensed cyclic compound being represented by one of Formulae 1-1 to 1-8 described herein.

20 Claims, 4 Drawing Sheets

(51) Int. Cl.
| C07F 9/576 | (2006.01) |
| C07D 405/10 | (2006.01) |
| C07D 401/04 | (2006.01) |
| C07D 221/18 | (2006.01) |
| C07F 9/6558 | (2006.01) |
| C07F 9/6568 | (2006.01) |
| H01L 51/50 | (2006.01) |
| H01L 51/52 | (2006.01) |

(52) U.S. Cl.
CPC ...... *H01L 51/0067* (2013.01); *H01L 51/5072* (2013.01); *H01L 51/5221* (2013.01)

(56) References Cited

U.S. PATENT DOCUMENTS

| 6,596,415 | B2 | 7/2003 | Shi et al. |
| 2003/0165715 | A1 | 9/2003 | Yoon et al. |
| 2004/0239237 | A1 | 12/2004 | Matsusue et al. |
| 2007/0122657 | A1 | 5/2007 | Klubek et al. |
| 2008/0030125 | A1 | 2/2008 | Boerner et al. |
| 2010/0001301 | A1 | 1/2010 | Karg et al. |

FOREIGN PATENT DOCUMENTS

| JP | 2012-028711 A | 2/2012 |
| KR | 2003-0041968 A | 5/2003 |
| KR | 10-0691543 B1 | 3/2007 |
| KR | 10-2007-0085377 A | 8/2007 |
| KR | 10-2010-0101315 A | 9/2010 |
| KR | 10-2012-0122982 A | 11/2012 |
| KR | 10-2013-0135178 A | 12/2013 |
| KR | 10-2015-0077271 A | 7/2015 |

OTHER PUBLICATIONS

Machine translation of KR 1020130135178, translation generated Feb. 2017, 29 pages.*

Korean Office Action dated Jul. 5, 2016 in Corresponding Korean Patent Application No. 10-2015-0018132.

Portela-Cubillo, et al., "Microwave-Assisted Syntheses of N-Heterocycles Using Alkenone-, Alkynone- and Aryl-carbonyl 0-Phenyl Oximes: Formal Synthesis of Neocryptolepine", J. Org. Chem., 2008, 73 (14), pp. 5558-5565.

Tang, et al., "Organic electroluminescent diodes", Appl. Phys. Lett., 51, 913 (1987).

Adachi, et al., "Confinement of charge carriers and molecular excitons within 5nmthick emitter layer in organic electroluminescent devices with a double heterostructure", Appl. Phys. Lett., 57, 531 (1990).

Sakamoto,et al., "Synthesis, Characterization, and Electron-Transport Property of Perfluorinated Phenylene Dendrimers", J. Am. Chem. Soc., 2000, 122 (8), 1832-1833.

Yamaguchi, et al., "Diphenylamino-Substituted 2,5-Diarylsiloles for Single-Layer Organic Electroluminescent Devices", Chem. Lett., 98 (2001).

Johansson, et al., "Solid-State Amplified Spontaneous Emission in Some Spiro-Type Molecules: A New Concept for the Design of Solid-State Lasing Molecules", Adv. Mater. 10 (1998) 1136.

Tao, et al., "Sharp green electroluminescence from 1H-pyrazolo[3,4-b]quinoline-based light-emitting diodes", Appl. Phys. Lett. 77 (2000) 1575.

Chemspider_Chemicalstructure_Dibenzo(C,F)Quinoline, http://www.chemspider.com/Chemical-Structure.4953810.html?rid=c3ef054f-ae35-4e, Mar. 11, 2014.

Korean Office Action dated Jul. 11, 2016 in Corresponding Korean Patent Application No. 10-2015-0153807.

Korean Notice of Allowance dated Jan. 23, 2017 in corresponding Korean Patent Application No. 10-2015-0018132.

Korean Notice of Allowance dated Jan. 23, 2017 in corresponding Korean Patent Application No. 10-2015-0153807.

Provisional double patenting rejection over claims of the above-identified application; USPTO Office action dated Jan. 31, 2017, in U.S. Appl. No. 14/309,367.

* cited by examiner

| 190 |
|-----|
| 150 |
| 110 |

| 190 |
| 150 |
| 110 |
| 210 |

| 220 |
|-----|
| 190 |
| 150 |
| 110 |

| 220 |
|---|
| 190 |
| 150 |
| 110 |
| 210 |

CONDENSED CYCLIC COMPOUND AND ORGANIC LIGHT-EMITTING DEVICE INCLUDING THE SAME

CROSS-REFERENCE TO RELATED APPLICATIONS

Korean Patent Application No. 10-2014-0022880, filed on Feb. 26, 2014, in the Korean Intellectual Property Office, Korean Patent Application No. 10-2014-0105428, filed on Aug. 13, 2014, in the Korean Intellectual Property Office, and Korean Patent Application No. 10-2015-0018132, filed on Feb. 5, 2015, in the Korean Intellectual Property Office, and entitled: "Condensed Cyclic Compound and Organic Light-Emitting Device Including the Same," are incorporated by reference herein in their entirety.

BACKGROUND

1. Field

Embodiments relate to a condensed cyclic compound and an organic light-emitting device including the same.

2. Description of the Related Art

Organic light-emitting devices are self-emission devices that have wide viewing angles, high contrast ratios, short response times, and excellent brightness, driving voltage, and response speed characteristics, and produce multicolored images.

An organic light-emitting device may include a substrate and a first electrode on the substrate, and may have a structure of a hole transport region, an emission layer, an electron transport region, and a second electrode that are sequentially stacked in the stated order on the first electrode. Holes provided from the first electrode may move toward the emission layer through the hole transport region, and electrons provided from the second electrode may move toward the emission layer through the electron transport region. Carriers, such as holes and electrons, may be recombined in the emission layer to produce excitons. These excitons may change from an excited state to a ground state, thereby generating light.

SUMMARY

The embodiments ma provide a condensed cyclic compound and an organic light-emitting device including the same.

According to one or more exemplary embodiments, there is provided a condensed cyclic compound represented by one of Formulae 1-1 to 1-8 below:

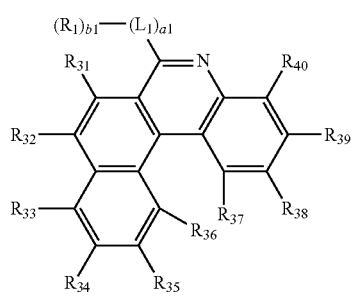

<Formula 1-1>

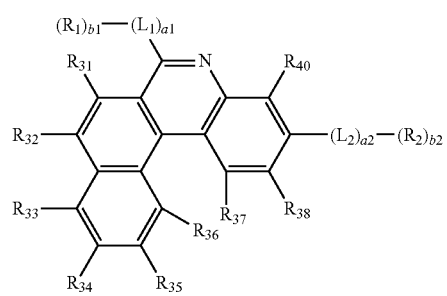

<Formula 1-2>

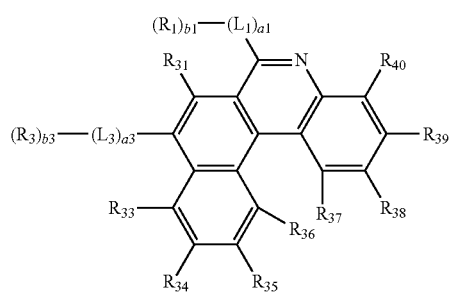

<Formula 1-3>

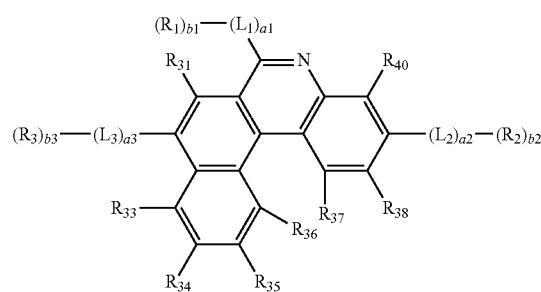

<Formula 1-4>

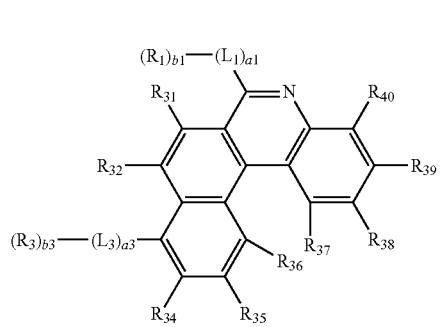

<Formula 1-5>

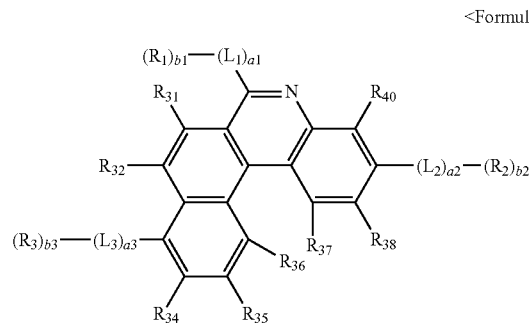

<Formula 1-6>

-continued

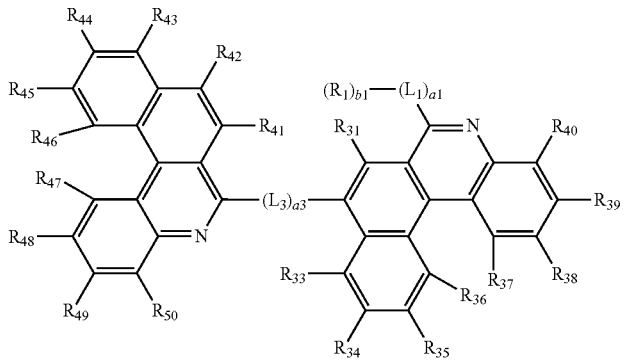

<Formula 1-7>

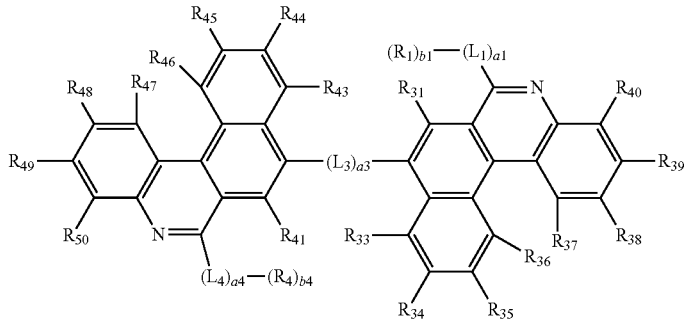

<Formula 1-8>

In Formulae 1-1 to 1-8, $L_1$ to $L_4$ may be each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, a substituted or unsubstituted divalent non-aromatic condensed heteropolycyclic group, *—P(=O)$R_{10}$—*', *—P(=S)$R_{11}$—*', *—S(=O)—*', and *—S(=O)$_2$—*', a1 to a4 may be each independently an integer selected from 1 to 5, $R_1$ to $R_4$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, *—P(=O)($R_{12}$)($R_5$), *—P(=S)($R_6$)($R_7$), *—S(=O)($R_8$), and *—S(=O)$_2$($R_9$), b1 to b4 may be each independently an integer selected from 0 to 5, $R_5$ to $R_{12}$ may be each independently selected from a hydrogen, a deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_{31}$ to $R_{50}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; and a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof.

However, the condensed cyclic compound of Formula 1-1 above may exclude compounds shown below:
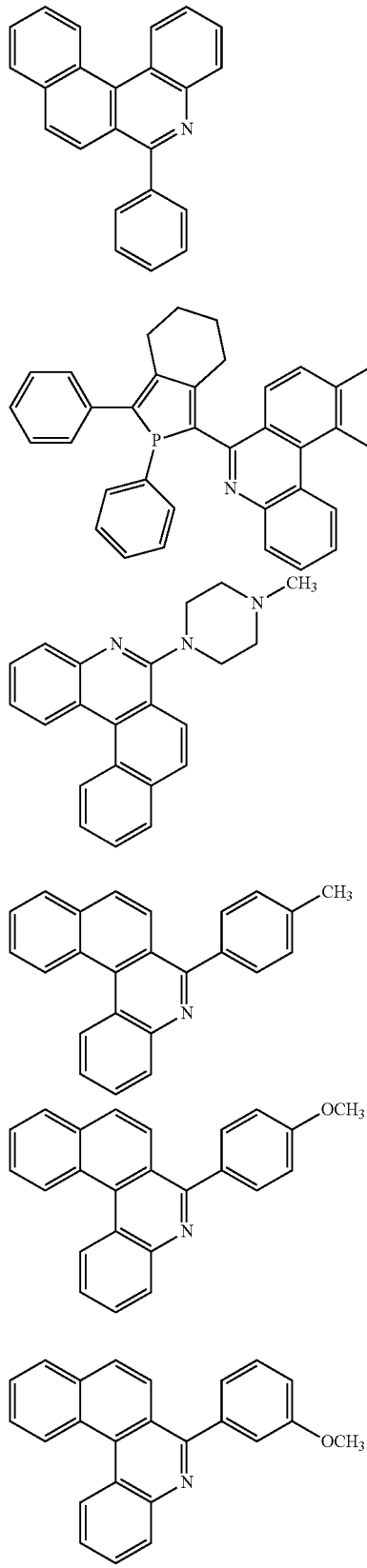
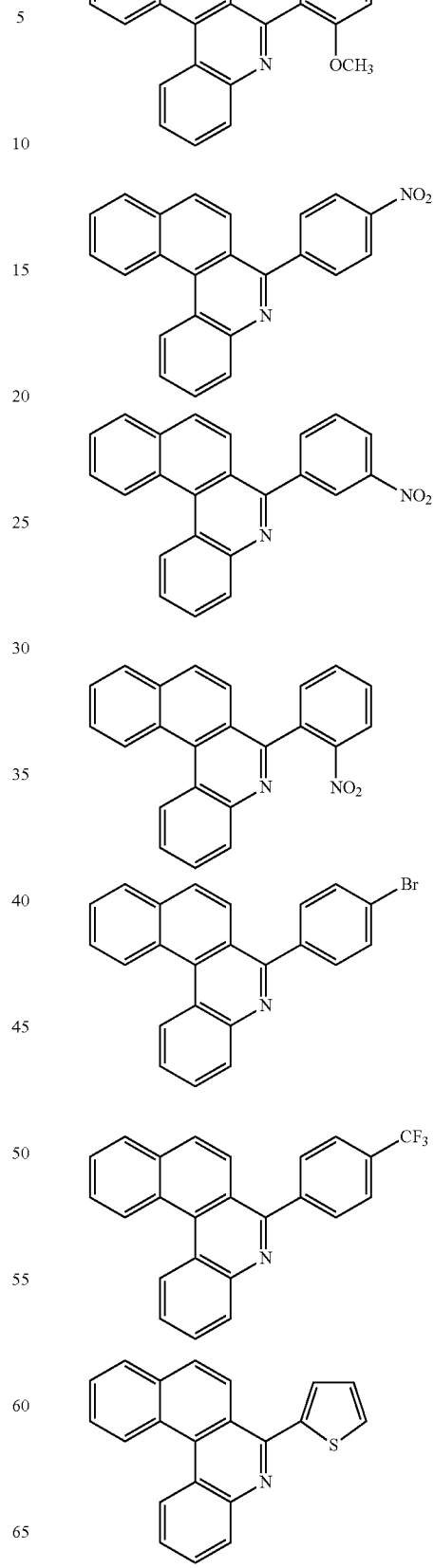

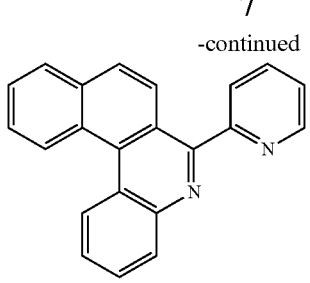

According to one or more exemplary embodiments, there is provided an organic light-emitting device including: a first electrode; a second electrode that is disposed facing the first electrode; and an organic layer that is disposed between the first electrode and the second electrode and includes an emission layer, wherein the organic layer includes at least one condensed cyclic compound shown above.

BRIEF DESCRIPTION OF THE DRAWINGS

Features will be apparent to those of skill in the art by describing in detail exemplary embodiments with reference to the attached drawings in which:

FIGS. 1 to 4 illustrate schematic views of organic light-emitting devices according to the embodiments.

DETAILED DESCRIPTION

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

In the drawing figures, the dimensions of layers and regions may be exaggerated for clarity of illustration. Like reference numerals refer to like elements throughout.

As used herein, the term "and/or" includes any and all combinations of one or more of the associated listed items. Expressions such as "at least one of," when preceding a list of elements, modify the entire list of elements and do not modify the individual elements of the list.

The embodiments may provide a condensed cyclic compound represented by one of Formulae 1-1 to 1-8 below.

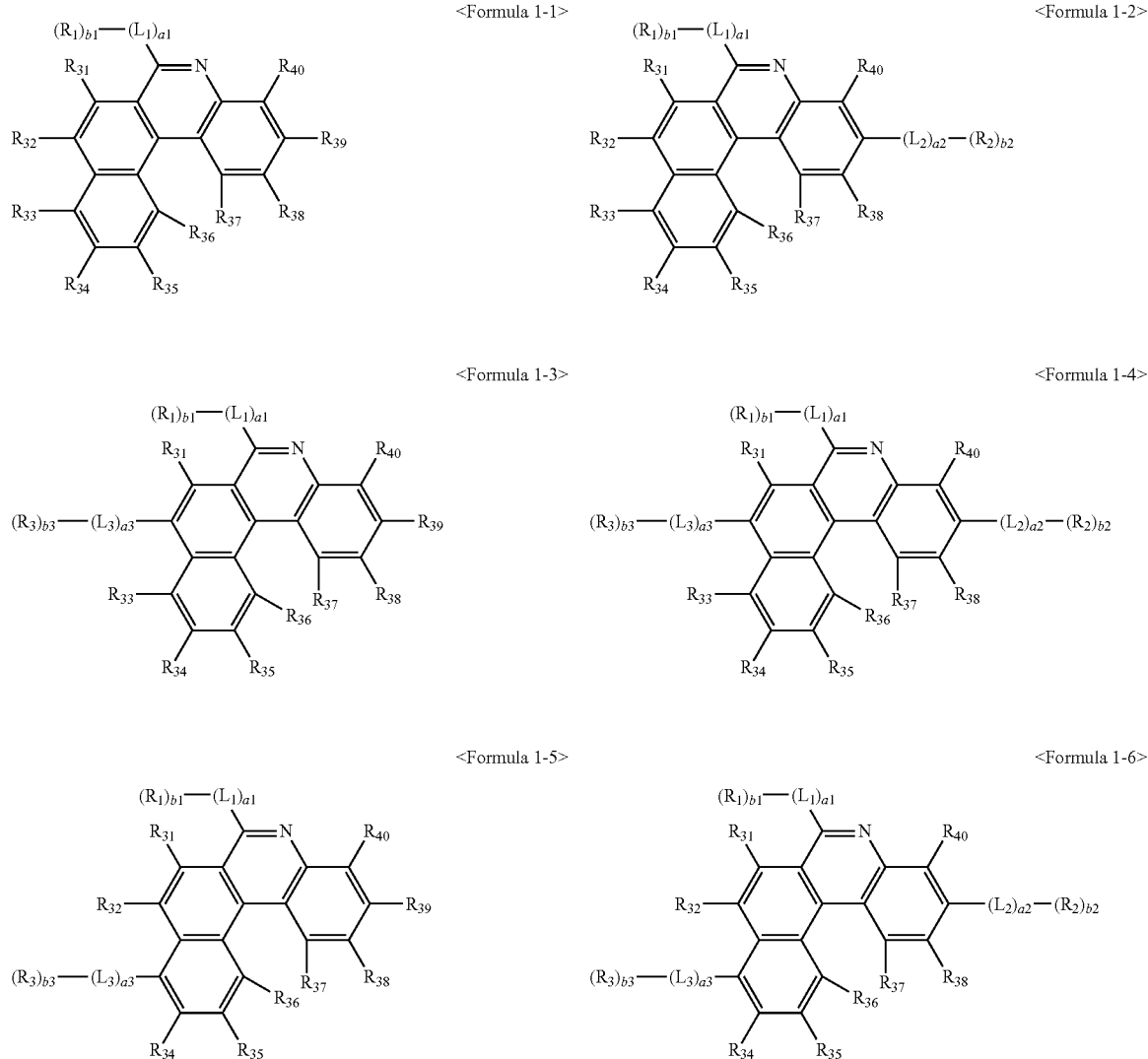

<Formula 1-7>

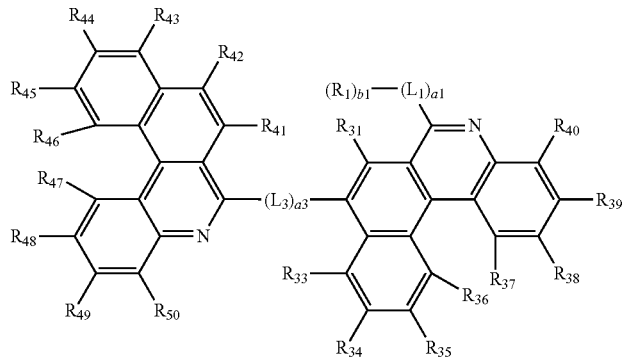

<Formula 1-8>

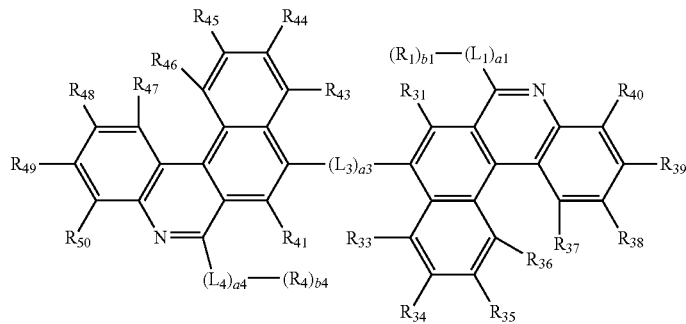

In Formulae 1-1 to 1-8, $L_1$ to $L_4$ may be each independently selected from or include a substituted or unsubstituted $C_3$-$C_{10}$ cycloalkylene group, a substituted or unsubstituted heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, a substituted or unsubstituted divalent non-aromatic condensed heteropolycyclic group, *—P(=O)$R_{10}$—*', *—P(=S)$R_{11}$—*', *—S(=O)—*', and *—S(=O)$_2$—*'.

For example, in Formulae 1-1 to 1-8, $L_1$ to $L_4$ may be each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, an imidazopyrimidinylene group, a benzoxanthenylene group (e.g., a benzo[kl]xanthenylene group), a benzonaphthofuranylene group, and a dinaphthofuranylene group;

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, an imidazopyrimidinylene group, a benzoxanthenylene group (e.g., a benzo[kl]xanthenylene group), a benzonaphthofuranylene group, and a dinaphthofuranylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a biphenyl group, a terphenyl group, a phenyl group substituted with a $C_1$-$C_{20}$ alkyl group, and —Si($Q_{31}$)($Q_{32}$)($Q_{33}$); and

*—P(=O)$R_{10}$—*', *—P(=S)$R_{11}$—*', *—S(=O)—*', and *—S(=O)$_2$—*', and $Q_{31}$ to $Q_{33}$ and $R_{10}$ and $R_{11}$ may be each independently selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, an imidazopyrimidinyl group, a biphenyl group, a terphenyl group, and a phenyl group substituted with a $C_1$-$C_{20}$ alkyl group.

In an implementation, in Formulae 1-1 to 1-8, $L_1$ to $L_4$ may be each independently selected from:

a phenylene group, a naphthylene group, a fluorenylene group, a phenalenylene group, a phenanthrenylene group, an anthracenylene group, a triphenylenylene group, a pyrenylene group, a chrysenylene group, a pyridinylene group, a pyrazinylene group, a pyrimidinylene group, a quinolinylene group, an isoquinolinylene group, a quinoxalinylene group, a quinazolinylene group, a carbazolylene group, a triazinylene group, a dibenzofuranylene group, a dibenzothiophenylene group, a benzoxanthenylene group (e.g., a benzo[kl]xanthenylene group), and a dinaphthofuranylene group;

a phenylene group, a naphthylene group, a fluorenylene group, a phenalenylene group, a phenanthrenylene group, an anthracenylene group, a triphenylenylene group, a pyrenylene group, a chrysenylene group, a pyridinylene group, a pyrazinylene group, a pyrimidinylene group, a quinolinylene group, an isoquinolinylene group, a quinoxalinylene group, a quinazolinylene group, a carbazolylene group, a triazinylene group, a dibenzofuranylene group, a dibenzothiophenylene group, a benzoxanthenylene group (e.g., a benzo[kl]xanthenylene group), and a dinaphthofuranylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzoxanthenyl group (e.g., a benzo[kl]xanthenyl group), a dinaphthofuranyl group, a biphenyl group, a terphenyl group, a phenyl group substituted with a $C_1$-$C_{20}$ alkyl group, and —Si($Q_{31}$)($Q_{32}$)($Q_{33}$); and

*—P(=S)$R_{11}$—*', *—S(=O)—*', and *—S(=O)$_2$—*', and *—P(=O)$_2$—*', and $Q_{31}$ to $Q_{33}$ may be each independently selected from a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and a phenyl group substituted with a $C_1$-$C_{20}$ alkyl group, and $R_{10}$ and $R_{11}$ may be each independently selected from a phenyl group, a naphthyl group, a fluorenyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzoxanthenyl group (e.g., a benzo[kl]xanthenyl group), a dinaphthofuranyl group, a biphenyl group, a terphenyl group, and a phenyl group substituted with a $C_1$-$C_{20}$ alkyl group.

In the Formulae, * and *' may represent binding sites to neighboring atoms.

In an implementation, in Formulae 1-1 to 1-8, $L_1$ to $L_4$ may be each independently selected from groups represented by Formulae 3-1 to 3-49 below, *—P(=O)R$_{10}$—*', *—P(=S)R$_{11}$—*', *—S(=O)—*', and *—S(=O)$_2$—*'.

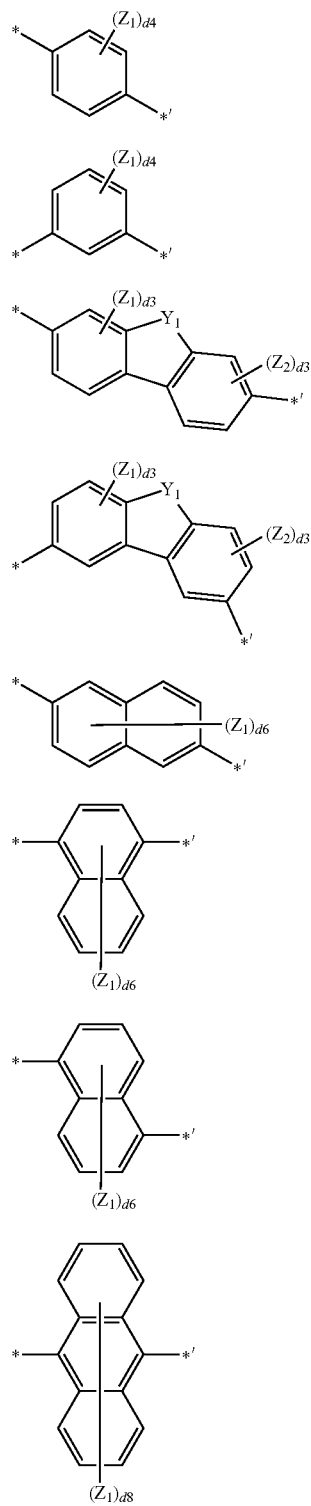

Formula 3-1
Formula 3-2
Formula 3-3
Formula 3-4
Formula 3-5
Formula 3-6
Formula 3-7
Formula 3-8

-continued

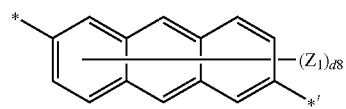

Formula 3-9

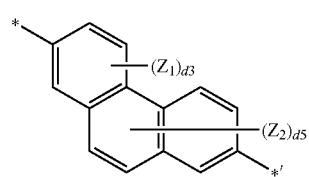

Formula 3-10

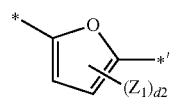

Formula 3-11

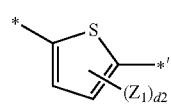

Formula 3-12

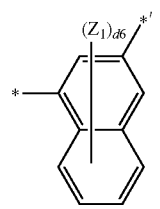

Formula 3-13

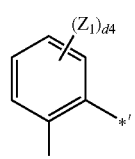

Formula 3-14

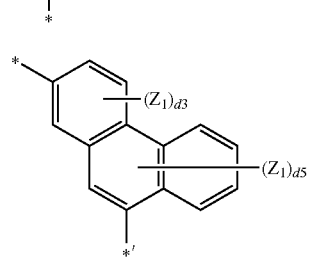

Formula 3-15

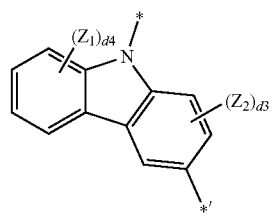

Formula 3-16

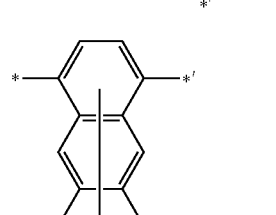

Formula 3-17

-continued
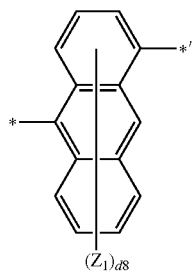
Formula 3-18
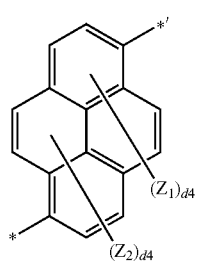
Formula 3-19
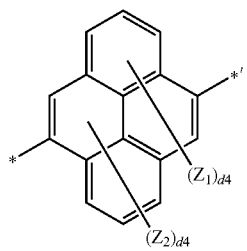
Formula 3-20
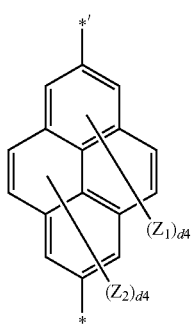
Formula 3-21
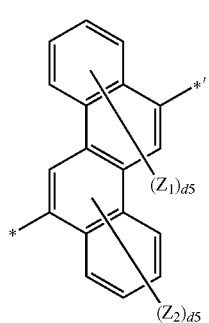
Formula 3-22
-continued
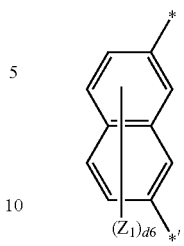
Formula 3-23
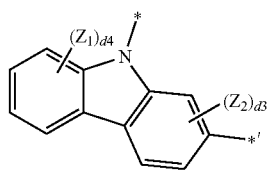
Formula 3-24
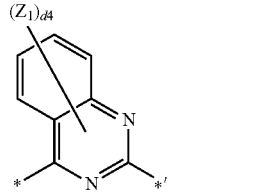
Formula 3-25
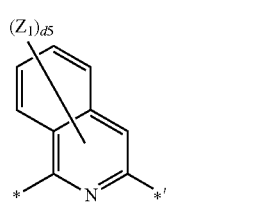
Formula 3-26
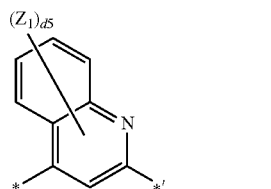
Formula 3-27
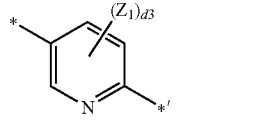
Formula 3-28
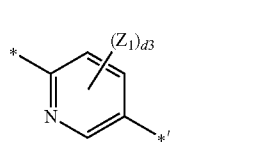
Formula 3-29
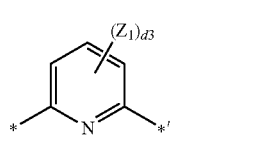
Formula 3-30
Formula 3-31

-continued
Formula 3-32
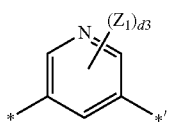
Formula 3-33
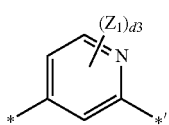
Formula 3-34
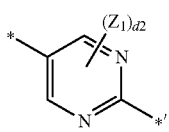
Formula 3-35
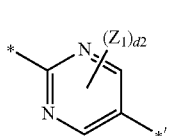
Formula 3-36
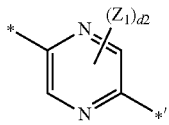
Formula 3-37
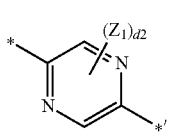
Formula 3-38
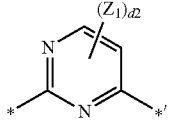
Formula 3-39
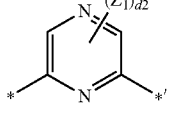
Formula 3-40
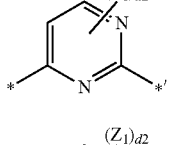
Formula 3-41
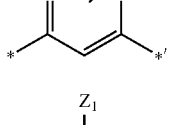
Formula 3-42
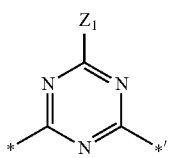
Formula 3-43
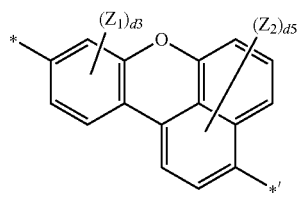
Formula 3-44
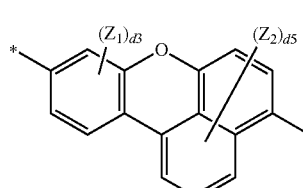
Formula 3-45
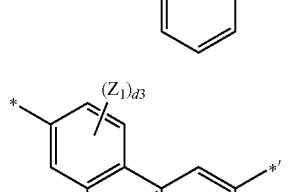
Formula 3-46
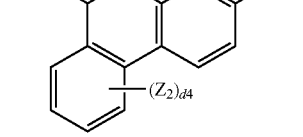
Formula 3-47
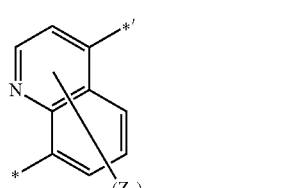
Formula 3-48
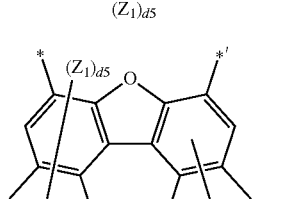
Formula 3-49
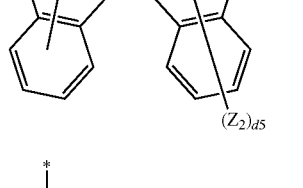
In Formulae 3-1 to 3-49,
$Y_1$ may be O, S, $C(Z_3)(Z_4)$, $N(Z_5)$, or $Si(Z_6)(Z_7)$;
$Z_1$ to $Z_7$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, a phenyl group substituted with a $C_1$-$C_{20}$ alkyl group, and —Si($Q_{31}$)($Q_{32}$)($Q_{33}$), $Q_{31}$ to $Q_{33}$ may be each independently selected from a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and a phenyl group substituted with a $C_1$-$C_{20}$ alkyl group, $R_{10}$ and $R_{11}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, an imidazopyrimidinyl group, a biphenyl group, a terphenyl group, and phenyl group substituted with a $C_1$-$C_{20}$ alkyl group, d2 may be 1 or 2, d3 may be an integer selected from 1 to 3, d4 may be an integer selected from 1 to 4, d5 may be an integer selected from 1 to 5, d6 may be an integer selected from 1 to 6, d8 may be an integer selected from 1 to 8, and

* and *' may indicate a binding site to a neighboring atom.

In Formulae 1-1 to 1-8, a1 to a4 may be each independently an integer selected from 1 to 5, and a1 may indicate the number of $L_1$. When a1 is 2 or more, 2 or more $L_1$(s) may be identical to or different from each other. Descriptions of a2 to a4 may be understood by referring to the descriptions presented in connection with a1 and compound structures of Formulae 1-1 to 1-8.

In an implementation, in Formulae 1-1 to 1-8, a1 to a4 may be each independently 1, 2, or 3.

In an implementation, in Formulae 1-1 to 1-8, a1 to a4 may be each independently 1 or 2.

In Formulae 1-1 to 1-8, $R_1$ to $R_4$ may be each independently selected from or include a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, *—P(=O)($R_{12}$)($R_5$), *—P(=S)($R_6$)($R_7$), *—S(=O)($R_8$), and *—S(=O)$_2$($R_9$).

In an implementation, in Formulae 1-1 to 1-8, $R_1$ to $R_4$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a benzoxanthenyl group (e.g., a benzo[kl]xanthenyl group), a benzonaphthofuranyl group, and a dinaphthofuranyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a benzoxanthenyl group (e.g., a benzo[kl]xanthenyl group), a benzonaphthofuranyl group, and a dinaphthofuranyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a biphenyl group, a terphenyl group, a phenyl group substituted with a $C_1$-$C_{20}$ alkyl group, and —Si($Q_{31}$)($Q_{32}$)($Q_{33}$); and

*—P(=O)($R_{12}$)($R_5$), *—P(=S)($R_6$)($R_7$), *—S(=O)($R_8$), and *—S(=O)$_2$($R_9$), and $Q_{31}$ to $Q_{33}$, $R_5$ to $R_9$ and $R_{12}$ may be each independently selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, an imidazopyrimidinyl group, a biphenyl group, a terphenyl group, and a phenyl group substituted with a $C_1$-$C_{20}$ alkyl group.

In an implementation, in Formulae 1-1 to 1-8, $R_1$ to $R_4$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, a fluorenyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzoxanthenyl group (e.g., a benzo[kl]xanthenyl group), and a dinaphthofuranyl group;

a phenyl group, a naphthyl group, a fluorenyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzoxanthenyl group (e.g., a benzo[kl]xanthenyl group), and a dinaphthofuranyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzoxanthenyl group (e.g., a benzo[kl]xanthenyl group), a dinaphthofuranyl group, a biphenyl group, a terphenyl group, a phenyl group substituted with a $C_1$-$C_{20}$ alkyl group, and —Si($Q_{31}$)($Q_{32}$)($Q_{33}$); and

*—P(=O)(R$_{12}$)(R$_5$), *—P(=S)(R$_6$)(R$_7$), *—S(=O)(R$_8$), and *—S(=O)$_2$(R$_9$), Q$_{31}$ to Q$_{33}$ may be each independently selected from a C$_1$-C$_{10}$ alkyl group, a C$_1$-C$_{10}$ alkoxy group, a phenyl group, a naphthyl group, a pyridinyl group, a pyrimidinyl group, a triazinyl group, a biphenyl group, a terphenyl group, and a phenyl group substituted with a C$_1$-C$_{20}$ alkyl group, and R$_5$ to R$_9$ and R$_{12}$ may be each independently selected from a phenyl group, a naphthyl group, a fluorenyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzoxanthenyl group (e.g., a benzo[kl]xanthenyl group), a dinaphthofuranyl group, a biphenyl group, a terphenyl group, and a phenyl group substituted with a C$_1$-C$_{20}$ alkyl group.

In an implementation, in Formulae 1-1 to 1-8, R$_1$ to R$_4$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a C$_1$-C$_{20}$ alkyl group, and a C$_1$-C$_{20}$ alkoxy group;

a C$_1$-C$_{20}$ alkyl group and a C$_1$-C$_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

groups represented by Formulae 5-1 to 5-96 (e.g., Formulae 5-1 to 5-90 and 5-92 to 5-96) below; and

*—P(=O)(R$_{12}$)(R$_5$), *—P(=S)(R$_6$)(R$_7$), *—S(=O)(R$_8$), and *—S(=O)$_2$(R$_9$),

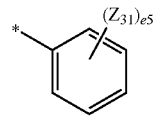

Formula 5-1

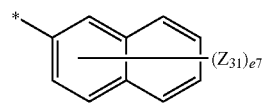

Formula 5-2

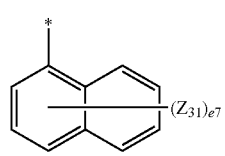

Formula 5-3

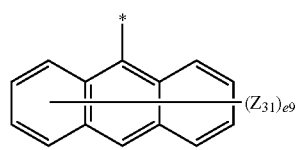

Formula 5-4

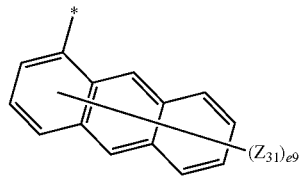

Formula 5-5

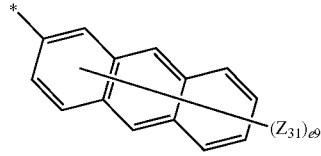

Formula 5-6

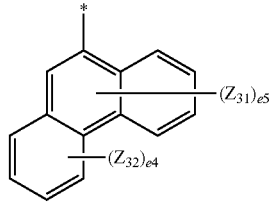

Formula 5-7

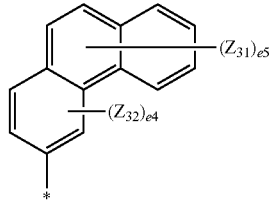

Formula 5-8

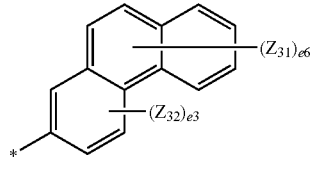

Formula 5-9

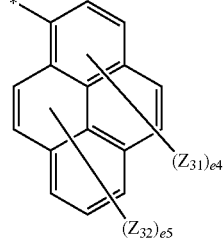

Formula 5-10

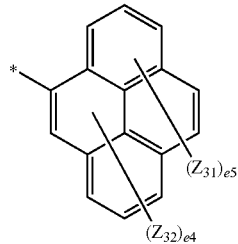

Formula 5-11

-continued
Formula 5-12 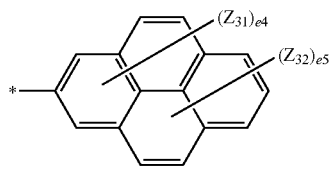
Formula 5-13 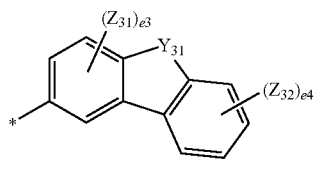
Formula 5-14 
Formula 5-15 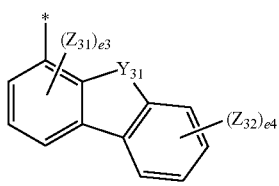
Formula 5-16 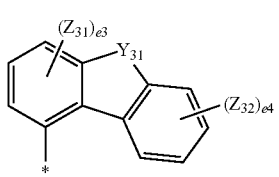
Formula 5-17 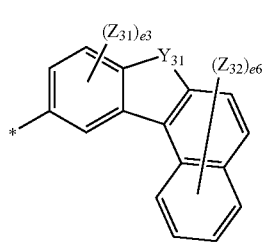
Formula 5-18 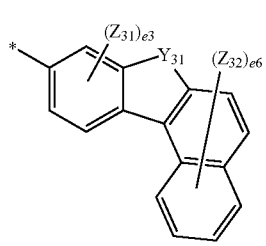
Formula 5-19 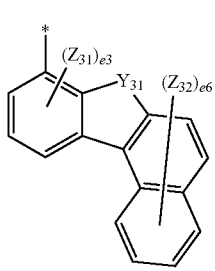
-continued
Formula 5-20 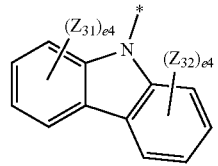
Formula 5-21 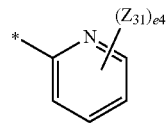
Formula 5-22 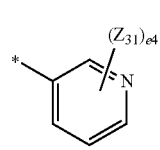
Formula 5-23 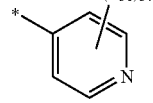
Formula 5-24 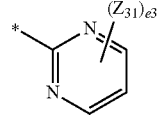
Formula 5-25 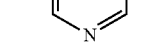
Formula 5-26 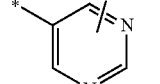
Formula 5-27 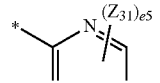
Formula 5-28 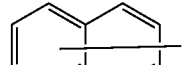
Formula 5-29 
Formula 5-30 

-continued
Formula 5-31
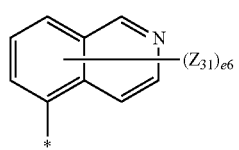
Formula 5-32
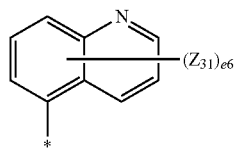
Formula 5-33
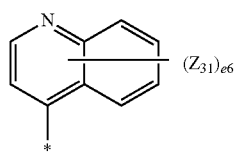
Formula 5-34
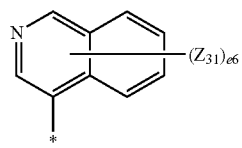
Formula 5-35
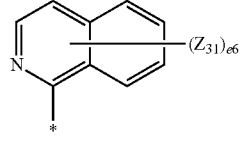
Formula 5-36
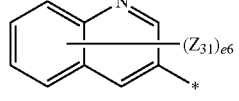
Formula 5-37
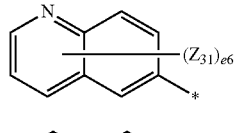
Formula 5-38
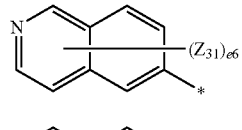
Formula 5-39
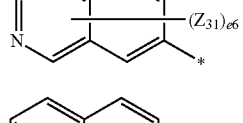
Formula 5-40
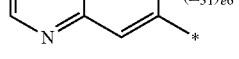
Formula 5-41
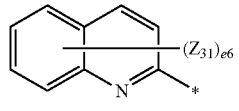
Formula 5-42
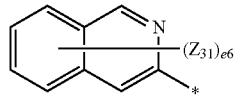
-continued
Formula 5-43
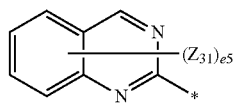
Formula 5-44
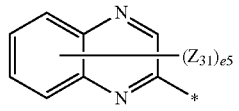
Formula 5-45
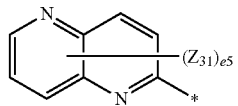
Formula 5-46
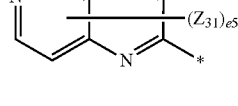
Formula 5-47
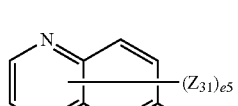
Formula 5-48
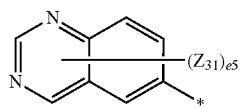
Formula 5-49
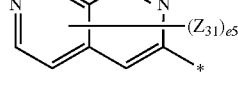
Formula 5-50
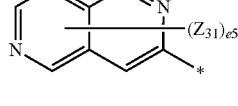
Formula 5-51
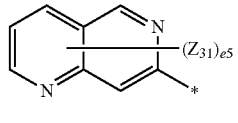
Formula 5-52
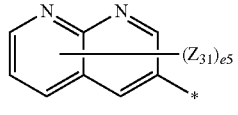
Formula 5-53
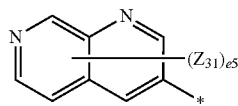
Formula 5-54
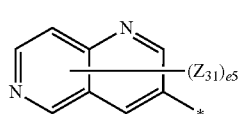
Formula 5-55

-continued
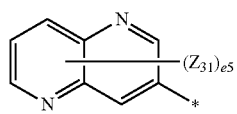
Formula 5-56
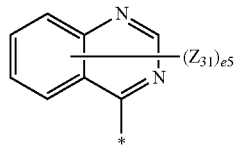
Formula 5-57
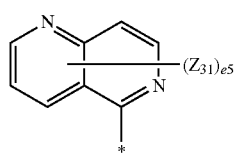
Formula 5-58
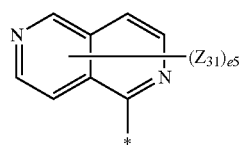
Formula 5-59
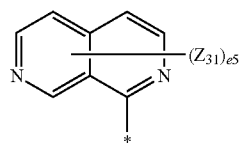
Formula 5-60
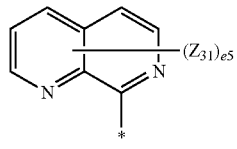
Formula 5-61
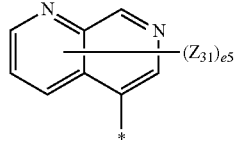
Formula 5-62
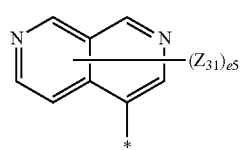
Formula 5-63
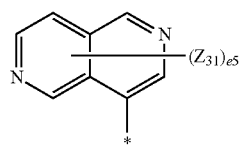
Formula 5-64
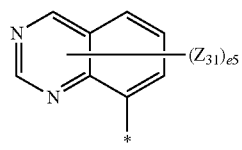
Formula 5-65
-continued
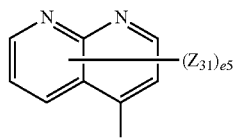
Formula 5-66
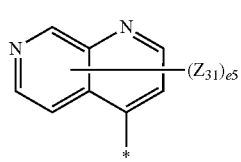
Formula 5-67
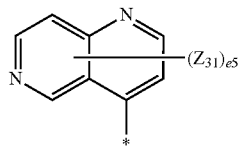
Formula 5-68
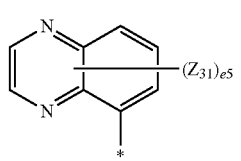
Formula 5-69
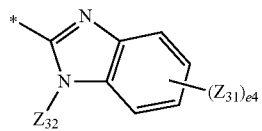
Formula 5-70
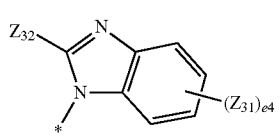
Formula 5-71
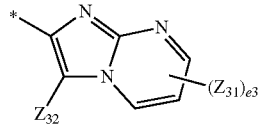
Formula 5-72
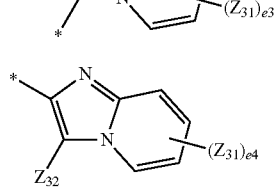
Formula 5-73
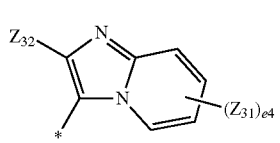
Formula 5-74
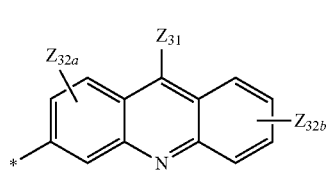
Formula 5-75
Formula 5-76

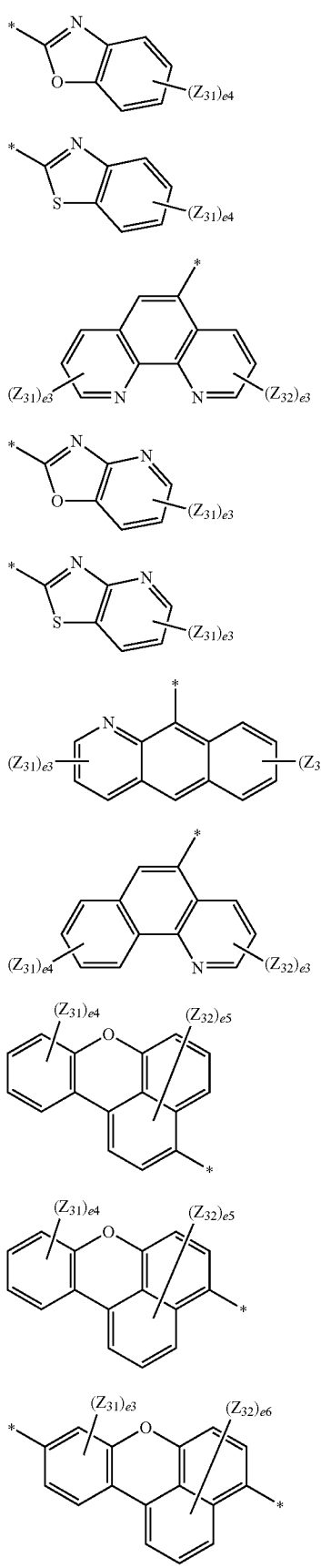
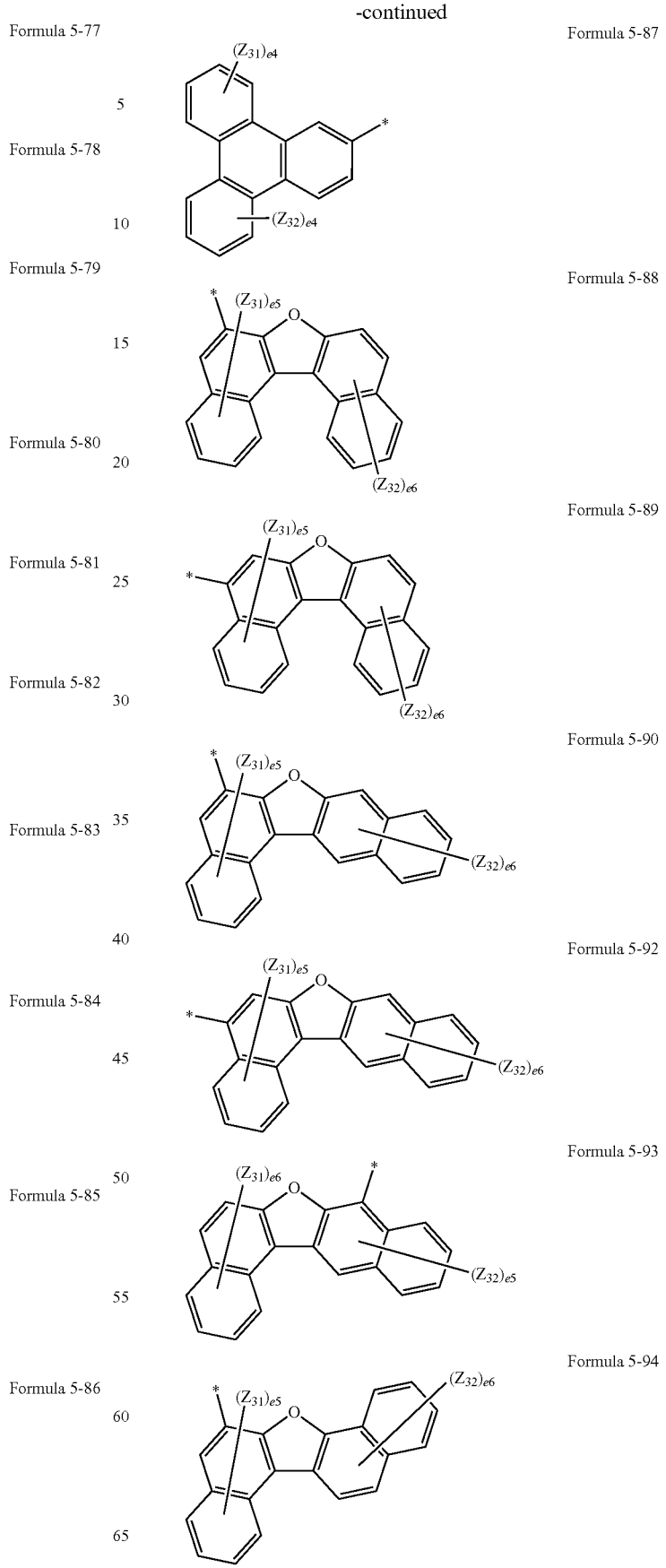

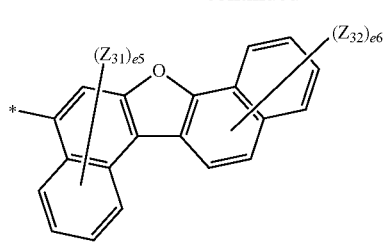

Formula 5-95

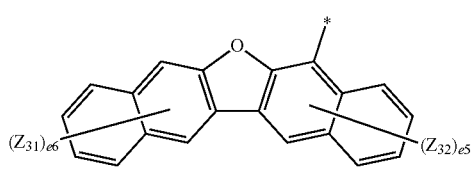

Formula 5-96

In Formulae 5-1 to 5-96, $Y_{31}$ may be O, S, $C(Z_{33})(Z_{34})$, $N(Z_{35})$, or $Si(Z_{36})(Z_{37})$, $Z_{31}$ to $Z_{37}$, $Z_{32a}$, and $Z_{32b}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, a phenyl group substituted with a $C_1$-$C_{20}$ alkyl group, and —$Si(Q_{31})(Q_{32})(Q_{33})$, $Q_{31}$ to $Q_{33}$ may be each independently selected from a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and a phenyl group substituted with a $C_1$-$C_{20}$ alkyl group, $R_5$ to $R_9$ and $R_{12}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, an imidazopyrimidinyl group, a biphenyl group, a terphenyl group, and a phenyl group substituted with a $C_1$-$C_{20}$ alkyl group, e3 may be an integer selected from 1 to 3,
e4 may be an integer selected from 1 to 4,
e5 may be an integer selected from 1 to 5,
e6 may be an integer selected from 1 to 6,
e7 may be an integer selected from 1 to 7,
e8 may be an integer selected from 1 to 8,
e9 may be an integer selected from 1 to 9, and
* may indicate a binding site to a neighboring atom.

In Formulae 1-1 to 1-8, b1 to b4 may be each independently an integer selected from 0 to 5, and b1 may indicate the number of $R_1$. When b1 is 2 or more, 2 or more $R_1$(s) may be identical to or different from each other. Descriptions of b2 to b4 may be understood by referring to the descriptions presented in connection with b1 and compound structures of Formulae 1-1 to 1-8.

In an implementation, in Formulae 1-1 to 1-8, b1 to b4 may be each independently 0, 1, 2, or 3.

In an implementation, in Formulae 1-1 to 1-8, b1 to b4 may be each independently 0, 1, or 2.

$R_5$ to $R_{12}$ used herein may be each independently selected from or include a hydrogen, a deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group. Descriptions of $R_4$ to $R_{11}$ may be understood by referring to the descriptions provided herein.

In Formulae 1-1 to 1-8, $R_{31}$ to $R_{50}$ may be each independently selected from:

a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; and a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof.

For example, in Formulae 1-1 to 1-8, $R_{31}$ to $R_{50}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{10}$ alkyl group, and a $C_1$-$C_{10}$ alkoxy group.

In an implementation, in Formulae 1-1 to 1-8, $R_{31}$ to $R_{50}$ may be hydrogen.

In an implementation, the condensed cyclic compound represented by Formula 1-1 above may exclude the compounds shown below.

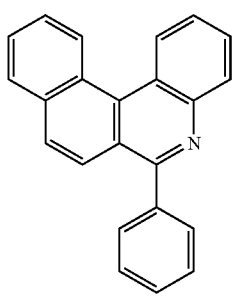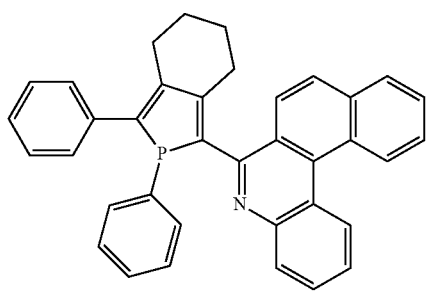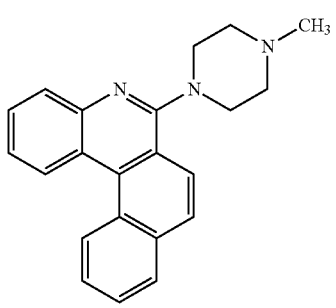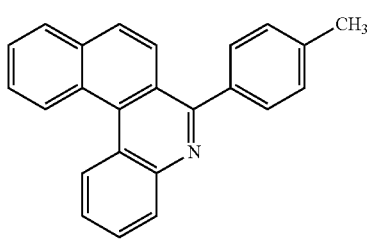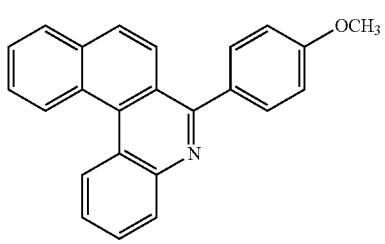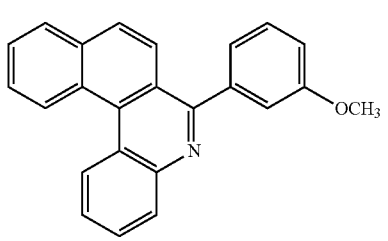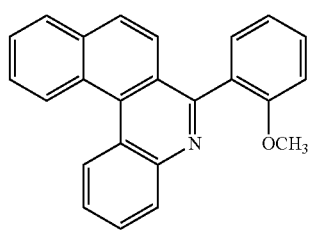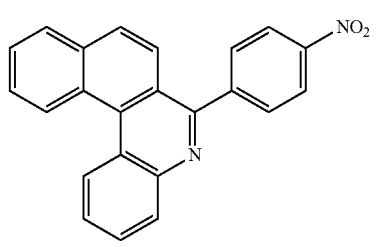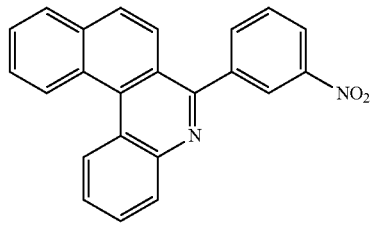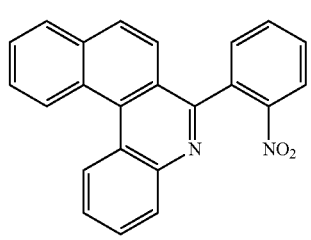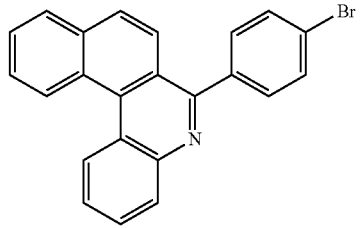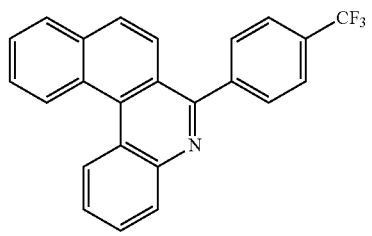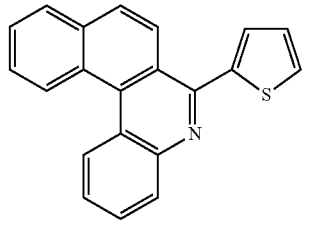

-continued

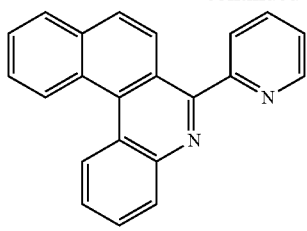

In an implementation, the condensed cyclic compound may be represented by one of Formulae 1-3 to 1-8 above.

In an implementation, the condensed cyclic compound may be represented by Formula 1-1 above, and in Formula 1-1, $R_1$ may be selected from:

a cyano group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a benzoxanthenyl group (e.g., a benzo[kl]xanthenyl group), a benzonaphthofuranyl group, and a dinaphthofuranyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a benzoxanthenyl group (e.g., a benzo[kl]xanthenyl group), a benzonaphthofuranyl group, and a dinaphthofuranyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a biphenyl group, a terphenyl group, a phenyl group substituted with a $C_1$-$C_{20}$ alkyl group, and —Si($Q_{31}$)($Q_{32}$)($Q_{33}$); and

*—P(=O)($R_{12}$)($R_5$), *—P(=S)($R_6$)($R_7$), *—S(=O)($R_8$), and *—S(=O)$_2$($R_9$), $Q_{31}$ to $Q_{33}$, $R_5$ to $R_9$ and $R_{12}$ may be each independently selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, an imidazopyrimidinyl group, a biphenyl group, a terphenyl group, and a phenyl group substituted with a $C_1$-$C_{20}$ alkyl group, and b1 may be 1, 2, or 3.

In an implementation, the condensed cyclic compound may be one of the compounds shown below.
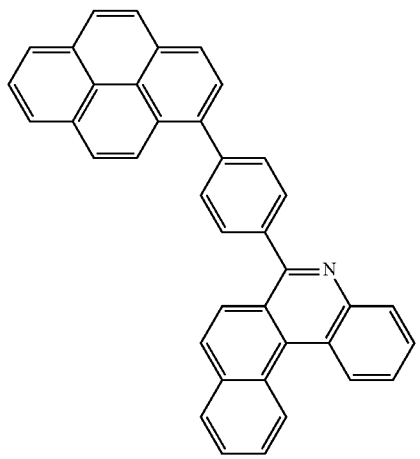
1A
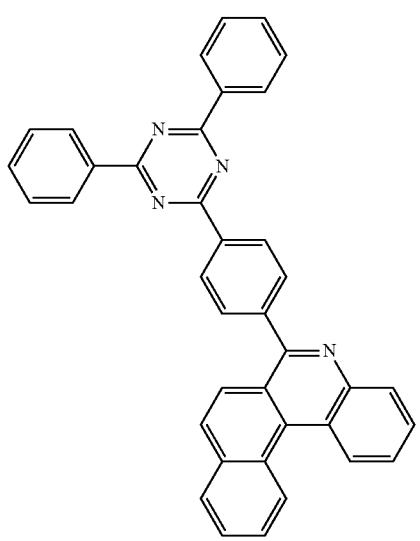
2A
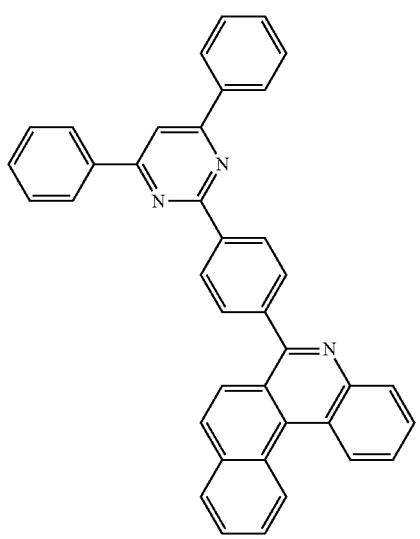
3A
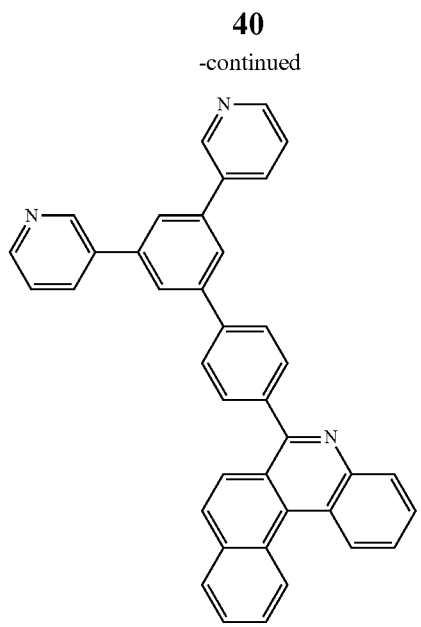
4A
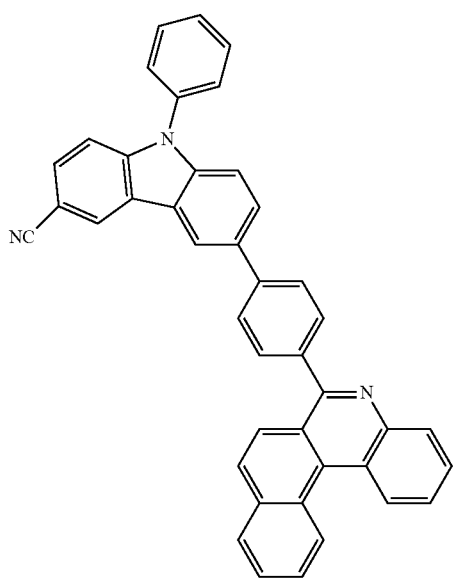
5A
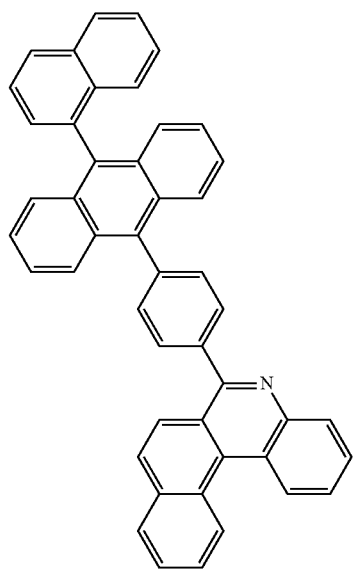
6A 7A 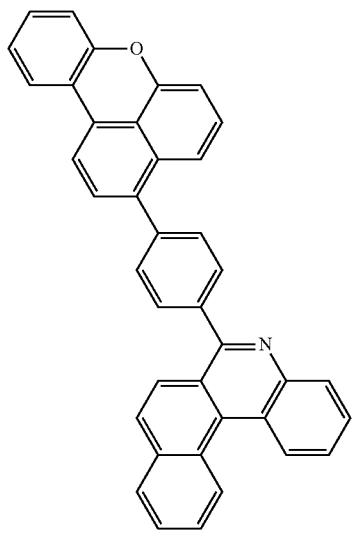
8A 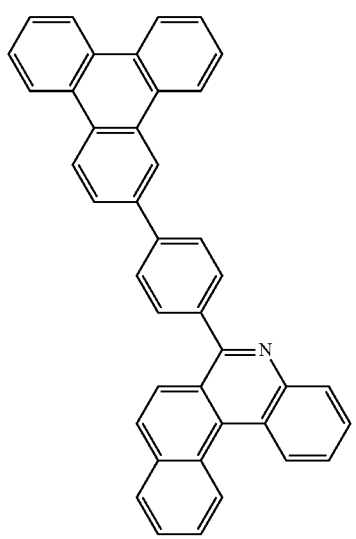
9A 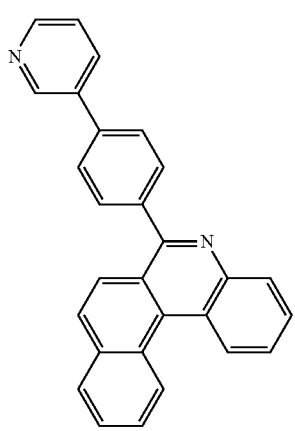
10A 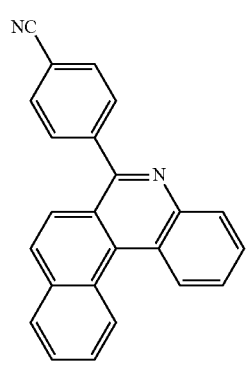
11A 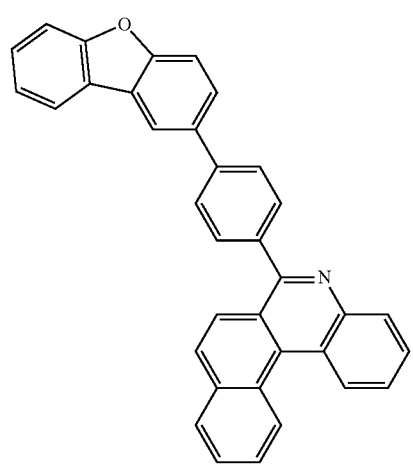
12A 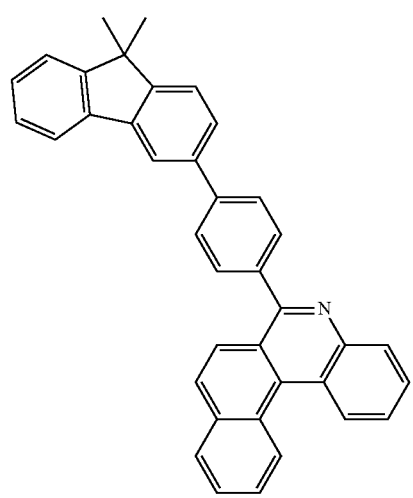

13A
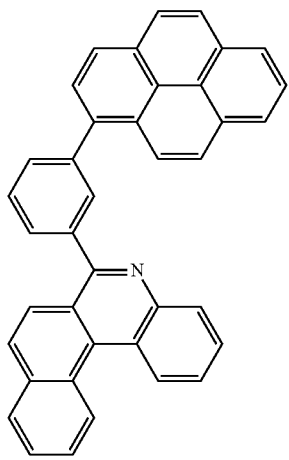
14A
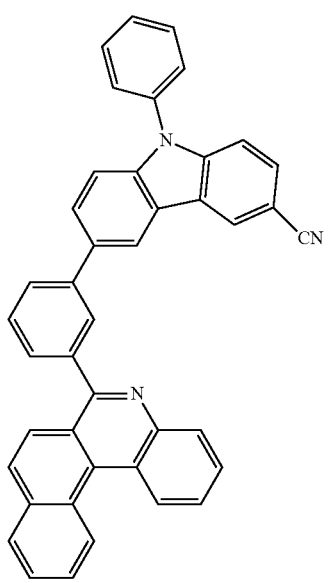
15A
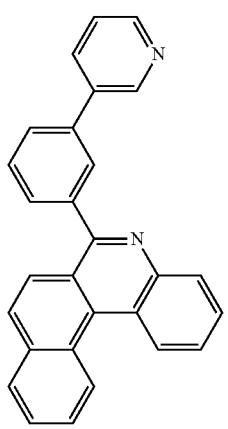
16A
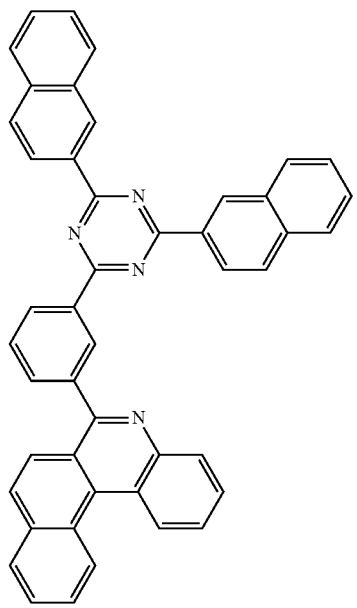
17A
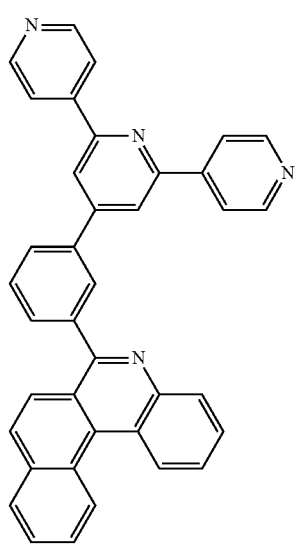
18A
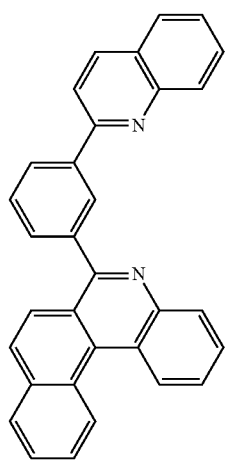

19A
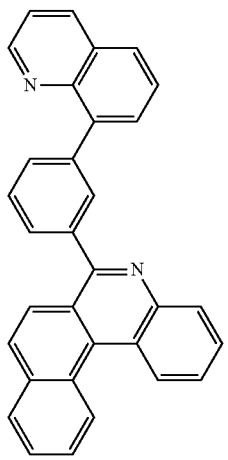
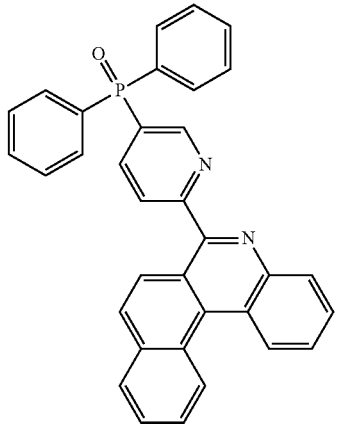
20A
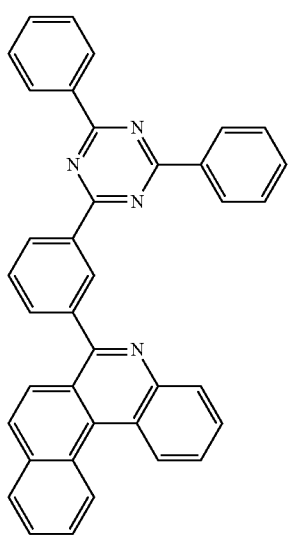
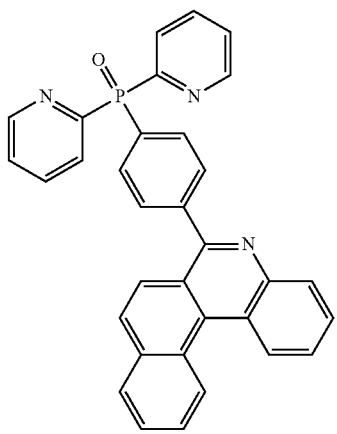
21A
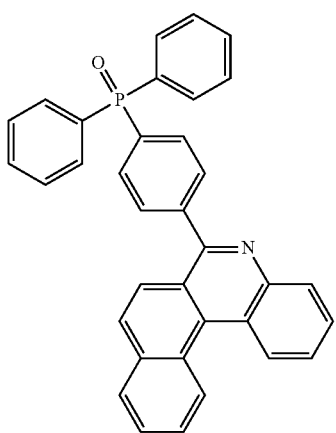
22A
23A
24A
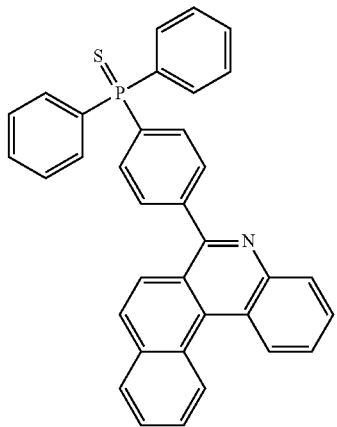

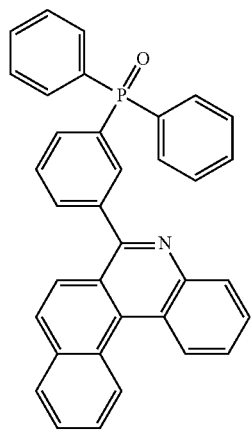
25A
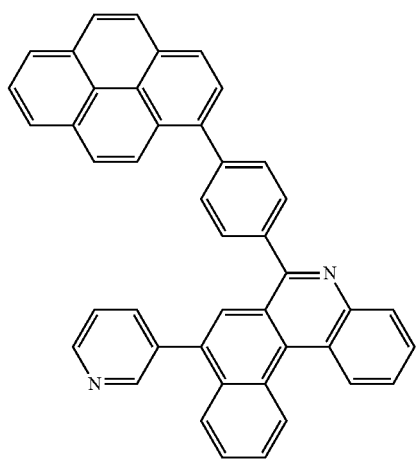
26A
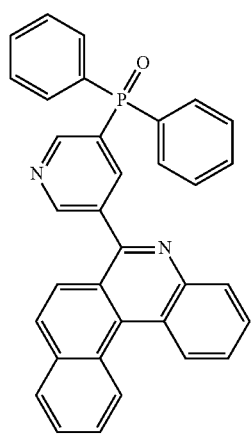
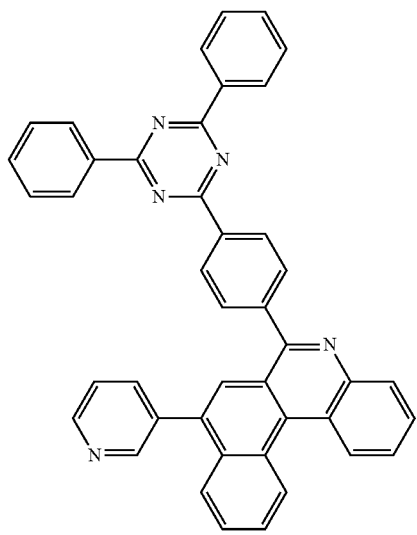
29A
27A
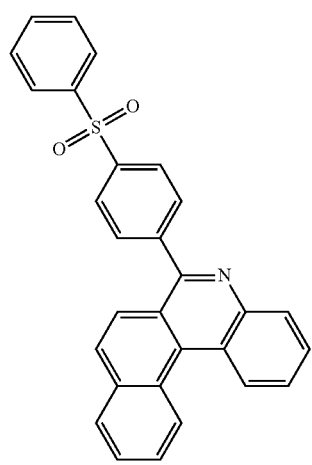
30A
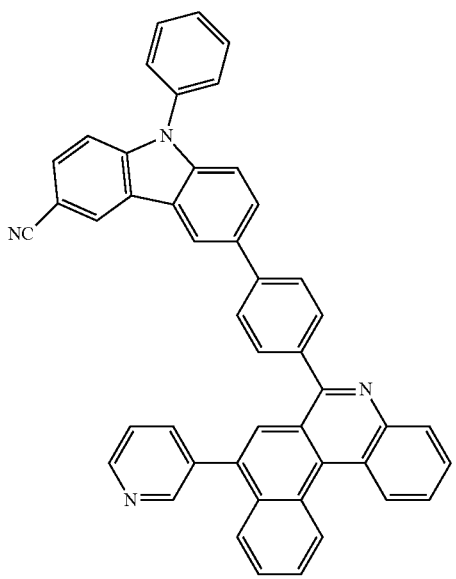

31A
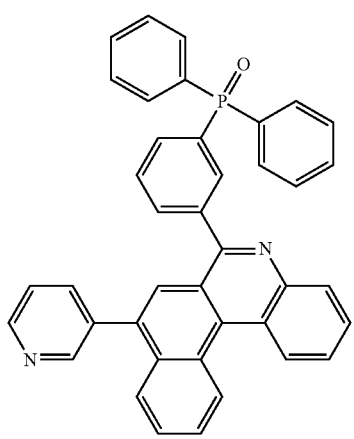
32A
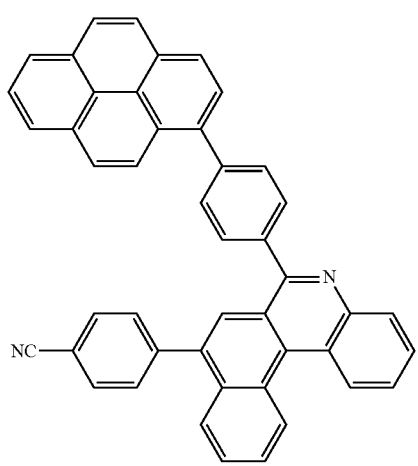
33A
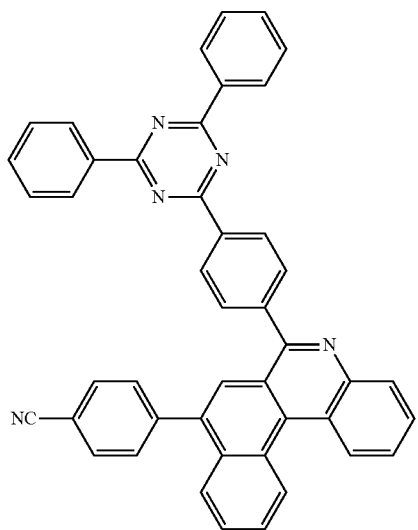
34A
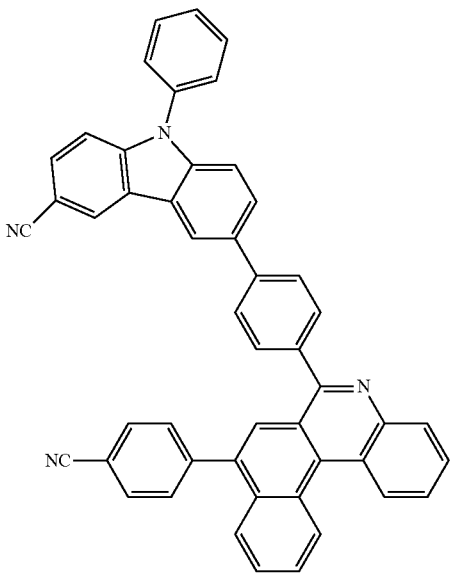
35A
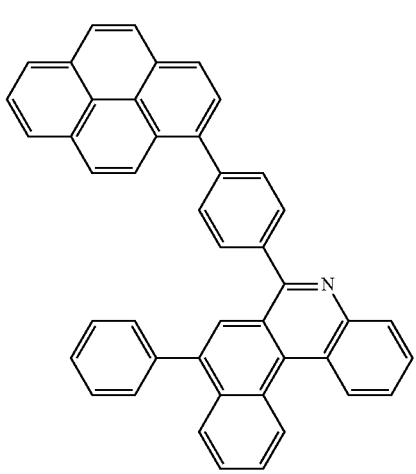
36A
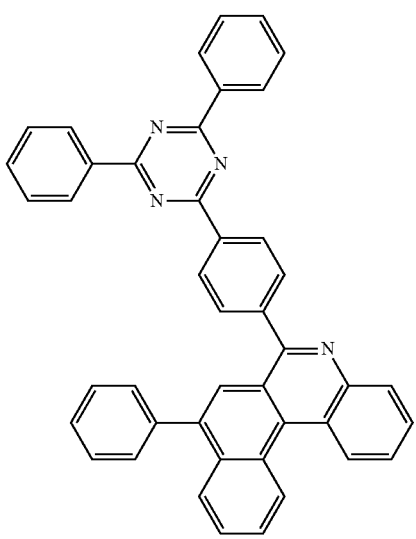

37A 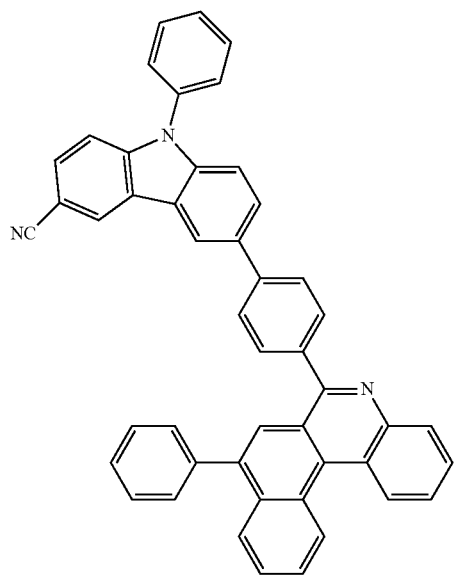
38A 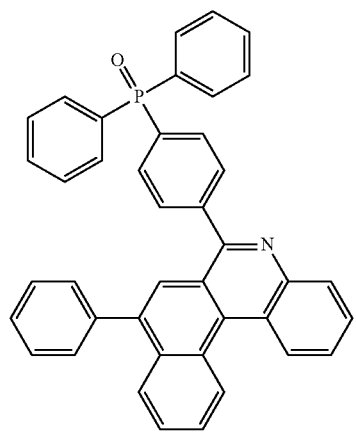
39A 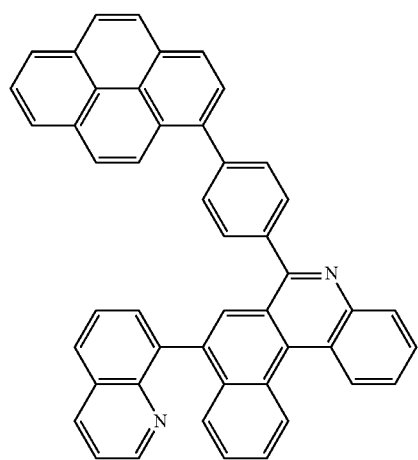
40A 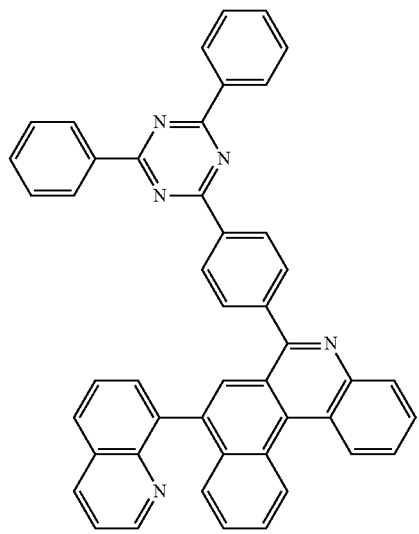
41A 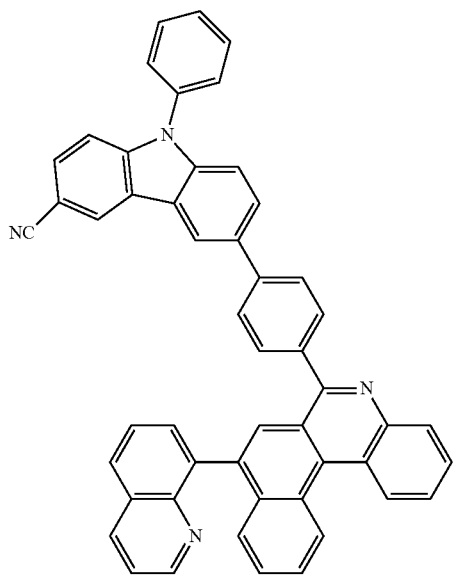
42A 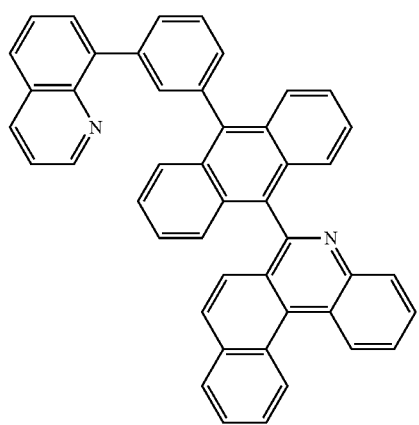

43A
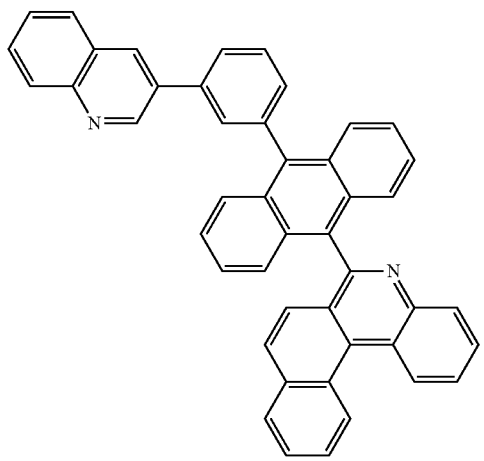
44A
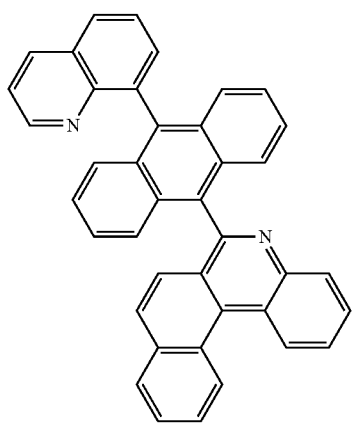
45A
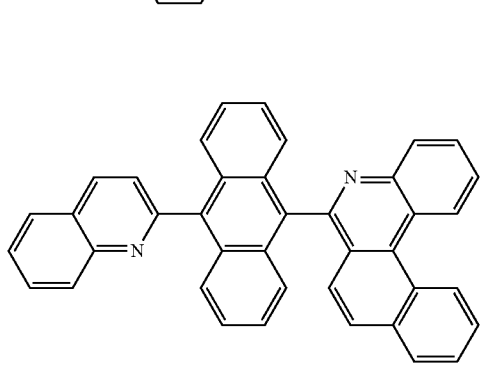
46A
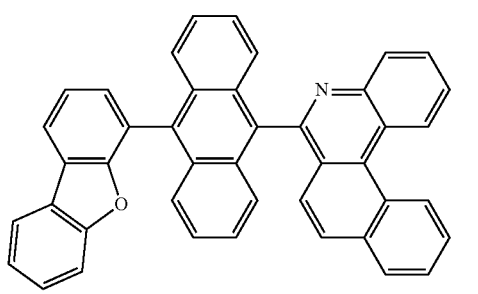
47A
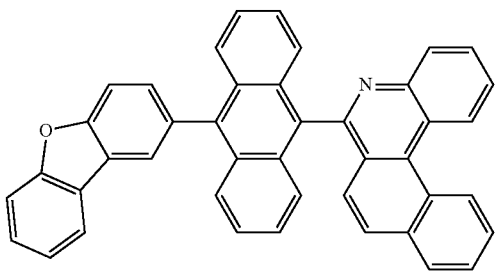
48A
49A
50A
51A

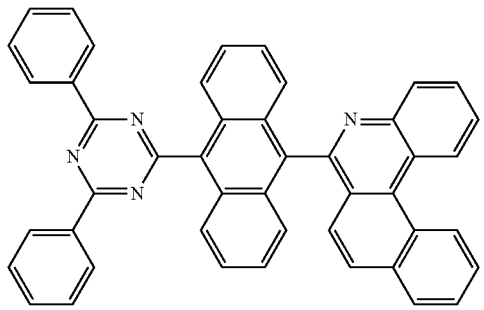
52A
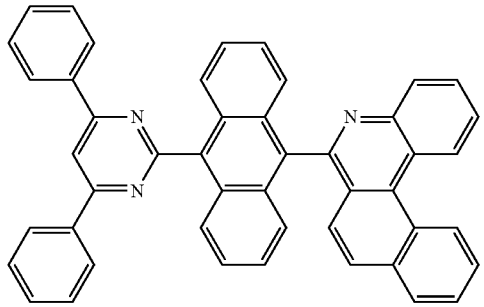
53A
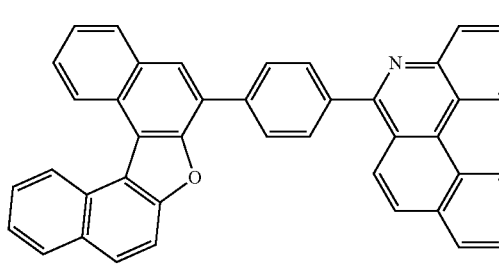
54A
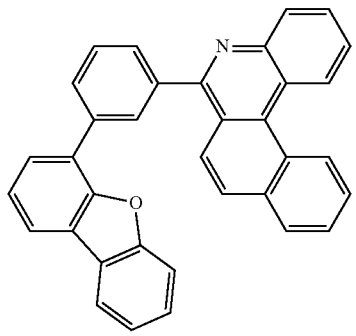
55A
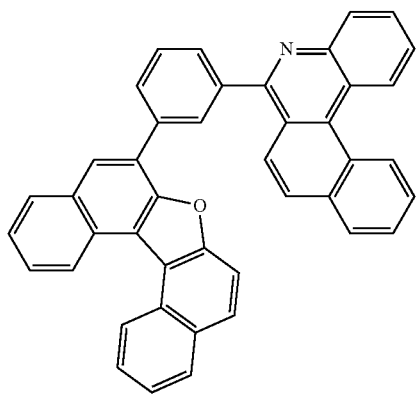
56A
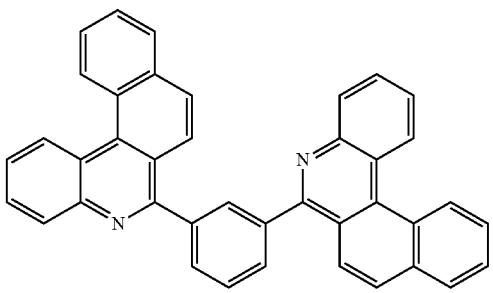
57A
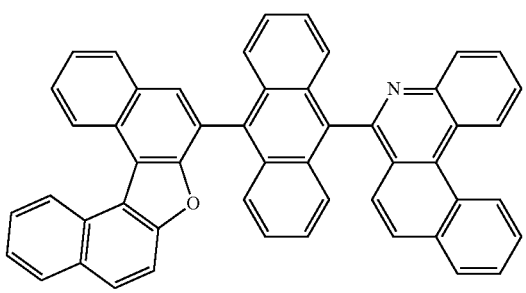
58A
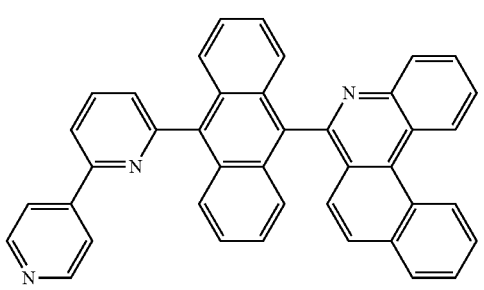
59A
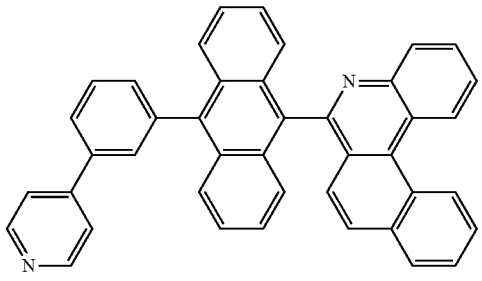
60A
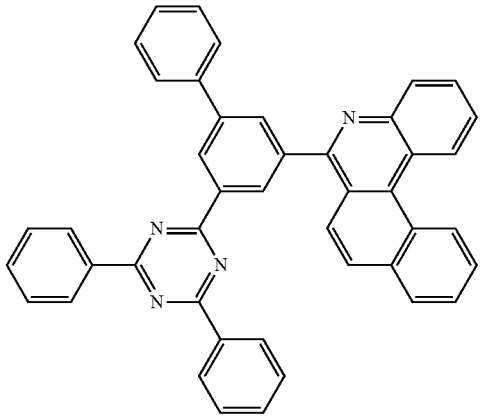
61A

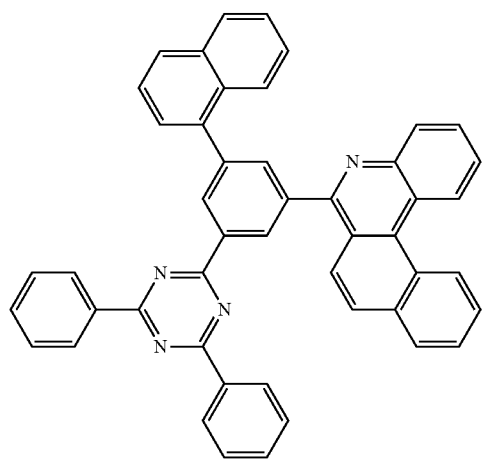
62A
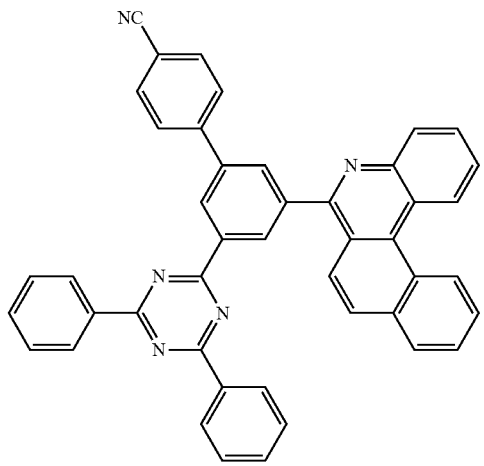
65A
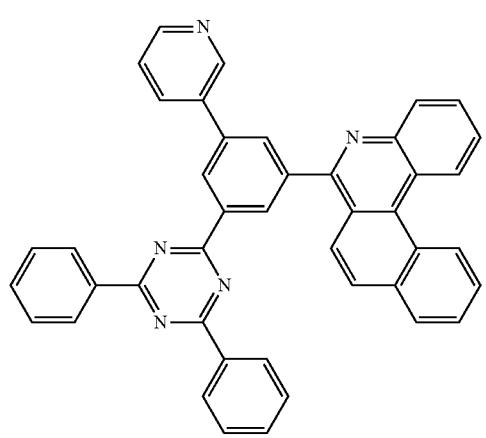
63A
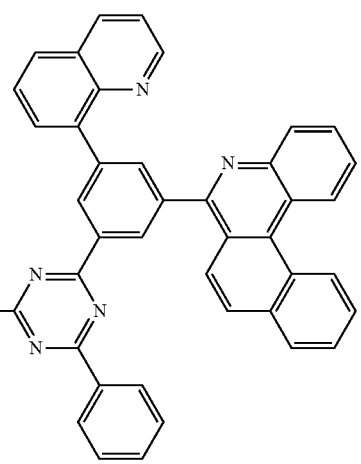
66A
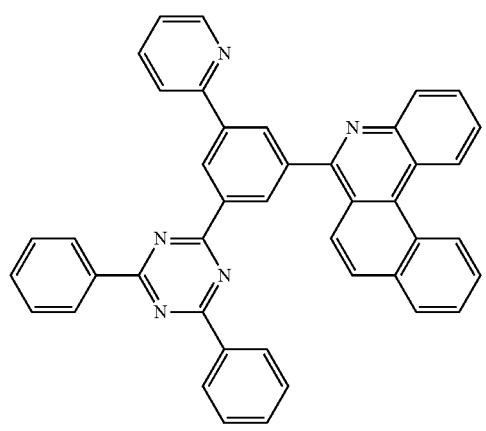
64A
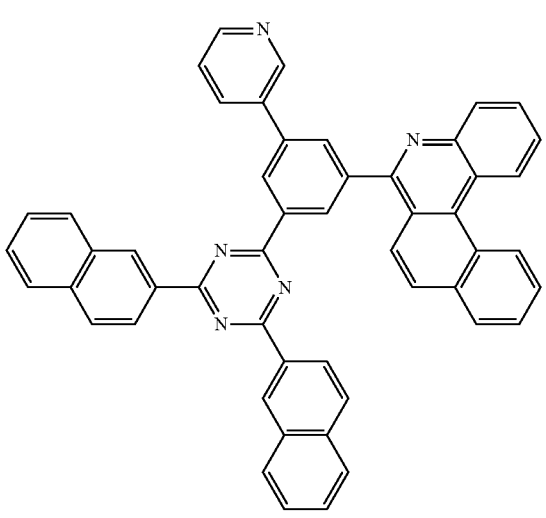
67A

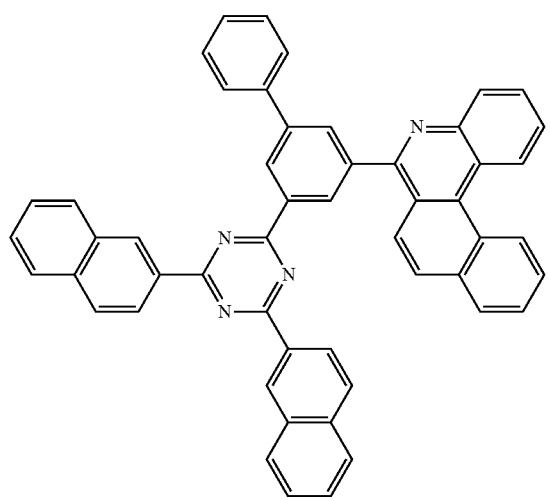
68A
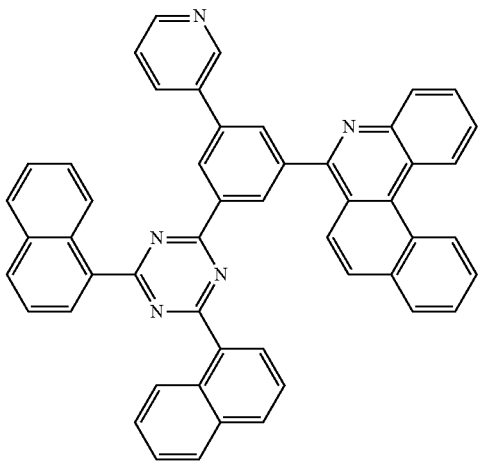
71A
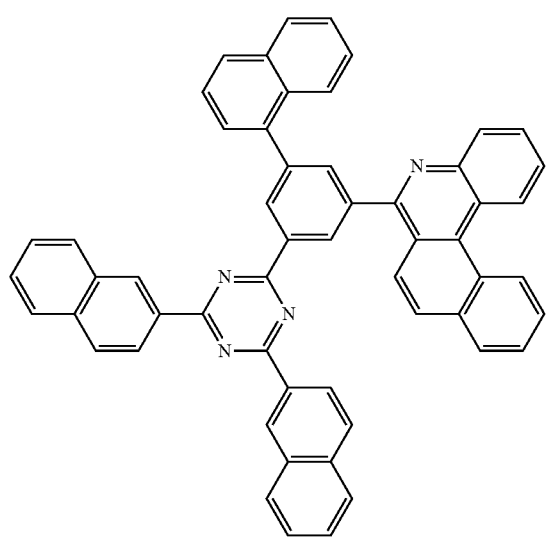
69A
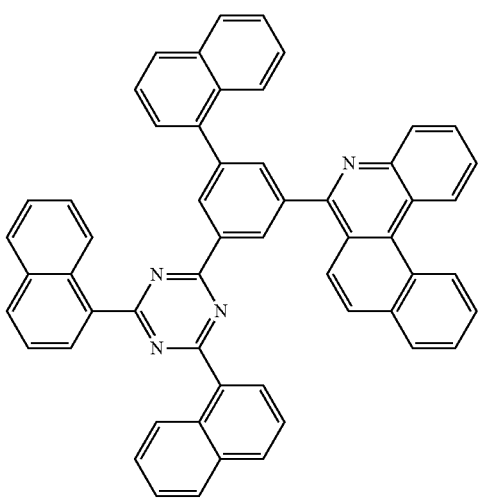
72A
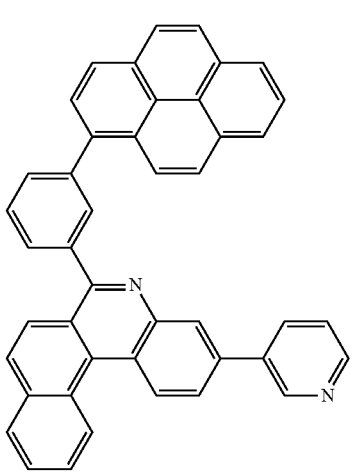
70A
73A 74A
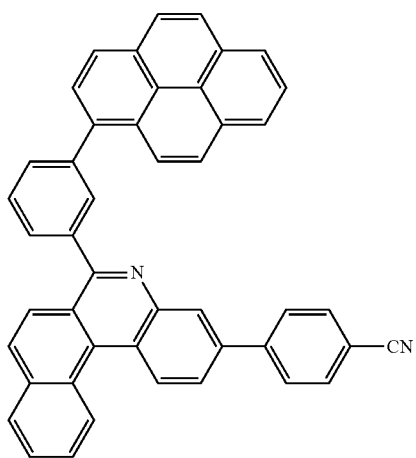
75A
77A
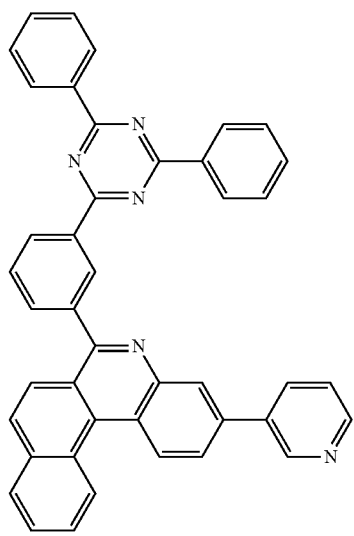
78A
76A
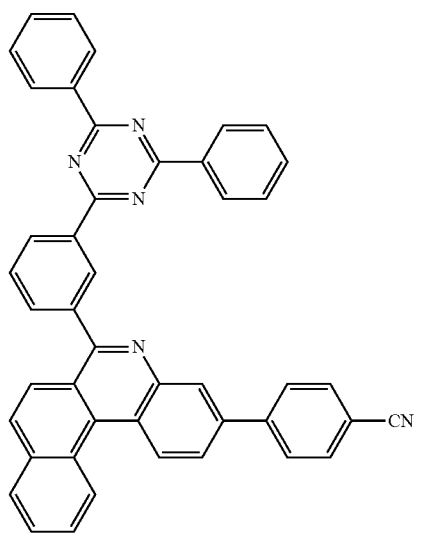
79A
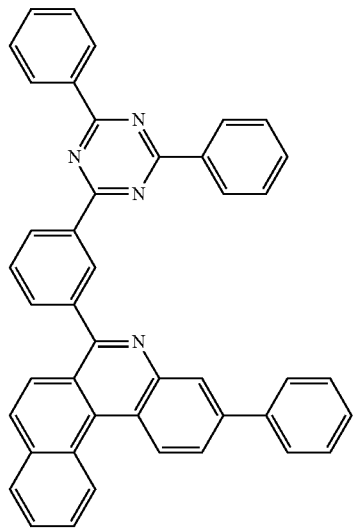

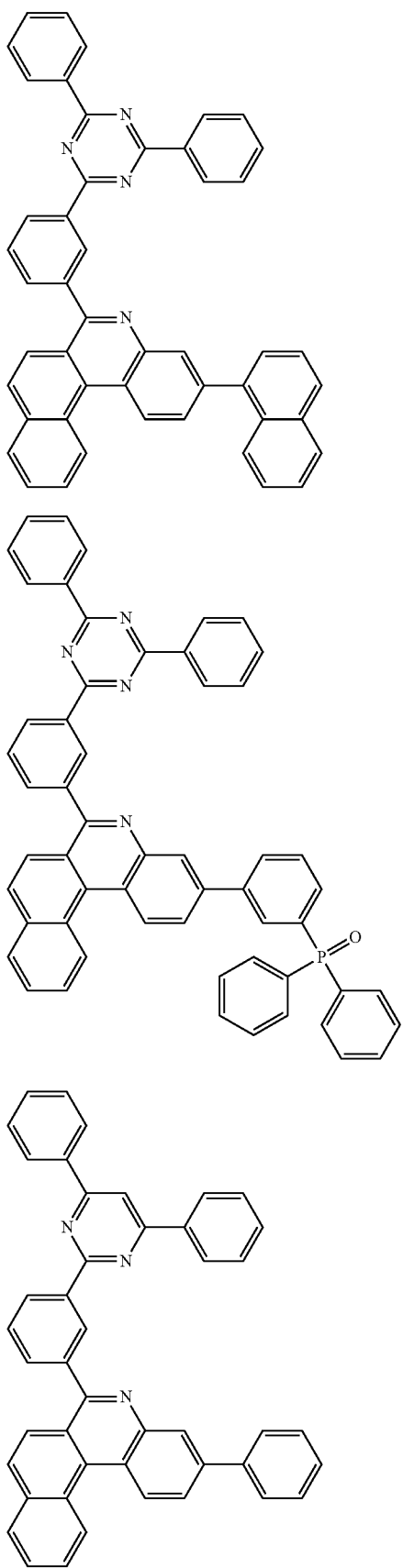
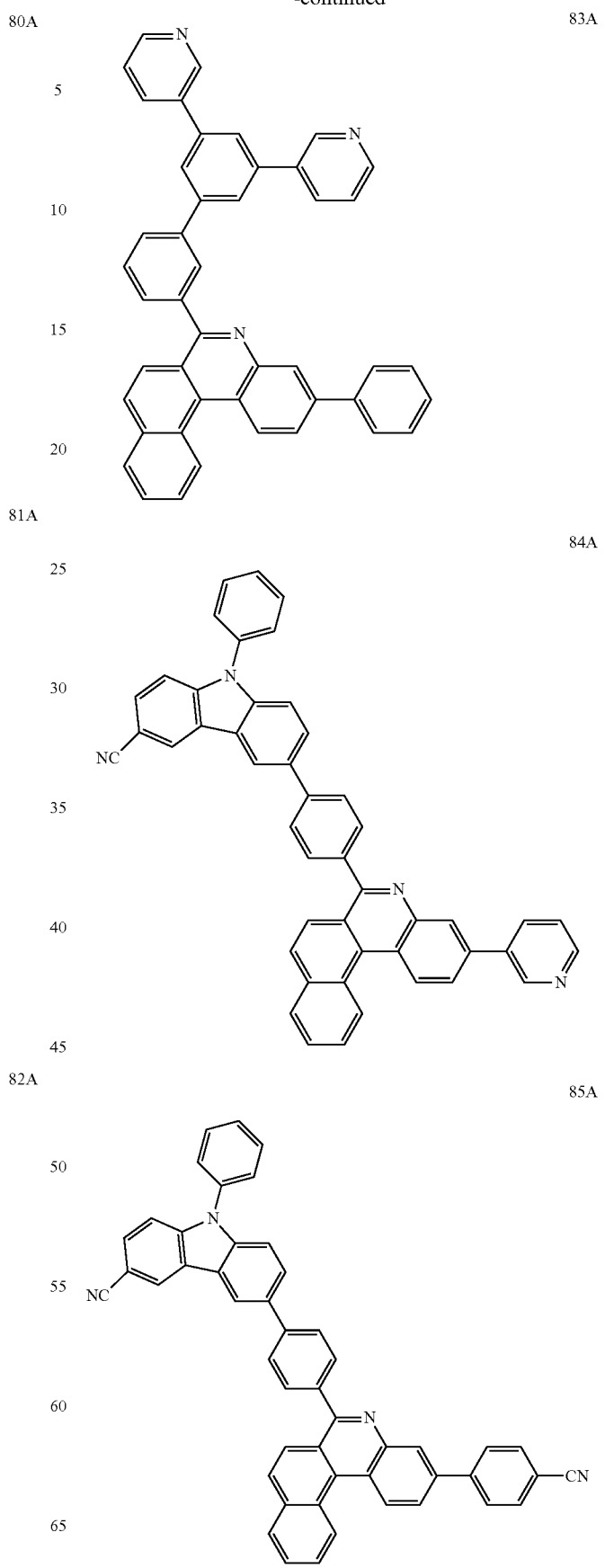

86A
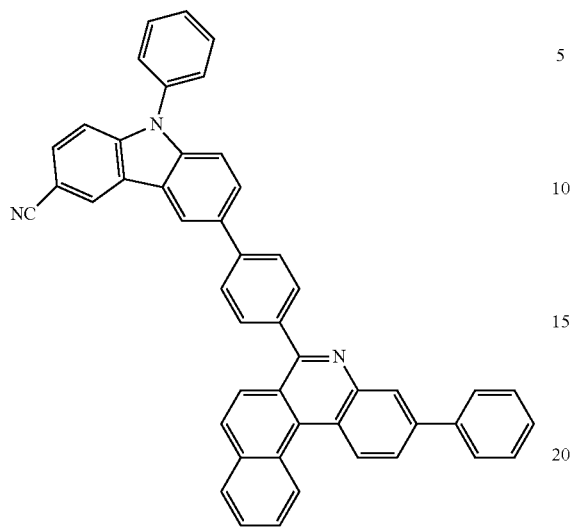
87A
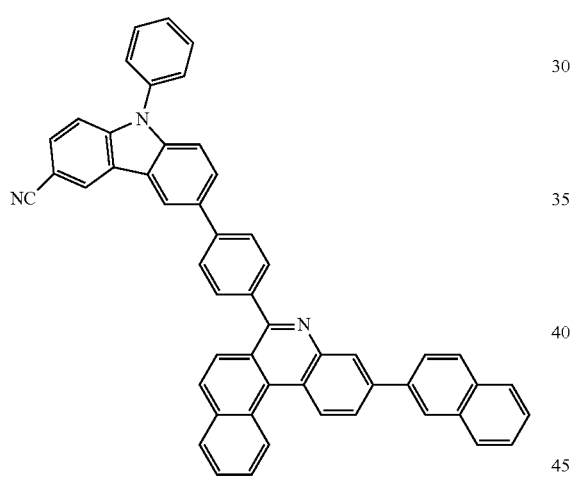
1B
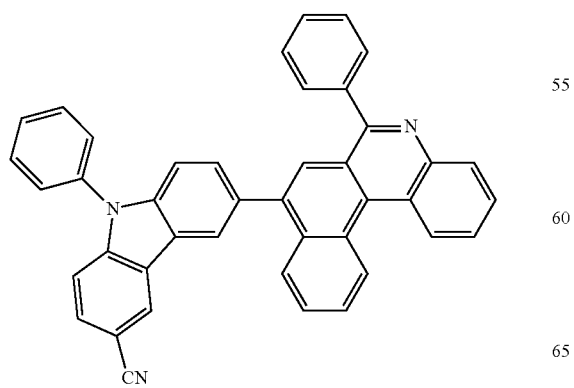
2B
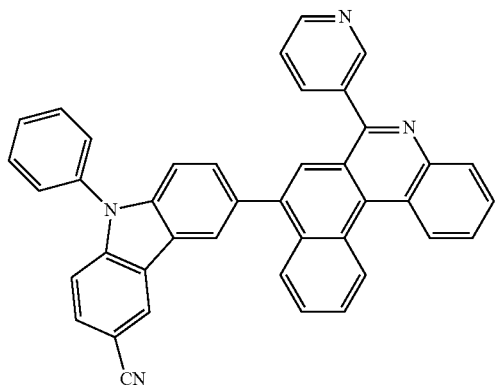
3B
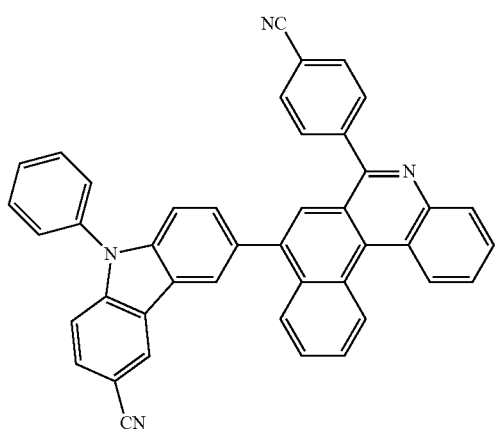
4B
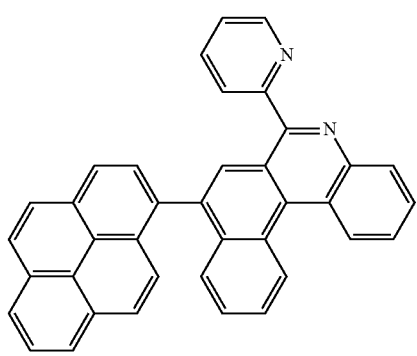
5B
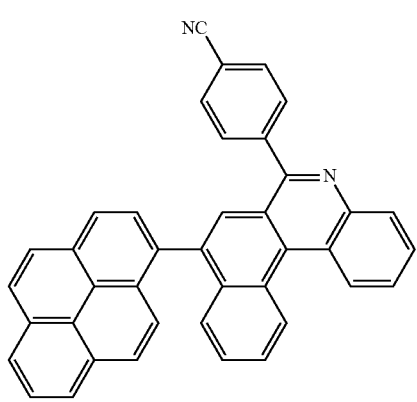

-continued
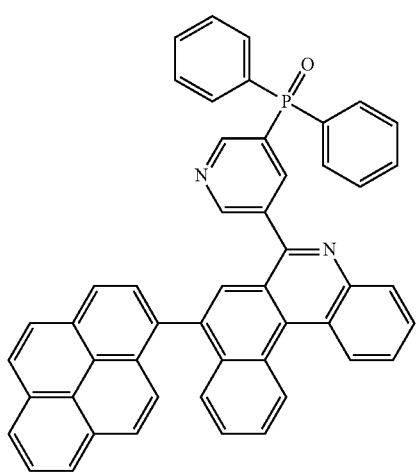
6B
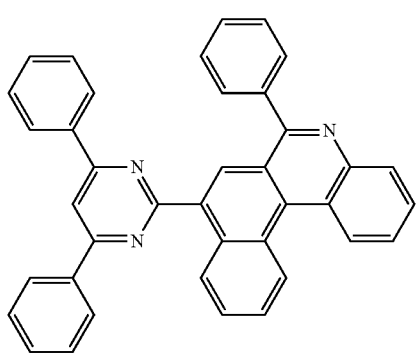
7B
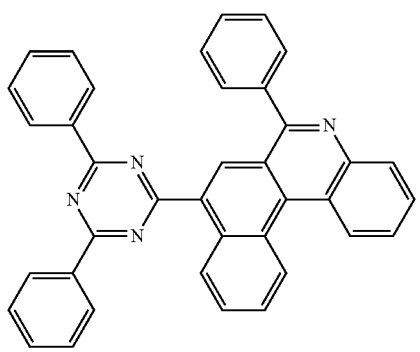
8B
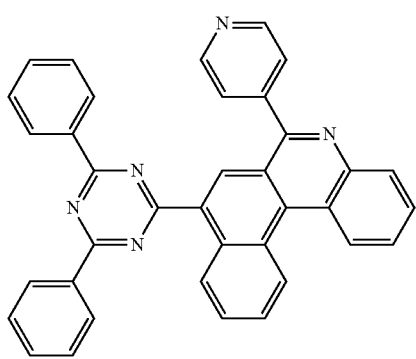
9B
-continued
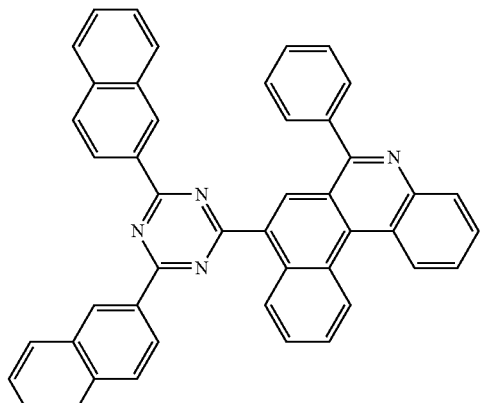
10B
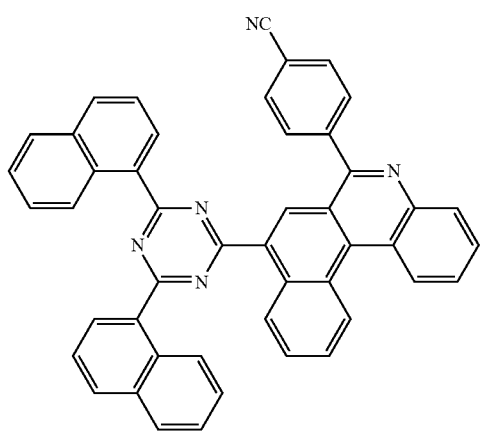
11B
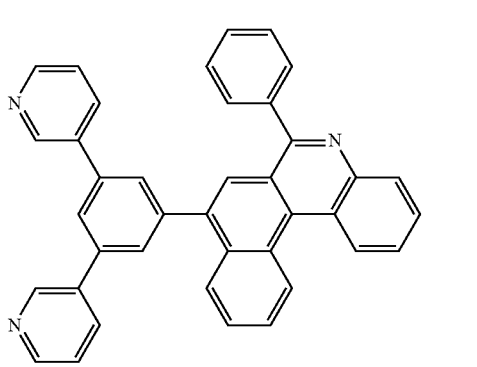
12B
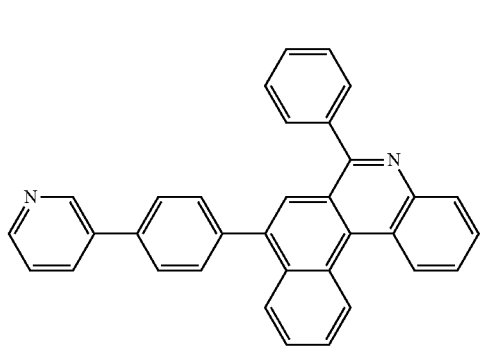
13B 14B
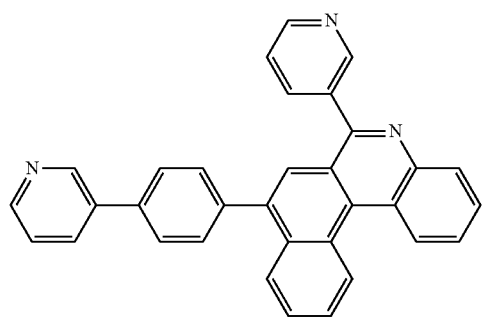
18B
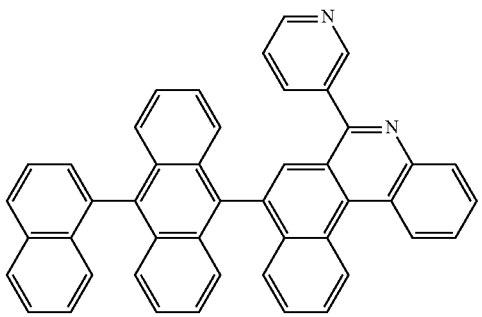
15B
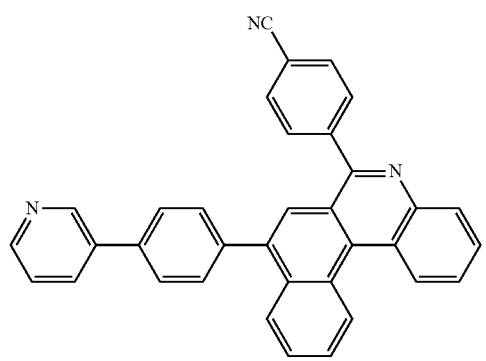
19B
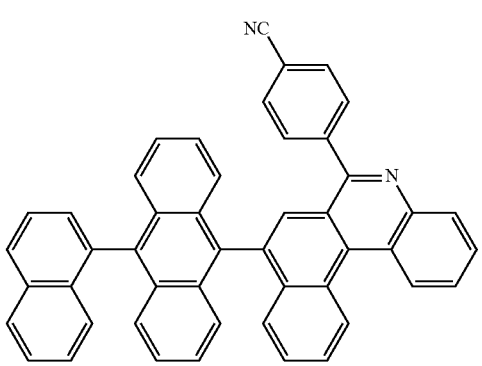
16B
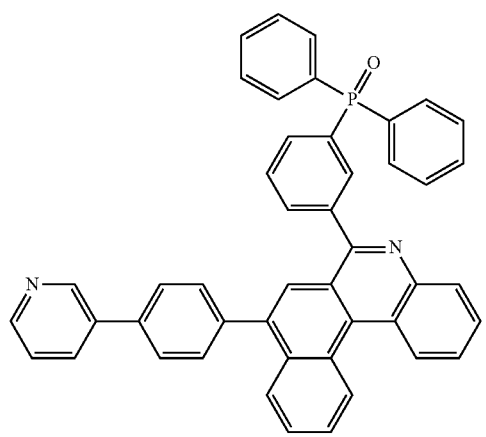
20B
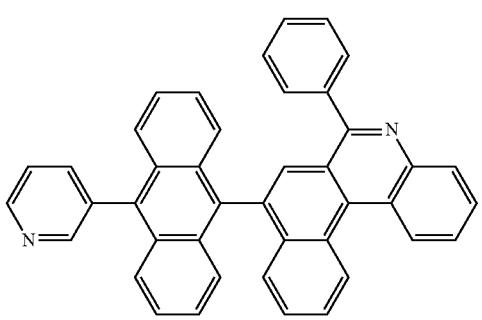
17B
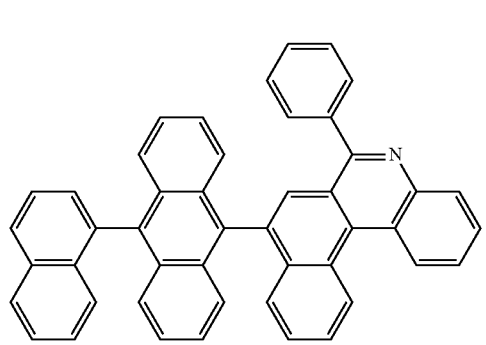
21B
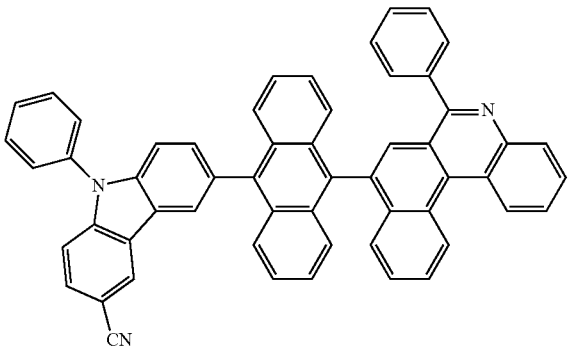

22B
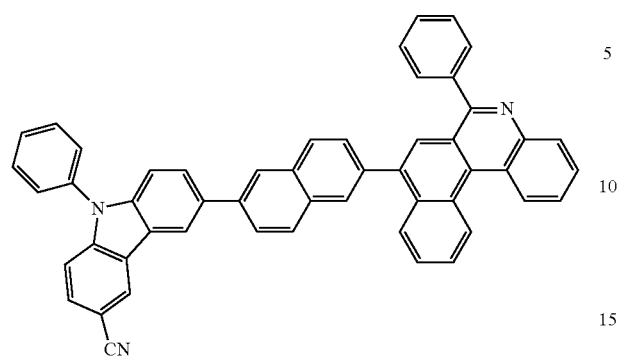
23B
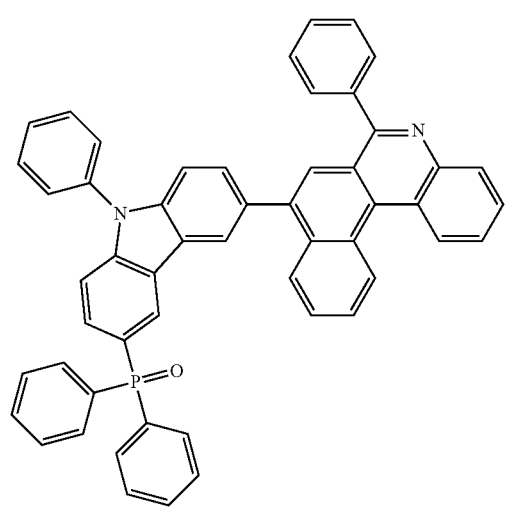
24B
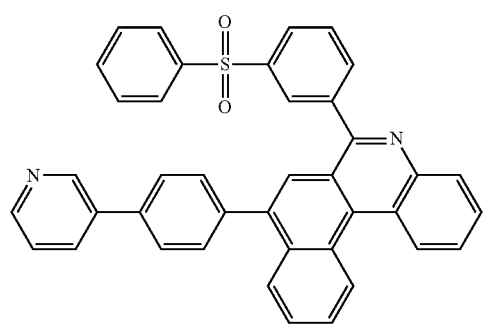
25B
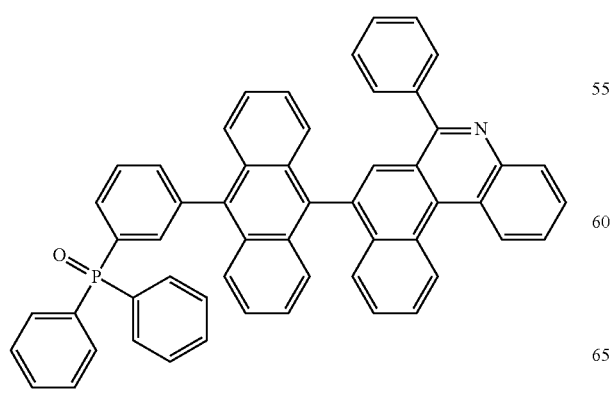
26B
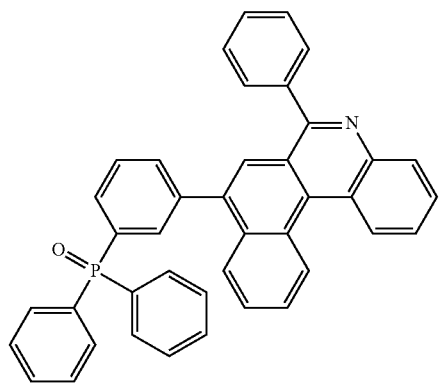
27B
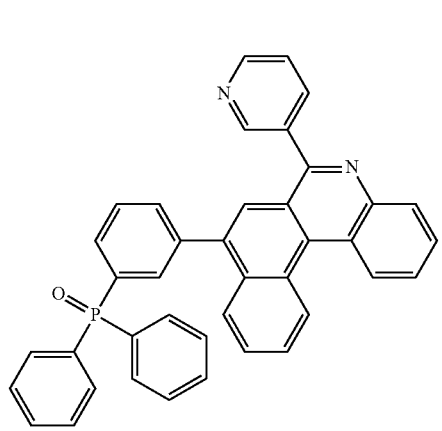
28B
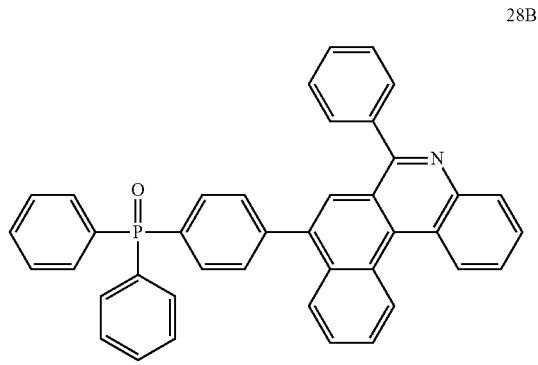
29B
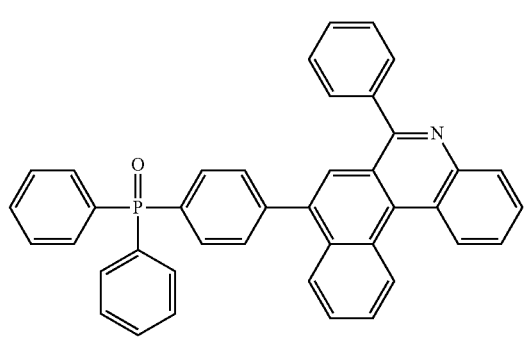

30B
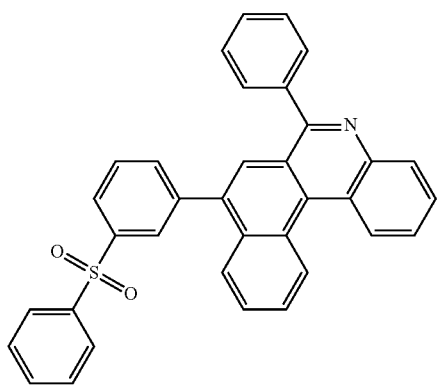
35B
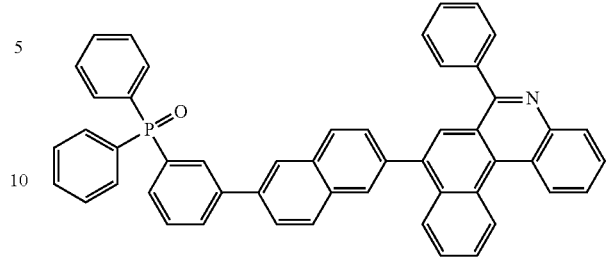
31B
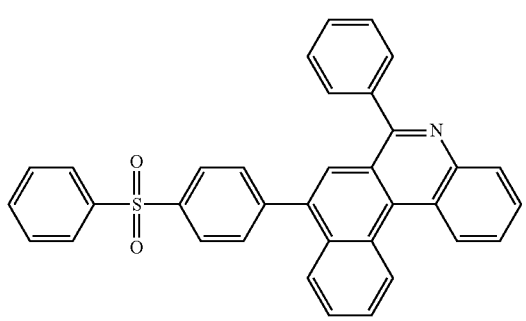
36B
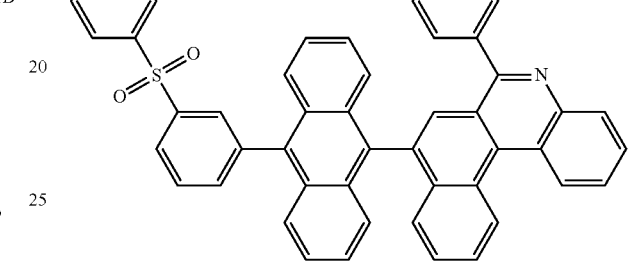
32B
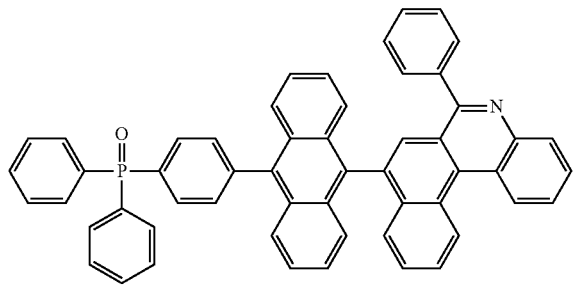
37B
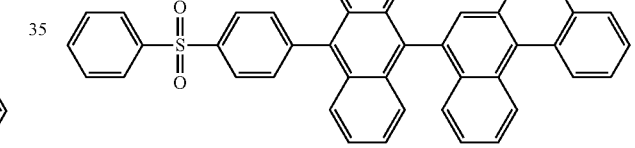
33B
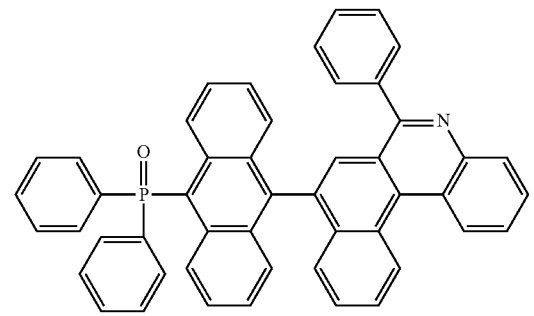
28B
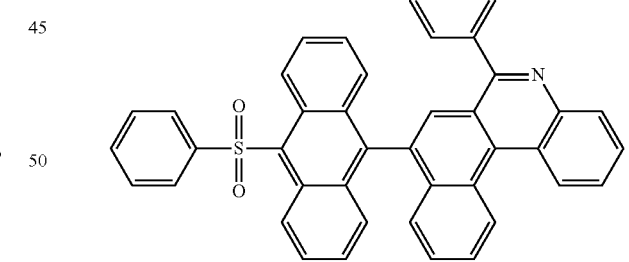
34B
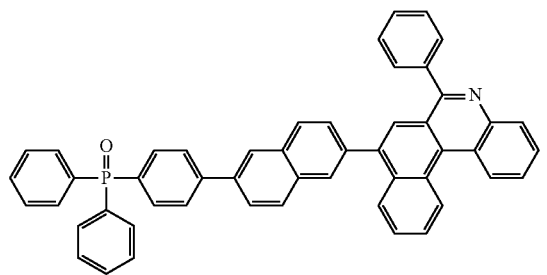
39B
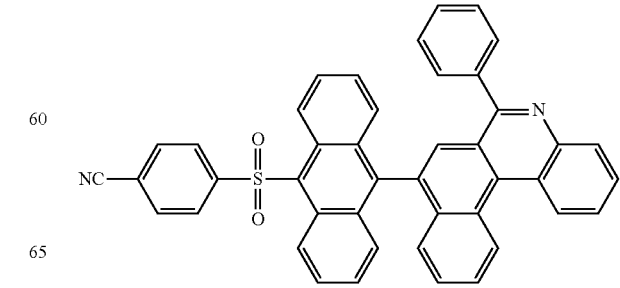

40B
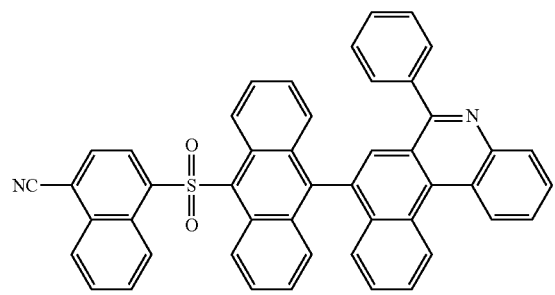
41B
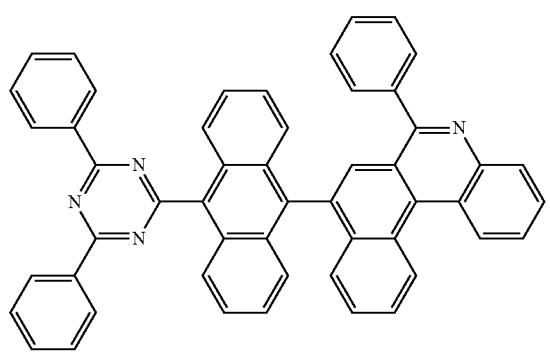
42B
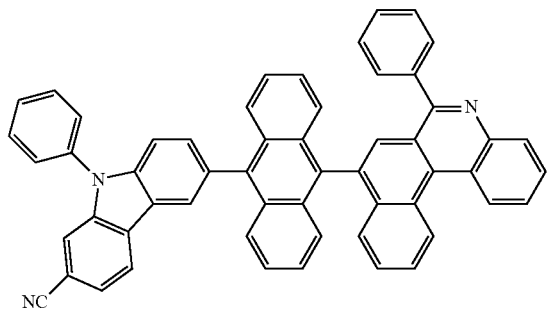
43B
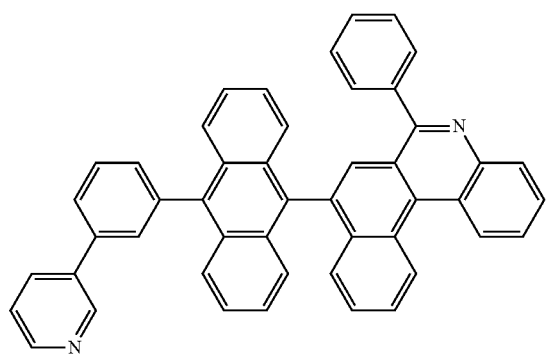
44B
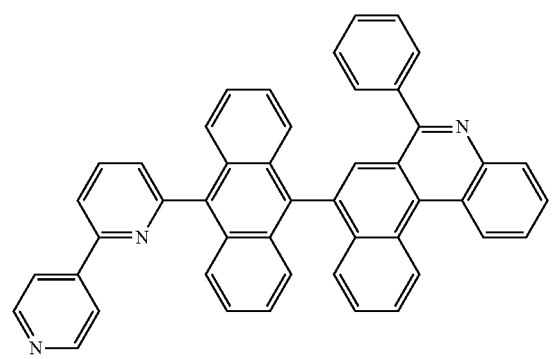
45B
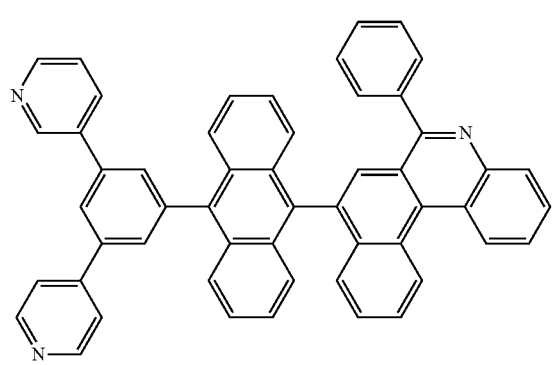
46B
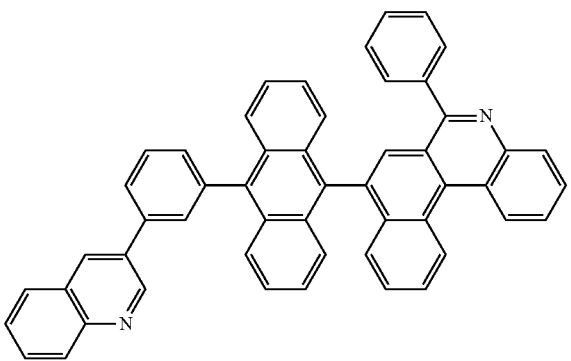
47B
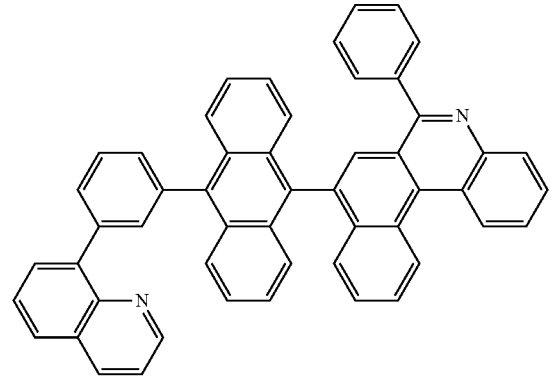

48B
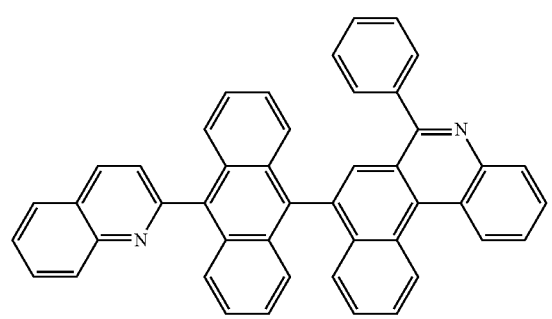
49B
52B
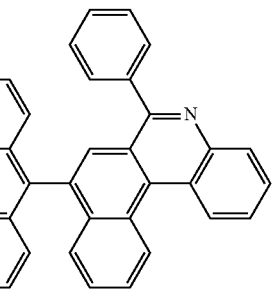
53B
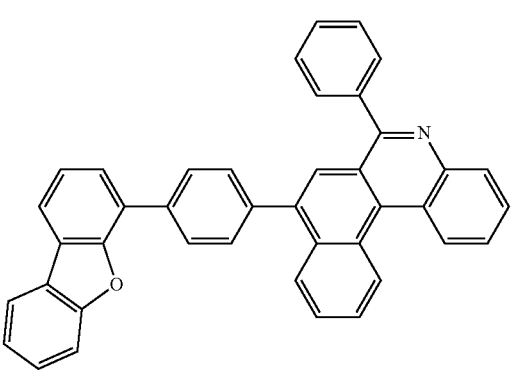
50B
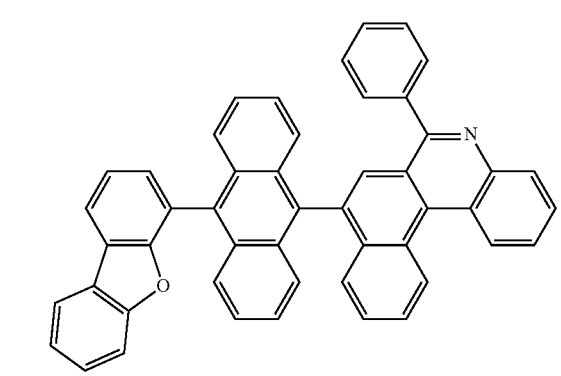
54B
51B
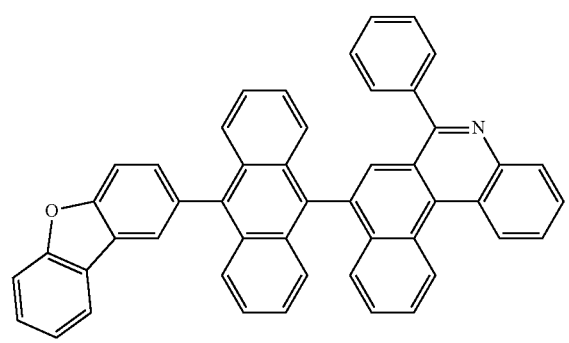
55B
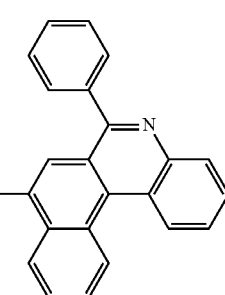

56B
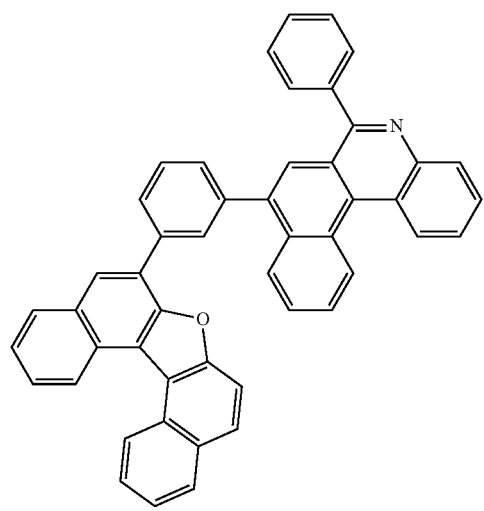
57B
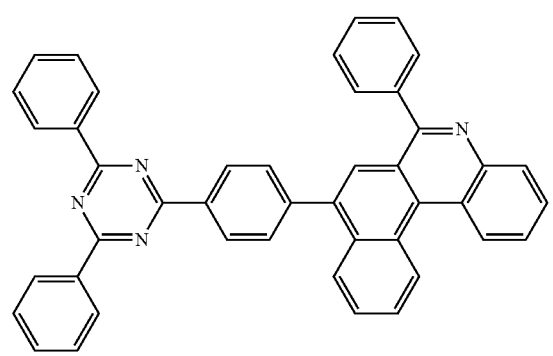
58B
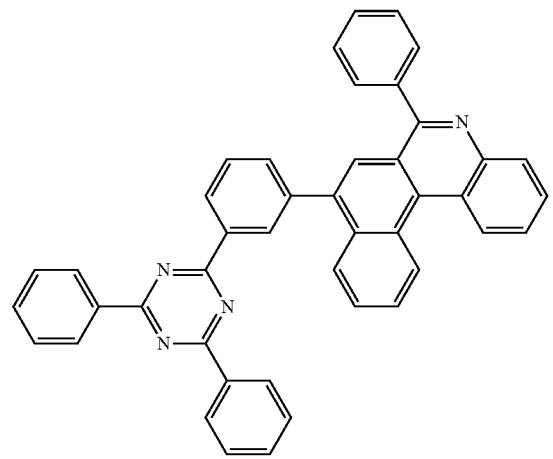
59B
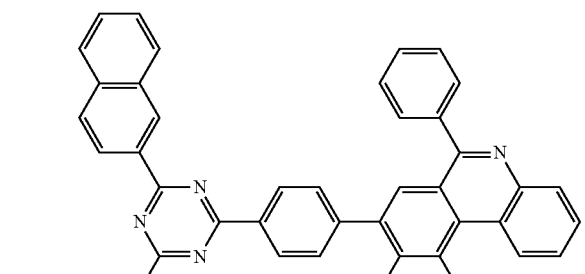
60B
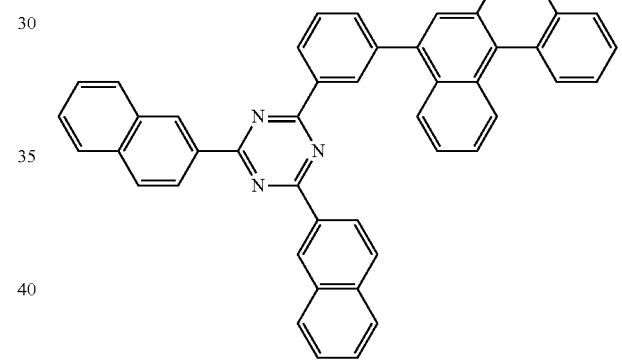
61B
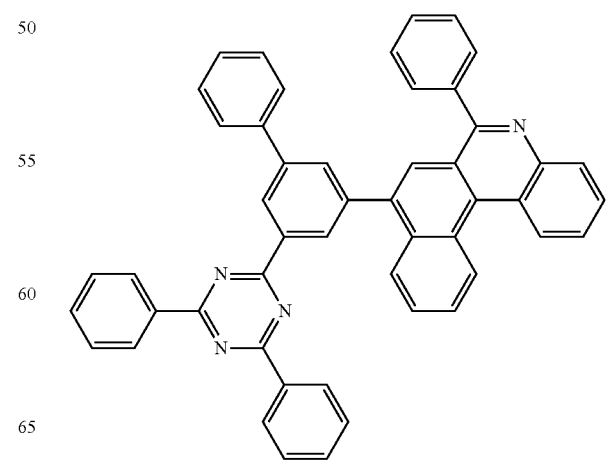

62B
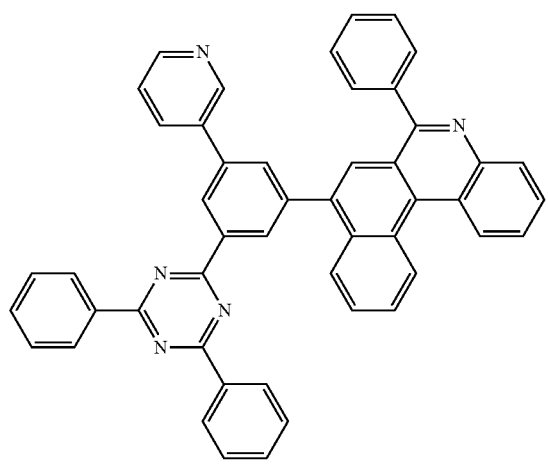
63B
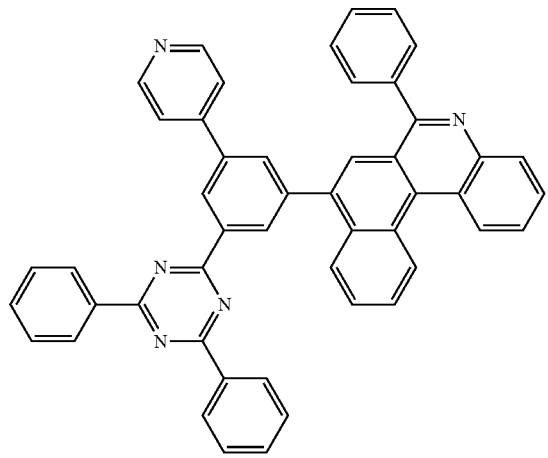
64B
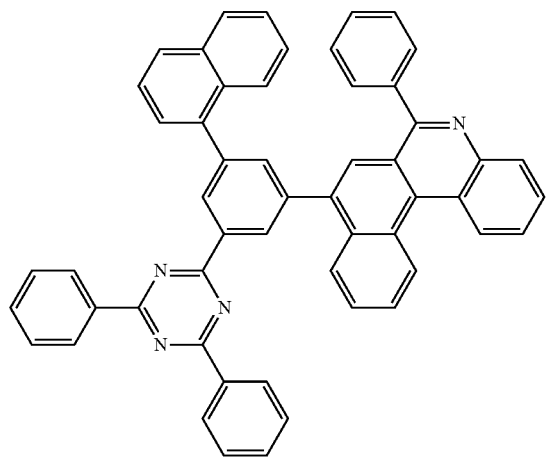
65B
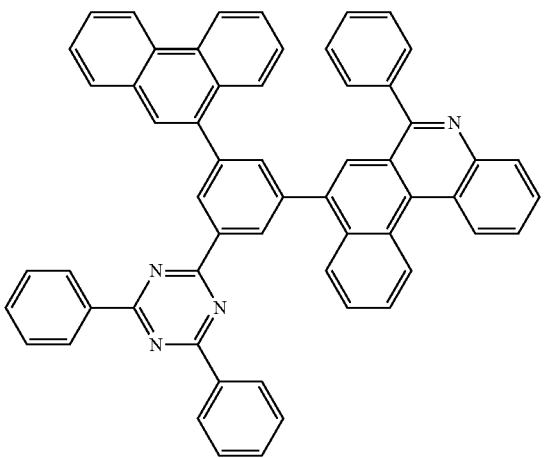
66B
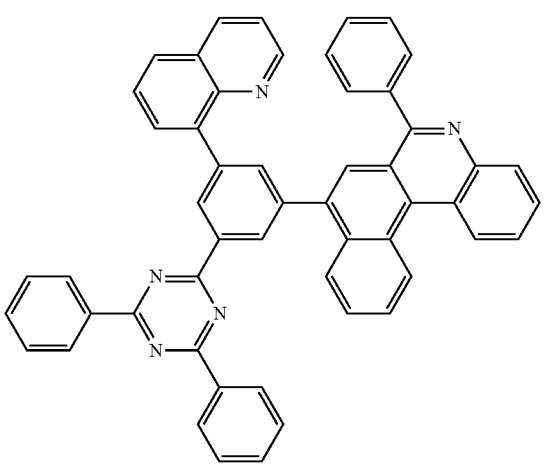
67B
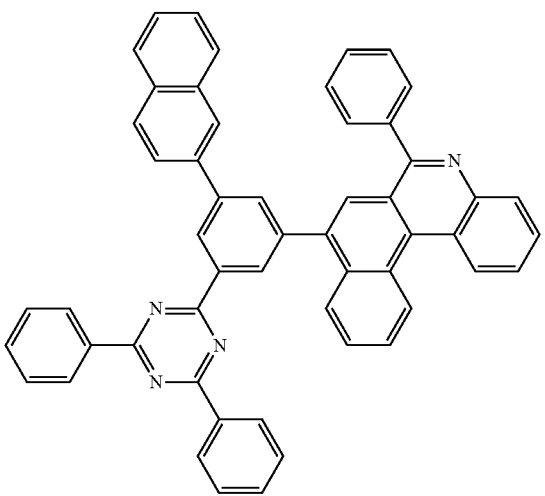

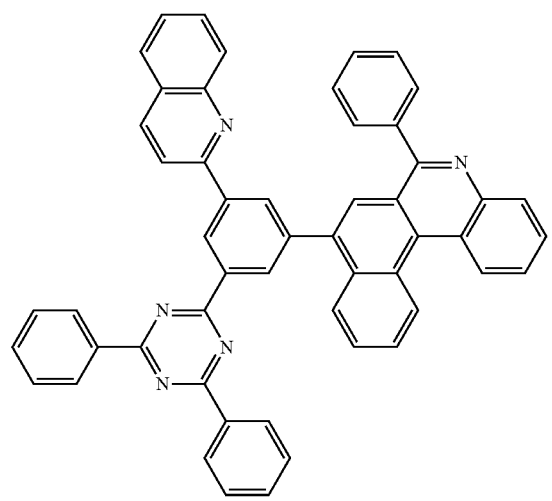
68B
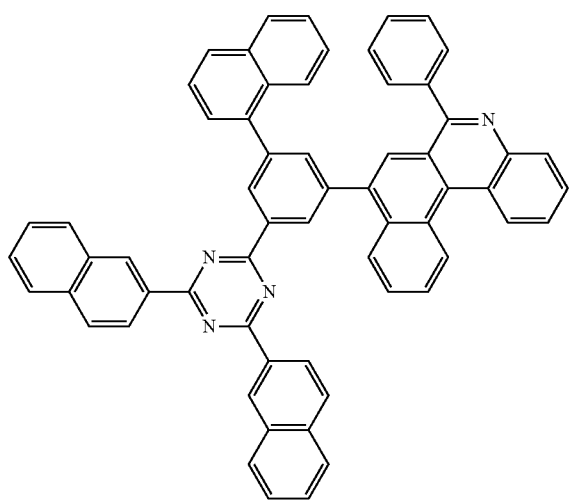
71B
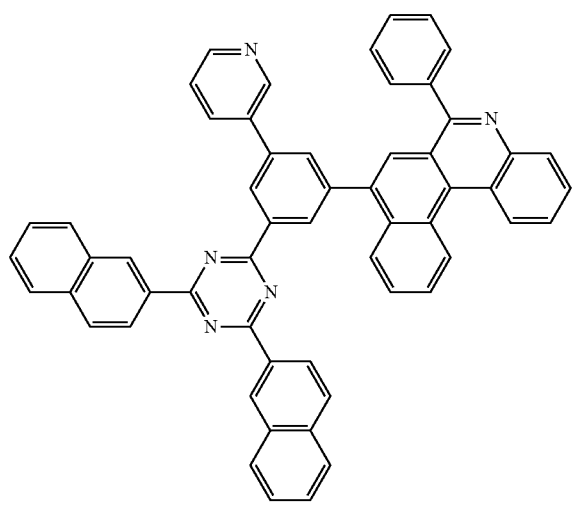
69B
70B
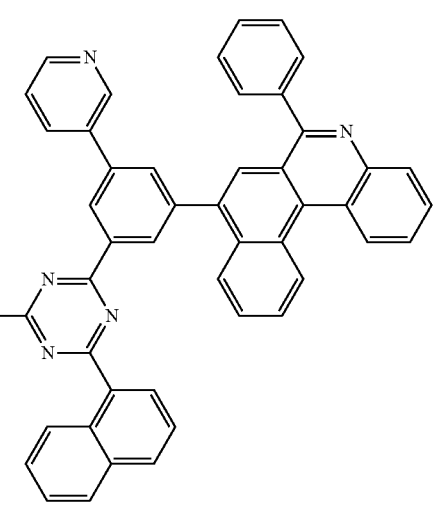
72B
73B

74B
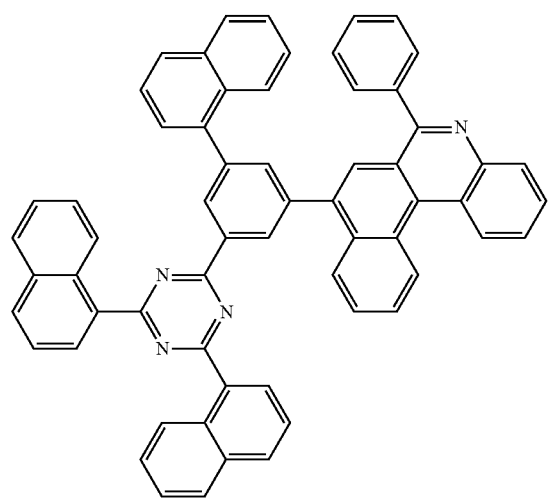
75B
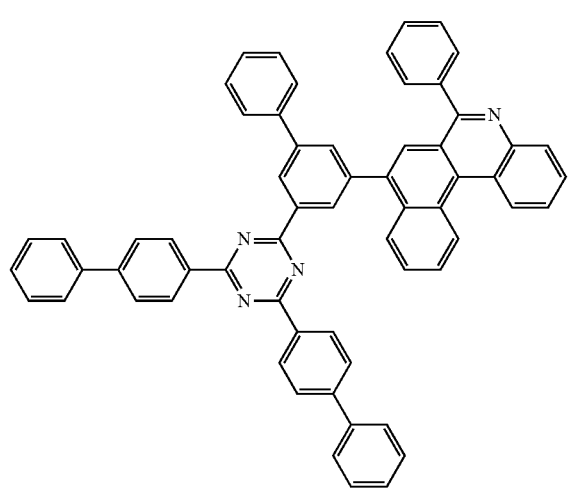
76B
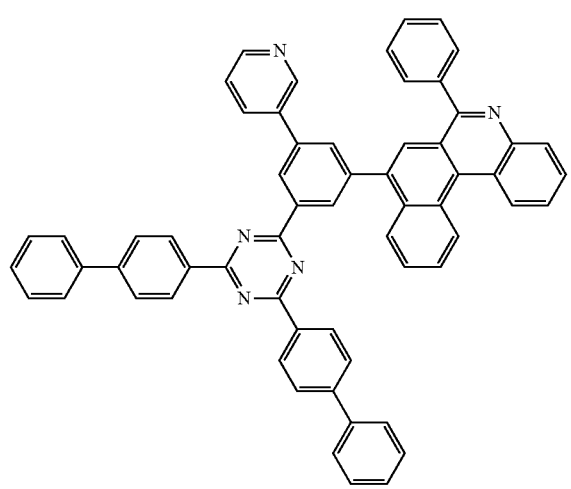
77B
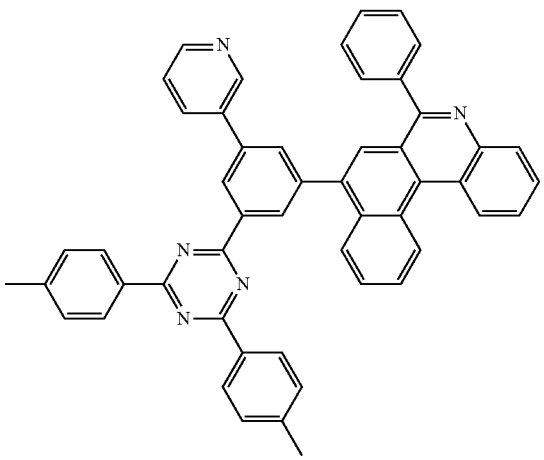
78B
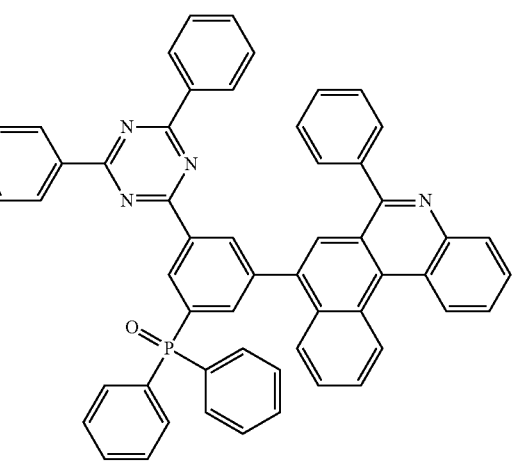
79B
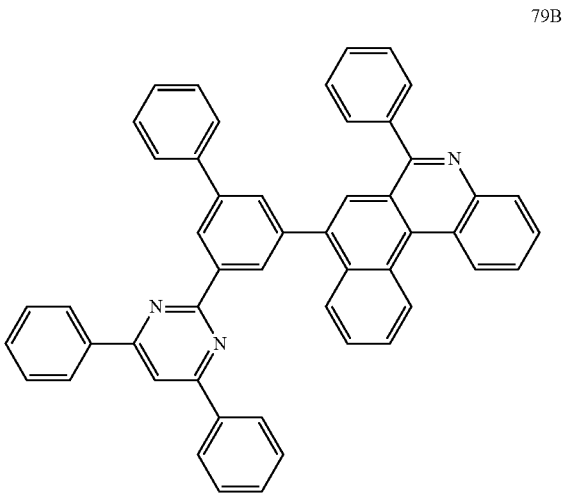

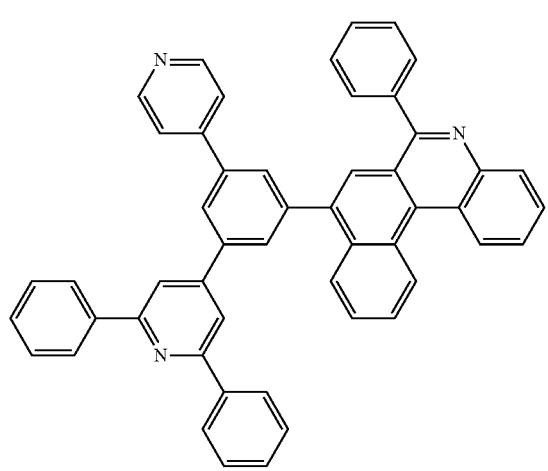
80B
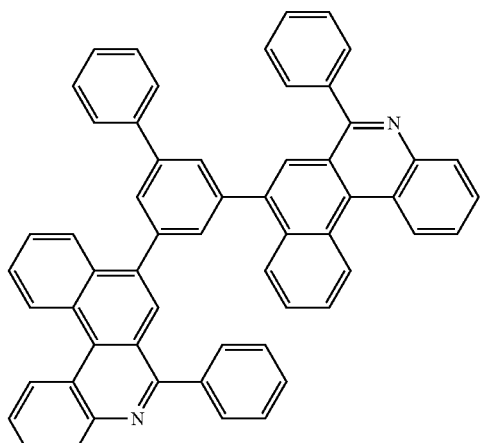
83B
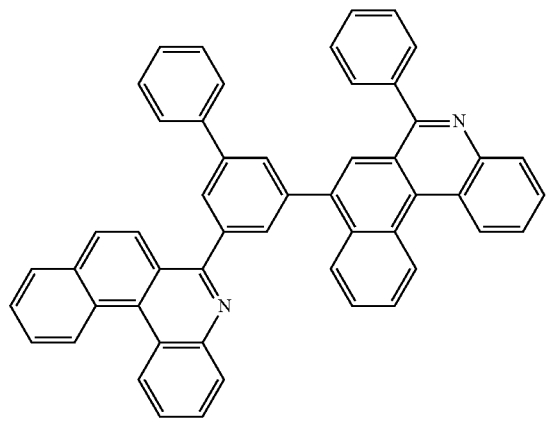
81B
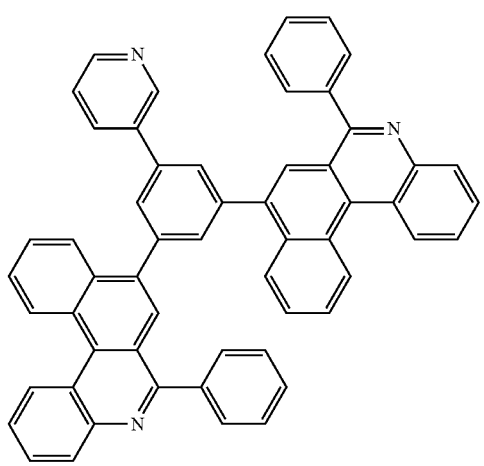
84B
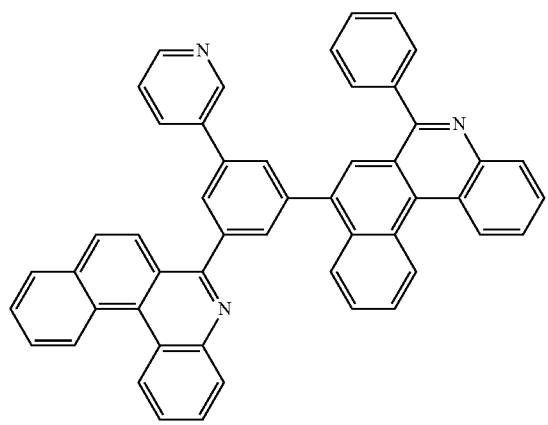
82B
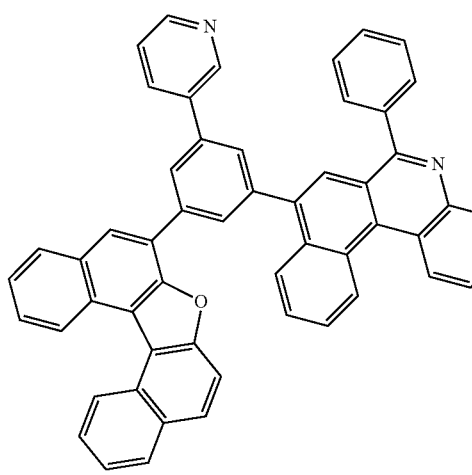
85B -continued
86B
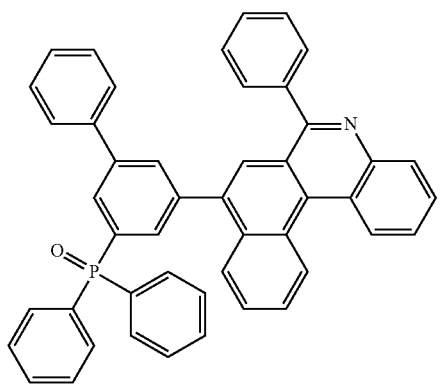
87B
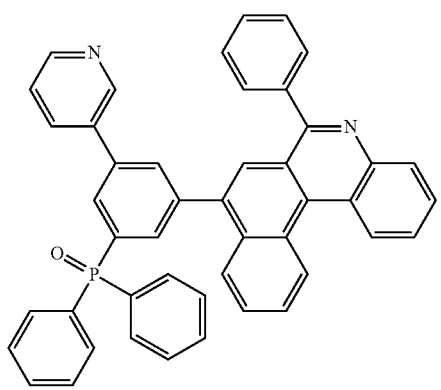
88B
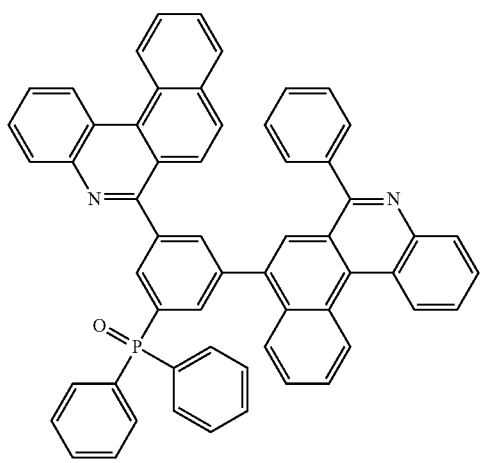
1C
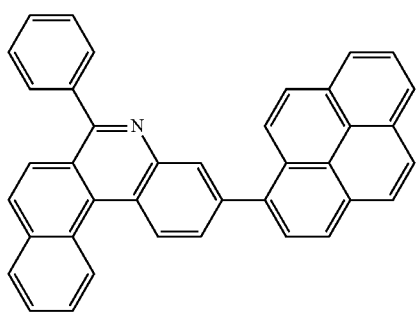
-continued
2C
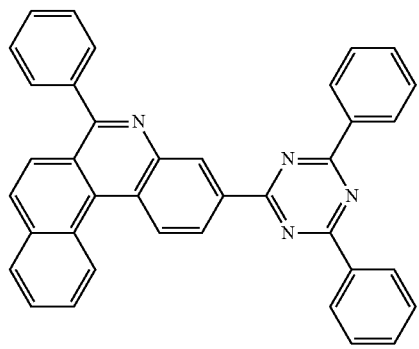
3C
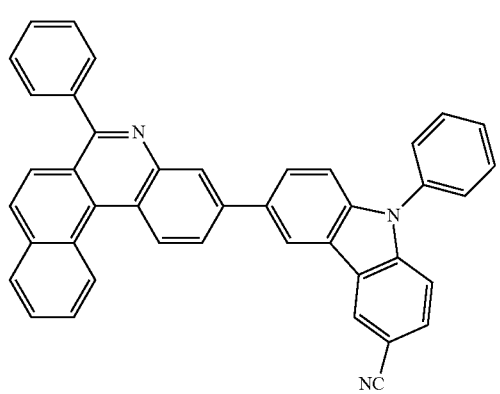
4C
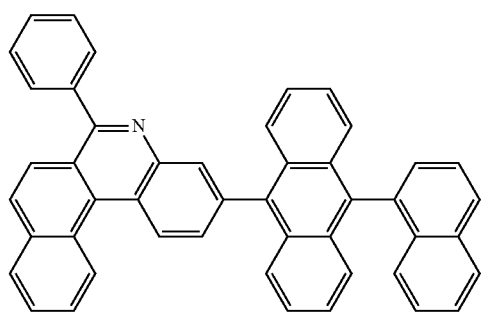
5C
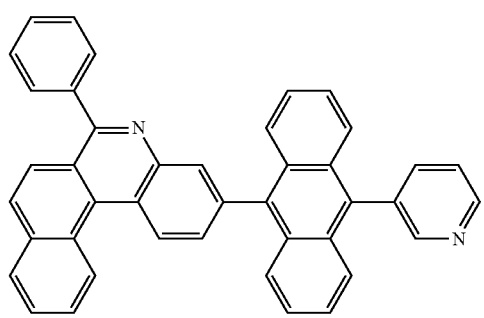

91
-continued
6C
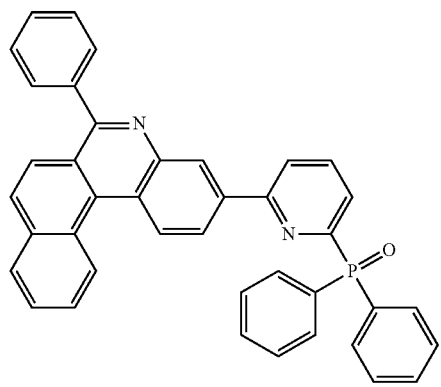
7C
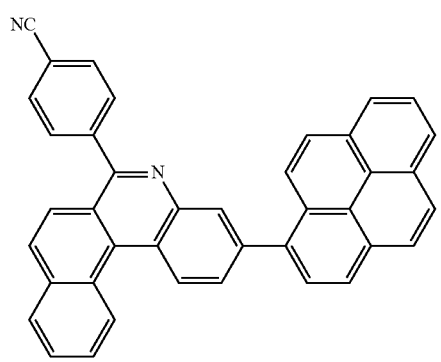
8C
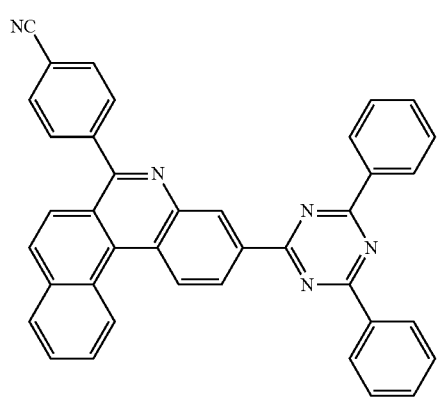
9C
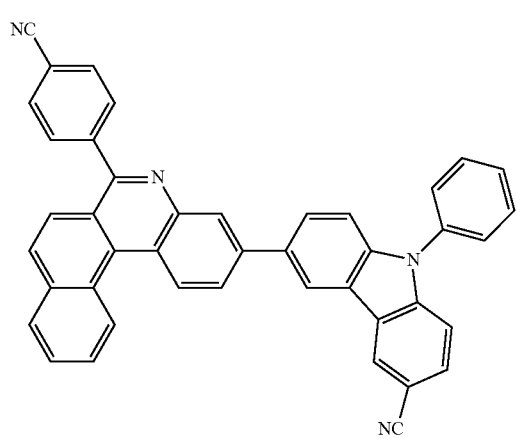
92
-continued
10C
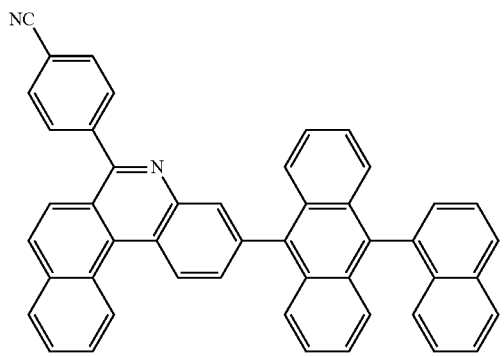
11C
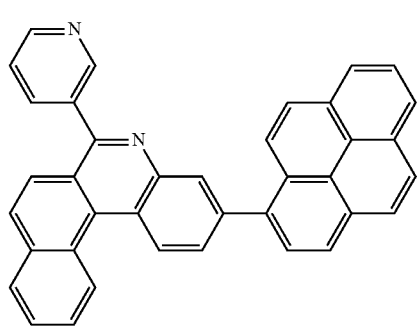
12C
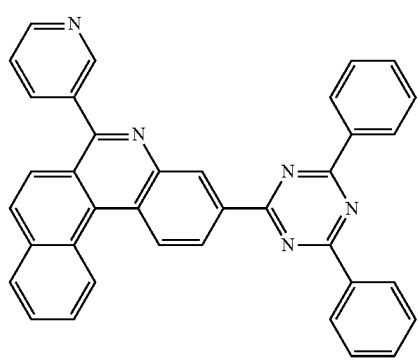
13C
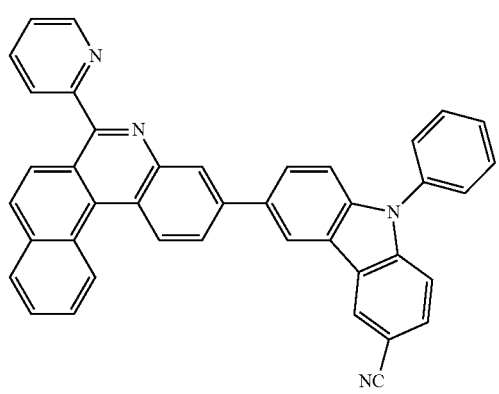

14C
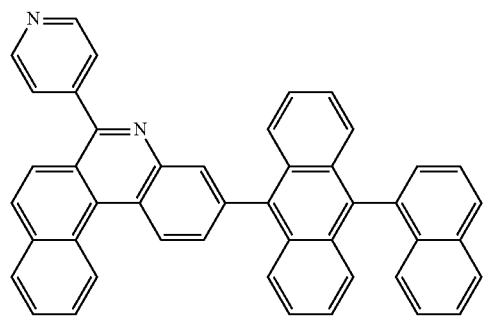
15C
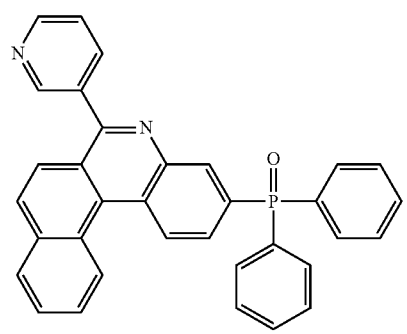
16C
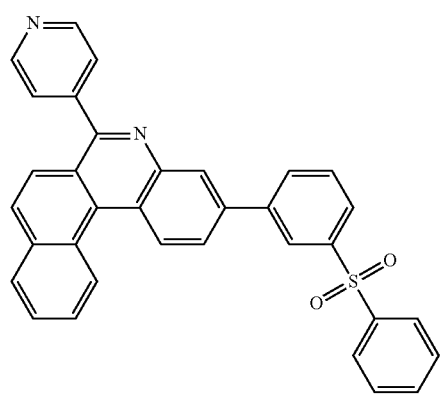
17C
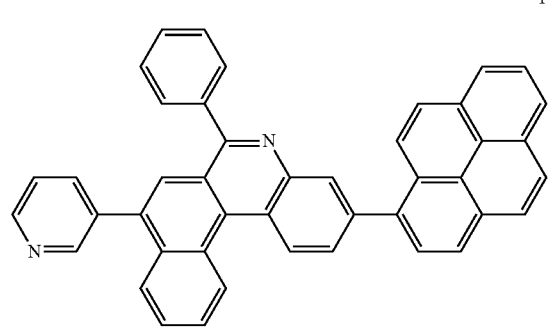
18C
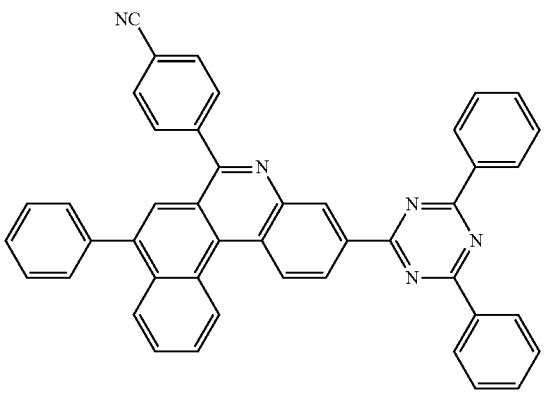
19C
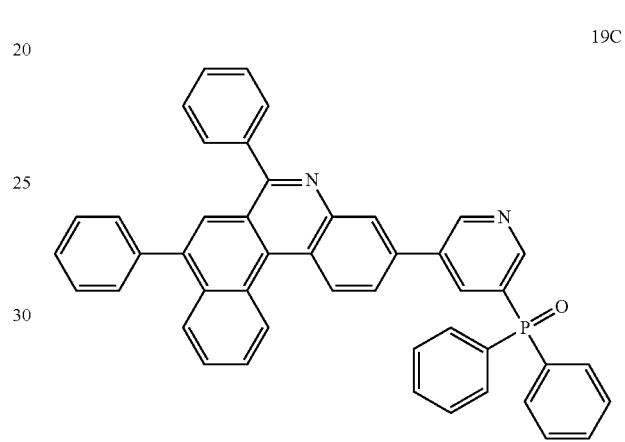
20C
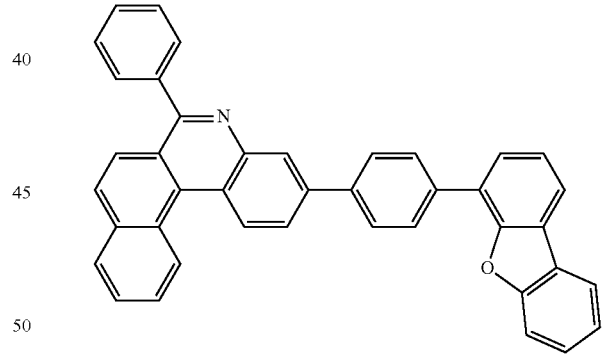
21C
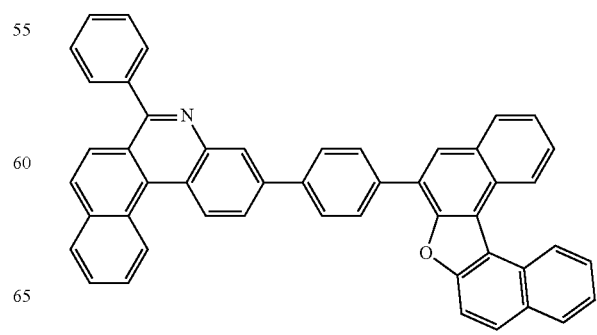

22C
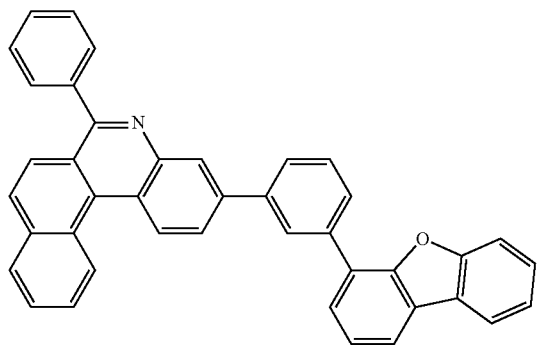
23C
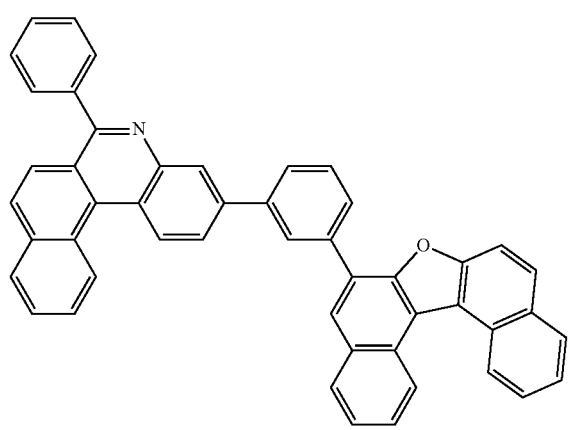
24C
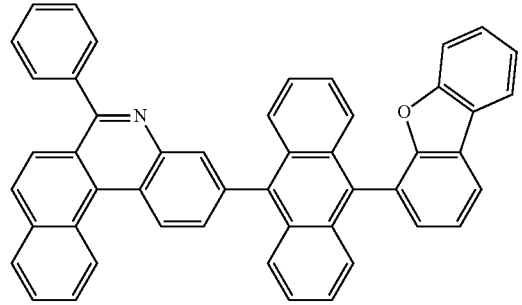
25C
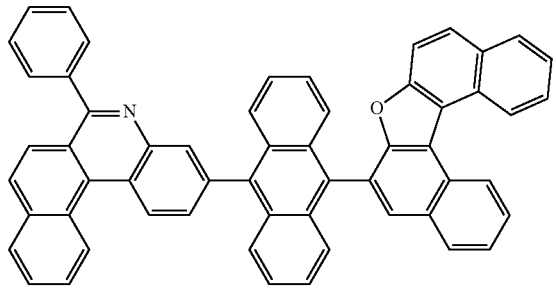
26C
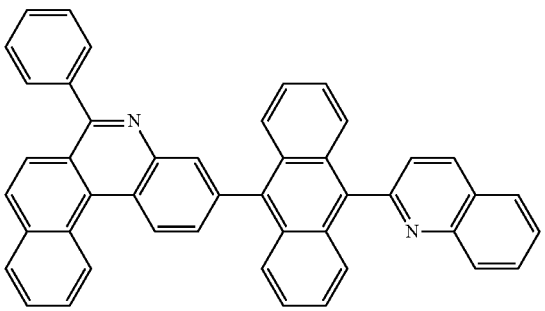
27C
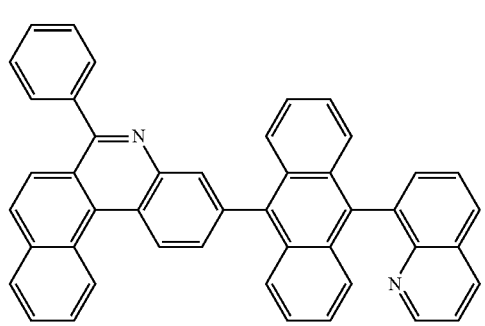
28C
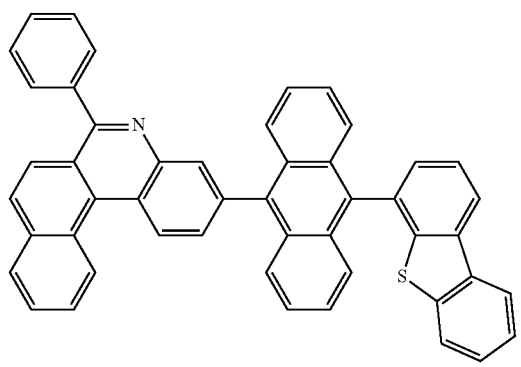
29C
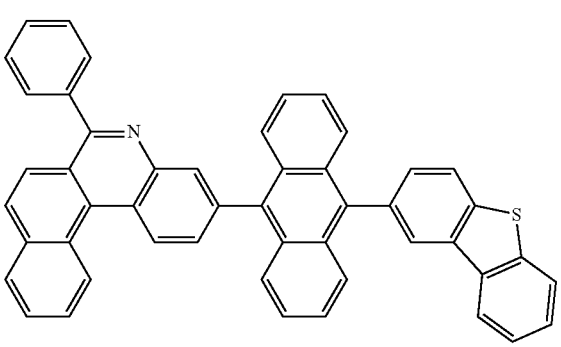

30C
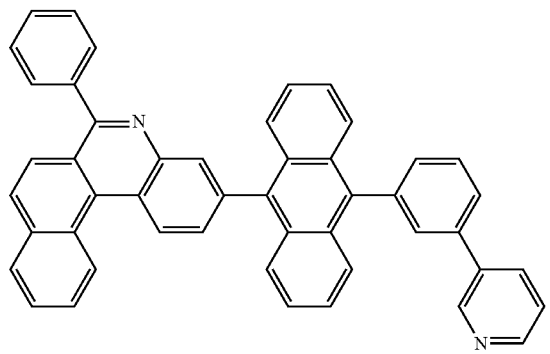
31C
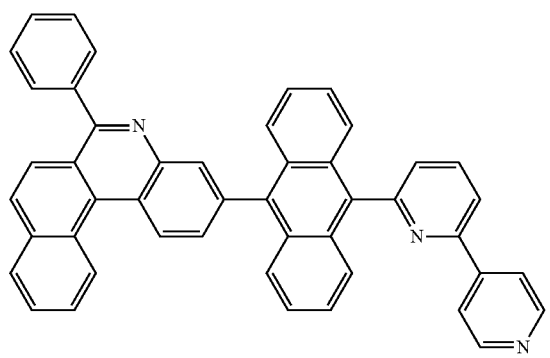
32C
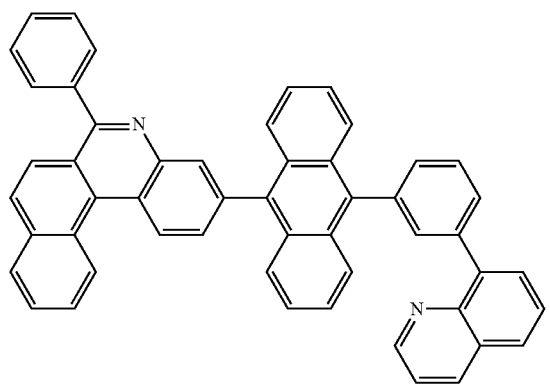
33C
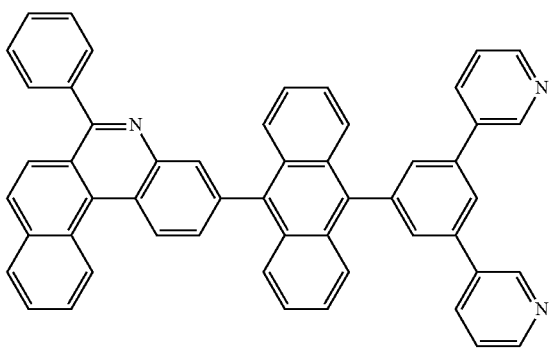
34C
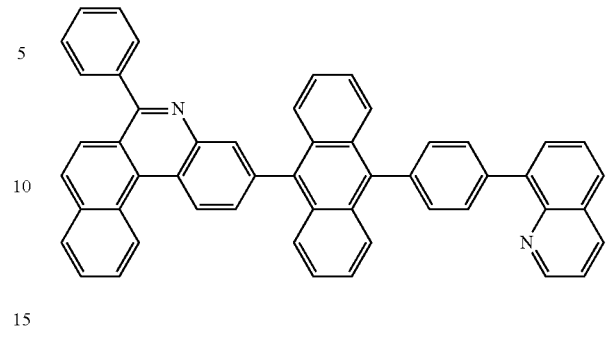
35C
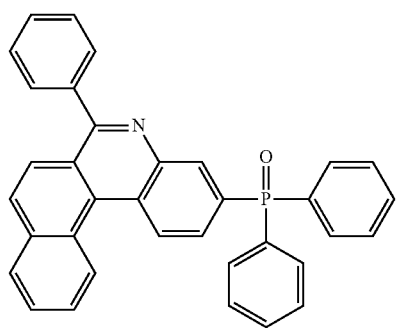
36C
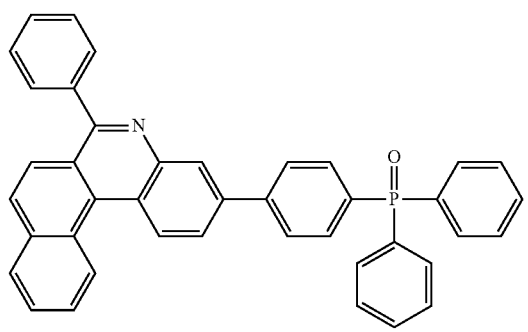
37C
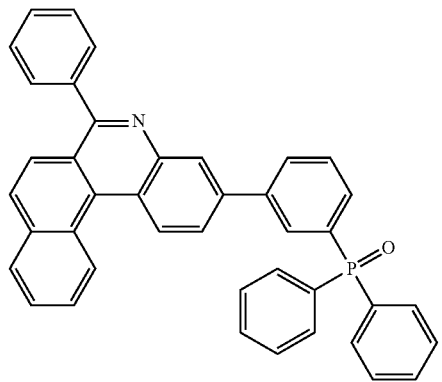

99
-continued
38C
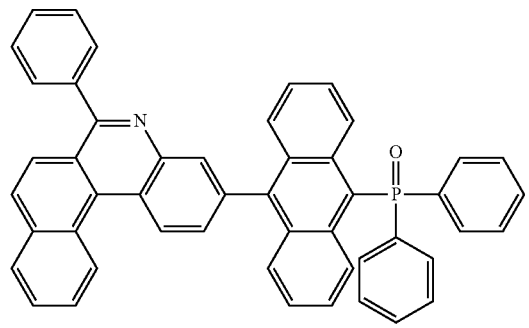
39C
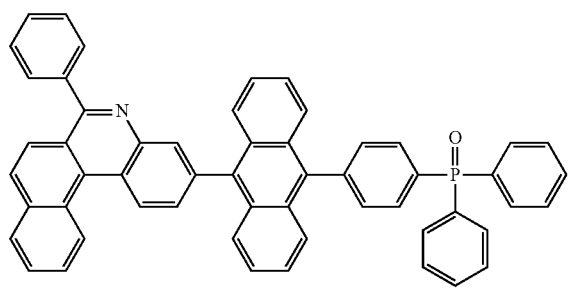
40C
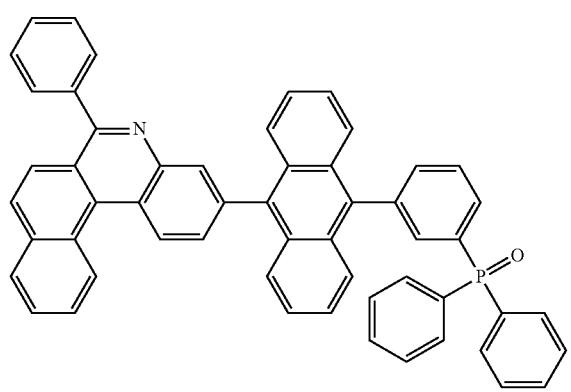
41C
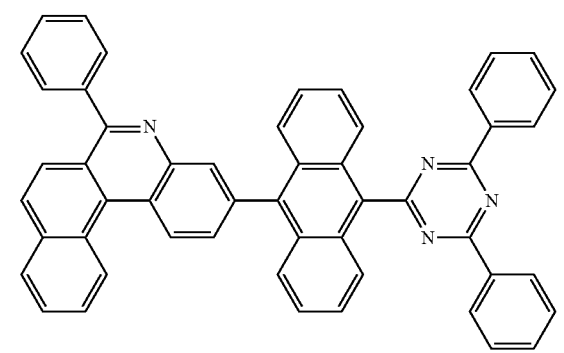
100
-continued
42C
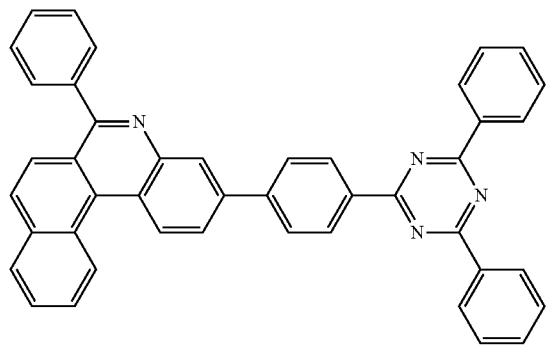
43C
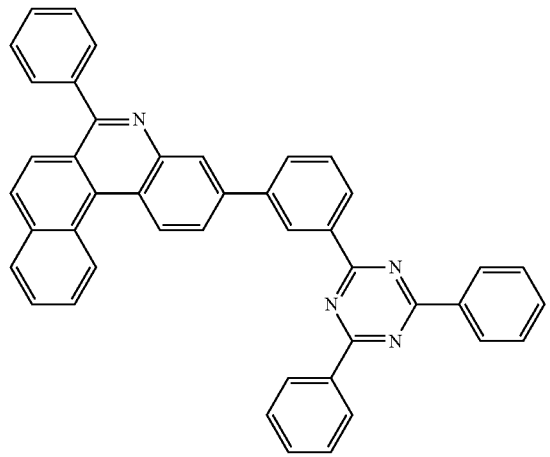
44C
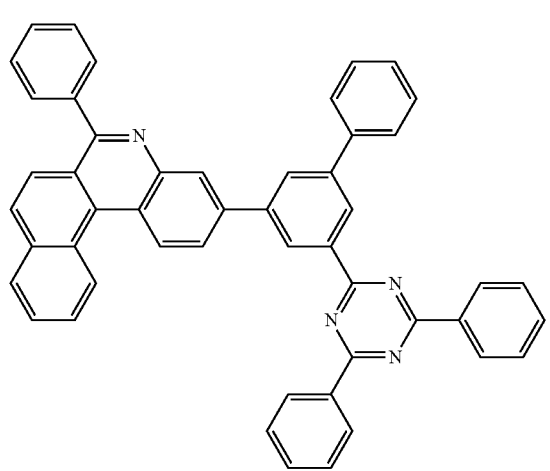

-continued
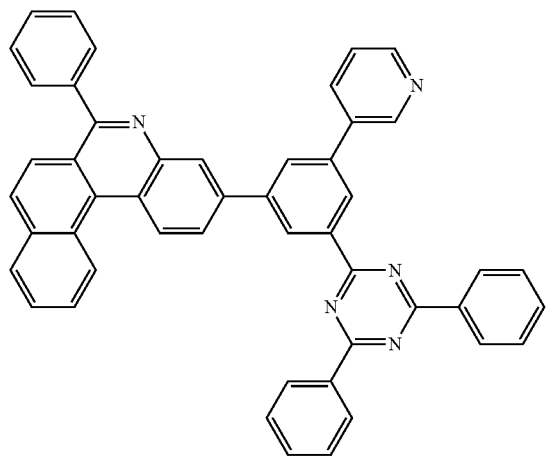
45C
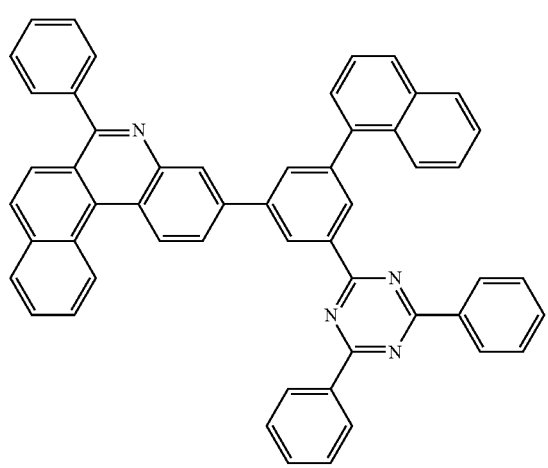
46C
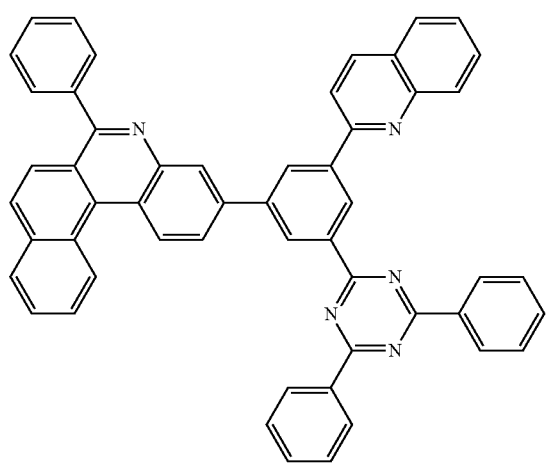
47C
-continued
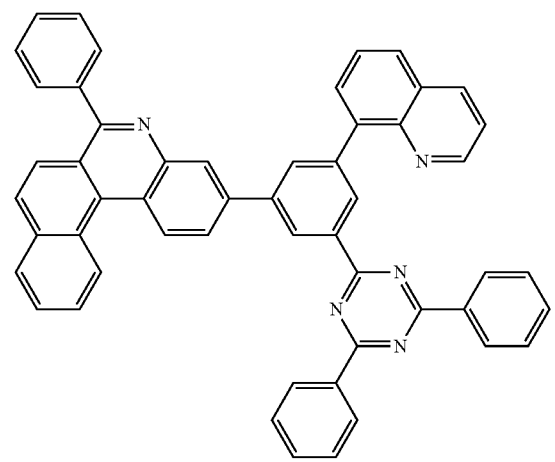
48C
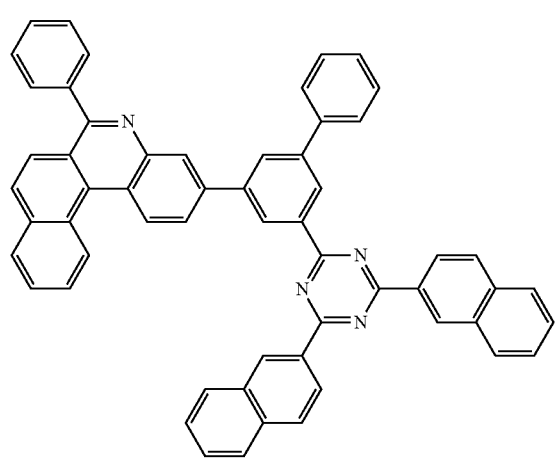
49C
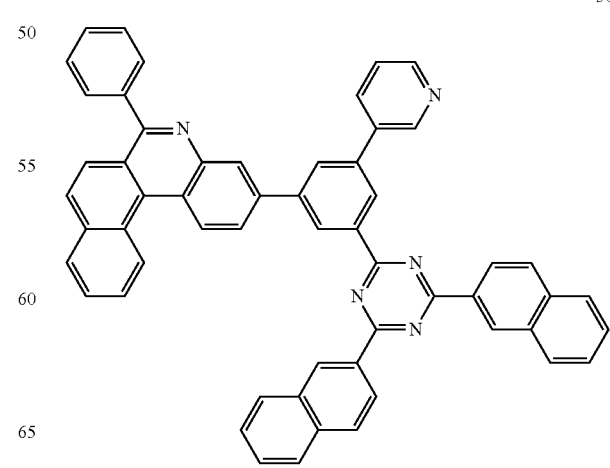
50C

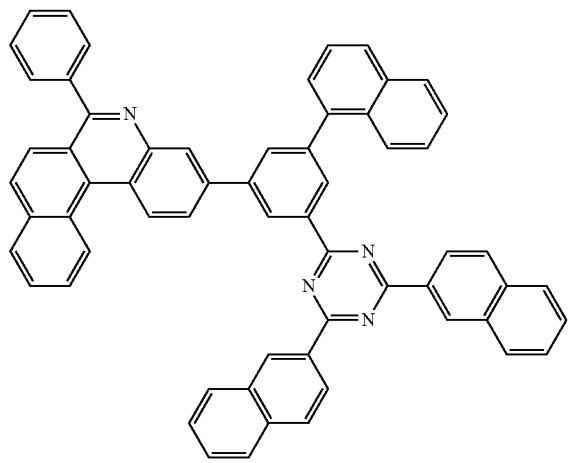
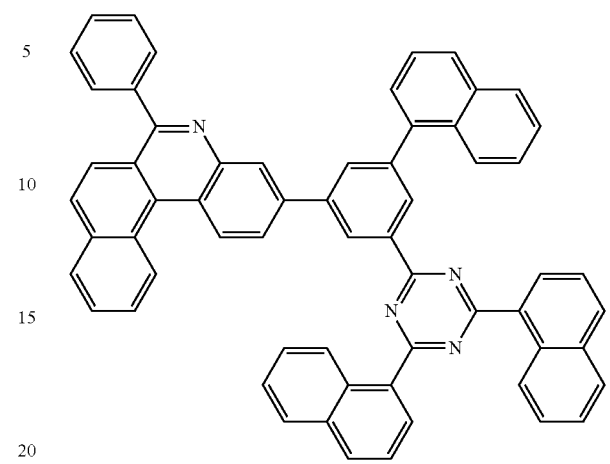
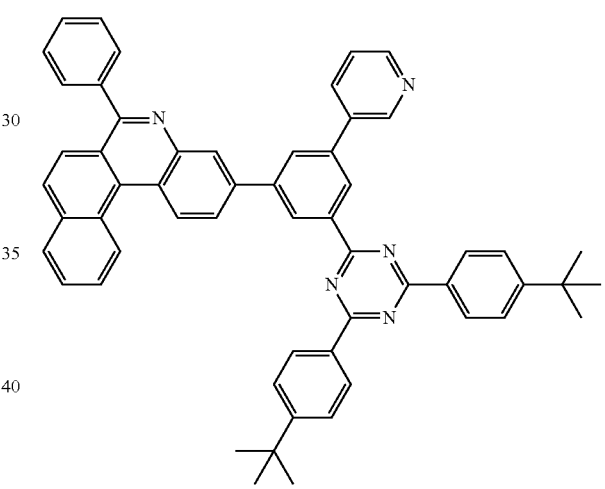
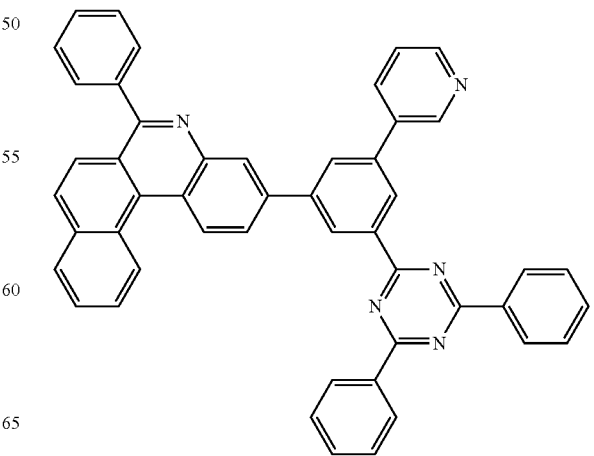

1D
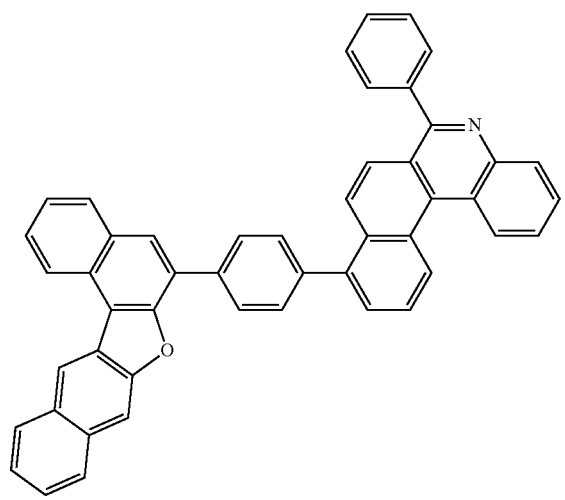
2D
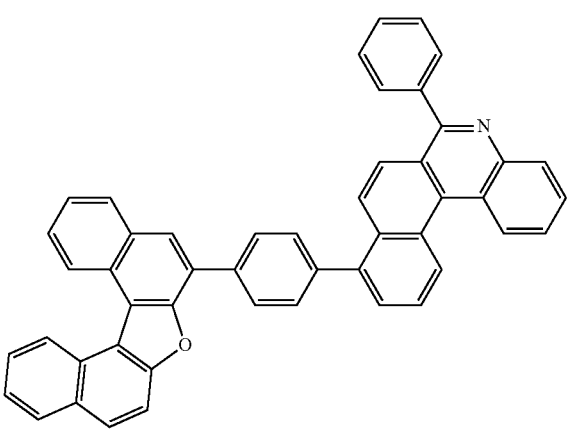
3D
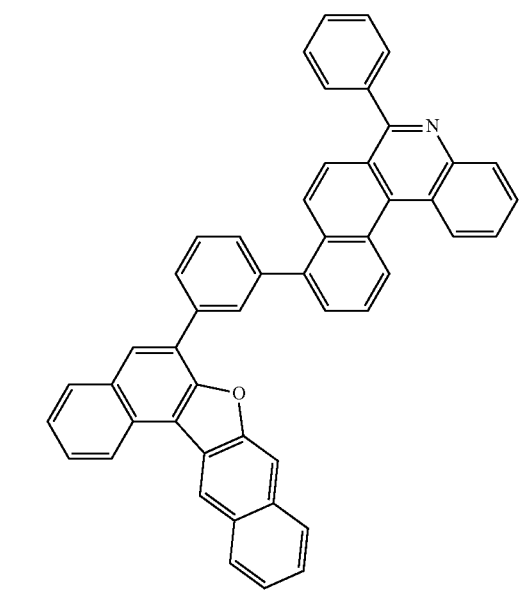
4D
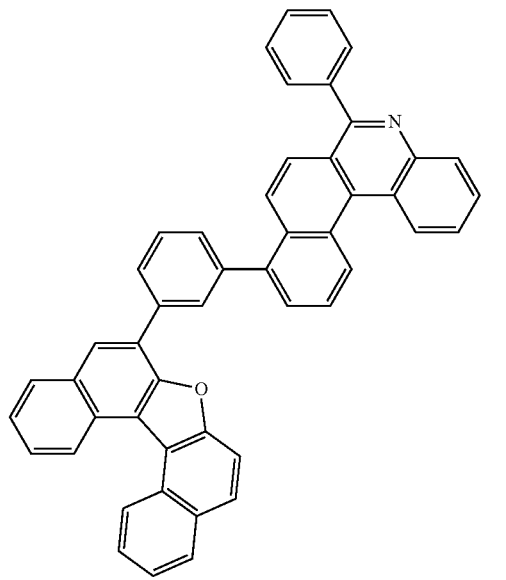
5D
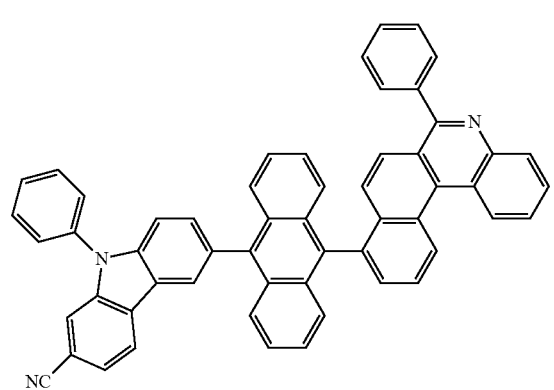
6D
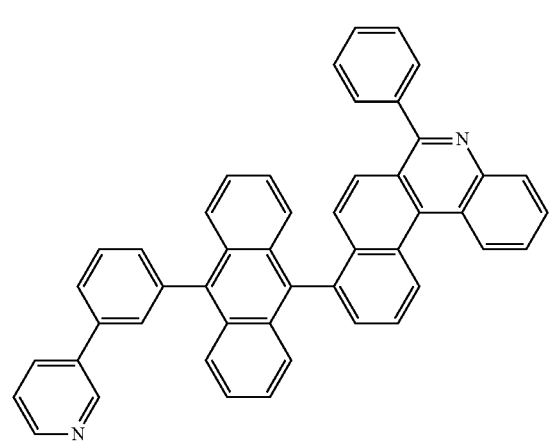

-continued
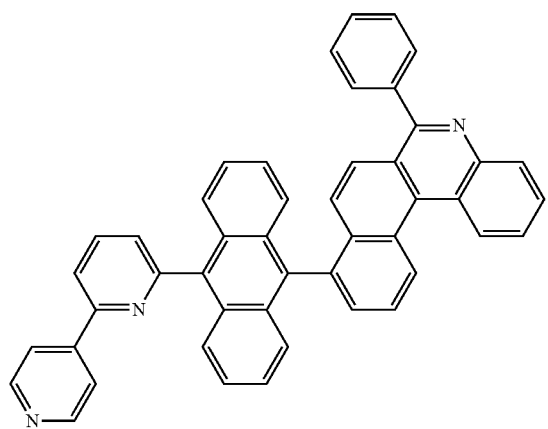
7D
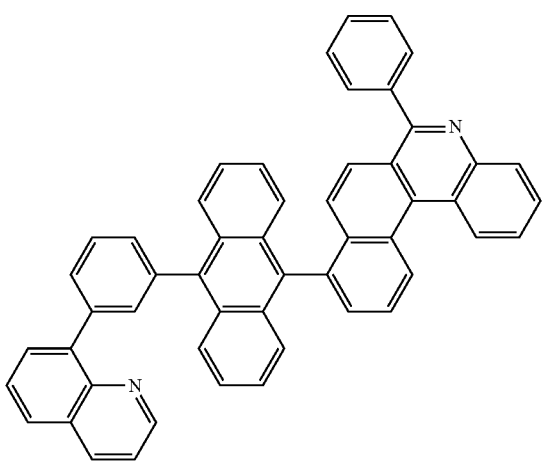
10D
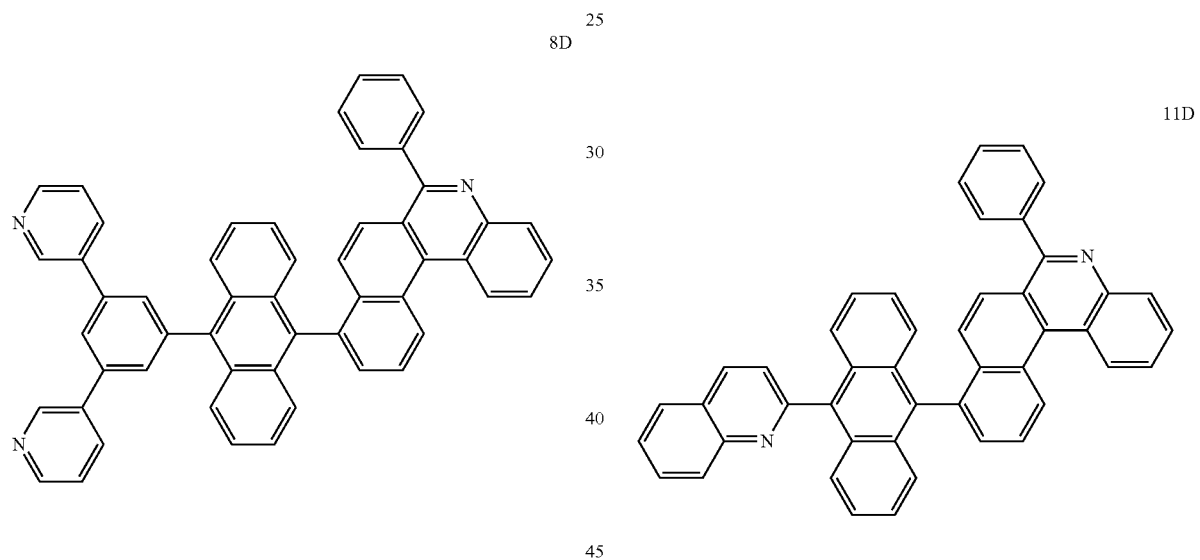
8D
11D
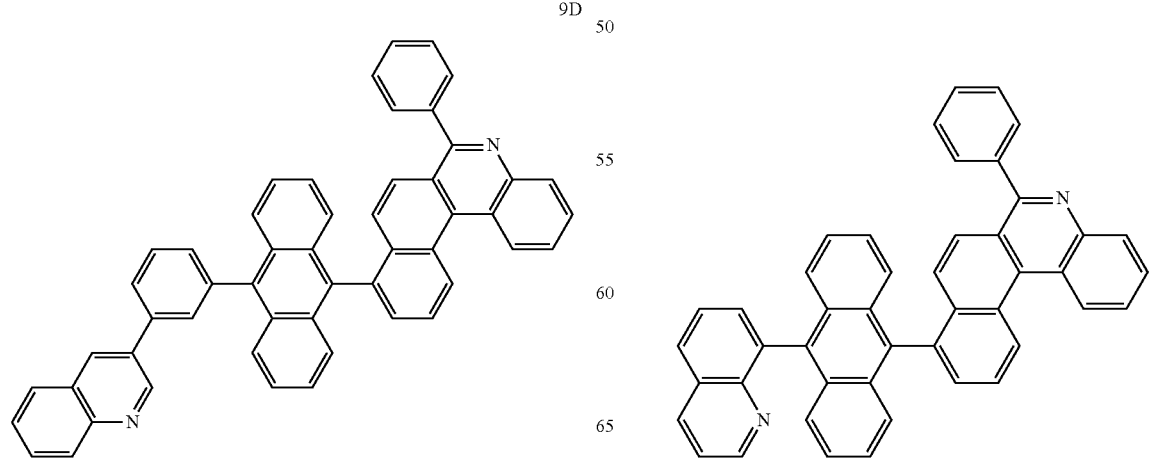
9D
12D

13D
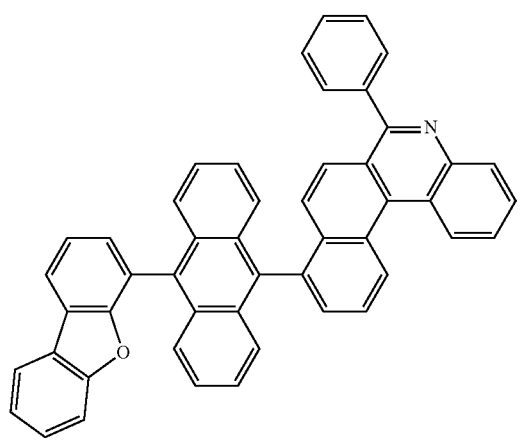
14D
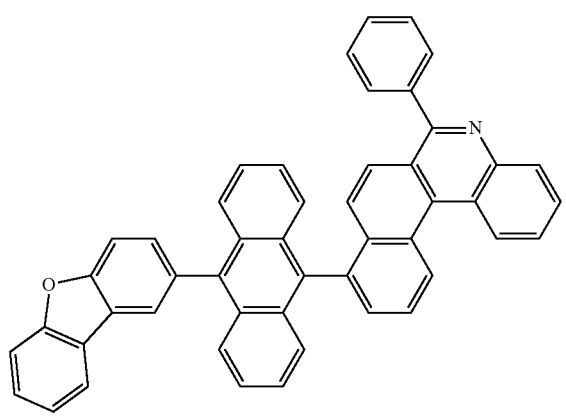
15D
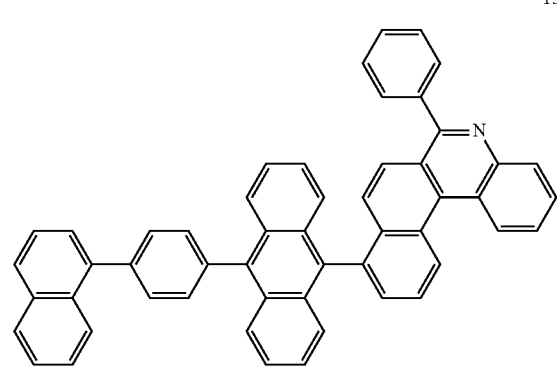
16D
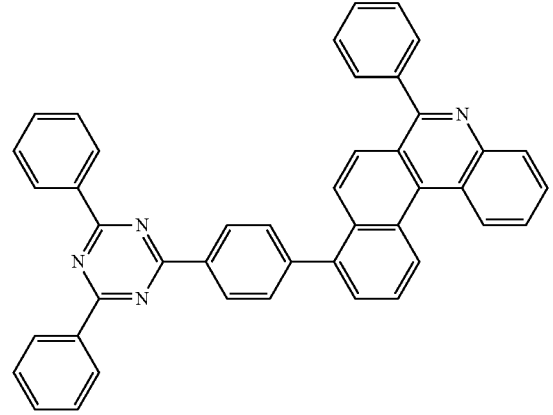
17D
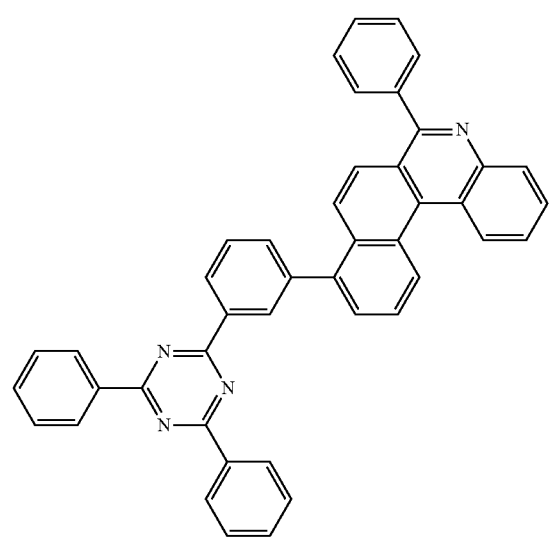
18D
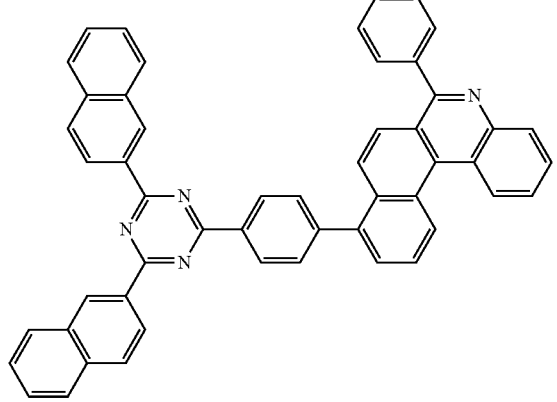

19D
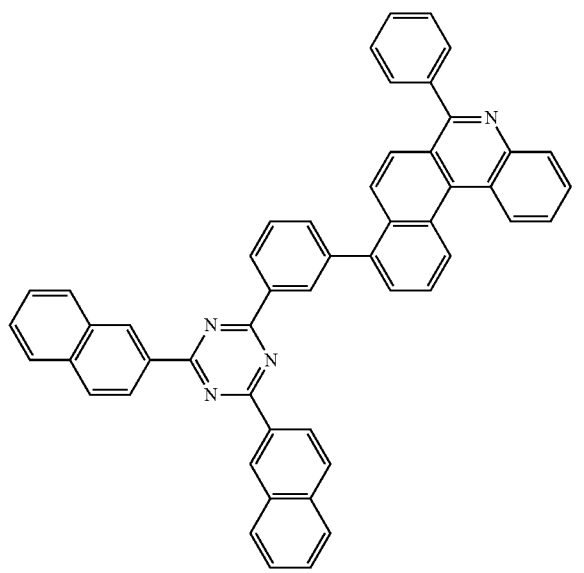
20D
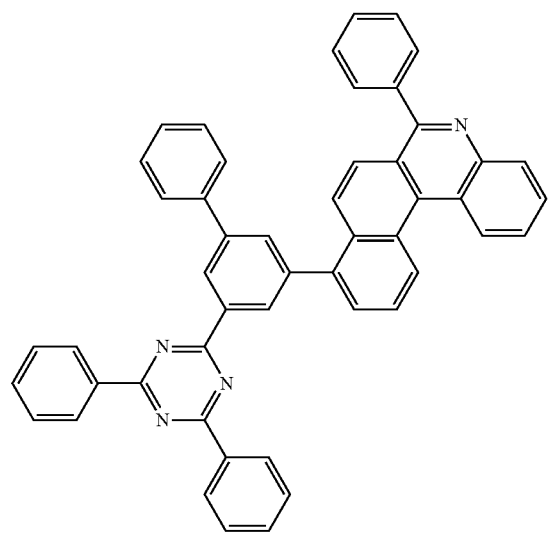
21D
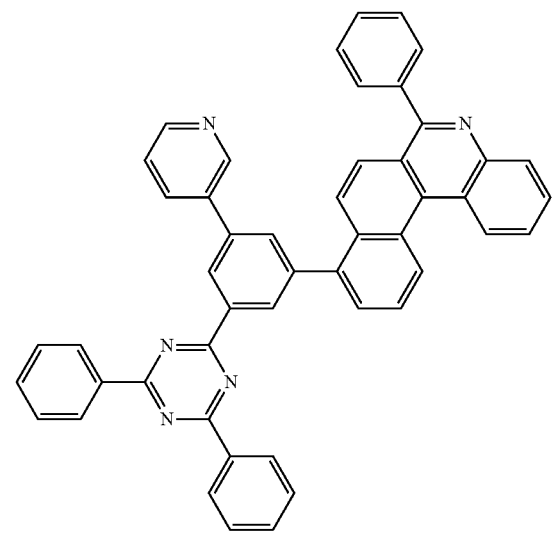
22D
23D
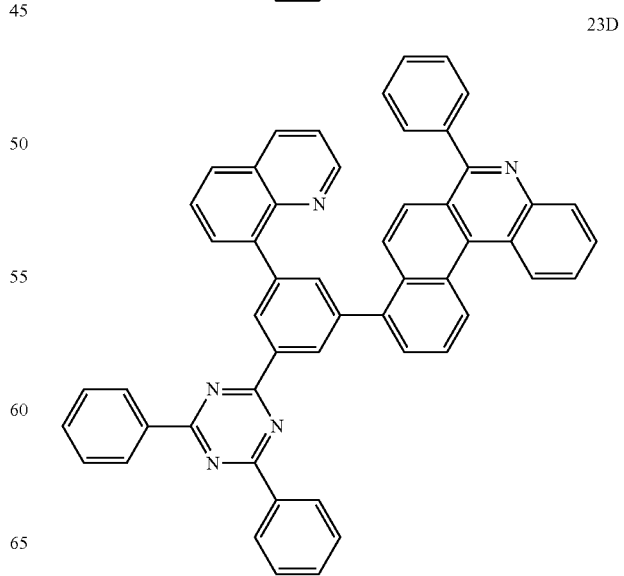

24D
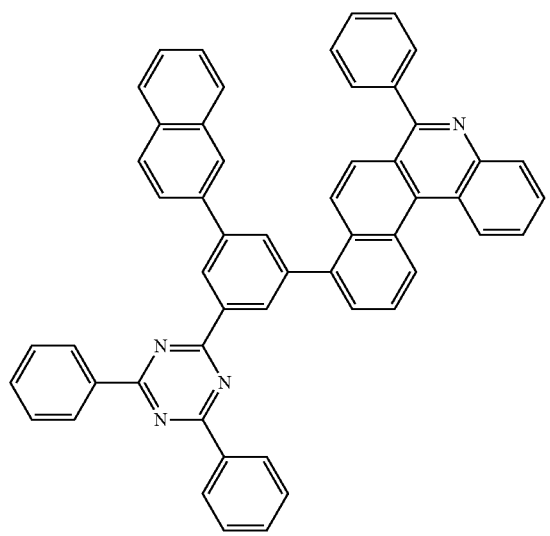
25D
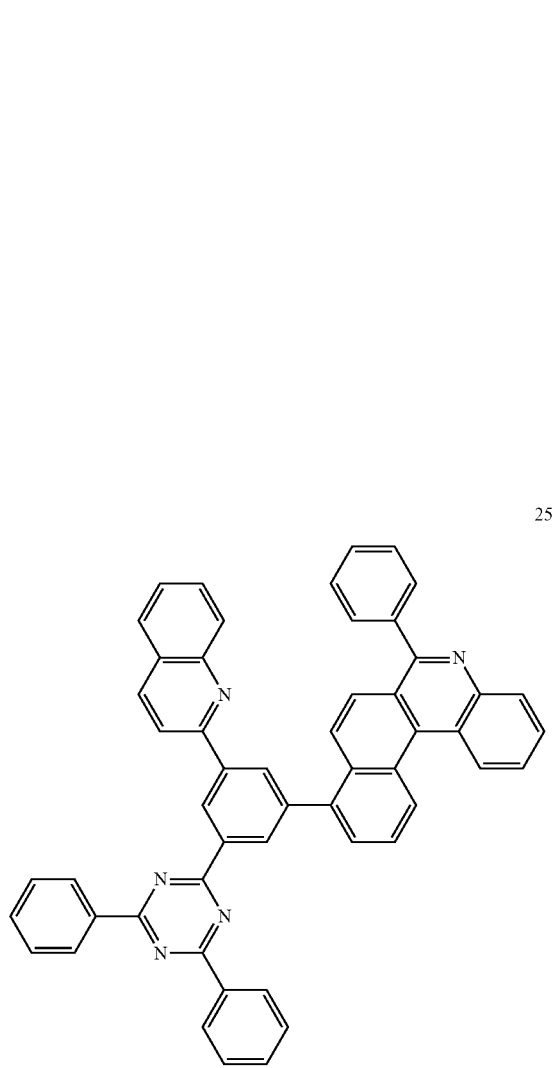
26D
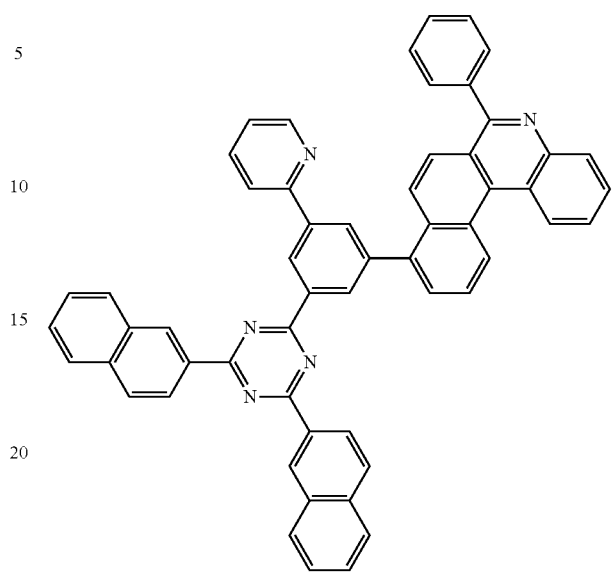
27D
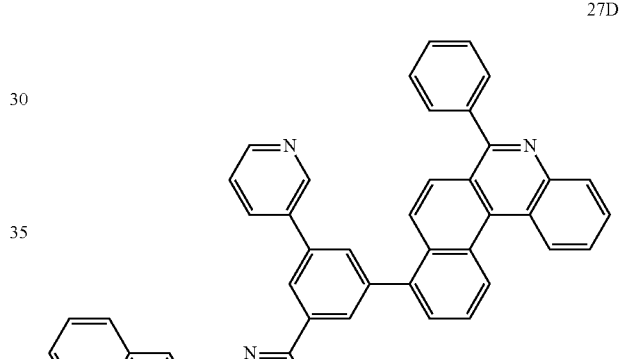
28D
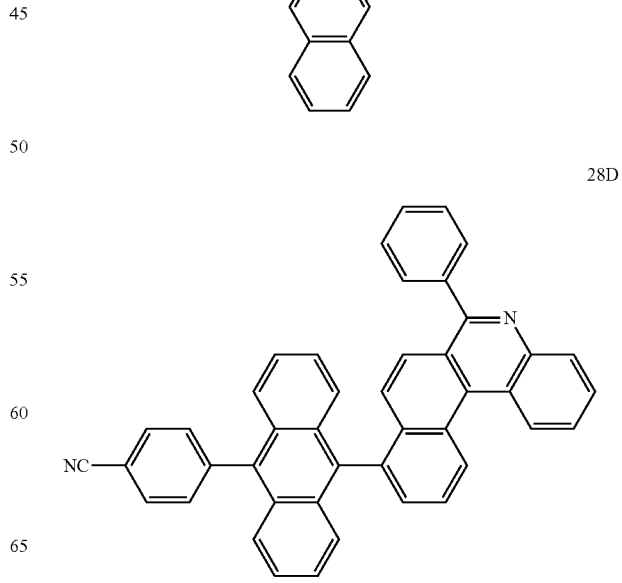

29D

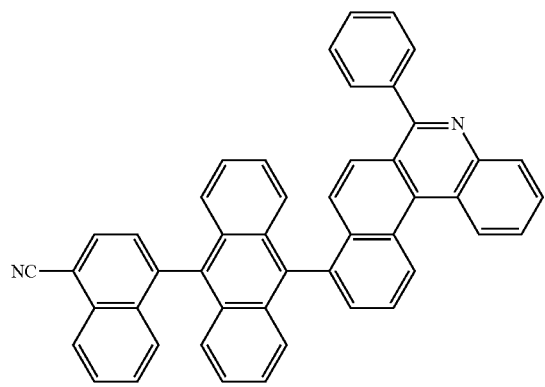

30D

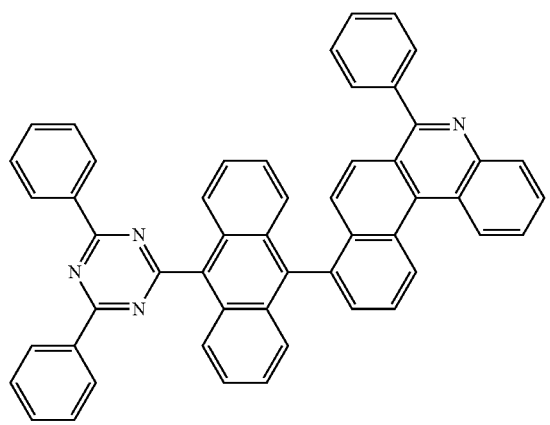

The condensed cyclic compound represented by one of Formulae 1-1 to 1-8 above may have excellent charge transport capability and thermal stability. Accordingly an organic light-emitting device including the condensed cyclic represented by one of Formulae 1-1 to 1-8 above may have low driving voltage, high efficiency, high brightness, and long lifespan.

A method of synthesizing the condensed cyclic compounds of Formulae 1-1 to 1-8 above may be understood, e.g., based on Examples Synthesis Examples described later.

At least one of the condensed cyclic compounds of Formulae 1-1 to 1-8 may be used or included between a pair of electrodes included in an organic light-emitting device. For example, the condensed cyclic compound of one of Formulae 1-1 to 1-8 may be included in at least one of an electron transport region and an emission layer of an organic light-emitting device. Alternatively, the condensed cyclic compound of one of Formulae 1-1 to 1-8 may be used as a material used to form a capping layer, the capping layer being positioned on an outer side of a pair of electrodes included in the organic light-emitting device.

Accordingly, there is provided an organic light-emitting device including: a first electrode; a second electrode disposed acing the first electrode; and an organic layer disposed between the first electrode and the second electrode and including an emission layer, wherein the organic layer includes at least one of the condensed cyclic compounds of Formulae 1-1 to 1-8.

The expression "(an organic layer) includes at least one of the condensed cyclic compounds" used herein may include a case in which "(an organic layer) includes at least one condensed cyclic compound of Formulae 1-1 to 1-8 above or a case in which (an organic layer) includes two or more different condensed cyclic compounds of Formulae 1-1 to 1-8 above".

For example, the organic layer may include, as the condensed cyclic compound, only Compound 2A above. In this regard, Compound 2A may exist in an electron transport layer included in the organic light-emitting device. Alternatively, the organic layer may include, as the condensed cyclic compound, Compound 2A and Compound 14A above. Here, Compound 2A and Compound 14A may be situated in either an identical layer (for example, Compound 2A and Compound 14A may all exist in an electron transport layer), or different layers (for example, Compound 2A may exist in an electron transport layer and Compound 14A may exist in an emission layer).

The organic layer may include i) a hole transport region that is disposed between the first electrode (i.e., an anode) and the emission layer and includes at least one of a hole injection layer (HIL), a hole transport layer (HTL), a buffer layer, and an electron blocking layer (EBL); and ii) an electron transport region that is disposed between the emission layer and the second electrode (i.e., a cathode) and includes at least one of a hole blocking layer (HBL), an electron transport layer (ETL), and an electron injection layer (EIL). At least one of the condensed cyclic compounds of Formulae 1-1 to 1-8 may be included in at least one of the electron transport region and the emission layer. For example, the electron transport region of the organic light-emitting device may include an ETL, and the ETL may include at least one of the condensed cyclic compounds of Formulae 1-1 to 1-8.

The organic light-emitting device may further include at least one of a first capping layer and a second capping layer, wherein the first capping layer is disposed on a path where light generated in the emission layer is extracted through the first electrode, and the second capping layer is disposed on a path where light generated in the emission layer is extracted through the second electrode. In an implementation, at least one of the first capping layer and the second capping layer may include at least one of the condensed cyclic compounds of Formulae 1-1 to 1-8 above.

For example, the organic light-emitting device may have i) a structure in which the first electrode, the organic layer, the second electrode, and the second capping layer are sequentially stacked in the stated order, ii) a structure in which the first capping layer, the first electrode, the organic layer, and the second electrode are sequentially stacked in the stated order, or iii) a structure in which the first capping layer, the first electrode, the organic layer, the second electrode, and the second capping layer are sequentially stacked in the stated order. In an implementation, at least one of the first capping layer and the second capping layer may include at least one of the condensed cyclic compounds of Formulae 1-1 to 1-8 above.

The term "organic layer" used herein may refer to a single layer and/or a plurality of layers disposed between the first electrode and the second electrode of the organic light-emitting device. A material included in the "organic layer" is not limited to an organic material.

Figure 1:
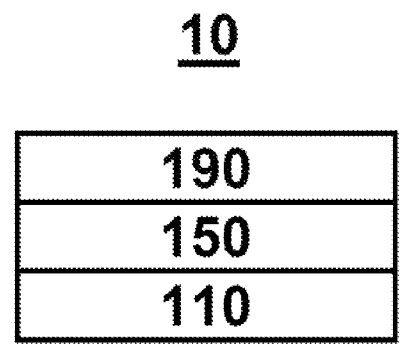

FIG. 1 illustrates a schematic cross-sectional view of an organic light-emitting device 10 according to an embodiment. The organic light-emitting device 10 may include a first electrode 110, an organic layer 150, and a second electrode 190.

Hereinafter, a structure and a method of manufacturing the organic light-emitting device 10 according to an embodiment will be described in connection with FIG. 1.

In FIG. 1, a substrate may be additionally disposed under the first electrode 110 or on the second electrode 190. The substrate may be a glass substrate or a transparent plastic substrate, each of which has excellent mechanical strength, thermal stability, transparency, surface smoothness, ease of handling, and water-proofness.

The first electrode 110 may be formed by, e.g., depositing or sputtering a material for forming the first electrode 110 on the substrate. When the first electrode 110 is an anode, the material for forming the first electrode 110 may be selected from materials having a high work function to facilitate hole injection. The first electrode 110 may be a reflective electrode, a semi-transmissive electrode, or a transmissive electrode. The material for forming the first electrode 110 may be, for example, indium tin oxide (ITO), indium zinc oxide (IZO), tin oxide ($SnO_2$), or zinc oxide (ZnO), each of which has excellent transparency and conductivity. In an implementation, to form the first electrode 110 that is a semi-transmissive electrode or a reflective electrode, the material for forming the first electrode 110 may be at least one selected from magnesium (Mg), aluminum (Al), aluminum-lithium (Al—Li), calcium (Ca), magnesium-indium (Mg—In), and magnesium-silver (Mg—Ag).

The first electrode 110 may have a single-layer structure or a multi-layer structure consisting of a plurality of layers. For example, the first electrode 110 may have a triple-layer structure of ITO/Ag/ITO, but the structure of the first electrode 110 is not limited thereto.

The organic layer 150 may be disposed on the first electrode 110, and may include the emission layer.

The organic layer 150 may further include a hole transport region and an electron transport region, wherein the hole transport region is disposed between the first electrode and the emission layer and the electron transport region is disposed between the emission layer and the second electrode.

The hole transport region may include at least one of an HIL, an HTL, a buffer layer, and an EBL, and the electron transport region may include at least one of an HBL, an ETL, and an EIL.

The hole transport region may have a single-layer structure consisting of a single material, a singly-layer structure consisting of a plurality of different materials, or a multi-layer structure consisting of a plurality of different materials.

For example, the hole transport region may have a single-layer structure consisting of a plurality of different materials, or a structure of HIL/HTL, a structure of HIL/HTL/buffer layer, a structure of HIL/buffer layer, a structure of HTL/buffer layer, or a structure of HIL/HTL/EBL, each of which layers are sequentially stacked in the stated order from the first electrode 110.

When the hole transport region include an HIL, the HIL may be formed on the first electrode 110 by using various methods, such as vacuum deposition, spin coating, casting, a Langmuir-Blodgett (LB) method, ink-jet printing, layer printing, and laser induced thermal imaging (LITI).

When the HIL is formed by vacuum deposition, deposition conditions may include, e.g., a deposition temperature of about 100° C. to about 500° C., a vacuum pressure of about $10^{-8}$ torr to about $10^{-3}$ torr, and/or a deposition rate of about 0.01 Å/sec to about 100 Å/sec, which are determined according to a compound that is used to form the HIL and a structure of the HIL.

When the HIL is formed by spin coating, coating conditions may include, e.g., a coating speed of about 2,000 rpm to about 5,000 rpm and/or a temperature at which a heat treatment is performed of about 80° C. to about 200° C., which are determined according to a compound that is used to form the HIL and a structure of the HIL.

When the hole transport region includes an HTL, the HTL may be formed on the first electrode 110 or the HIL by using various methods, such as vacuum deposition, spin coating, casting, an LB method, and LITI. When the HTL is formed by vacuum deposition and spin coating, deposition and coating conditions may be determined by referring to those applied to form the HIL.

In an implementation, the hole transport region may include at least one of m-MTDATA, TDATA, 2-TNATA, NPB, β-NPB, TPD, Spiro-TPD, Spiro-NPB, methylated-NPB, TAPC, HMTPD, 4,4',4"-tris(N-carbazolyl)triphenylamine (TCTA), polyaniline/dodecylbenzenesulfonic acid:polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), polyaniline/poly(4-styrenesulfonate) (PANI/PSS), a compound represented by Formula 201 below, and a compound represented by Formula 202 below:

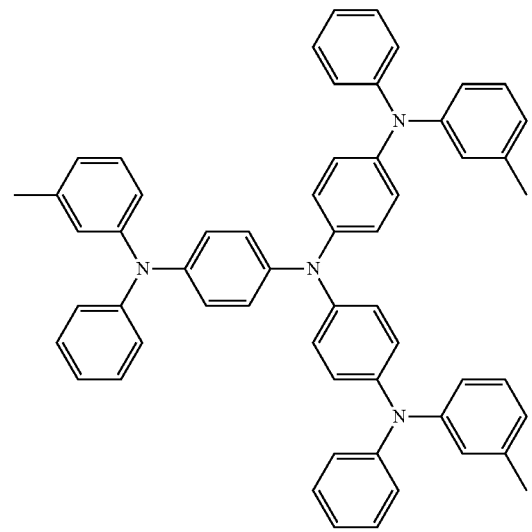

m-MTDATA

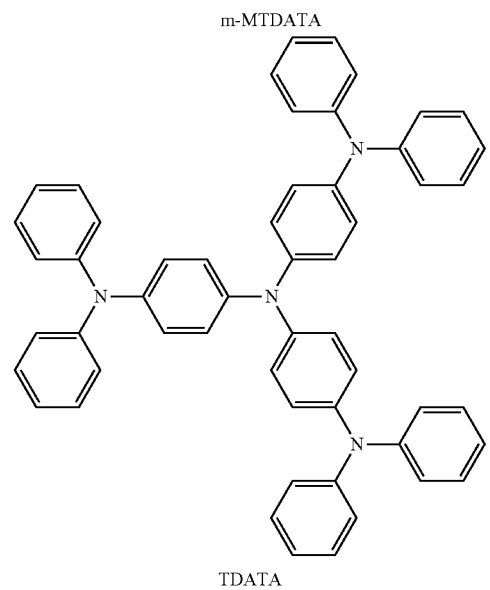

TDATA

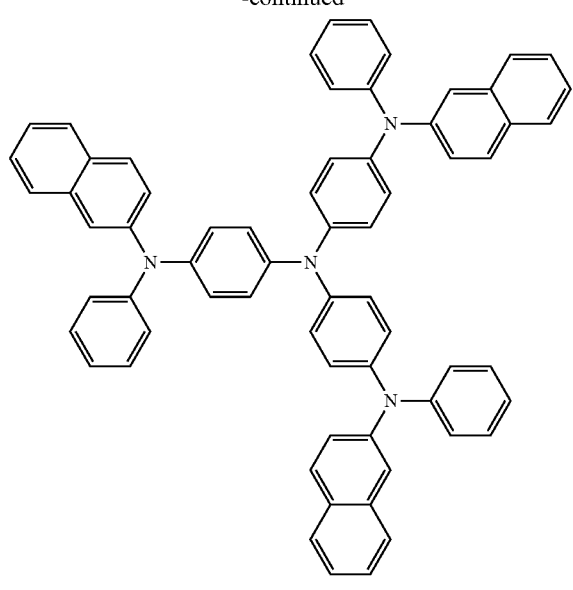
2-TNATA
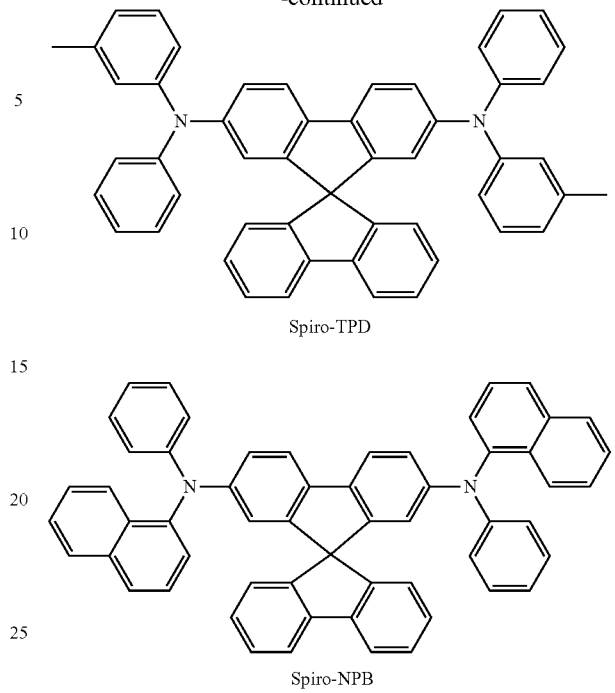
Spiro-TPD
Spiro-NPB
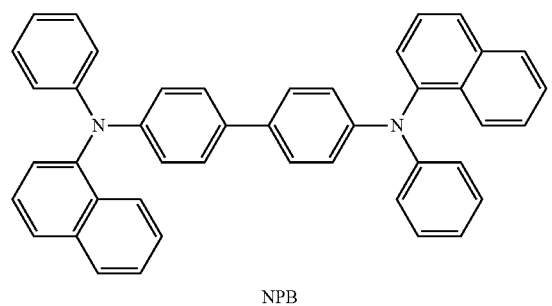
NPB
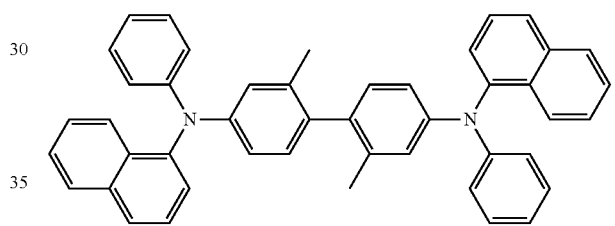
methylated NPB
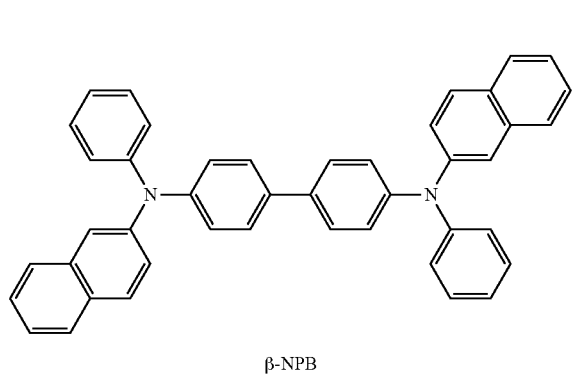
β-NPB
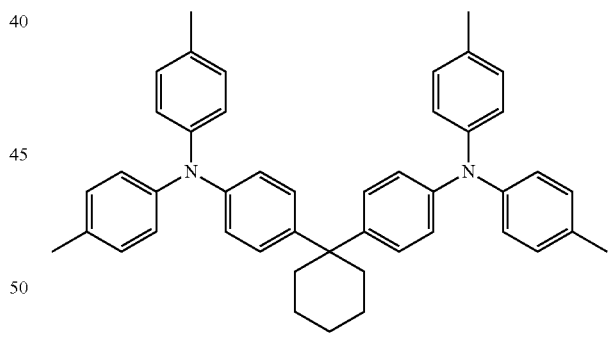
TAPC
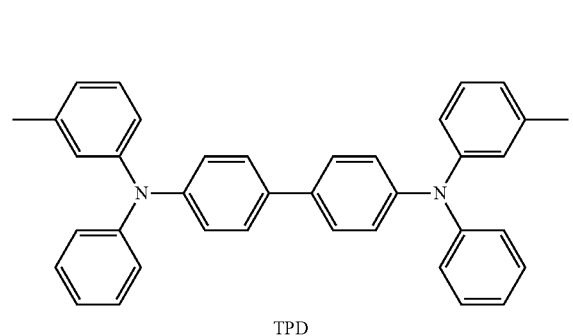
TPD
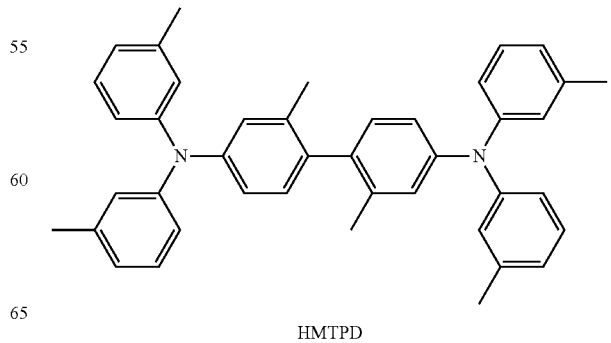
HMTPD

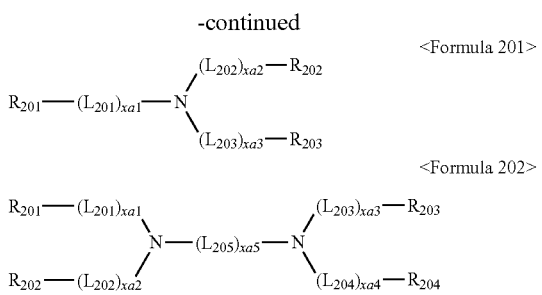

<Formula 201>

<Formula 202>

In Formulae 201 and 202, descriptions of $L_{201}$ to $L_{205}$ may be each independently understood by referring to the description provided herein in connection with $L_1$, xa1 to xa4 may be each independently selected from 0, 1, 2, and 3, xa5 may be selected from 1, 2, 3, 4, and 5, and $R_{201}$ to $R_{204}$ may be each independently selected from a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group.

For example, in Formulae 201 and 202, $L_{201}$ to $L_{205}$ may be each independently selected from a phenylene group, a naphthylene group, a fluorenylene group, a spiro-fluorenylene group, a benzofluorene group, a dibenzofluorene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group, xa1 to xa4 may be each independently 0, 1, or 2, xa5 may be 1, 2, or 3, $R_{201}$ to $R_{204}$ may be each independently selected from a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, but embodiments are not limited thereto.

The compound of Formula 201 above may be represented by Formula 201A below:

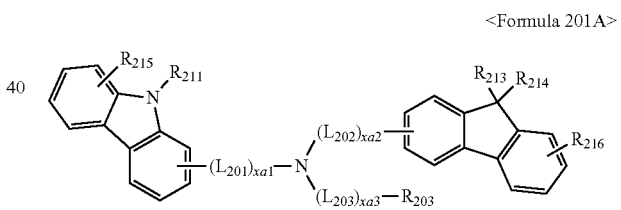

<Formula 201A>

For example, the compound of Formula 201 above may be represented by Formula 201A-1 below, but is not limited thereto:

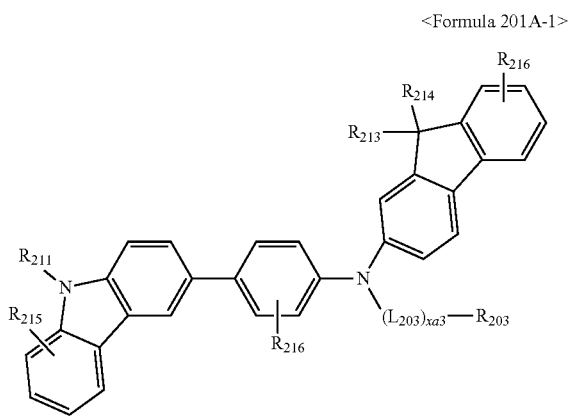

<Formula 201A-1>

The compound of Formula 202 above may be represented by Formula 202A below, but is not limited thereto:

<Formula 202A>

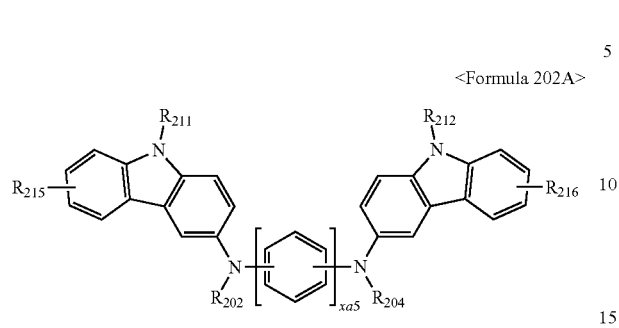

In Formulae 201A, 201A-1, and 202A above, descriptions of $L_{201}$ to $L_{203}$, xa1 to xa3, xa5, and $R_{202}$ to $R_{204}$ may be understood by referring to descriptions provided herein, and descriptions of $R_{211}$ and $R_{212}$ may be understood by referring to the description provided herein in connection with $R_{203}$. Here, $R_{213}$ to $R_{216}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, and a monovalent non-aromatic condensed heteropolycyclic group.

The compounds of Formulae 201 and 202 above may include Compounds HT1 to HT20 below.

HT1

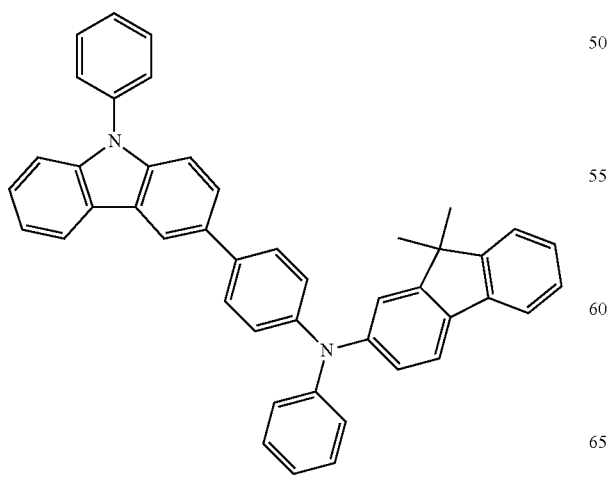

HT2

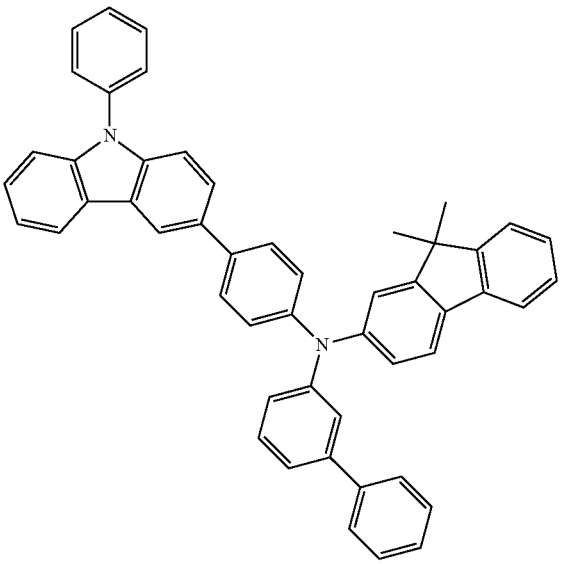

HT3

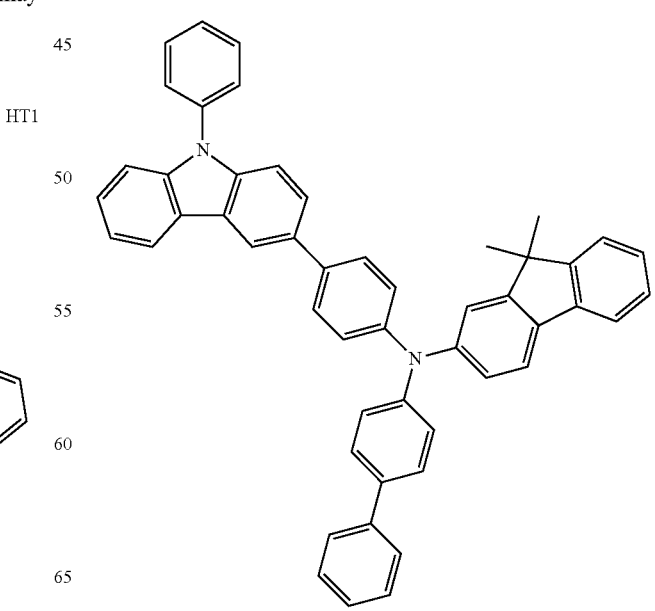

HT4
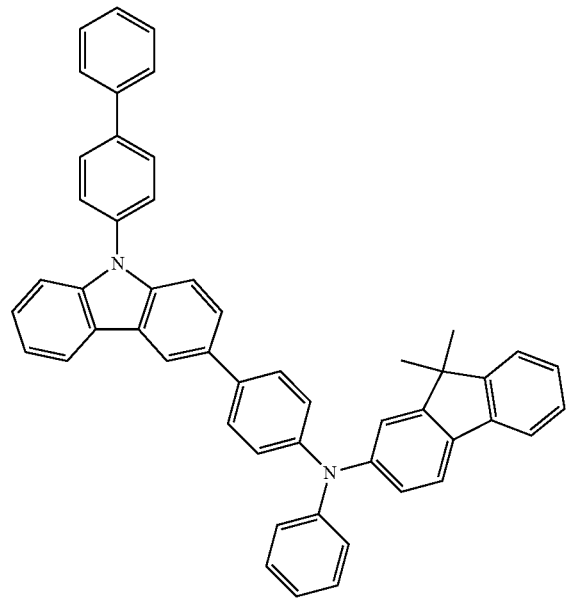
HT5
HT6
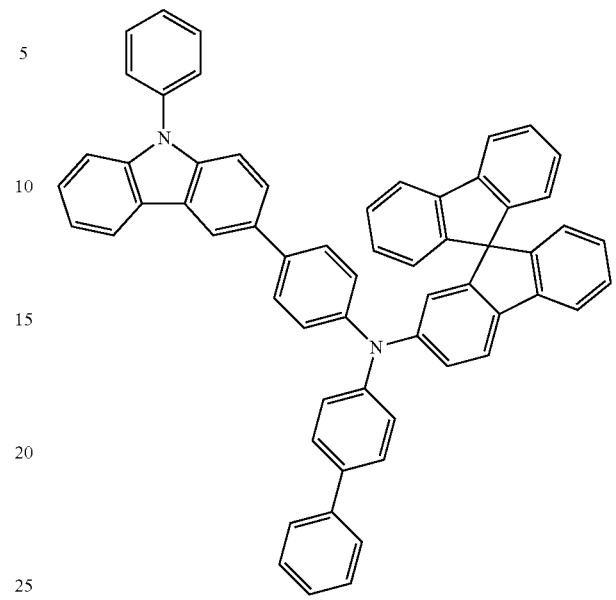
HT7
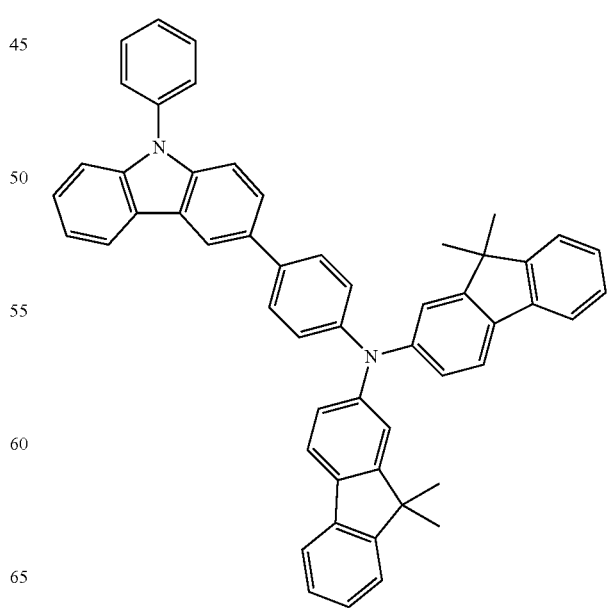

HT8
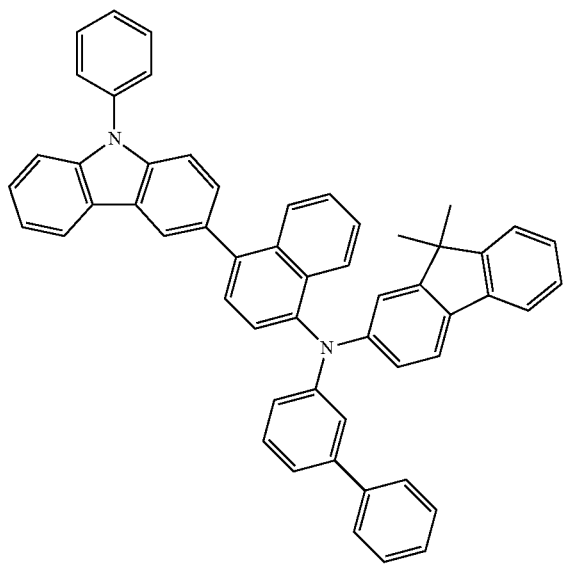
HT10
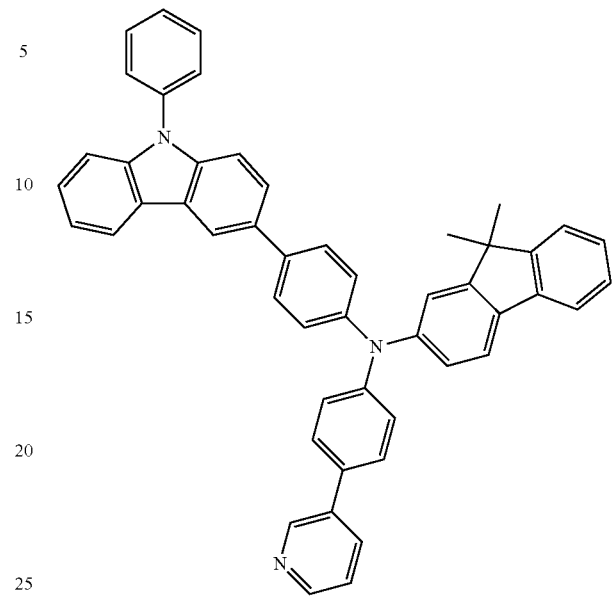
HT9
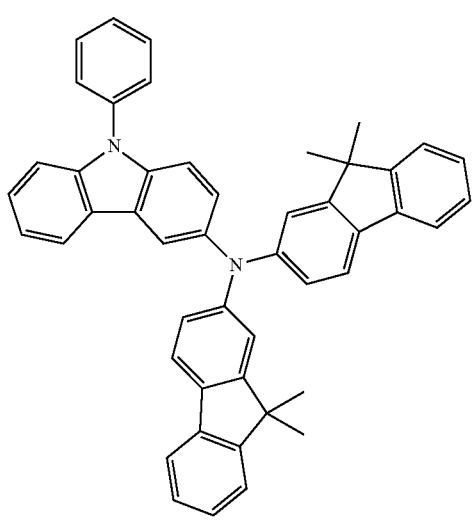
HT11
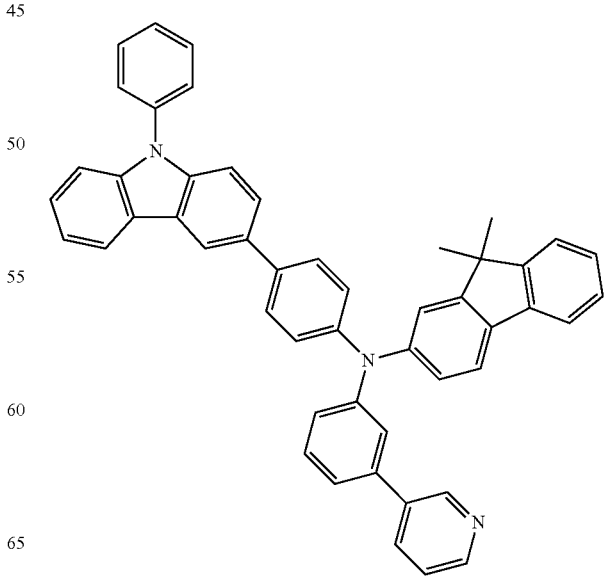

-continued
HT12
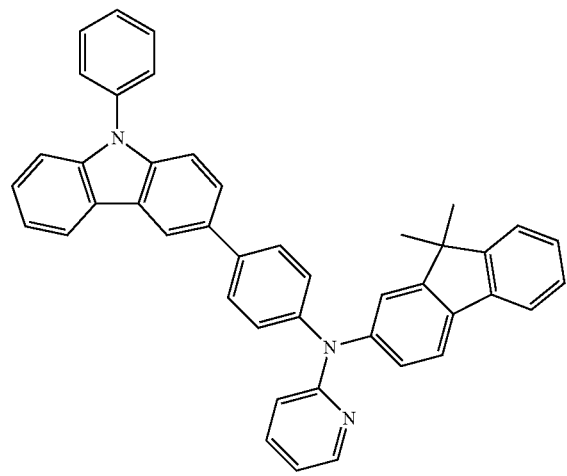
HT13
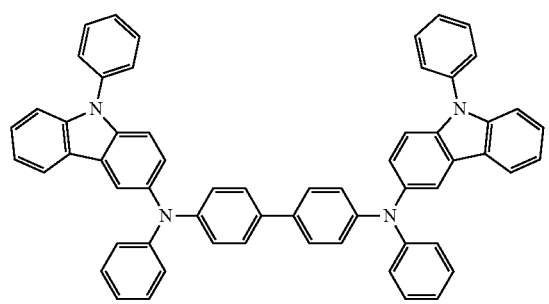
HT14
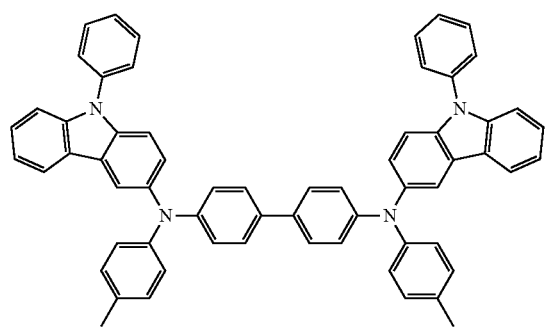
HT15
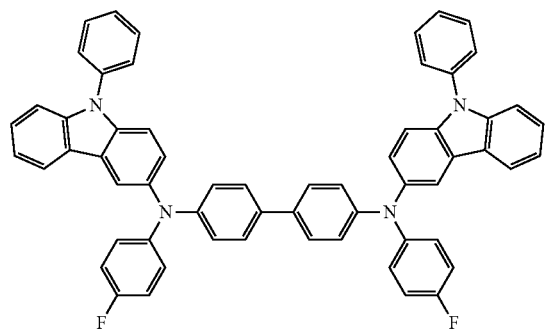
-continued
HT16
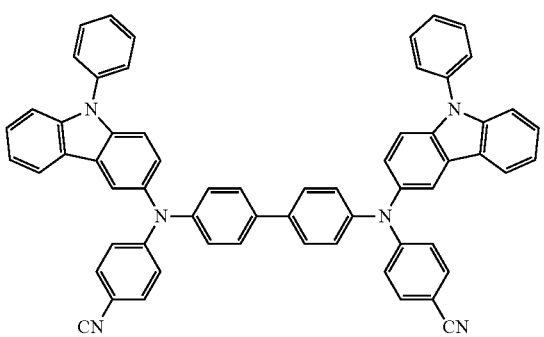
HT17
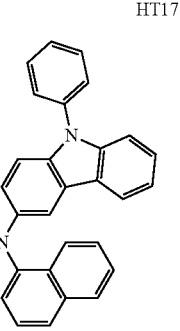
HT18
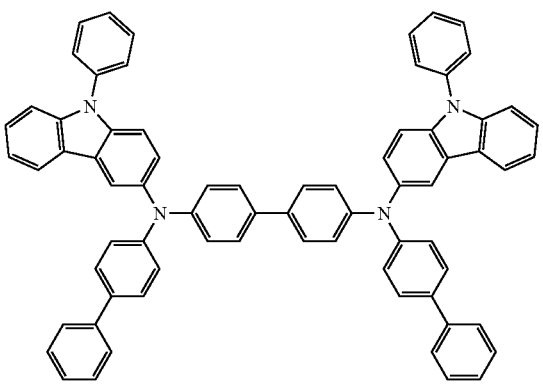
HT19
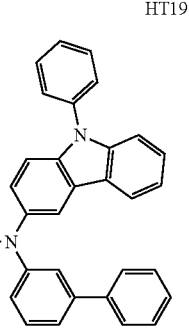

-continued

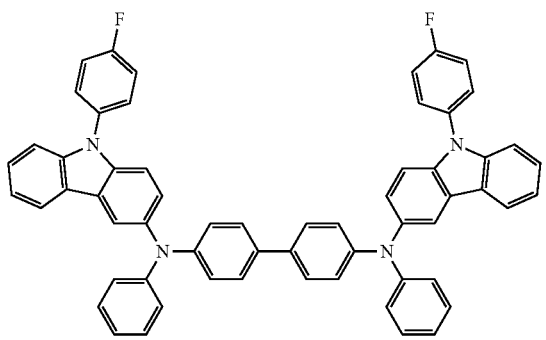
HT20

A thickness of the hole transport region may be from about 100 Å to about 10,000 Å, e.g., about 100 Å to about 1,000 Å. When the hole transport region includes both an HIL and an HTL, a thickness of the HIL may be from about 100 Å to about 10,000 Å, e.g., about 100 Å to about 1,000 Å, and a thickness of the HTL may be from about 50 Å to about 2,000 Å, e.g., about 100 Å to about 1,500 Å. When the thicknesses of the hole transport region, the HIL, and the HTL are within these ranges, satisfactory hole transporting characteristics may be obtained without a substantial increase in driving voltage.

The hole transport region may further include, in addition to the materials described above, a charge-generation material for the improvement of conductive characteristics. The charge-generation material may be homogeneously or non-homogeneously dispersed in the hole transport region.

The charge-generation material may be, e.g., a p-dopant. The p-dopant may include, e.g., one of a quinone derivative, a metal oxide, and a cyano group-containing compound. Non-limiting examples of the p-dopant are a quinone derivative such as tetracyanoquinonedimethane (TCNQ) or 2,3,5,6-tetrafluoro-tetracyano-1,4-benzoquinonedimethane (F4-TCNQ); a metal oxide such as a tungsten oxide or a molybdenum oxide; and a cyano group-containing compound such as Compounds HT-D1 and HP-1 below, but are not limited thereto:

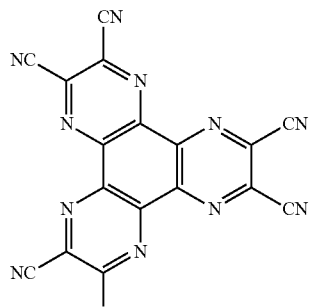
<Compound HT-D1>

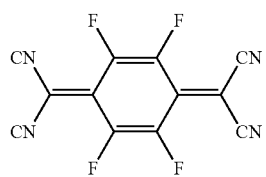
<F4-TCNQ>

The hole transport region may further include, in addition to the HIL and the HTL, at least one of a buffer layer and an EBL. The buffer layer may compensate for an optical resonance distance of light according to a wavelength of the light emitted from the emission layer, and thus may improve light-emission efficiency. In this regard, a material that is included in the hole transport region may be used as a material that is included in the buffer layer. The EBL may serve as a layer that prevents electrons from being injected from the electron transport region.

The emission layer may be formed on the first electrode 110 or the hole transport region by using various methods, e.g., vacuum deposition, spin coating, casting, an LB method, LITI. When the emission layer is formed by vacuum deposition and spin coating, deposition and coating conditions may be determined by referring to those applied to form the HIL.

When the organic light-emitting device 10 is a full-color organic light-emitting device, the emission layer, may be patterned into a red emission layer, a green emission layer, and a blue emission layer, according to an individual sub-pixel. In an implementation, the emission layer may have a structure of a red emission layer, a green emission layer, and a blue emission layer, each of which layers are sequentially stacked in the stated order. In this regard, a material emitting red light, a material emitting green light, and a material emitting blue light may have a mixed structure without having division of layers, thereby emitting white light.

The emission layer may include a host and a dopant. The host may include at least one of an anthracene-based or -containing compound, an arylamine-based or -containing compound, and a styryl-based or -containing compound.

In an implementation, the host may include a compound represented by Formula 301 below.

$$Ar_{301}-[(L_{301})_{xb1}-R_{301}]_{xb2} \qquad <Formula\ 301>$$

In Formula 301, $Ar_{301}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, and —Si($Q_{301}$)($Q_{302}$)($Q_{303}$) (wherein $Q_{301}$ to $Q_{303}$ may be each independently selected from a hydrogen, a $C_1$-$C_{60}$ alkyl group, a $C_2$-$C_{60}$ alkenyl group, a $C_6$-$C_{60}$ aryl group, and a $C_1$-$C_{60}$ heteroaryl group), description of $L_{301}$ may be understood by referring to the description provided herein in connection with $L_1$, $R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, and a triazinyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl, xb1 may be selected from 0, 1, 2, and 3, and xb2 may be selected from 1, 2, 3, and 4.

For example, in Formula 301 above, $L_{301}$ may be selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, and a chrysenylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, $R_{301}$ may be selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but embodiments are not limited thereto.

In an implementation, the host may include a compound represented by Formula 301A below:

<Formula 301A>

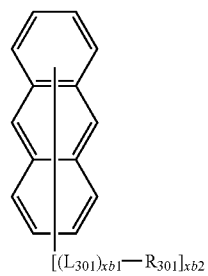

$[(L_{301})_{xb1}-R_{301}]_{xb2}$

Descriptions of substituents on Formula 301A may be understood by referring to the description provided herein.

In an implementation, the compound of Formula 301 above may include at least one of Compounds H1 to H42 below.

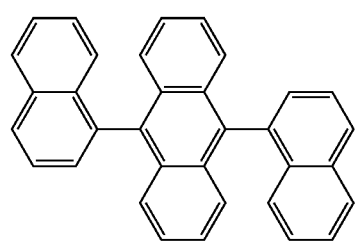

H1

H2 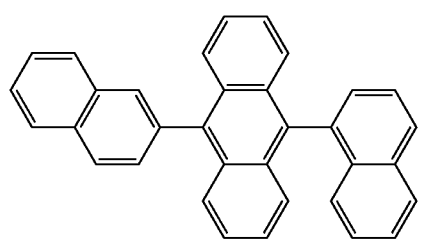
H3 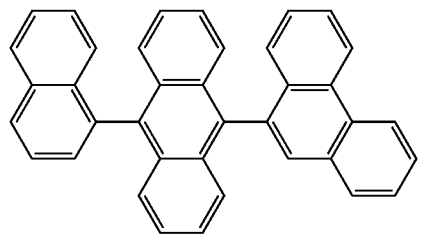
H4 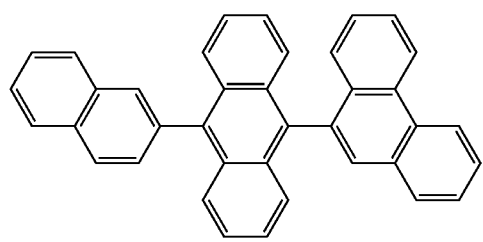
H5 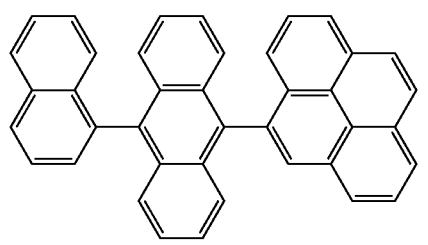
H6 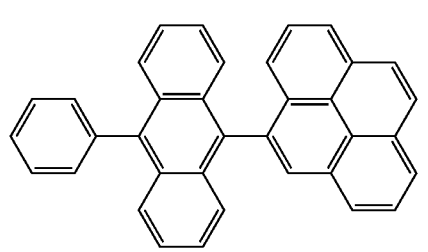
H7 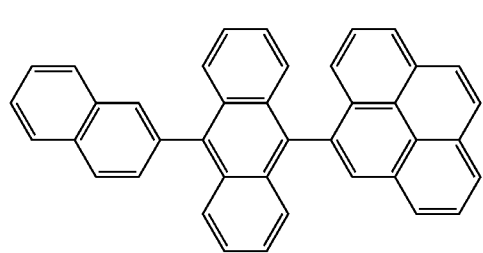
H8 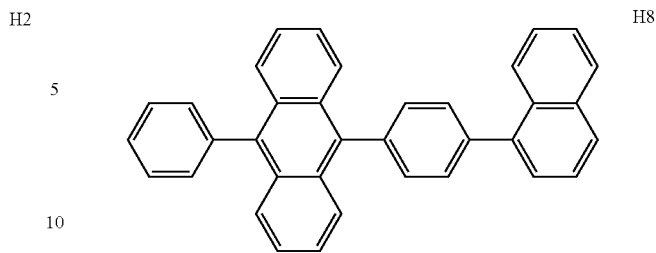
H9 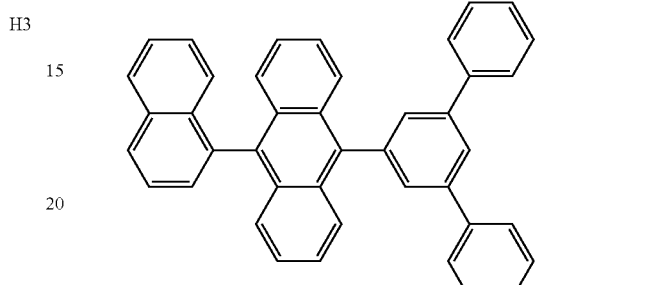
H10 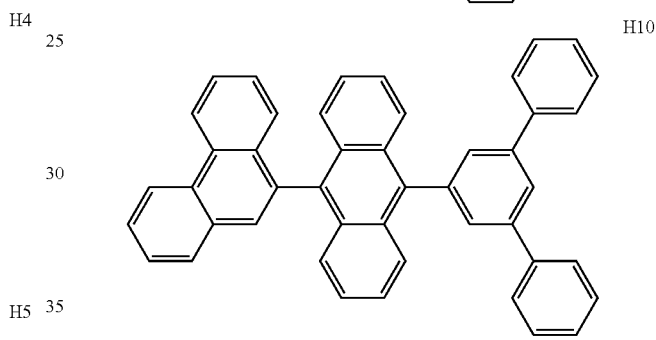
H11 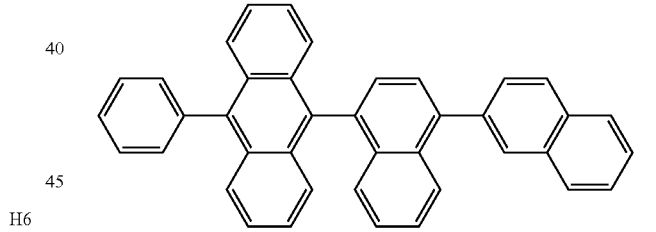
H12 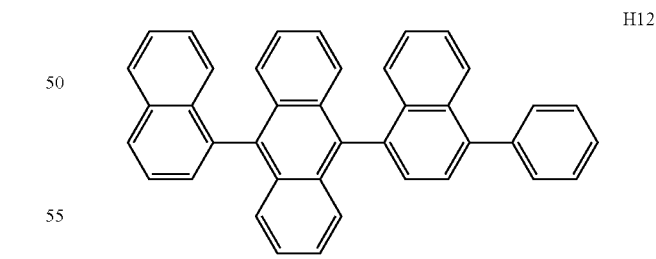
H13 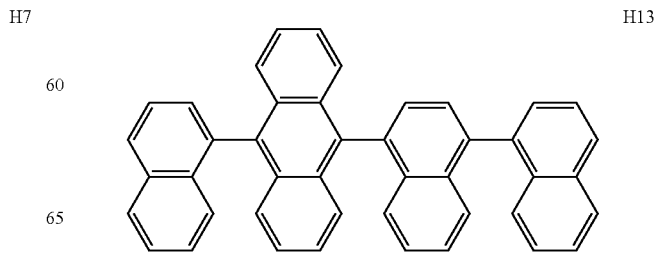

-continued
H14
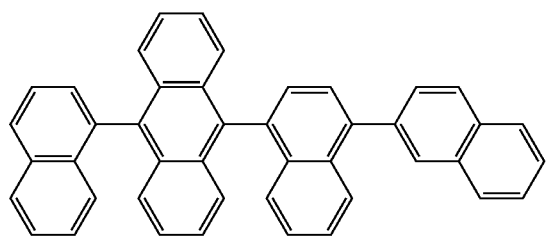
H15
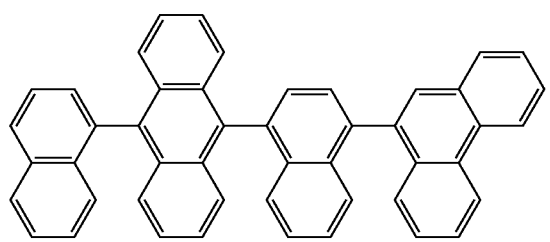
H16
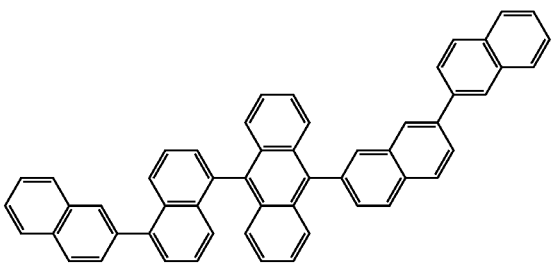
H17
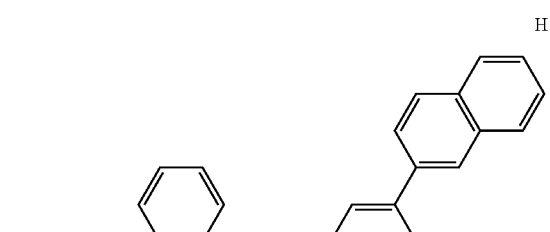
H18
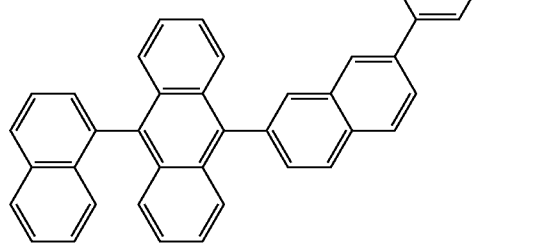
-continued
H19
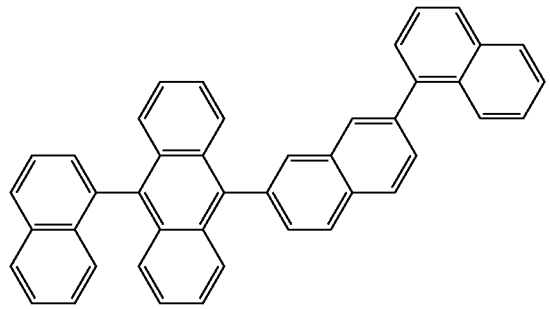
H20
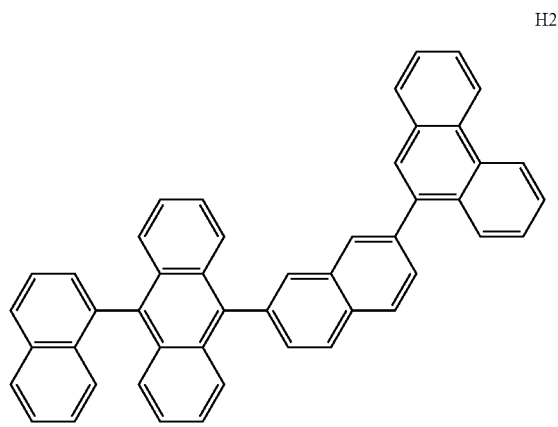
H21
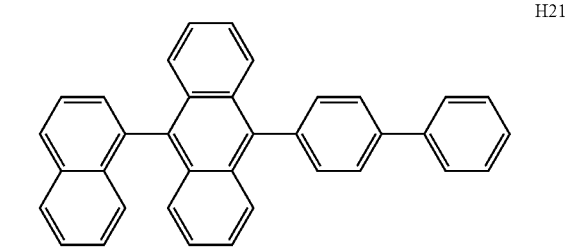
H22
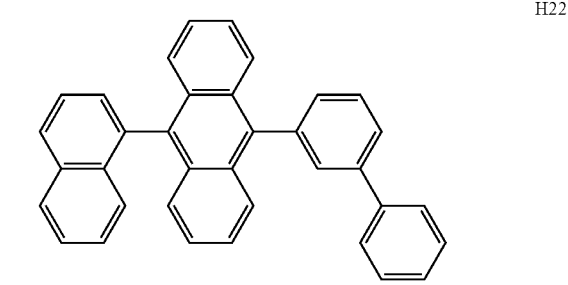
H23
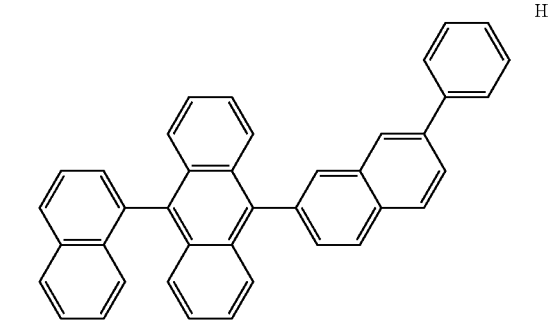

-continued
H24
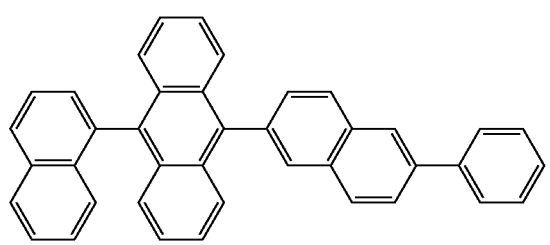
H25
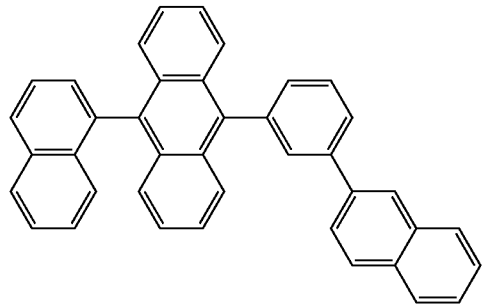
H26
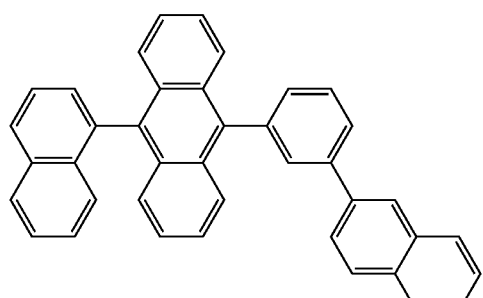
H27
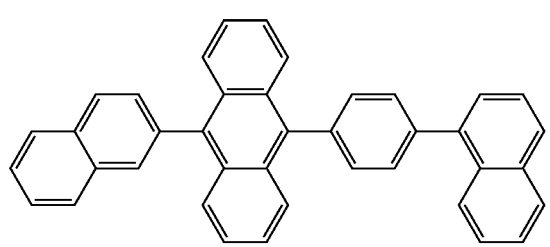
H28
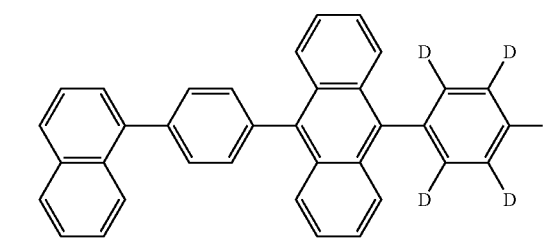
H29
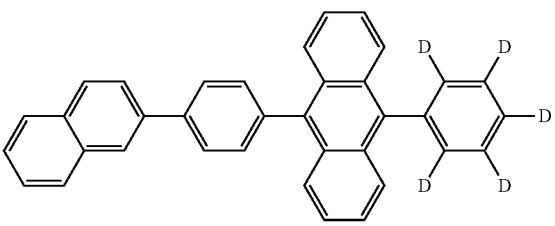
-continued
H30
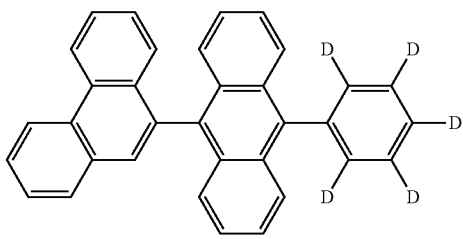
H31
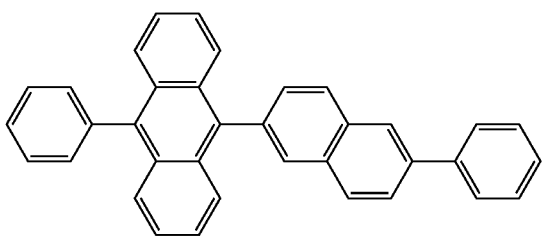
H32
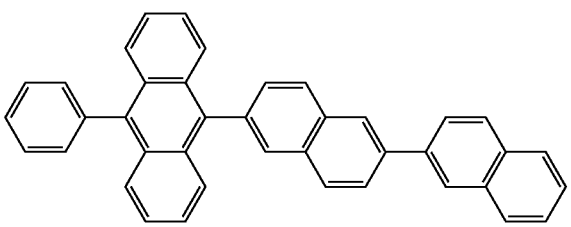
H33
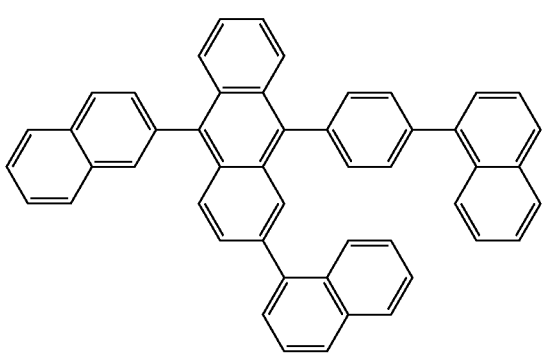
H34
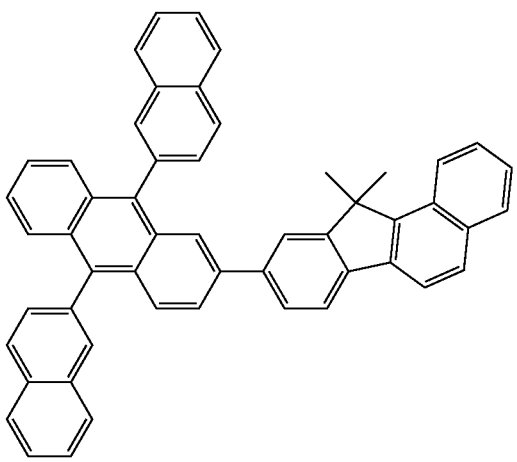

H35
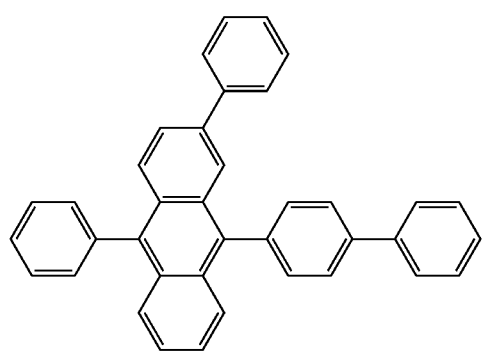
H36
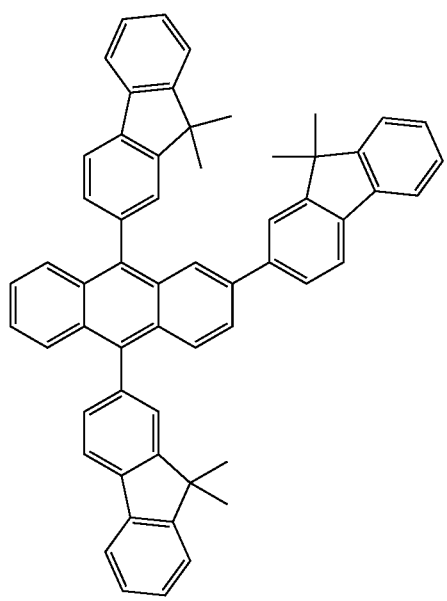
H37
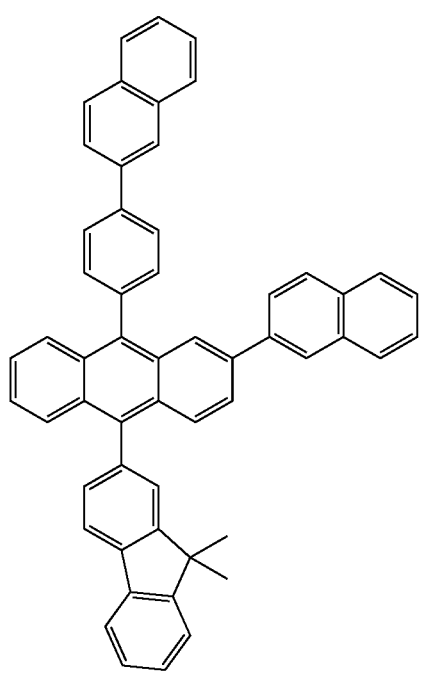
H38
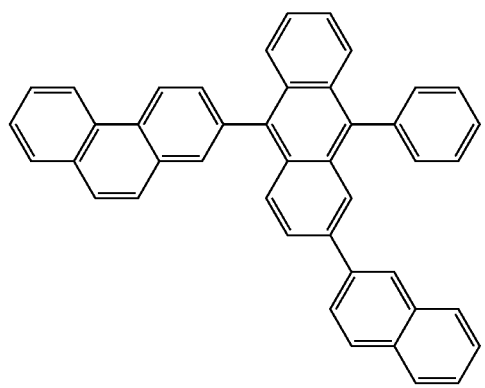
H39
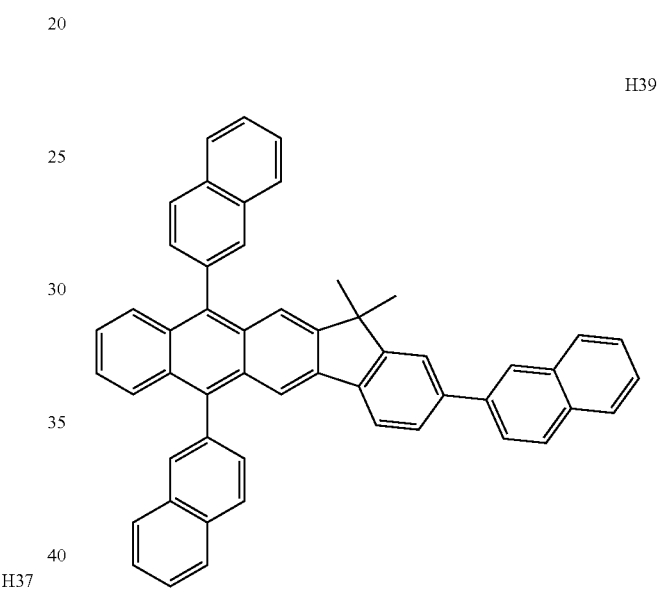
H40
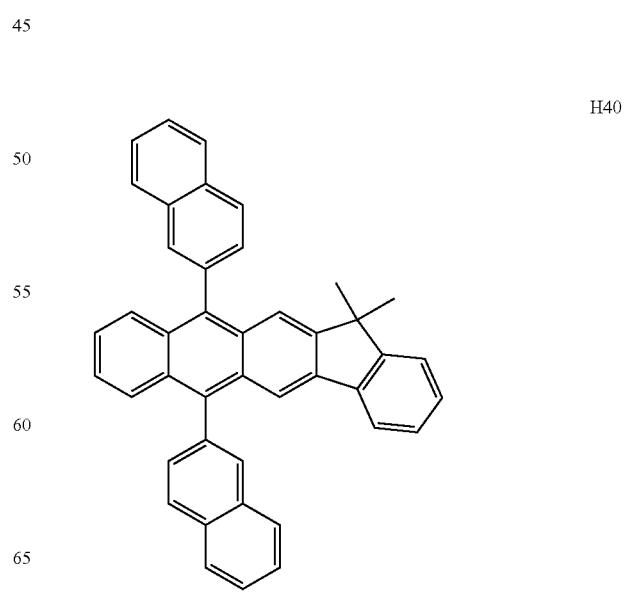

H41
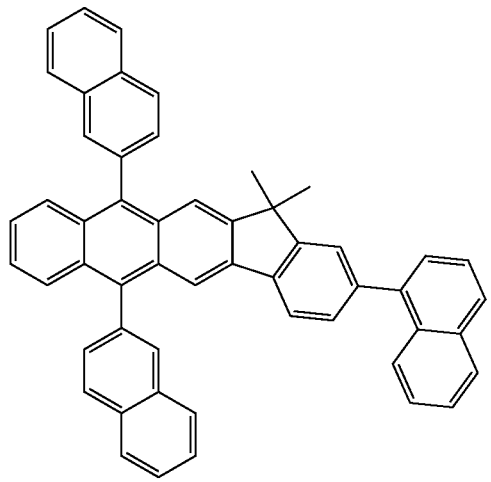
H42
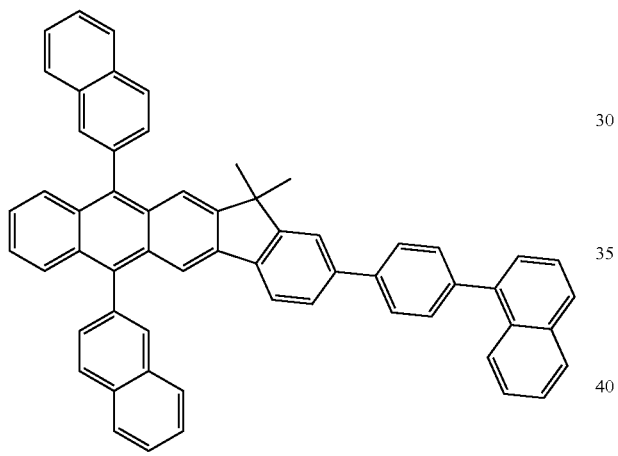
H44
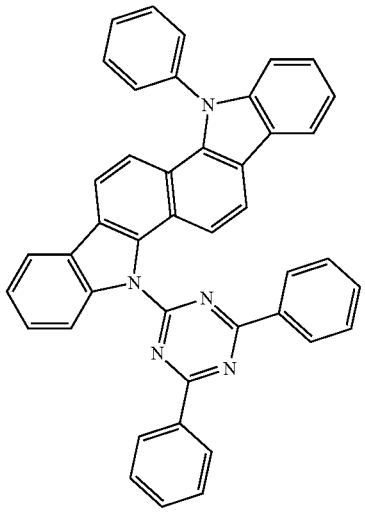
H45
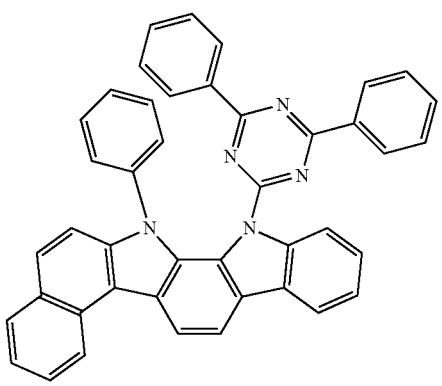
In an implementation, the host may include at least one of Compounds H43 to H49 below.
H43
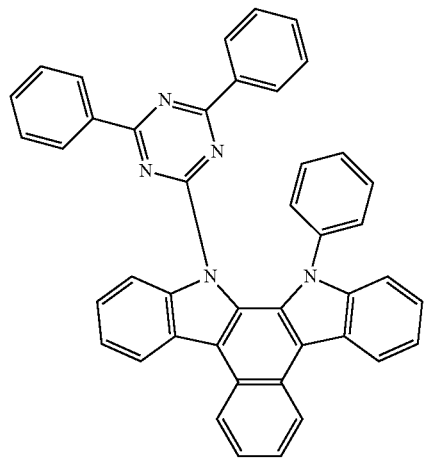
H46
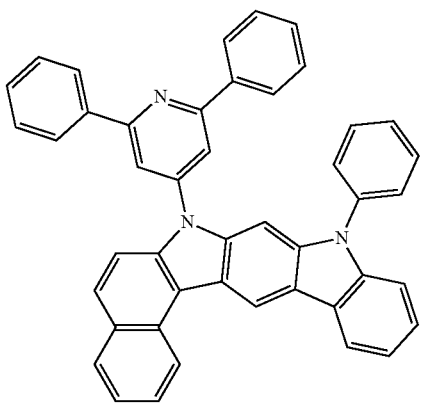

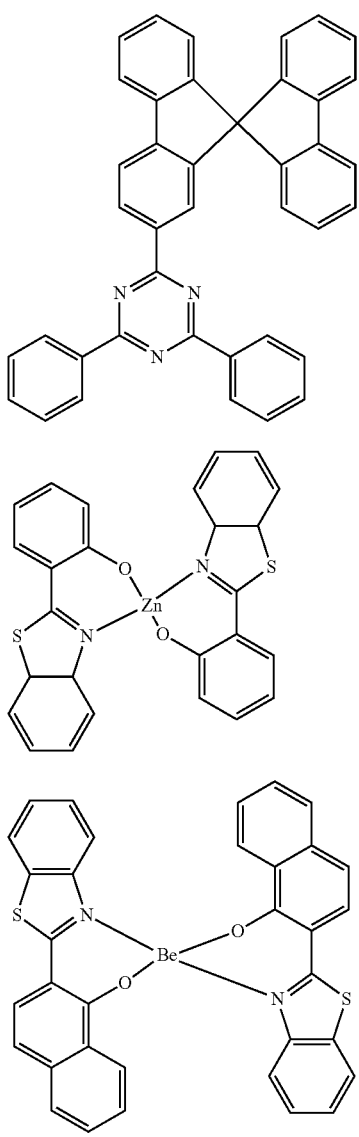
In an implementation, the host may include one of the compounds shown below.
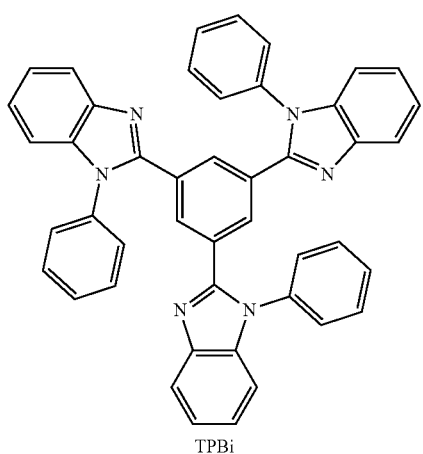
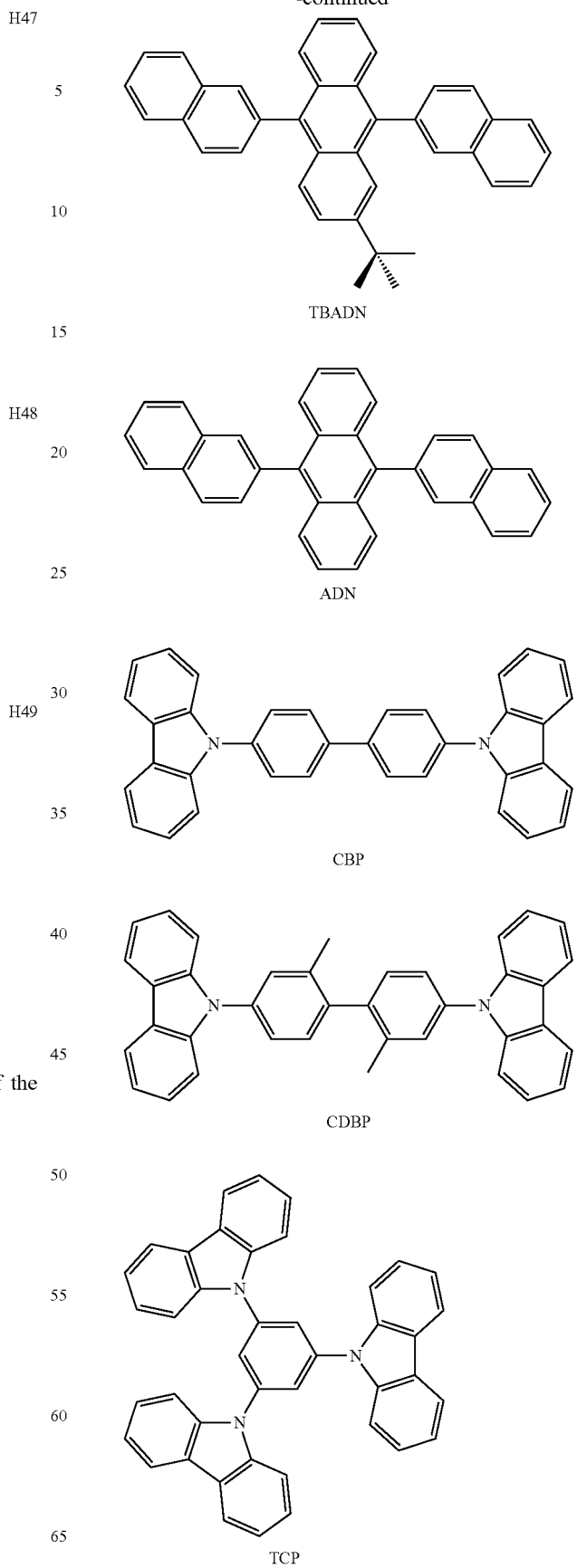

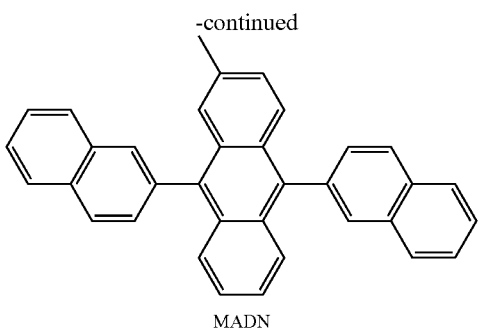

MADN

The dopant included in the emission layer may include a phosphorescent dopant or a fluorescent dopant.

The phosphorescent dopant may include an organic metal complex represented by Formula 401 below.

<Formula 401>

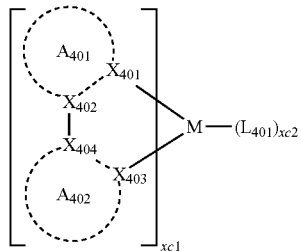

In Formula 401 above,

M may be selected from iridium (Ir), platinum (Pt), osmium (Os), titanium (Ti), zirconium (Zr), hafnium (Hf), europium (Eu), terbium (Tb), and thulium (Tm), $X_{401}$ to $X_{404}$ may be each independently nitrogen or carbon, $A_{401}$ and $A_{402}$ rings may be each independently selected from a substituted or unsubstituted benzene, a substituted or unsubstituted naphthalene, a substituted or unsubstituted fluorene, a substituted or unsubstituted spiro-fluorene, a substituted or unsubstituted indene, a substituted or unsubstituted pyrrole, a substituted or unsubstituted thiophene, a substituted or unsubstituted furan, a substituted or unsubstituted imidazole, a substituted or unsubstituted pyrazole, a substituted or unsubstituted thiazole, a substituted or unsubstituted isothiazole, a substituted or unsubstituted oxazole, a substituted or unsubstituted isooxazole, a substituted or unsubstituted pyridine, a substituted or unsubstituted pyrazine, a substituted or unsubstituted pyrimidine, a substituted or unsubstituted pyridazine, a substituted or unsubstituted quinoline, a substituted or unsubstituted isoquinoline, a substituted or unsubstituted benzoquinoline, a substituted or unsubstituted quinoxaline, a substituted or unsubstituted quinazoline, a substituted or unsubstituted carbazole, a substituted or unsubstituted benzoimidazole, a substituted or unsubstituted benzofuran, a substituted or unsubstituted benzothiophene, a substituted or unsubstituted isobenzothiophene, a substituted or unsubstituted benzooxazole, a substituted or unsubstituted isobenzooxazole, a substituted or unsubstituted triazole, a substituted or unsubstituted oxadiazole, a substituted or unsubstituted triazine, a substituted or unsubstituted dibenzofuran, and a substituted or unsubstituted dibenzothiophene, at least one of substituents of the substituted benzene, the substituted naphthalene, the substituted fluorene, the substituted spiro-fluorene, the substituted indene, the substituted pyrrole, the substituted thiophene, the substituted furan, the substituted imidazole, the substituted pyrazole, the substituted thiazole, the substituted isothiazole, the substituted oxazole, the substituted isooxazole, the substituted pyridine, the substituted pyrazine, the substituted pyrimidine, the substituted pyridazine, the substituted quinoline, the substituted isoquinoline, the substituted benzoquinoline, the substituted quinoxaline, the substituted quinazoline, the substituted carbazole, the substituted benzoimidazole, the substituted benzofuran, the substituted benzothiophene, the substituted isobenzothiophene, the substituted benzooxazole, the substituted isobenzooxazole, the substituted triazole, the substituted oxadiazole, the substituted triazine, the substituted dibenzofuran, and substituted dibenzothiophene may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{401}$)($Q_{402}$), —Si($Q_{403}$)($Q_{404}$)($Q_{405}$), and —B($Q_{406}$)($Q_{407}$);

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group;

a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, and a monovalent non-aromatic condensed heteropolycyclic group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, —N($Q_{411}$)($Q_{412}$), —Si($Q_{413}$)($Q_{414}$)($Q_{415}$), and —B($Q_{416}$)($Q_{417}$); and —N($Q_{421}$)($Q_{422}$), —Si($Q_{423}$)($Q_{424}$)($Q_{425}$), and —B($Q_{426}$)($Q_{427}$), $L_{401}$ may be an organic ligand, xc1 may be 1, 2, or 3, and xc2 may be 0, 1, 2, or 3.

In an exemplary embodiment, $L_{401}$ may be a monovalent organic ligand, a divalent organic ligand, or a trivalent organic ligand. For example, $L_{401}$ may be selected from a halogen ligand (e.g., Cl or F), a diketone ligand (e.g., acetylacetonate, 1,3-diphenyl-1,3-propanedionate, 2,2,6,6-tetramethyl-3,5-heptanedionate, or hexafluoroacetonate), a carboxylic acid ligand (e.g., picolinate, dimethyl-3-pyrazolecarboxylate, or benzoate), a carbon monoxide ligand, an isonitrile ligand, a cyano ligand, and a phosphorus ligand (e.g., phosphine or phosphite).

In an implementation, $Q_{401}$ to $Q_{407}$, $Q_{411}$ to $Q_{417}$, and $Q_{421}$ to $Q_{427}$ may be each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group.

When $A_{401}$ in Formula 401 has 2 or more substituents, 2 or more substituents of $A_{401}$ may be bonded to each other to form a saturated ring or an unsaturated ring.

When $A_{402}$ in Formula 401 has 2 or more substituents, 2 or more substituents of $A_{402}$ may be bonded to each other to form a saturated ring or an unsaturated ring.

When xc1 in Formula 401 is 2 or more, a plurality of ligands

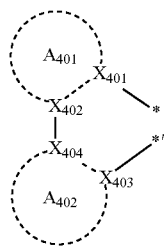

in Formula 401 may be identical to or different from each other. When xc1 in Formula 401 is 2 or more, $A_{401}$ and $A_{402}$ may be each independently bonded to $A_{401}$ and $A_{402}$ of other neighboring ligands, directly or via a linking group (e.g., a $C_1$-$C_5$ alkylene group, —N(R')— (wherein R' may be a $C_1$-$C_{10}$ alkyl group or a $C_6$-$C_{20}$ aryl group), or —C(=O)—).

The phosphorescent dopant may be, e.g., selected from Compounds PD1 to PD75 below.

PD1
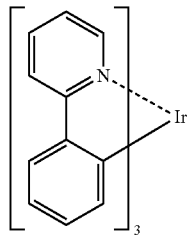

PD2
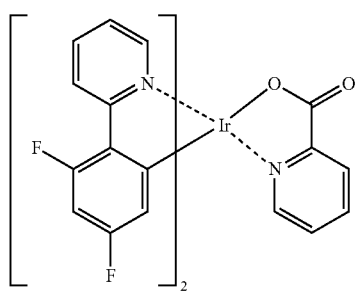

PD3
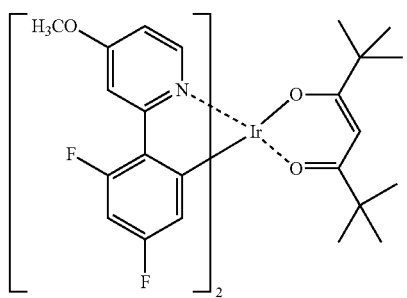

PD4
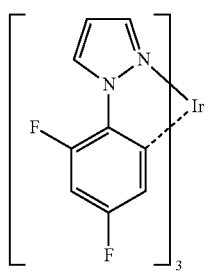

PD5
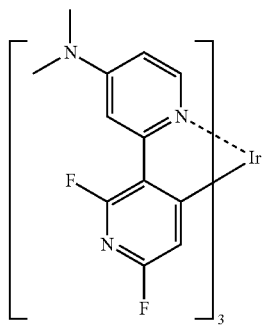

PD6
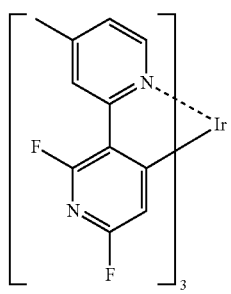

PD7
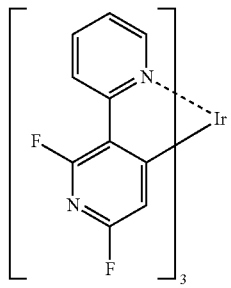

PD8
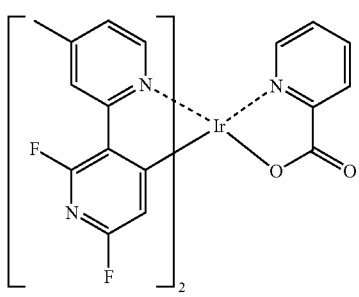
PD9
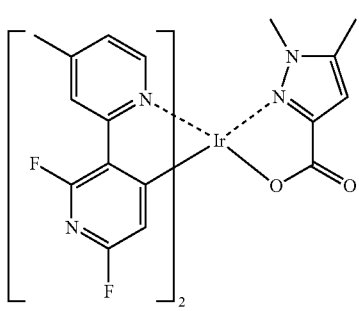
PD10
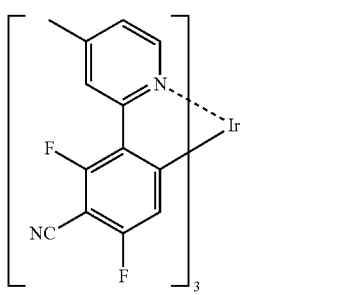
PD11
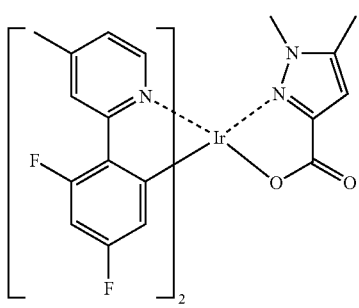
PD12
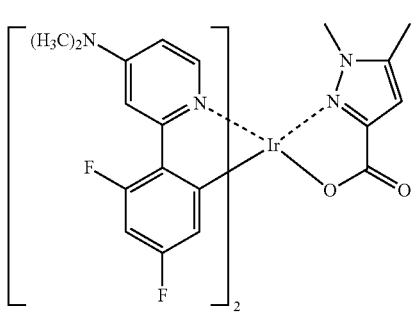
PD13
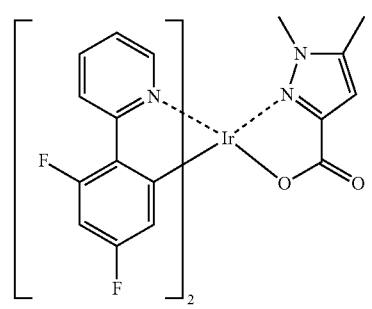
PD14
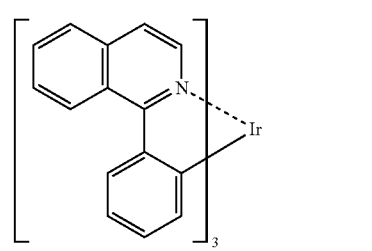
PD15
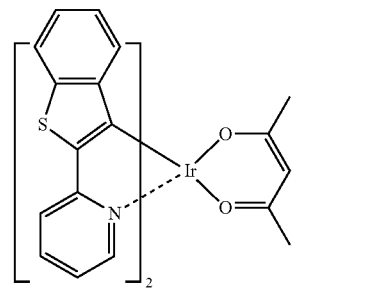
PD16
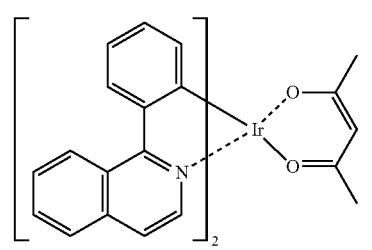
PD17
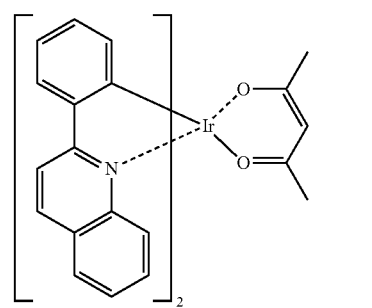

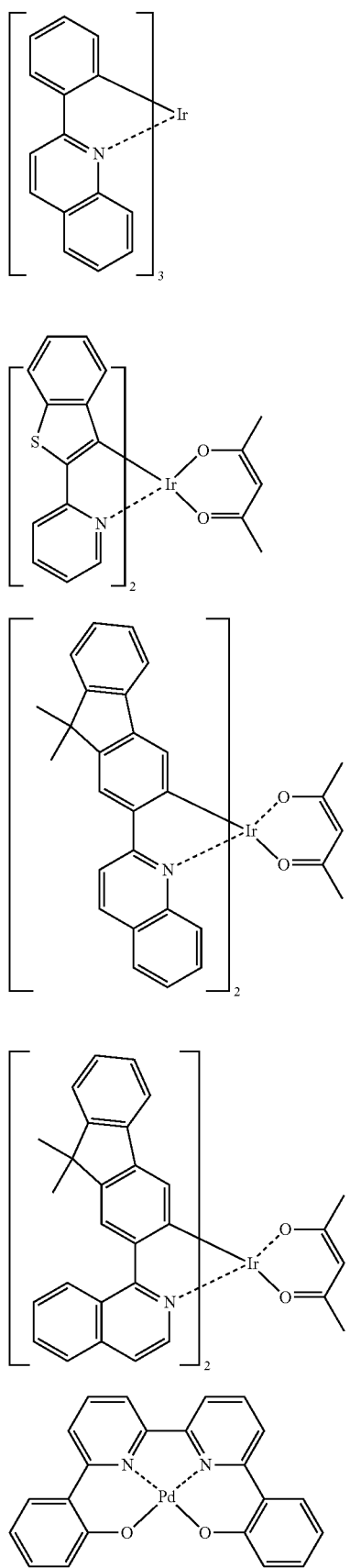
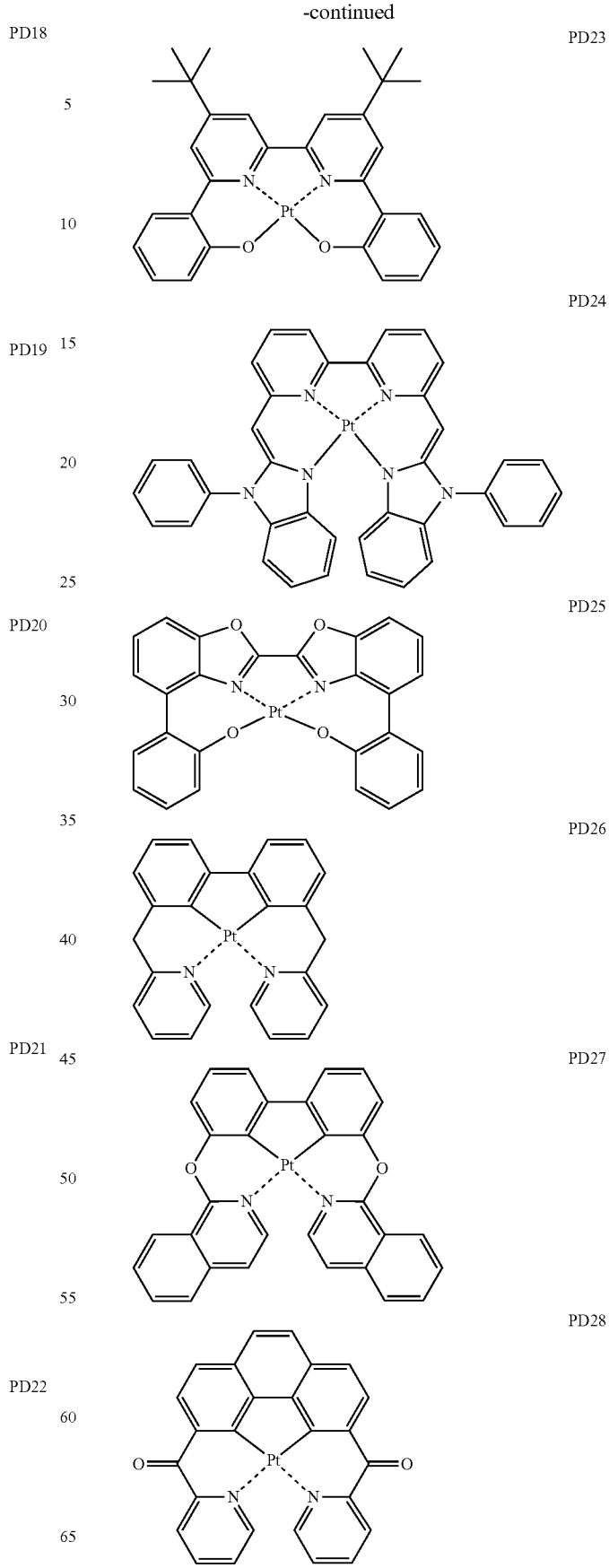

-continued
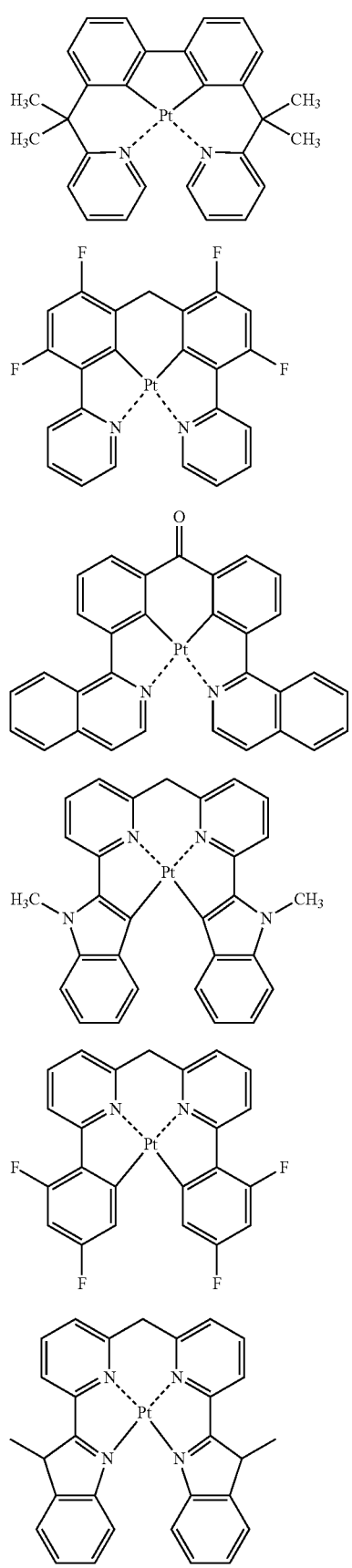
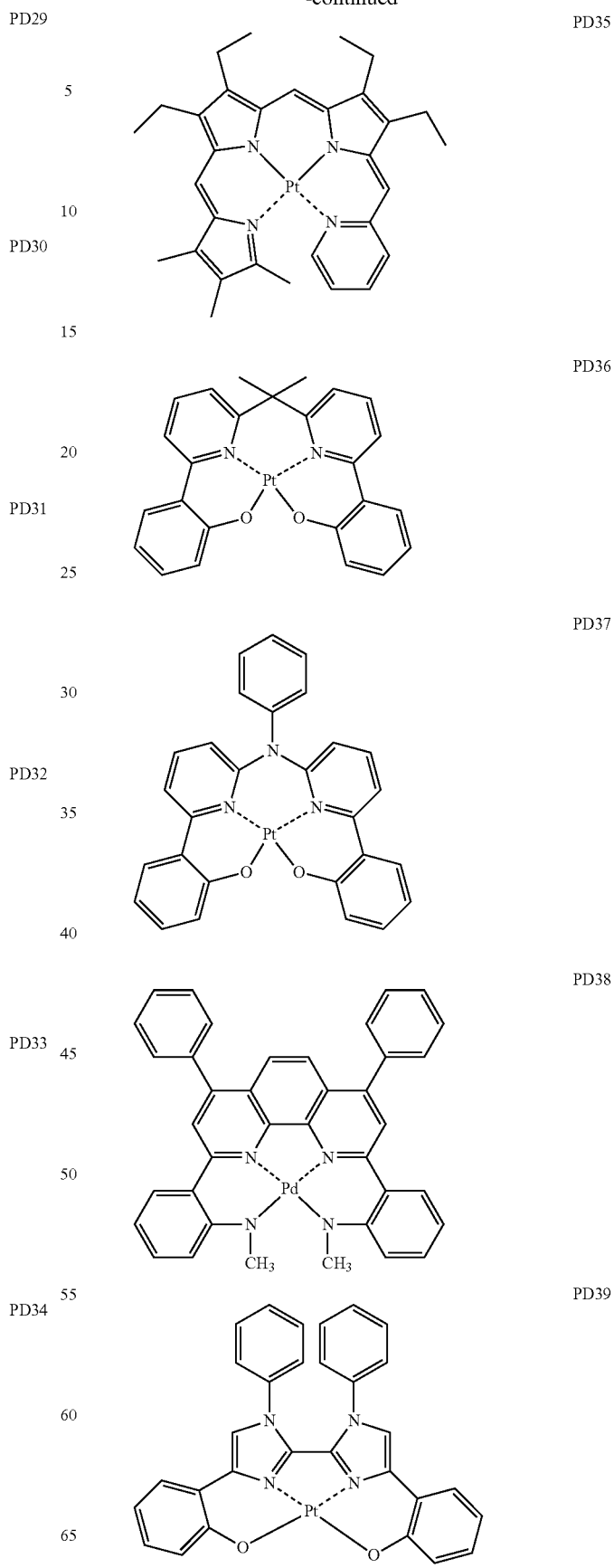

PD40 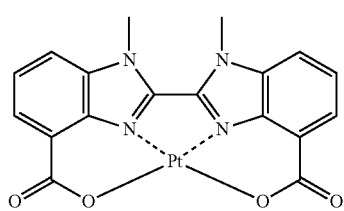
PD41 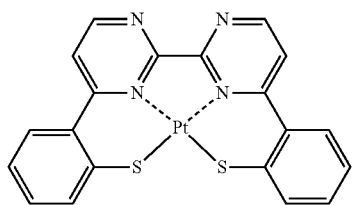
PD42 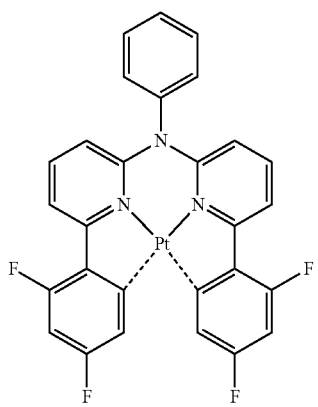
PD43 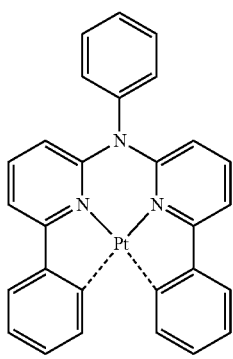
PD44 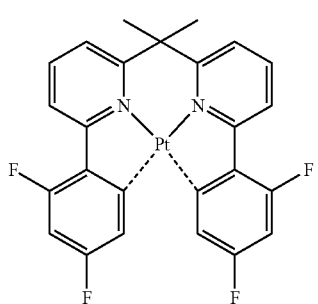
PD45 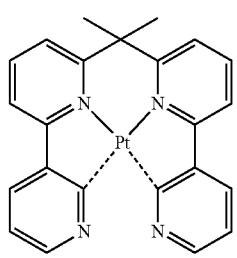
PD46 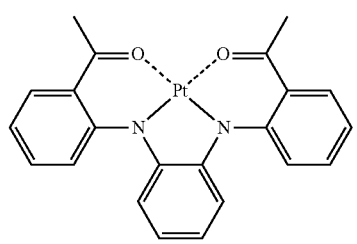
PD47 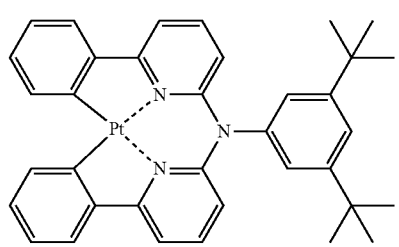
PD48 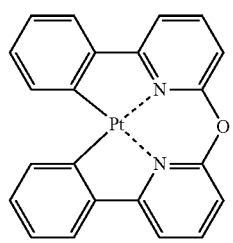
PD49 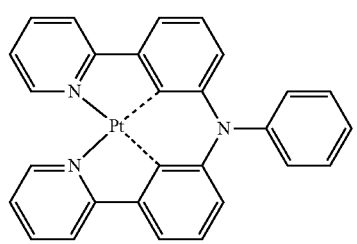
PD50

PD51 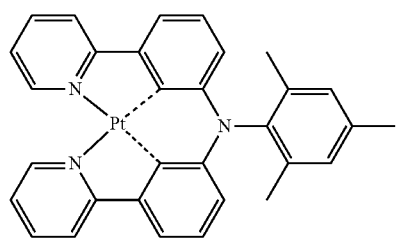
PD52 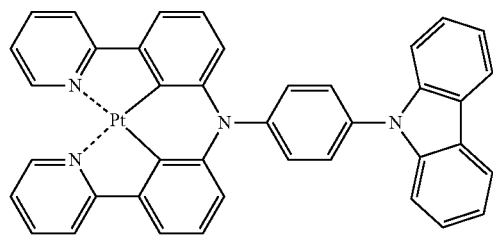
PD53 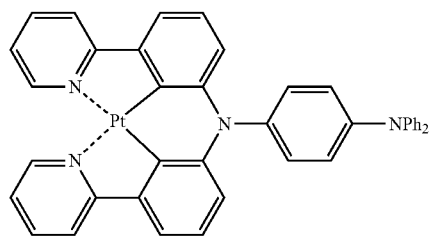
PD54 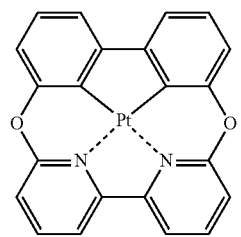
PD55 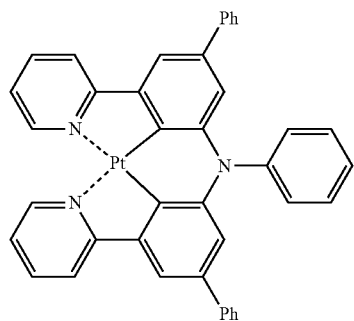
PD56 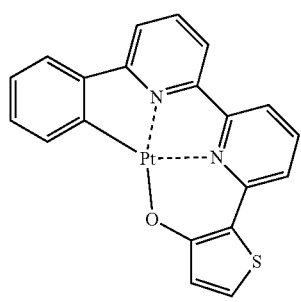
PD57 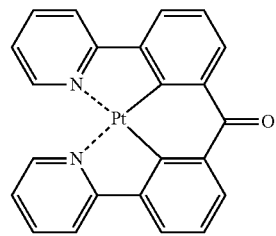
PD58 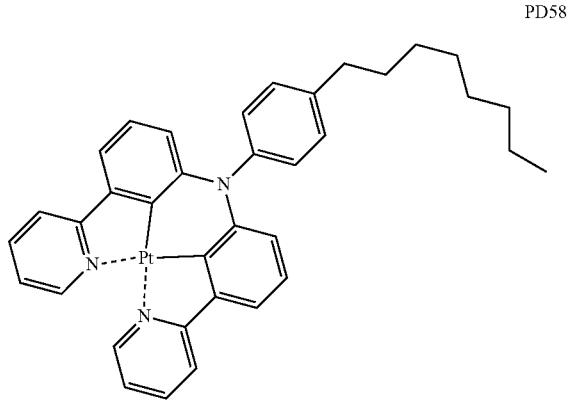
PD59 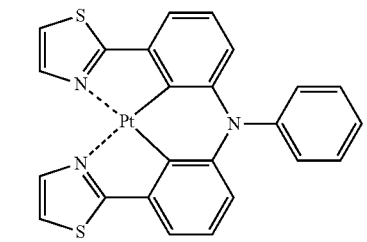
PD60 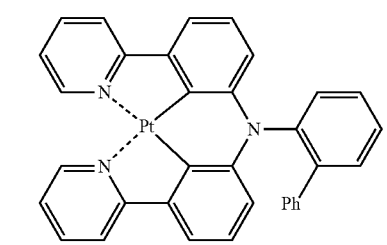
PD61 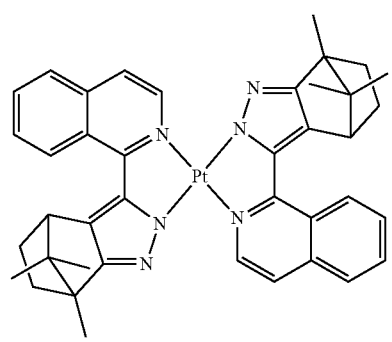

PD62 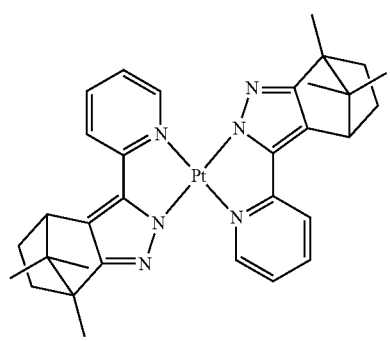
PD63 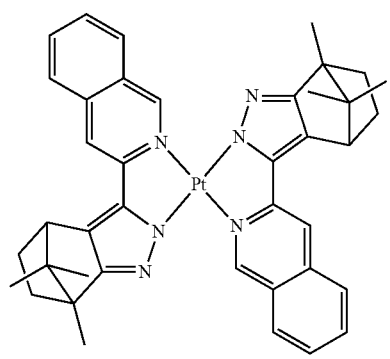
PD64 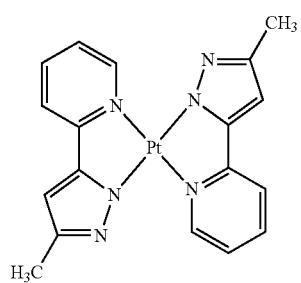
PD65 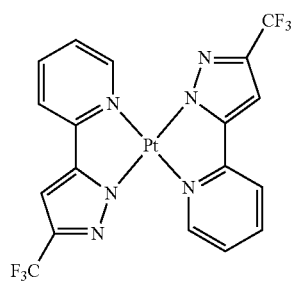
PD66 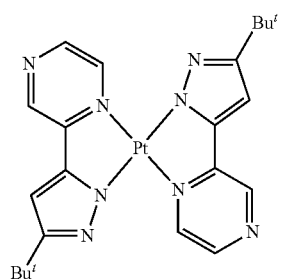
PD67 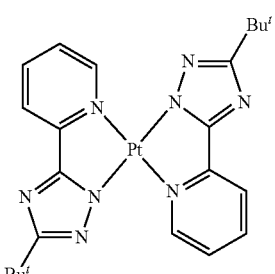
PD68 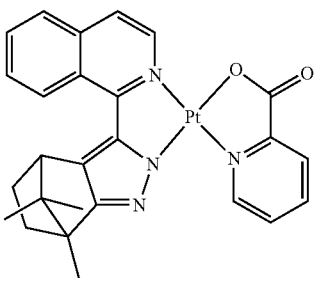
PD69 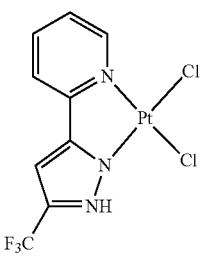
PD70 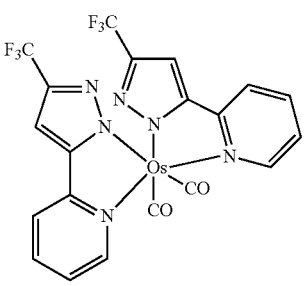
PD71 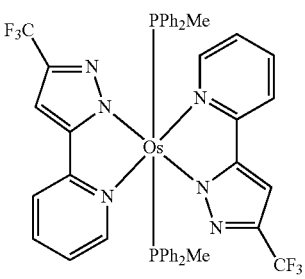

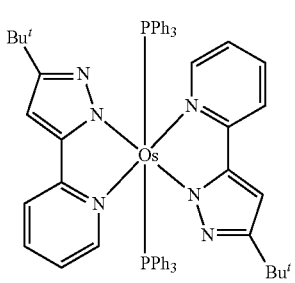
PD72

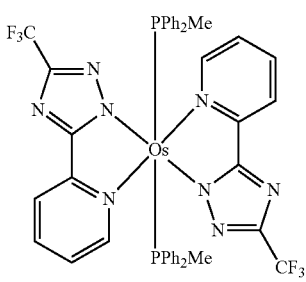
PD73

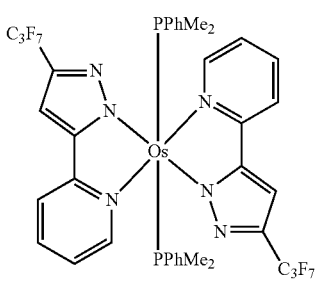
PD74

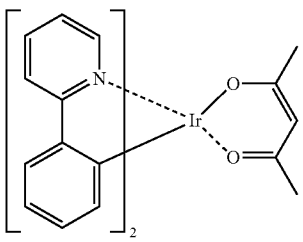
PD75

The fluorescent dopant may include a compound represented by Formula 501 below:

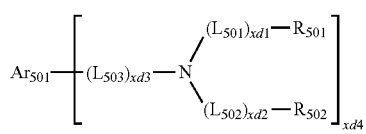
<Formula 501>

In Formula 501,

Ar$_{501}$ may be selected from:

a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, a naphthacene, a picene, a perylene, a pentaphene, and an indenoanthracene; and a naphthalene, a heptalene, a fluorene, a spiro-fluorene, a benzofluorene, a dibenzofluorene, a phenalene, a phenanthrene, an anthracene, a fluoranthene, a triphenylene, a pyrene, a chrysene, naphthacene, a picene, a perylene, a pentaphene, and an indenoanthracene, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_2$-$C_{10}$ heterocycloalkyl group, a $C_3$-$C_{10}$ cycloalkenyl group, a $C_2$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, a monovalent non-aromatic condensed polycyclic group, a monovalent non-aromatic condensed heteropolycyclic group, and —Si($Q_{501}$)($Q_{502}$)($Q_{503}$) (wherein $Q_{501}$ to $Q_{503}$ may be each independently selected from a hydrogen, a $C_1$-$C_{60}$ alkyl group, a $C_2$-$C_{60}$ alkenyl group, a $C_6$-$C_{60}$ aryl group, and a $C_2$-$C_{60}$ heteroaryl group), descriptions of $L_{501}$ to $L_{503}$ may be understood by referring to the description provided herein in connection with $L_1$, $R_{501}$ and $R_{502}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazole group, a triazinyl group, a dibenzofuranyl group, and a dibenzothiophenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a dibenzofuranyl group, and a dibenzothiophenyl group, xd1 to xd3 may be each independently selected from 0, 1, 2, and 3, and xd4 may be selected from 1, 2, 3, and 4.

The fluorescent host may include at least one of Compounds FD1 to FD9 below.

FD1
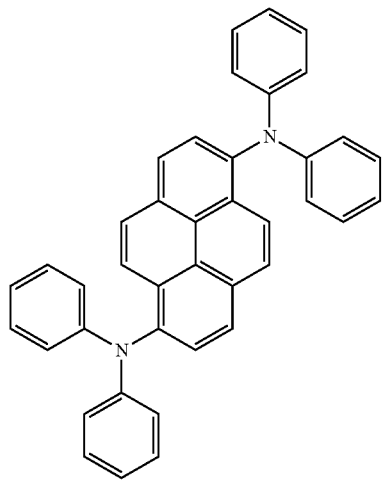
FD2
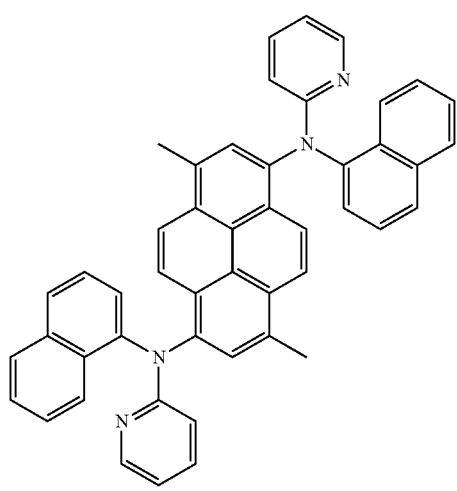
FD3
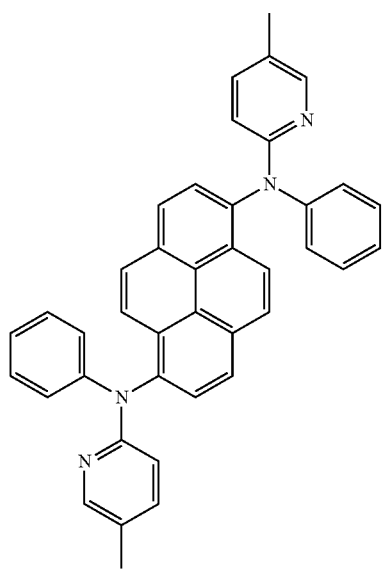
FD4
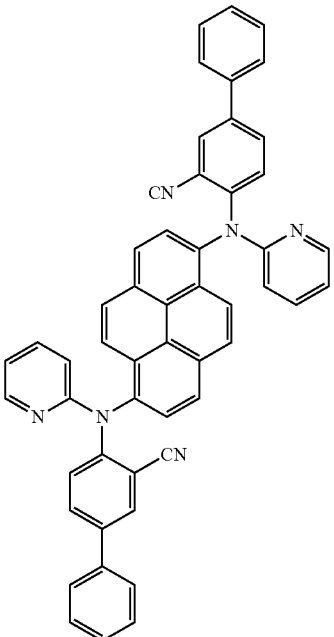
FD5
FD6
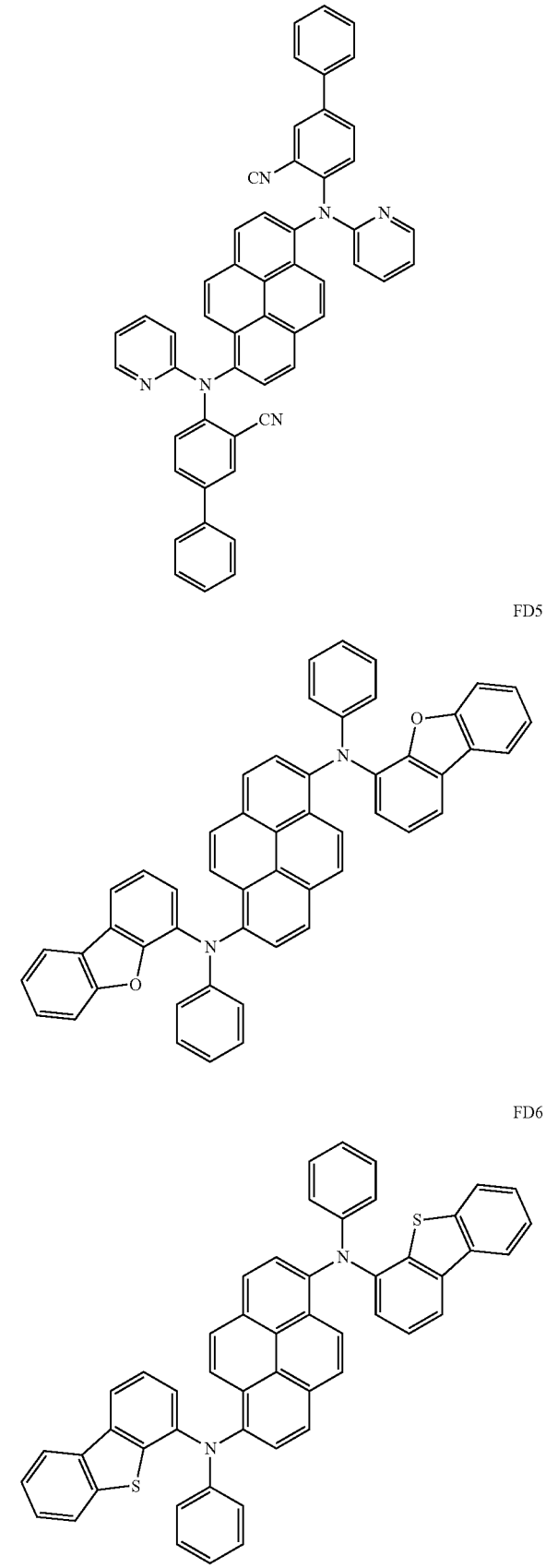

FD7

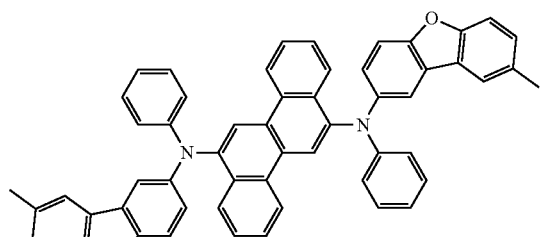

FD8

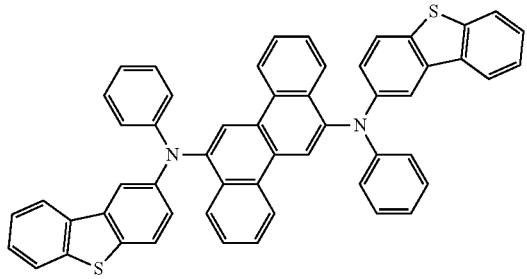

DPVBi

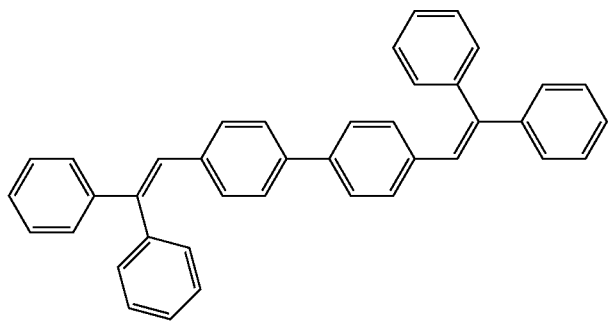

DPAVBi

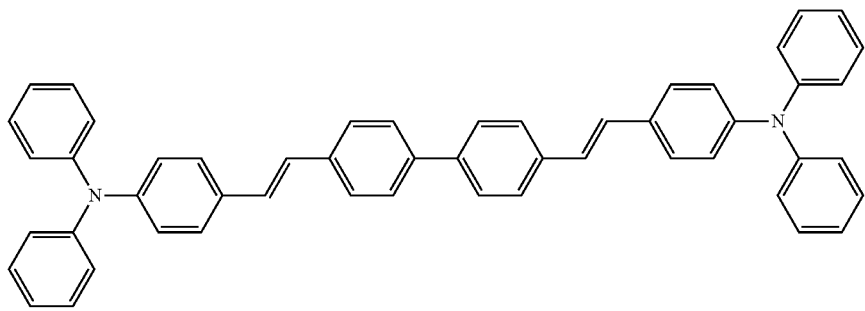

<Compound FD9>

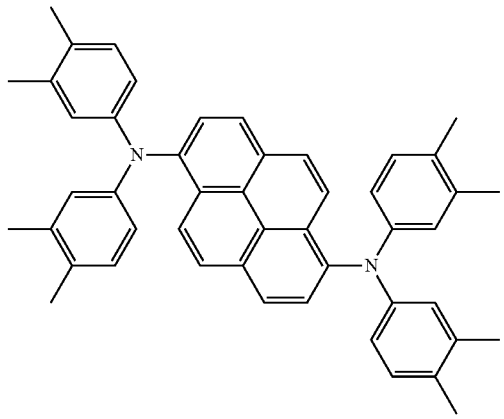

When the emission layer includes a host and a dopant, an amount of the dopant may be from about 0.01 to about 15 parts by weight, based on 100 parts by weight of the host.

A thickness of the emission layer may be from about 100 Å to about 1,000 Å, e.g., about 200 Å to about 600 Å. When the thickness of the emission layer is within these ranges, excellent emission characteristics may be obtained without a substantial increase in driving voltage.

In an implementation, the fluorescent dopant may be selected from the compounds shown below.

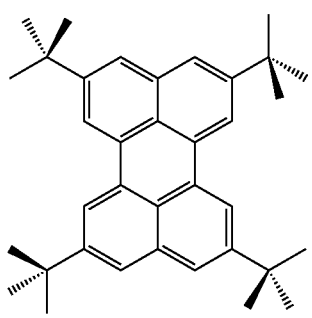
TBPe

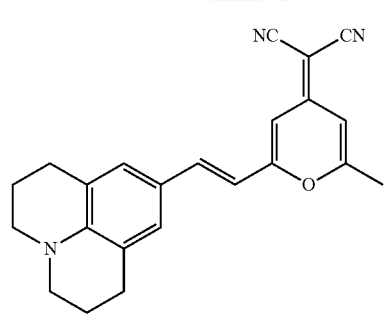
DCM

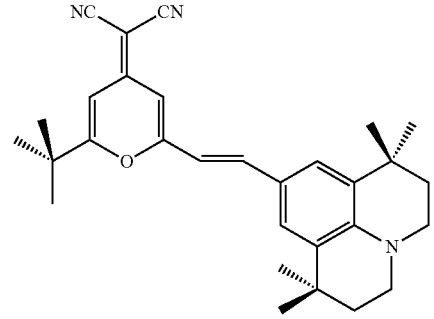
DCJTB

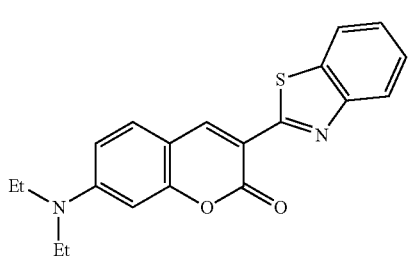
Coumarin 6

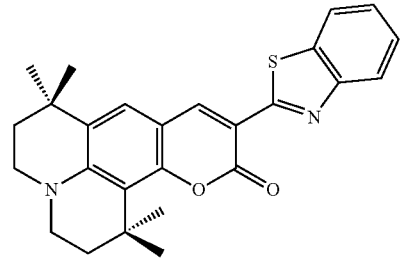
C545T

Next, the electron transport region may be disposed on the emission layer.

In an implementation, the electron transport region may include at least one of, e.g., an HBL, an ETL, and an EIL.

For example, the electron transport region may have a structure of ETL/EIL or a structure of HBL/ETL/EIL, each of which layers are sequentially stacked in the stated order from the emission layer.

In an implementation, the organic layer 150 of the organic light-emitting device 10 may include the electron transport region that is disposed between the emission layer and the second electrode 190.

The electron transport region may include at least one of the condensed cyclic compounds of Formulae 1-1 to 1-8 above.

When the electron transport region includes an HBL, the HBL may be formed on the emission layer by using various methods, such as vacuum deposition, spin coating, casting, an LB method, and LITI. When the HBL is formed by vacuum deposition and spin coating, deposition and coating conditions may be determined by referring to those applied to form the HIL.

The HBL may include, e.g., at least one of BCP and Bphen below.

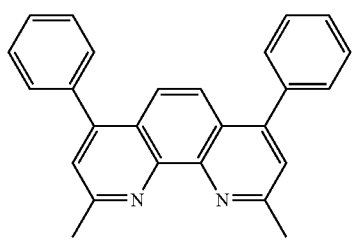
BCP

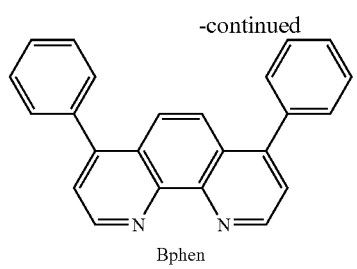
Bphen

A thickness of the HBL may be from about 20 Å to about 1,000 Å, e.g., about 30 Å to about 300 Å. When the thickness of the HBL is within these ranges, excellent hole blocking characteristics may be obtained without a substantial increase in driving voltage.

The electron transport region may include an ETL, and the ETL may be formed on the emission layer or the HBL by using various methods, e.g., vacuum deposition, spin coating, casting, an LB method, and LITI. When the ETL is formed by vacuum deposition and spin coating, deposition and coating conditions may be determined by referring to those applied to form the HIL.

The ETL may include at least one of the condensed cyclic compounds of Formulae 1-1 to 1-8 above.

A thickness of the ETL may be from about 100 Å to about 1,000 Å, e.g., about 150 Å to about 500 Å. When the thickness of the ETL is within these ranges, excellent electron transporting characteristics may be obtained without a substantial increase in driving voltage.

The ETL may further include, in addition to the materials described above, a metal-containing material.

The metal-containing material may include a Li complex. The Li complex may include, for example, Compound ET-D1 (e.g., lithium quinolate (LiQ) or ET-D2 below:

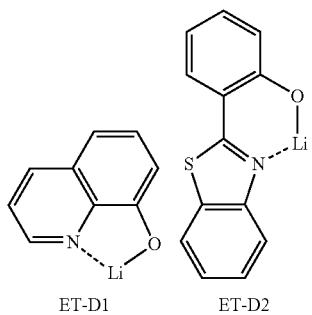

ET-D1          ET-D2

The electron transport region may include an EIL that facilitates electron injection from the second electrode 190.

The EIL may be formed on the ETL by using various methods, e.g., vacuum deposition, spin coating, casting, an LB method, LITI. When the EIL is formed by vacuum deposition and spin coating, deposition and coating conditions may be determined by referring to those applied to form the HIL.

The EIL may include at least one selected from LiF, NaCl, CsF, $Li_2O$, BaO, and LiQ.

A thickness of the EIL may be from about 1 Å to about 100 Å, e.g., about 3 Å to about 90 Å. When the thickness of the EIL is within these ranges, satisfactory electron injecting characteristics may be obtained without a substantial increase in driving voltage.

The second electrode 190 may be disposed on the organic layer 150. The second electrode 190 may be a cathode, which is an electron injection electrode. In an implementation, a material for forming the second electrode 190 may be a material having a low work function, such as a metal, an alloy, an electrically conductive compound, or a mixture thereof. Examples of the material for forming the second electrode 190 may include lithium (Li), magnesium (Mg), aluminum (Al), aluminum-lithium (Al—Li), calcium (Ca), magnesium-indium (Mg—In), and magnesium-silver (Mg—Ag). In an implementation, the material for forming the second electrode 190 may include ITO or IZO. The second electrode 190 may be a semi-transmissive electrode or a transmissive electrode.

Figure 2:
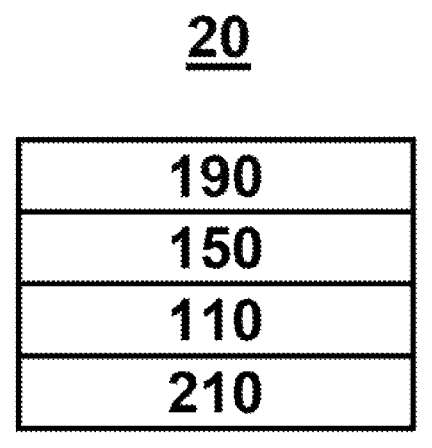
Figure 3:
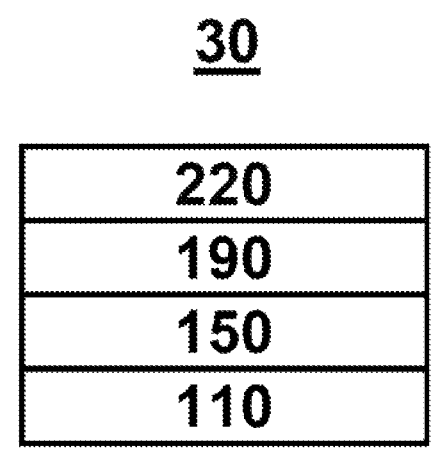
Figure 4:
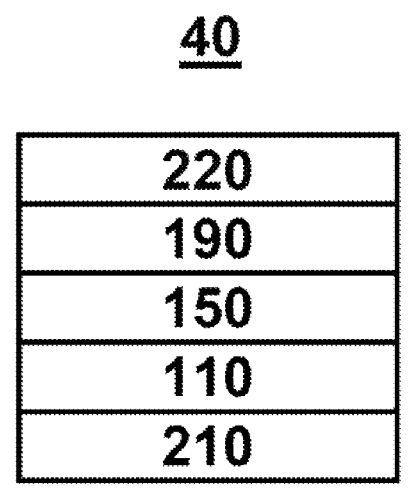

FIG. 2 illustrates a schematic view of an organic light-emitting device 20 according to an embodiment, the organic light-emitting device 20 having a structure of a first capping layer 210, a first electrode 110, an organic layer 150, and a second electrode 190, which are sequentially stacked in the stated order. FIG. 3 illustrates a schematic view of an organic light-emitting device 30 according to an embodiment, the organic light-emitting device 30 having a structure of a first electrode 110, an organic layer 150, a second electrode 190, and a second capping layer 220, which are sequentially stacked in the stated order. FIG. 4 illustrates a schematic view of an organic light-emitting device 40 according to an embodiment, the organic light-emitting device 40 having a structure of the a first capping layer 210, a first electrode 110, an organic layer 150, a second electrode 190, and a second capping layer 220, which are sequentially stacked in the stated order.

In FIGS. 2 to 4, the first electrode 110, the organic layer 150, and the second electrode 190 may be described in connection with FIG. 1.

In the organic layer 150 of the organic light-emitting devices 20 and 40, light generated from the emission layer may be emitted to the outside through the first electrode 110, which may be a semi-transmissive electrode or a transmissive electrode, and the first capping layer 210. In the organic layer 150 of the organic light-emitting devices 30 and 40, light generated from the emission layer may be emitted to the outside through the second electrode 190, which may be a semi-transmissive electrode or a transmissive electrode, and the second capping layer 220.

The first capping layer 210 and the second capping layer 220 may help improve external light emission efficiency, according to the principle of constructive interference.

In an implementation, the first capping layer 210 of FIG. 2 and the second capping layer 220 of FIG. 3 may include at least one of the condensed cyclic compounds of Formulae 1-1 to 1-8 above.

In an implementation, at least one of the first capping layer 210 and the second capping layer 220 of FIG. 4 may include at least one of the condensed cyclic compounds of Formulae 1-1 to 1-8 above.

In an implementation, the organic layer 150 of FIGS. 2 to 4 may not include the condensed cyclic compounds of Formulae 1-1 to 1-8 above.

Hereinafter, the organic light-emitting devices according to exemplary embodiments are described in detail with reference to FIGS. 1 to 4.

A $C_1$-$C_{60}$ alkyl group used herein refers to a linear or branched aliphatic hydrocarbon monovalent group having 1 to 60 carbon atoms, and detailed examples thereof are a methyl group, an ethyl group, a propyl group, an isobutyl group, a sec-butyl group, a ter-butyl group, a pentyl group, an iso-amyl group, and a hexyl group. A $C_1$-$C_{60}$ alkylene group used herein refers to a divalent group having the same structure as the $C_1$-$C_{60}$ alkyl group.

A $C_1$-$C_{60}$ alkoxy group used herein refers to a monovalent group represented by —$OA_{101}$ (wherein $A_{101}$ is the $C_1$-$C_{60}$ alkyl group), and detailed examples thereof are a methoxy group, an ethoxy group, and an isopropyloxy group.

A $C_2$-$C_{60}$ alkenyl group used herein refers to a hydrocarbon group formed by substituting at least one carbon double bond in the middle or terminal of the $C_2$-$C_{60}$ alkyl group, and detailed examples thereof are an ethenyl group, a prophenyl group, and a butenyl group. A $C_2$-$C_{60}$ alkenylene group used herein refers to a divalent group having the same structure as the $C_2$-$C_{60}$ alkenyl group.

A $C_2$-$C_{60}$ alkynyl group used herein refers to a hydrocarbon group formed by substituting at least one carbon triple bond in the middle or terminal of the $C_2$-$C_{60}$ alkyl group, and detailed examples thereof are an ethynyl group and a propynyl group. A $C_2$-$C_{60}$alkynylene group used herein refers to a divalent group having the same structure as the $C_2$-$C_{60}$ alkynyl group.

A $C_3$-$C_{10}$ cycloalkyl grouped herein refers to a monovalent hydrocarbon monocyclic group having 3 to 10 carbon atoms, and detailed examples thereof are a cyclopropyl group, a cyclobutyl group, a cyclopentyl group, a cyclohexyl group, and a cycloheptyl group. A $C_3$-$C_{10}$ cycloalkylene group used herein refers to a divalent group having the same structure as the $C_3$-$C_{10}$ cycloalkyl group.

A $C_1$-$C_{10}$ heterocycloalkyl group used herein refers to a monovalent monocyclic group having at least one heteroatom selected from N, O, Si, P and S as a ring-forming atom and 1 to 10 carbon atoms, and detailed examples thereof are a tetrahydrofuranyl group and a tetrahydrothiophenyl group. A $C_1$-$C_{10}$ heterocycloalkylene group used herein refers to a divalent group having the same structure as the $C_1$-$C_{10}$ heterocycloalkyl group.

A $C_3$-$C_{10}$ cycloalkenyl group used herein refers to a monovalent monocyclic group that has 3 to 10 carbon atoms and at least one double bond in the ring thereof and does not have aromaticity, and detailed examples thereof are a cyclopentenyl group, a cyclohexenyl group, and a cycloheptenyl group. A $C_3$-$C_{10}$ cycloalkenylene group used herein refers to a divalent group having the same structure as the $C_3$-$C_{10}$ cycloalkenyl group.

A $C_1$-$C_{10}$ heterocycloalkenyl group used herein refers to a monovalent monocyclic group that has at least one heteroatom selected from N, O, Si, P, and S as a ring-forming atom, 1 to 10 carbon atoms, and at least one double bond in its ring. Detailed examples of the $C_1$-$C_{10}$ heterocycloalkenyl group are a 2,3-hydrofuranyl group and a 2,3-hydrothiophenyl group. A $C_1$-$C_{10}$ heterocycloalkenylene group used herein refers to a divalent group having the same structure as the $C_1$-$C_{10}$ heterocycloalkenyl group.

A $C_6$-$C_{60}$ aryl group used herein refers to a monovalent group having a carbocyclic aromatic system having 6 to 60 carbon atoms, and a $C_6$-$C_{60}$ arylene group used herein refers to a divalent group having a carbocyclic aromatic system having 6 to 60 carbon atoms. Detailed examples of the $C_6$-$C_{60}$ aryl group are a phenyl group, a naphthyl group, an anthracenyl group, a phenanthrenyl group, a pyrenyl group, and a chrysenyl group. When the $C_6$-$C_{60}$ aryl group and the $C_6$-$C_{60}$ arylene group each include two or more rings, these rings may be fused to each other.

A $C_1$-$C_{60}$ heteroaryl group used herein refers to a monovalent group having a carbocyclic aromatic system that has at least one heteroatom selected from N, O, Si, P, and S as a ring-forming atom, and 1 to 60 carbon atoms. A $C_1$-$C_{60}$ heteroarylene group used herein refers to a divalent group having a carbocyclic aromatic system that has at least one heteroatom selected from N, O, P, and S as a ring-forming atom, and 1 to 60 carbon atoms. Detailed examples of the $C_1$-$C_{60}$ heteroaryl group are a pyridinyl group, a pyrimidinyl group, a pyrazinyl group, a pyridazinyl group, a triazinyl group, a quinolinyl group, and an isoquinolinyl group. When the $C_1$-$C_{60}$ heteroaryl group and the $C_1$-$C_{60}$ heteroarylene group each include two or more rings, these rings may be fused to each other.

A $C_6$-$C_{60}$ aryloxy group used herein indicates —$OA_{102}$ (wherein $A_{102}$ is the $C_6$-$C_{60}$ aryl group), and a $C_6$-$C_{60}$ arylthio group used herein indicates —$SA_{103}$ (wherein $A_{103}$ is the $C_6$-$C_{60}$ aryl group).

A monovalent non-aromatic condensed polycyclic group (e.g., a group having 8 to 60 carbon atoms) used herein refers to a monovalent group that has two or more rings condensed to each other, has carbon atoms only as a ring-forming atom, and has non-aromaticity in the entire molecular structure. A detailed example of the monovalent non-aromatic condensed polycyclic group is a fluorenyl group. A divalent non-aromatic condensed polycyclic group used herein refers to a divalent group having the same structure as the monovalent non-aromatic condensed polycyclic group.

A monovalent non-aromatic condensed heteropolycyclic group (e.g., a group having 1 to 60 carbon atoms) used herein refers to a monovalent group that has two or more rings condensed to each other, has heteroatoms as a ring-forming atom selected from N, O, Si, P, and S, in addition to C, and has non-aromaticity in the entire molecular structure. A detailed example of the monovalent non-aromatic condensed heteropolycyclic group is a carbazolyl group. A divalent non-aromatic condensed heteropolycyclic group used herein refers to a divalent group having the same structure as the monovalent non-aromatic condensed heteropolycyclic group.

At least one of substituents of the substituted $C_3$-$C_{10}$ cycloalkylene group, the substituted $C_1$-$C_{10}$ heterocycloalkylene group, the substituted $C_3$-$C_{10}$ cycloalkenylene group, the substituted $C_1$-$C_{10}$ heterocycloalkenylene group, the substituted $C_6$-$C_{60}$ arylene group, the substituted $C_1$-$C_{60}$ heteroarylene group, the substituted divalent non-aromatic condensed polycyclic group, the substituted divalent non-aromatic condensed heteropolycyclic group, the substituted $C_1$-$C_{60}$ alkyl group, the substituted $C_2$-$C_{60}$ alkenyl group, the substituted $C_2$-$C_{60}$ alkynyl group, the substituted $C_1$-$C_{60}$ alkoxy group, the substituted $C_3$-$C_{10}$ cycloalkyl group, the substituted $C_1$-$C_{10}$ heterocycloalkyl group, the substituted $C_3$-$C_{10}$ cycloalkenyl group, the substituted $C_1$-$C_{10}$ heterocycloalkenyl group, the substituted $C_6$-$C_{60}$ aryl group, the substituted $C_6$-$C_{60}$ aryloxy group, the substituted $C_6$-$C_{60}$ arylthio group, the substituted $C_1$-$C_{60}$ heteroaryl group, the substituted monovalent non-aromatic condensed polycyclic group, and the substituted monovalent non-aromatic condensed heteropolycyclic group may be selected from a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group;

a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group(aryloxy), a $C_6$-$C_{60}$ arylthio group(arylthio), a $C_1$-$C_{60}$ heteroaryl group, a monovalent non-aromatic condensed polycyclic group, a monovalent non-aromatic condensed heteropolycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, and a phenyl group substituted with a $C_1$-$C_{20}$ alkyl group;

a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, a biphenyl group, a terphenyl group, and a phenyl group substituted with a C1-C20 alkyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_6$-$C_{60}$ aryloxy group, a $C_6$-$C_{60}$ arylthio group, a $C_1$-$C_{60}$ heteroaryl group, a monovalent non-aromatic condensed polycyclic group, a monovalent non-aromatic condensed heteropolycyclic group, —$N(Q_{21})(Q_{22})$, —$Si(Q_{23})(Q_{24})(Q_{25})$, and —$B(Q_{26})(Q_{27})$; and —$N(Q_{31})(Q_{32})$, —$Si(Q_{33})(Q_{34})(Q_{35})$, and —$B(Q_{36})(Q_{37})$, and $Q_1$ to $Q_7$, $Q_{11}$ to $Q_{17}$, $Q_{21}$ to $Q_{27}$, and $Q_{31}$ to $Q_{37}$ may be each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_1$-$C_{10}$ heterocycloalkyl group, a $C_3$-$C_{10}$ cycloalkenyl group, a $C_1$-$C_{10}$ heterocycloalkenyl group, a $C_6$-$C_{60}$ aryl group, a $C_1$-$C_{60}$ heteroaryl group, a monovalent non-aromatic condensed polycyclic group, a monovalent non-aromatic condensed heteropolycyclic group, a biphenyl group, a terphenyl group, and a phenyl group substituted with a C1-C20 alkyl group.

The term "Ph" used herein refers to a phenyl group, the term "Me" used herein refers to a methyl group, the term "Et" used herein refers to an ethyl group, and the term "ter-Bu" or But used herein refers to a tert-butyl group.

The term "a biphenyl group" used herein refers to a monovalent substituent of which 2 benzene rings are connected to each other by a single bond, and the term "a terphenyl group" used herein refers to a monovalent substituent of which 3 benzene rings are connected to each other by a single bond.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

Hereinafter, the organic light-emitting device according to embodiments is described in detail with reference to Synthesis Example and Examples. The expression "B was used instead of A" used in describing Synthesis Examples means that a molar equivalent of A was identical to a molar equivalent of B.

EXAMPLE

Synthesis Example 1: Synthesis of Compound 2A

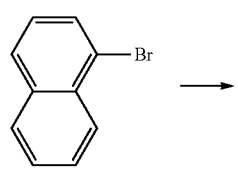

-continued

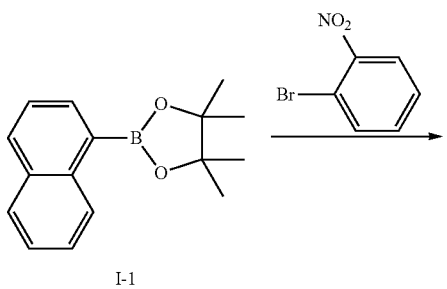
I-1

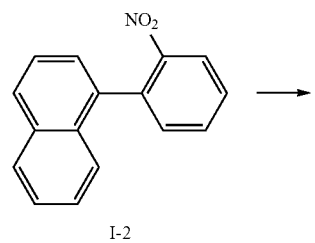
I-2

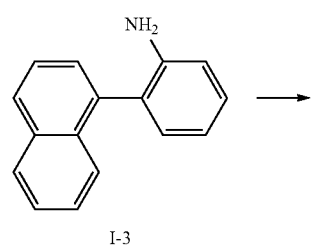
I-3

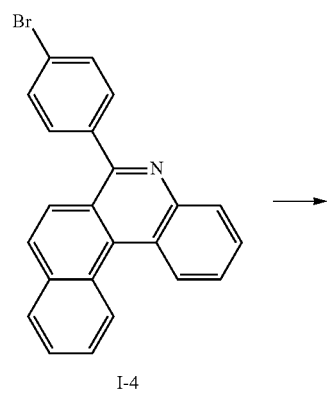
I-4

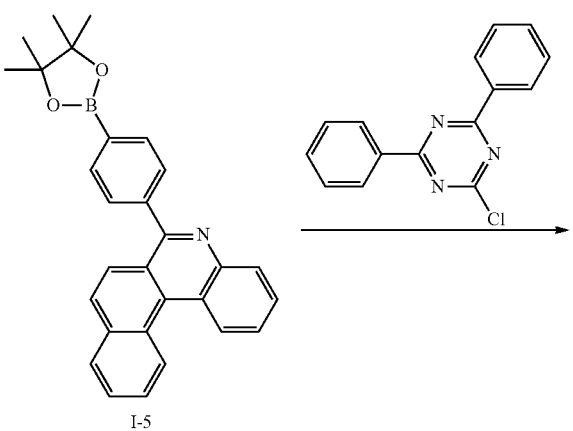
I-5

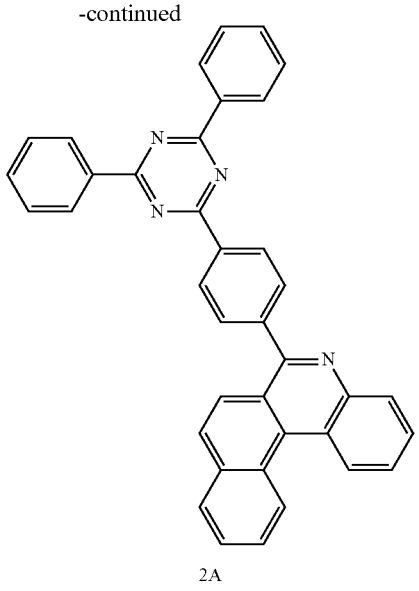

2A

Synthesis of Intermediate I-1

2.07 g (10 mmol) of 1-bromonaphthalene was dissolved in 30 mL of THF, and then, 4 mL (2.5 M in Hexane) of normal butyl lithium was added thereto at a temperature of −78° C. After 1 hour at the same temperature, 2.0 mL (10 mmol) of 2-isopropoxy-4,4,5,5-tetramethyl-1,3,2-dioxaborolane was added to the mixture. The resultant mixture was stirred for 5 hours at ambient temperature, and then, was washed out 3 three times with 30 mL of diethylether after adding water thereto. A diethyether layer obtained therefrom was dried by using MgSO$_4$, and then, dried again under reduced pressure, so as to obtain a product. The product was separation-purified by column chromatography to obtain 1.96 g (yield: 77%) of Intermediate I-1. The obtained compound was then identified by LC-MS.

$C_{16}H_{19}BO_2$: M+1 255.2

Synthesis of Intermediate I-2

2.54 g (10.0 mmol) of Intermediate I-1, 2.02 g (10.0 mmol) of 1-bromo-2-nitrobenzene, 0.58 g (0.50 mmol) of Pd(PPh$_3$)$_4$, 0.16 g (0.5 mmol) of tetrabutylammonium bromide (TBAB), and 3.18 g (30.0 mmol) of Na$_2$CO$_3$ were dissolved in 60 mL of a mixed solution of toluene/ethanol/H$_2$O (at a ratio of 3/3/1), and then, the mixture was stirred for 16 hours at a temperature of 80° C. The reaction solution was cooled to ambient temperature, and then, extracted three times each using 60 mL of water and 60 mL of diethylether. An organic layer obtained therefrom was dried by using magnesium sulfate, and the residues obtained by evaporating the solvent were separation-purified by silica gel column chromatography, so as to obtain 2.04 g (yield: 82%) of Intermediate I-2. The obtained compound was identified by LC-MS.

$C_{16}H_{11}NO_2$: M+1 250.1

Synthesis of Intermediate I-3

2.49 g (10.0 mmol) of Intermediate I-2, 3.56 g (30 mmol) of tin, and 5 mL (50 mmol, conc. 36.5%) of hydrochloric acid were dissolved in 60 mL of ethanol, and then, the mixed solution was stirred for 8 hours at a temperature of 100° C. The reaction solution was cooled to ambient temperature, and then, filtered under reduced pressure. In the filtrate obtained therefrom, 3 g of sodium hydroxide was dissolved in 10 mL of water, and the resultant mixture was extracted three times each using 60 mL of water and 60 mL of dichloromethane. An organic layer obtained therefrom was dried by using magnesium sulfate, and the residues obtained by evaporating the solvent were separation-purified by silica gel column chromatography, so as to obtain 1.97 g (yield: 90%) of Intermediate I-3. The obtained compound was identified by LC-MS.

$C_{16}H_{13}N$: M+1 220.1

Synthesis of Intermediate I-4

2.19 g (10 mmol) of Intermediate I-3 and 3.66 g (20 mmol) of 4-bromobenzaldehyde were dissolved in 10 mL of trifluoroacetic acid, and then, the mixed solution was stirred for 3 days in a seal tube at a temperature of 130° C. The reaction solution was cooled to ambient temperature, quenched with NaHCO$_3$, and extracted three times each using 60 mL of water and 60 mL of dichloromethane. An organic layer obtained therefrom was dried by using magnesium sulfate, and the residues obtained by evaporating the solvent were separation—purified by silica gel column chromatography, so as to obtain 1.92 g (yield: 50%) of Intermediate I-4. The obtained compound was identified by LC-MS.

$C_{23}H_{14}BrN$: M+1 384.0

Synthesis of Intermediate I-5

3.15 g (yield: 73%) of Intermediate I-5 was obtained in the same manner as in synthesizing Intermediate I-1, except that Intermediate I-4 was used instead of 1-bromonaphthalene. The obtained compound was identified by LC-MS.

$C_{29}H_{26}BNO_2$: M+1 432.2

Synthesis of Compound 2A 4.31 g (10 mmol) of Intermediate I-5, 2.68 g (10 mmol) of 2-chloro-4,6-diphenyl-1,3,5-triazine, 0.58 g (0.5 mmol) of tetrakis(triphenylphosphine)palladium (Pd(PPh$_3$)$_4$), and 4.14 g (30 mmol) of K$_2$CO$_3$ were dissolved in 60 mL of a mixed solution of THF/H$_2$O (at a volume ratio of 2/1), and then, the mixture was stirred for 16 hours at a temperature of 80° C. The reaction solution was cooled to ambient temperature, and then, extracted three times each using 40 mL of water and 50 mL of ethylether. An organic layer obtained therefrom was dried by using magnesium sulfate, and the residues obtained by evaporating the solvent were separation-purified by silica gel column chromatography, so as to obtain 3.38 g (yield: 63%) of Compound 2 Å. The obtained compound was identified by MS/FAB and $^1$H NMR.

$C_{38}H_{24}N_4$ cal. 536.20. found 536.19.

Synthesis Example 2: Synthesis of Compound 14A

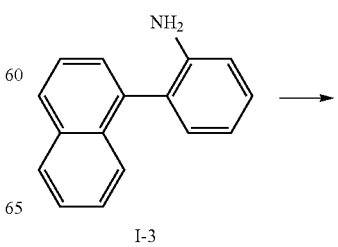

I-3

-continued

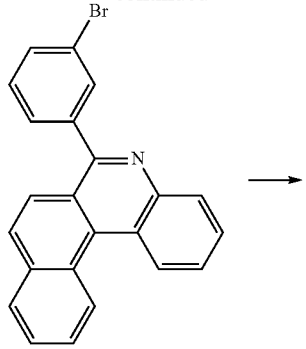
I-6

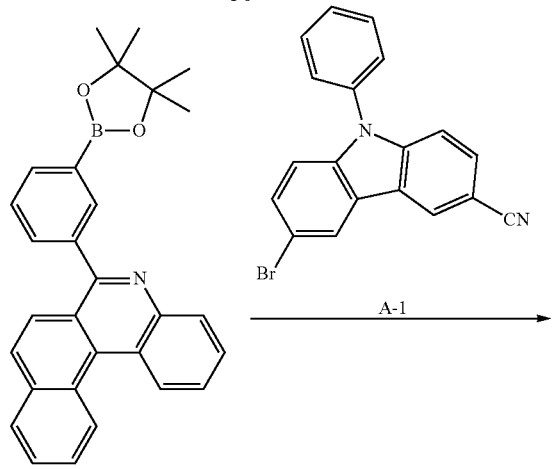
I-7

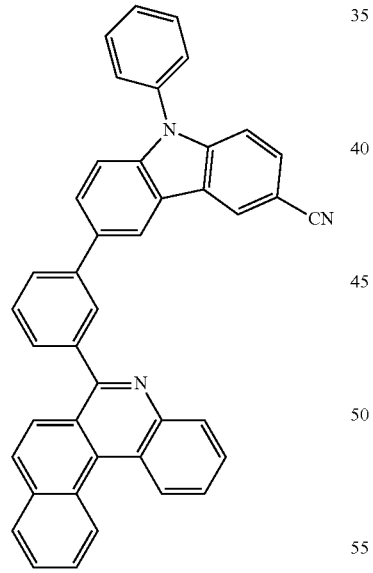
14A

Synthesis of Intermediate I-6

1.84 g (yield: 48%) of Intermediate I-6 was obtained in the same manner as in synthesizing Intermediate I-4 of Synthesis Example 1, except that 3-bromobenzaldehyde was used instead of 4-bromobenzaldehyde. The obtained compound was identified by LC-MS.

$C_{23}H_{14}BrN$: M+1 384.0

Synthesis of Intermediate I-7

3.11 g (yield: 72%) of Intermediate I-7 was obtained in the same manner as in synthesizing Intermediate I-5 of Synthesis Example 1, except that Intermediate I-6 was used instead of Intermediate I-4. The obtained compound was identified by LC-MS.

$C_{29}H_{26}BNO_2$: M+1 432.2

Synthesis of Compound 14A 3.83 g (yield: 67%) of Compound 14A was obtained in the same manner as in synthesizing Compound 2A of Synthesis Example 1, except that Intermediate I-7 and Intermediate A1 were used instead of Intermediate I-5 and 2-chloro-4,6-diphenyl-1,3,5-triazine, respectively. The obtained compound was identified by MS/FAB and $^1$H NMR.

$C_{42}H_{25}N_3$ cal. 571.20. found 571.21.

Synthesis Example 3: Synthesis of Compound 21A

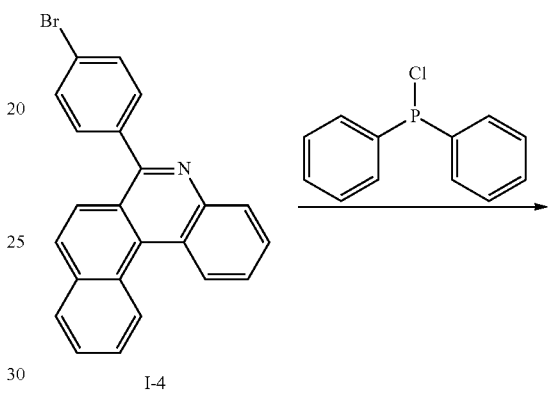
I-4

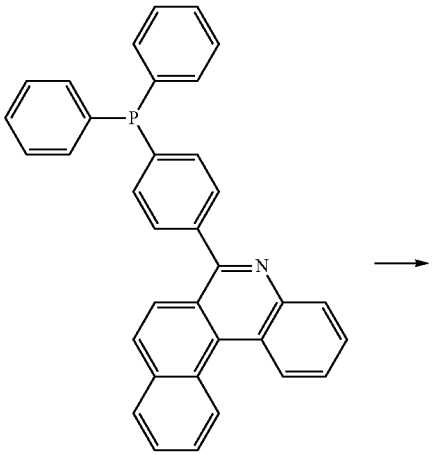
I-8

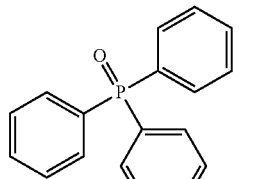

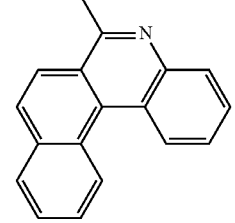
21A

181

Synthesis of Intermediate I-8

3.84 g (10 mmol) of Intermediate I-4 was dissolved in 30 mL of THF, and then, 4 mL (2.5 M in Hexane) of normal butyl lithium was added thereto at a temperature of −78° C. After 1 hour, 2.20 g (10 mmol) of chlorodiphenylphosphine was slowly added to the mixed solution. The resultant mixed solution was stirred for 3 hours until a temperature thereof increased to ambient temperature, and then, was washed out 3 three times with 30 mL of ethylacetate. An ethylacetate layer obtained therefrom was dried by using MgSO$_4$, and then, dried again under reduced pressure, so as to obtain Intermediate I-8.

Synthesis of Compound 21A

Intermediate I-8 was dissolved in 40 mL of dichloromethane, and then, 4 mL of hydrogen peroxide was added thereto. The mixed solution was stirred for 20 hours at ambient temperature, and the resultant mixed solution was washed out three times with 20 mL of dichloromethane after adding 20 mL of water thereto. An organic layer obtained therefrom was dried by using magnesium sulfate, and the residues obtained by evaporating the solvent were separation-purified by silica gel column chromatography, so as to obtain 3.74 g (yield: 74%) of Compound 21A. The obtained compound was identified by MS/FAB and $^1$H NMR.

C$_{35}$H$_{24}$NOP cal. 505.16. found 505.17.

Synthesis Example 4: Synthesis of Compound 55A

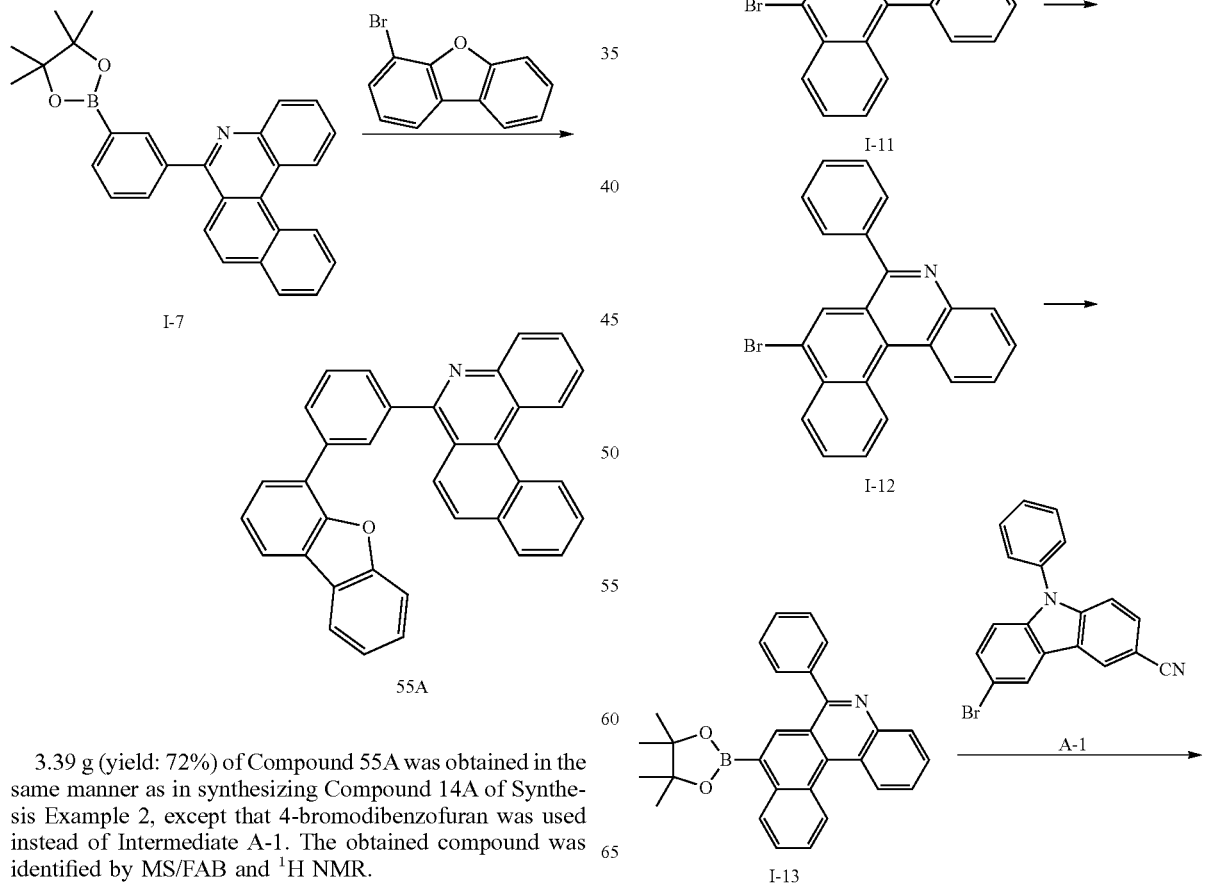

3.39 g (yield: 72%) of Compound 55A was obtained in the same manner as in synthesizing Compound 14A of Synthesis Example 2, except that 4-bromodibenzofuran was used instead of Intermediate A-1. The obtained compound was identified by MS/FAB and $^1$H NMR.

C$_{35}$H$_{21}$NO cal. 471.16. found 471.17.

182

Synthesis Example 5: Synthesis of Compound 1B

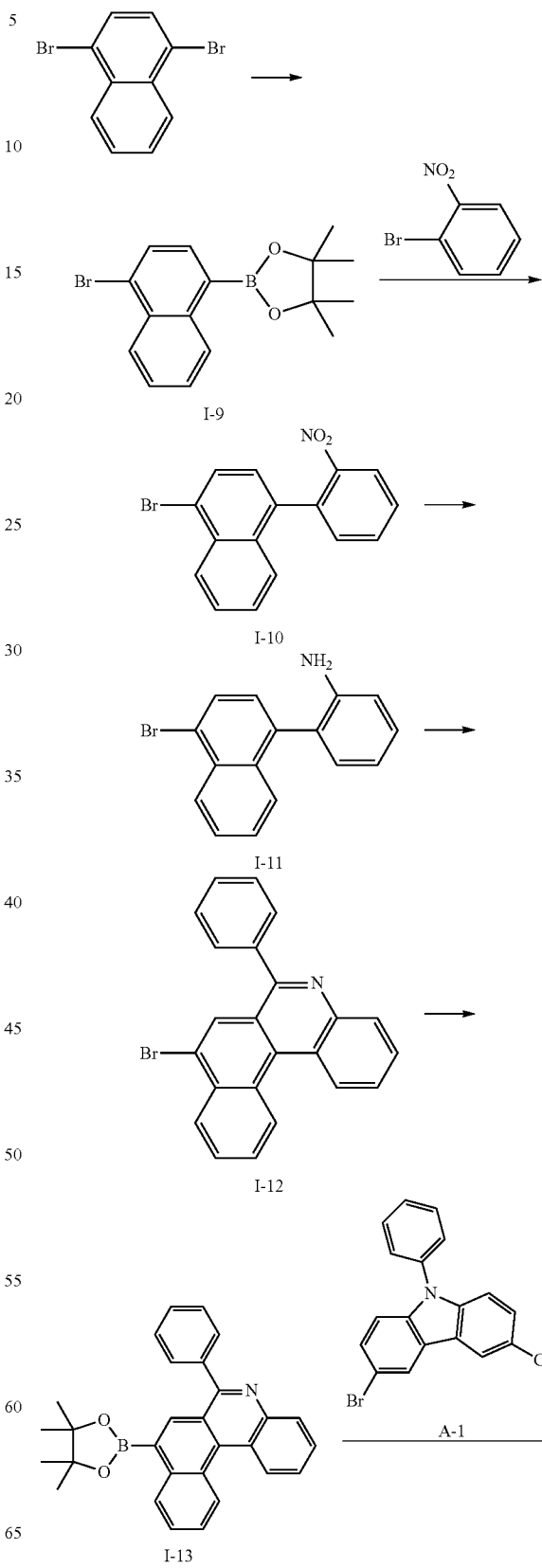

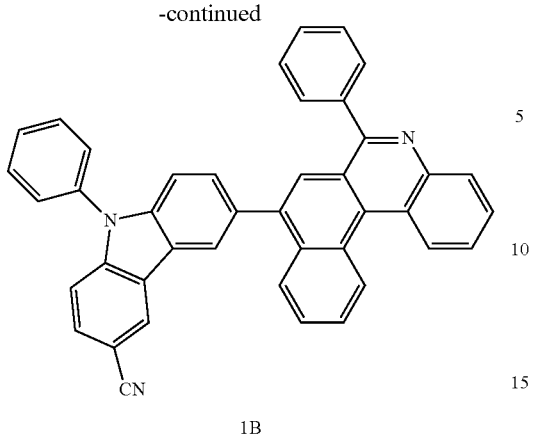

1B

Synthesis of Intermediate I-9

2.46 g (yield: 74%) of Intermediate I-9 was obtained in the same manner as in synthesizing Intermediate I-1 of Synthesis Example 1, except that 1,4-dibromonaphthalene was used instead of 1-bromonaphthalene. The obtained compound was identified by LC-MS.

$C_{16}H_{18}BBrO_2$: M+1 333.1

Synthesis of Intermediate I-10

2.63 g (yield: 80%) of Intermediate I-10 was obtained in the same manner as in synthesizing Intermediate I-2 of Synthesis Example 1, except that Intermediate I-9 was used instead of Intermediate I-1. The obtained compound was identified by LC-MS.

$C_{16}H_{10}BrNO_2$: M+1 328.0

Synthesis of Intermediate I-11

2.71 g (yield: 91%) of Intermediate I-11 was obtained in the same manner as in synthesizing Intermediate I-3 of Synthesis Example 1, except that Intermediate I-10 was used instead of Intermediate I-2. The obtained compound was identified by LC-MS.

$C_{16}H_{12}BrN$: M+1 298.0

Synthesis of Intermediate I-12

2.04 g (yield: 53%) of Intermediate I-12 was obtained in the same manner as in synthesizing Intermediate I-4 of Synthesis Example 1, except that benzaldehyde and Intermediate I-11 were used instead of 4-bromobenzaldehyde and Intermediate I-3. The obtained compound was identified by LC-MS.

$C_{23}H_{14}BrN$: M+1 384.0

Synthesis of Intermediate I-13

3.23 g (yield: 75%) of Intermediate I-13 was obtained in the same manner as in synthesizing Intermediate I-5 of Synthesis Example 1, except that Intermediate I-12 was used instead of Intermediate I-4. The obtained compound was identified by LC-MS.

$C_{29}H_{26}BNO_2$: M+1 432.2

Synthesis of Compound 1B 4.17 g (yield: 73%) of Compound 1B was obtained in the same manner as in synthesizing Compound 2A of Synthesis Example 1, except that Intermediate I-13 and Intermediate A-1 were used instead of Intermediate I-5 and 2-chloro-4,6-diphenyl-1,3,5-triazine, respectively. The obtained compound was identified by MS/FAB and $^1$H NMR.

$C_{42}H_{25}N_3$ cal. 571.20. found 571.22.

Synthesis Example 6: Synthesis of Compound 21B

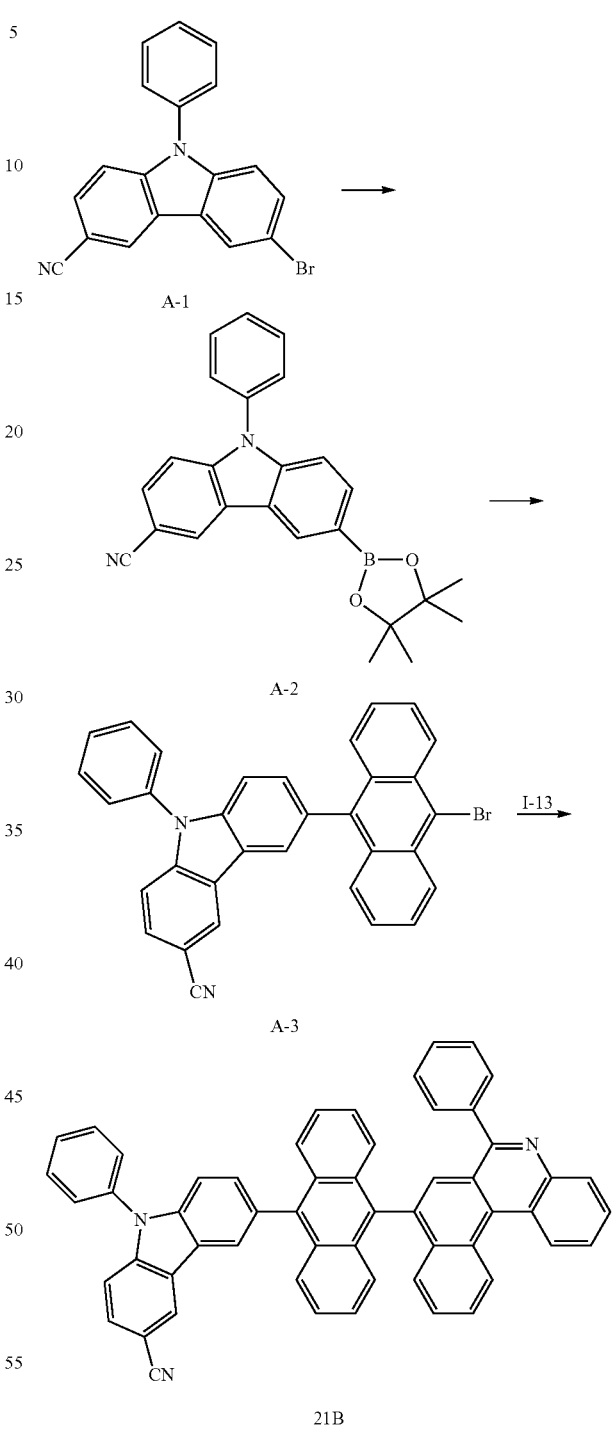

Synthesis of Intermediate A-2

2.76 g (yield: 70%) of Intermediate A-2 was obtained in the same manner as in synthesizing Intermediate I-1 of Synthesis Example 1, except that Intermediate A-1 was used instead of 1-bromonaphthalene. The obtained compound was identified by LC-MS.

$C_{25}H_{23}BN_2O_2$: M+1 395.2

Synthesis of Intermediate A-3

3.61 g (yield: 69%) of Intermediate A-3 was obtained in the same manner as in synthesizing Compound 2A of Synthesis Example 1, except that Intermediate A-2 and 9,10-dibromoanthracene were used instead of Intermediate I-5 and 2-chloro-4,6-diphenyl-1,3,5-triazine, respectively. The obtained compound was identified by LC-MS.

$C_{33}H_{19}BrN_2$: M+1 523.1

Synthesis of Compound 21B 5.61 g (yield: 75%) of Compound 21B was obtained in the same manner as in synthesizing Compound 2A of Synthesis Example 1, except that Intermediate I-13 and Intermediate A-3 were used instead of Intermediate I-5 and 2-chloro-4,6-diphenyl-1,3,5-triazine, respectively. The obtained compound was identified by MS/FAB and $^1$H NMR.

$C_{56}H_{33}N_3$ cal. 747.27. found 747.28.

Synthesis Example 7: Synthesis of Compound 25B

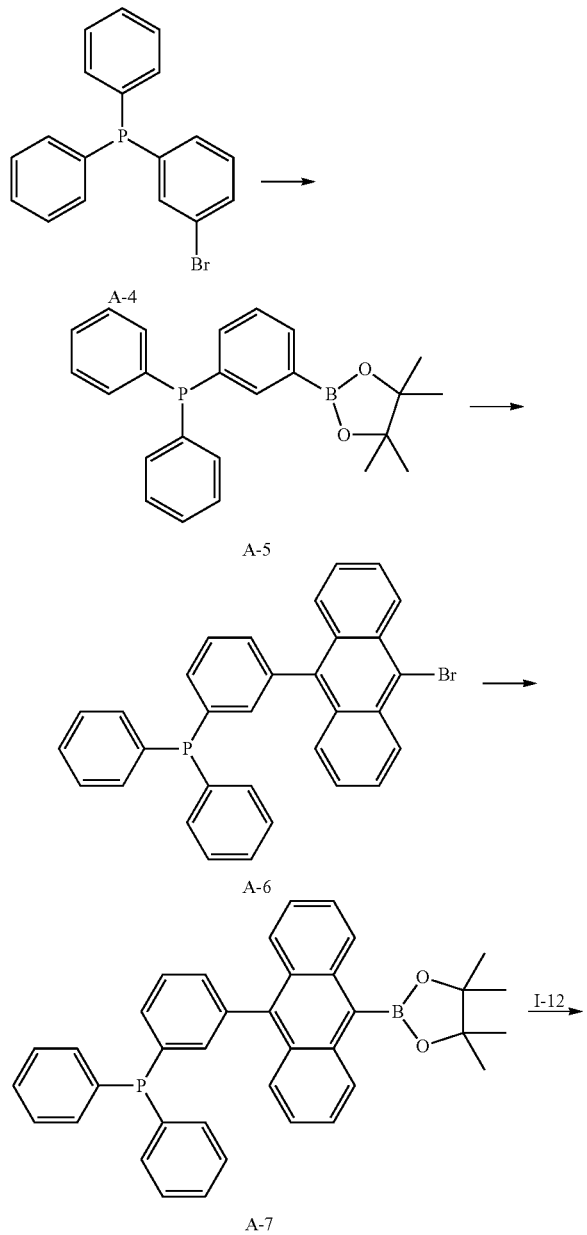

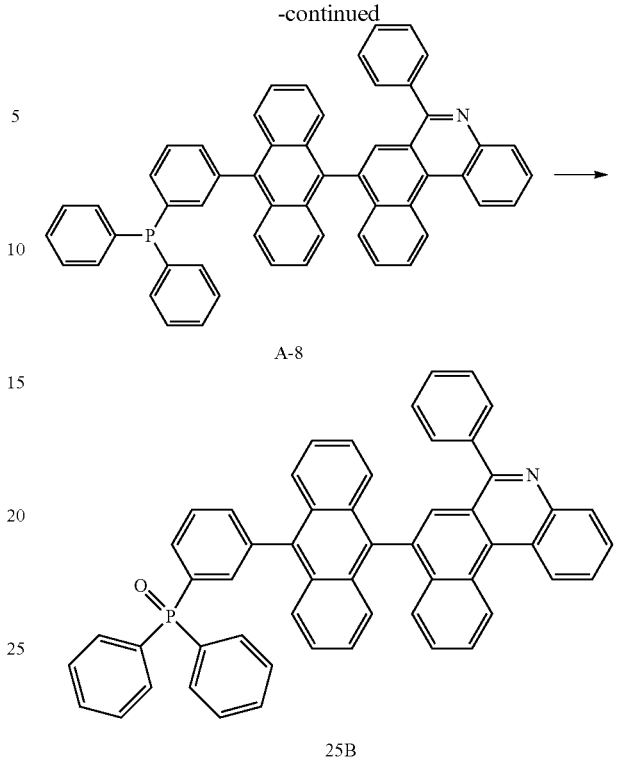

Synthesis of Intermediate A-4

2.36 g (10 mmol) of 1,3-dibromobenzene was dissolved in 30 mL of THF, and then, 4 mL (2.5 M in Hexane) of normal butyl lithium was added thereto at a temperature of −78° C. After 1 hour, 2.20 g (10 mmol) of chlorodiphenylphosphin was slowly added to the mixed solution. The resultant mixed solution was stirred for 3 hours until a temperature thereof increased to ambient temperature, and then, was washed out 3 three times with 30 mL of ethylacetate. An ethylacetate layer obtained therefrom was dried by using $MgSO_4$, and then, was separation-purified by silica gel column chromatography, so as to obtain 2.73 g (yield: 80%) of Intermediate A-4. The obtained compound was identified by LC-MS.

$C_{18}H_{14}BrP$: M+1 341.0

Synthesis of Intermediate A-5

2.06 g (yield: 53%) of Intermediate A-5 was obtained in the same manner as in synthesizing Intermediate I-1 of Synthesis Example 1, except that Intermediate A-4 was used instead of 1-bromonaphthalene. The obtained compound was identified by LC-MS.

$C_{24}H_{26}BO_2P$: M+1 389.2

Synthesis of Intermediate A-6

2.74 g (yield: 53%) of Intermediate A-6 was obtained in the same manner as in synthesizing Intermediate A-3 of Synthesis Example 6, except that Intermediate A-5 was used instead of Intermediate A-2. The obtained compound was identified by LC-MS.

$C_{32}H_{22}BrP$: M+1 517.1

Synthesis of Intermediate A-7

4.06 g (yield: 72%) of Intermediate A-7 was obtained in the same manner as in synthesizing Intermediate I-1 of Synthesis Example 1, except that Intermediate A-6 was used instead of 1-bromonaphthalene. The obtained compound was identified by LC-MS.

$C_{38}H_{34}BO_2P$: M+1 565.2

Synthesis of Intermediate A-8

5.49 g (yield: 74%) of Intermediate A-8 was obtained in the same manner as in synthesizing Compound 2A of Synthesis Example 1, except that Intermediate A-7 and Intermediate I-12 were used instead of Intermediate I-5 and 2-chloro-4,6-diphenyl-1,3,5-triazine, respectively. The obtained compound was identified by LC-MS.

$C_{55}H_{36}NP$: M+1 742.3

Synthesis of Compound 25B 3.71 g (5.0 mmol) of Intermediate A-8 was dissolved in 25 mL of dichloromethane, and then, 2 mL of hydrogen peroxide was added thereto. The mixed solution was stirred for 20 hours at ambient temperature, and the resultant mixed solution was extracted three times each using 20 mL of dichloromethane after adding 20 mL of water thereto. An organic layer was dried by using magnesium sulfate, and the residues obtained by evaporating the solvent were separation-purified by silica gel column chromatography, so as to obtain 2.88 g (yield: 76%) of Compound 25B. The obtained compound was identified by MS/FAB and $^1$H NMR.

$C_{55}H_{36}NOP$ cal. 757.25. found 757.24.

Synthesis Example 8: Synthesis of Compound 26B

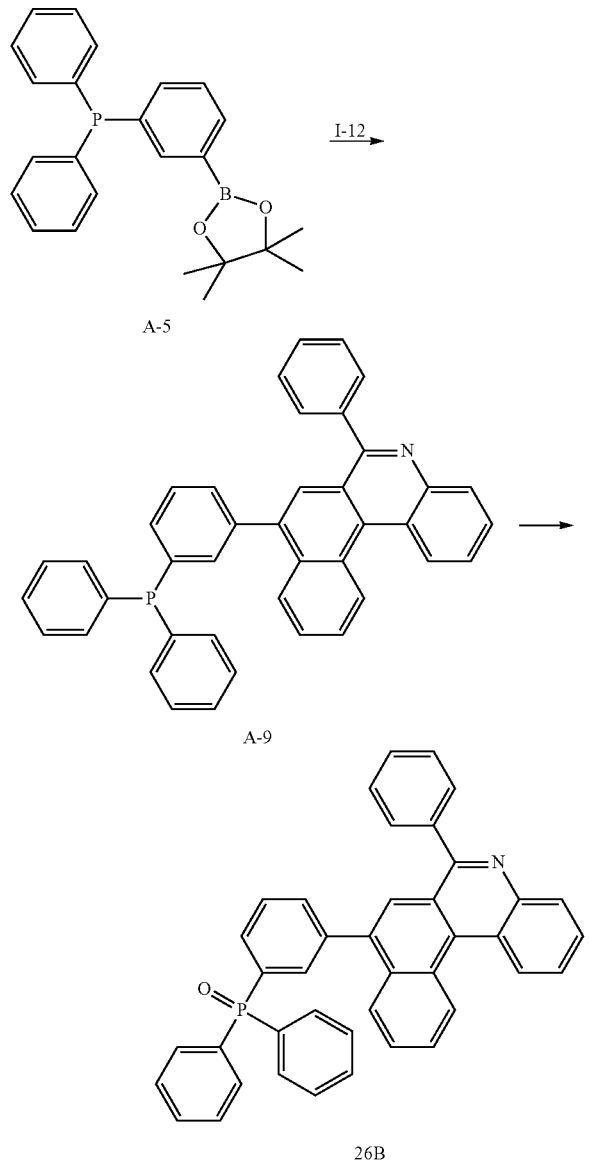

Synthesis of Intermediate A-9

3.73 g (yield: 66%) of Intermediate A-9 was obtained in the same manner as in synthesizing Intermediate A-8 of Synthesis Example 7, except that Intermediate A-5 was used instead of Intermediate A-7. The obtained compound was identified by LC-MS.

$C_{41}H_{28}NP$: M+1 566.2

Synthesis of Compound 26B 2.27 g (yield: 78%) of Compound 26B was obtained in the same manner as in synthesizing Compound 25B of Synthesis Example 7, except that Intermediate A-9 was used instead of Intermediate A-8. The obtained compound was identified by MS/FAB and $^1$H NMR.

$C_{41}H_{28}NOP$ cal. 581.19. found 581.20.

Synthesis Example 9: Synthesis of Compound 31B

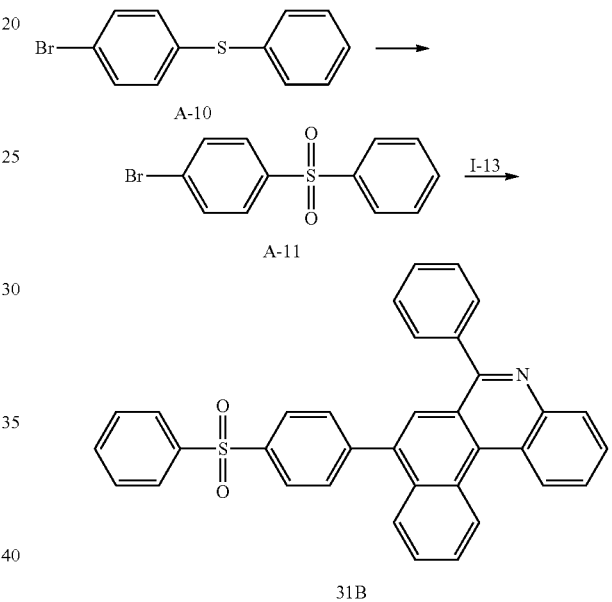

Synthesis of Intermediate A-10

1.10 g (10 mmol) of benzenethiol, 3.39 g (12 mmol) of 1-bromo-4-iodobenzene, 0.19 g (1.0 mmol) of CuI, and 2.76 g (20 mmol) of $K_2CO_3$ were dissolved in 50 mL of DMF, and then, the mixed solution was stirred for 16 hours at a temperature of 100° C. The resultant mixed solution was cooled to ambient temperature, and was extracted three times each using 40 mL of water and 40 mL of diethylether. An organic layer obtained therefrom was dried by using magnesium sulfate, and the residues obtained by evaporating the solvent were separation-purified by silica gel column chromatography, so as to obtain 1.86 g (yield: 70%) of Intermediate A-10. The obtained compound was identified by LC-MS.

$C_{12}H_9BrS$: M+1 265.0

Synthesis of Intermediate A-11

6.90 g (40 mmol) of m-CPBA was dissolved in 30 mL of dichloromethane at a temperature of 0° C., and then, the mixed solution was slowly added to a solution in which 2.65 g (10 mmol) of Intermediate A-10 was dissolved in 30 mL of dichloromethane. When a temperature of the resultant mixed solution increased to ambient temperature, the resultant mixed solution was stirred for 24 hours, and then, was stirred again for 30 minutes after adding 60 mL of a NaHCO₃ solution thereto. Afterwards, the reaction solution was extracted three times each using 30 mL of water and 30 mL of dichloromethane. An organic layer obtained therefrom was dried by using magnesium sulfate, and the residues obtained by evaporating the solvent were separation-purified by silica gel column chromatography, so as to obtain 2.38 g (yield: 80%) of Intermediate A-11. The obtained compound was identified by LC-MS. $C_{12}H_9BrO_2S$: M+1 296.9

Synthesis of Compound 31B 3.96 g (yield: 76%) of Compound 31B was obtained in the same manner as in synthesizing Compound 2A of Synthesis Example 1, except that Intermediate I-13 and Intermediate A-11 were used instead of Intermediate I-5 and 2-chloro-4,6-diphenyl-1,3,5-triazine, respectively. The obtained compound was identified by MS/FAB and ¹H NMR.

$C_{35}H_{23}NO_2S$ cal. 521.14. found 521.15.

Synthesis Example 10: Synthesis of Compound 32B

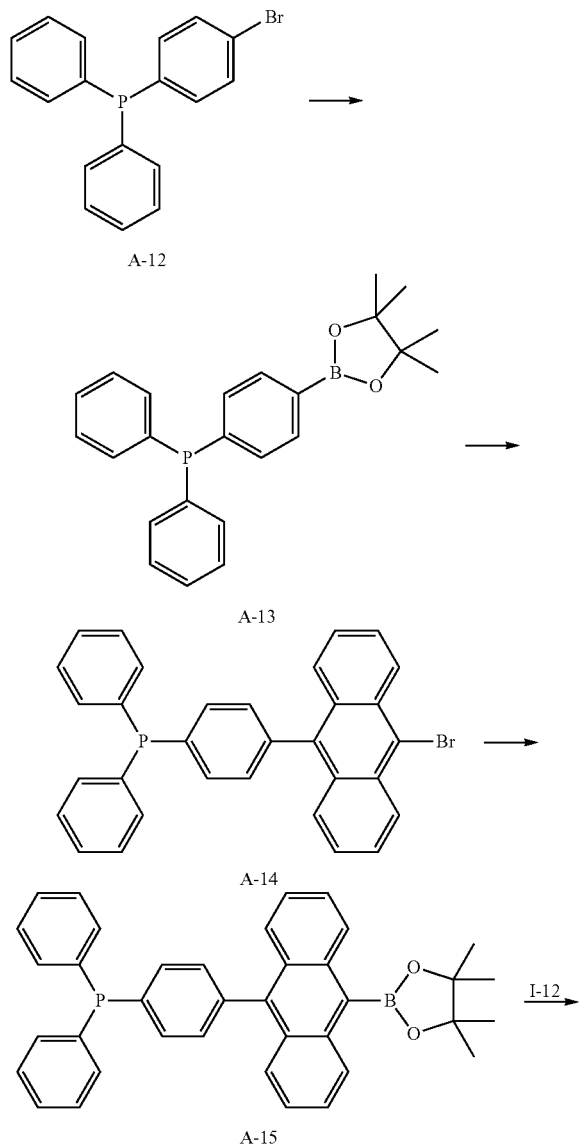

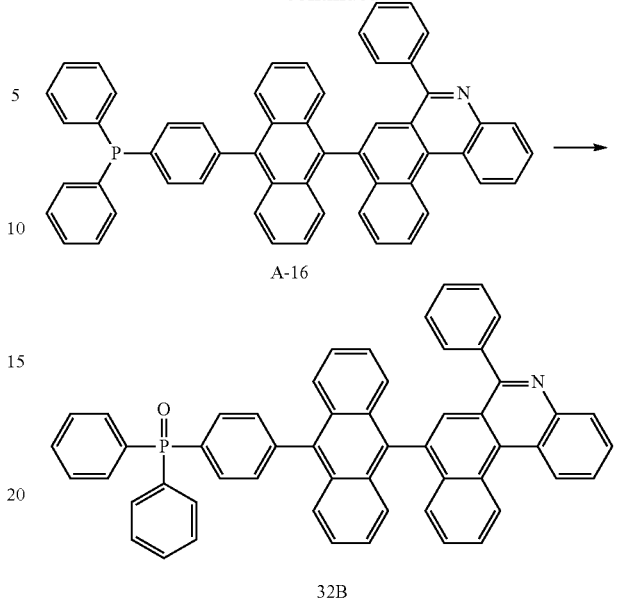

Synthesis of Intermediate A-12

2.76 g (yield: 81%) of Intermediate A-12 was obtained in the same manner as in synthesizing Intermediate A-4 of Synthesis Example 7, except that 1,4-dibromobenzene was used instead of 1,3-dibromobenzene. The obtained compound was identified by LC-MS.

$C_{18}H_{14}BrP$: M+1 341.0

Synthesis of Intermediate A-13

2.02 g (yield: 52%) of Intermediate A-13 was obtained in the same manner as in synthesizing Intermediate I-1 of Synthesis Example 1, except that Intermediate A-12 was used instead of 1-bromonaphthalene. The obtained compound was identified by LC-MS.

$C_{24}H_{26}BO_2P$: M+1 389.2

Synthesis of Intermediate A-14

2.74 g (yield: 53%) of Intermediate A-14 was obtained in the same manner as in synthesizing Intermediate A-3 of Synthesis Example 6, except that Intermediate A-13 was used instead of Intermediate A-2. The obtained compound was identified by LC-MS.

$C_{32}H_{22}BrP$: M+1 517.1

Synthesis of Intermediate A-15

4.18 g (yield: 74%) of Intermediate A-15 was obtained in the same manner as in synthesizing Intermediate I-1 of Synthesis Example 1, except that Intermediate A-14 was used instead of 1-bromonaphthalene. The obtained compound was identified by LC-MS.

$C_{38}H_{34}BO_2P$: M+1 565.2

Synthesis of Intermediate A-16

5.56 g (yield: 75%) of Intermediate A-16 was obtained in the same manner as in synthesizing Compound 2A of Synthesis Example 1, except that Intermediate A-15 and Intermediate I-12 were used instead of Intermediate I-5 and 2-chloro-4,6-diphenyl-1,3,5-triazine, respectively. The obtained compound was identified by LC-MS.

$C_{55}H_{36}NP$: M+1 742.3

Synthesis of Compound 32B 2.99 g (yield: 79%) of Compound 32B was obtained in the same manner as in synthesizing Compound 25B of Synthesis Example 7, except that Intermediate A-16 was used instead of Intermediate A-8. The obtained compound was identified by MS/FAB and ¹H NMR.

$C_{55}H_{36}NOP$ cal. 757.25. found 757.25.

Synthesis Example 11: Synthesis of Compound 33B

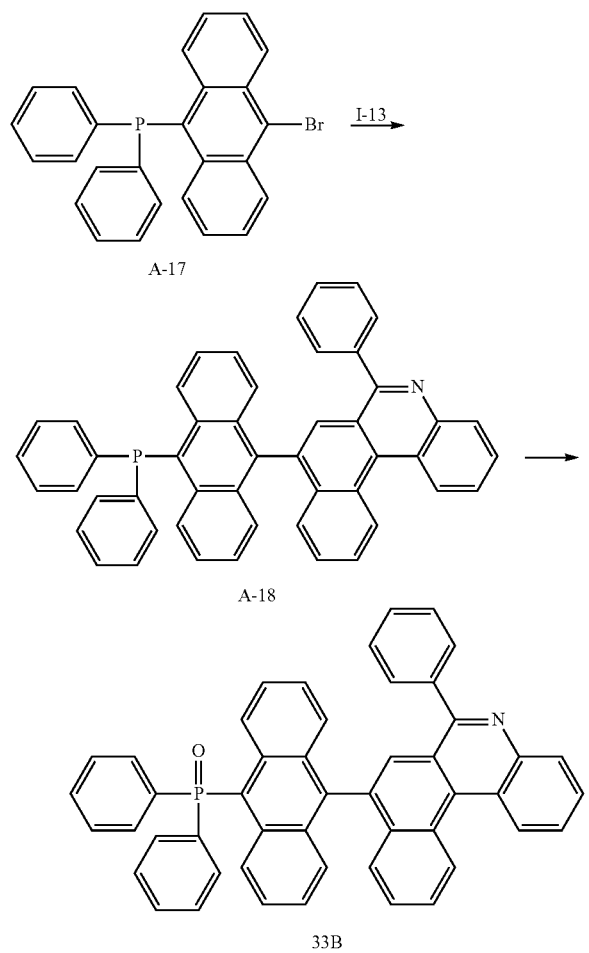

Synthesis of Intermediate A-17

2.96 g (yield: 67%) of Intermediate A-17 was obtained in the same manner as in synthesizing Intermediate A-4 of Synthesis Example 7, except that 9,10-dibromoanthracene was used instead of 1,3-dibromobenzene. The obtained compound was identified by LC-MS.

$C_{26}H_{18}BrP$: M+1 441.0

Synthesis of Intermediate A-18

5.06 g (yield: 76%) of Intermediate A-18 was obtained in the same manner as in synthesizing Compound 2A of Synthesis Example 1, except that Intermediate I-13 and Intermediate A-17 were used instead of Intermediate I-5 and 2-chloro-4,6-diphenyl-1,3,5-triazine, respectively. The obtained compound was identified by LC-MS.

$C_{49}H_{32}NP$: M+1 666.2

Synthesis of Compound 33B 2.66 g (yield: 78%) of Compound 33B was obtained in the same manner as in synthesizing Compound 25B of Synthesis Example 7, except that Intermediate A-18 was used instead of Intermediate A-8. The obtained compound was identified by MS/FAB and $^1$H NMR.

$C_{49}H_{32}NOP$ cal. 681.22. found 681.23.

Synthesis Example 12: Synthesis of Compound 37B

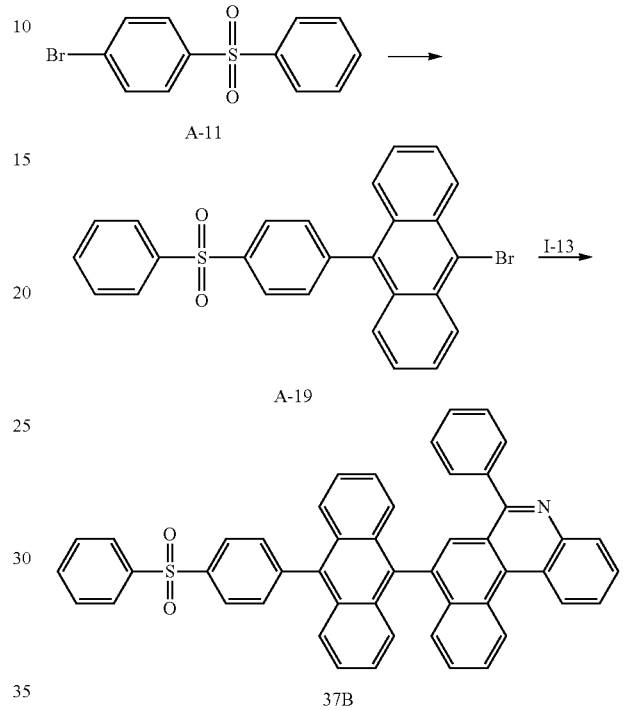

Synthesis of Intermediate A-19

2.93 g (yield: 62%) of Intermediate A-19 was obtained in the same manner as in synthesizing Compound 2A of Synthesis Example 1, except that 10-bromoanthracene-9-boronic acid and Intermediate A-11 were used instead of Intermediate I-5 and 2-chloro-4,6-diphenyl-1,3,5-triazine, respectively. The obtained compound was identified by LC-MS.

$C_{26}H_{17}BrO_2S$: M+1 473.0

Synthesis of Compound 37B 2.76 g (yield: 79%) of Compound 37B was obtained in the same manner as in synthesizing Compound 2A of Synthesis Example 1, except that Intermediate I-13 and Intermediate A-19 were used instead of Intermediate I-5 and 2-chloro-4,6-diphenyl-1,3,5-triazine, respectively. The obtained compound was identified by MS/FAB and $^1$H NMR.

$C_{49}H_{31}NO_2S$ cal. 697.21. found 697.20.

Synthesis Example 13: Synthesis of Compound 44B

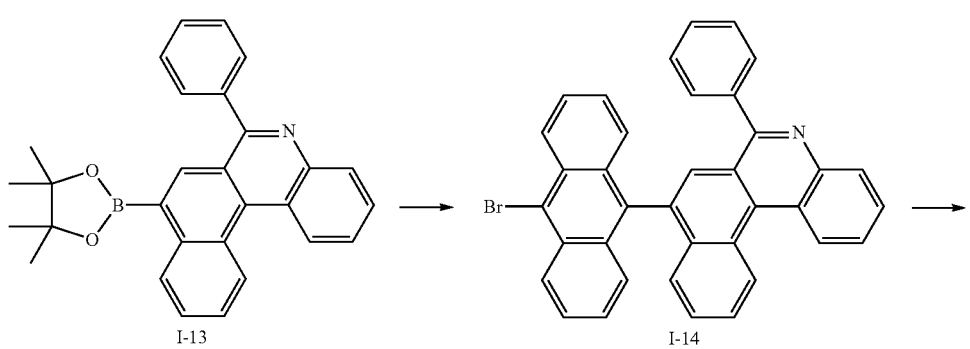

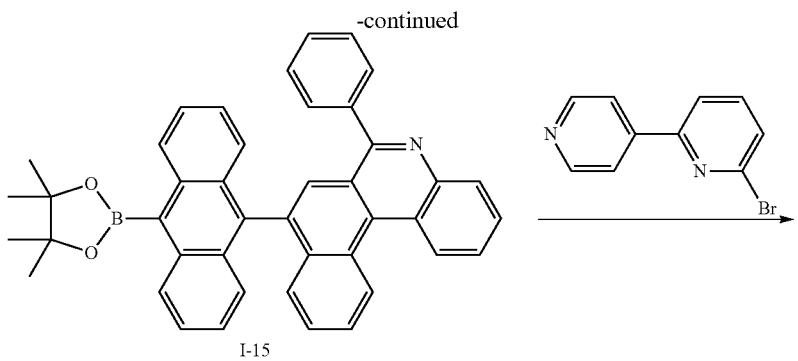

I-15

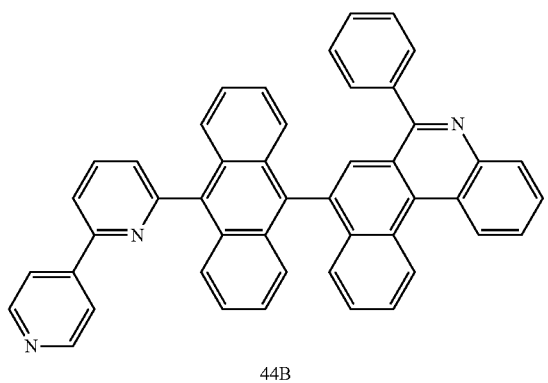

44B

Synthesis of Intermediate I-14

4.26 g (yield: 76%) of Intermediate I-14 was obtained in the same manner as in synthesizing Compound 2A of Synthesis Example 1, except that Intermediate I-13 and 9,10-dibromoanthracene were used instead of Intermediate I-5 and 2-chloro-4,6-diphenyl-1,3,5-triazine, respectively. The obtained compound was identified by LC-MS.

$C_{37}H_{22}BrN$: M+1 560.1

Synthesis of Intermediate I-15

4.74 g (yield: 78%) of Intermediate I-15 was obtained in the same manner as in synthesizing Intermediate I-1 of Synthesis Example 1, except that Intermediate I-14 was used instead of 1-bromonaphthalene. The obtained compound was identified by LC-MS.

$C_{43}H_{34}BNO_2$: M+1 608.3

Synthesis of Compound 44B 4.19 g (yield: 66%) of Compound 44B was obtained in the same manner as in synthesizing Compound 2A of Synthesis Example 1, except that Intermediate I-15 and 6-bromo-2,4'-dipyridine were used instead of Intermediate I-5 and 2-chloro-4,6-diphenyl-1,3,5-triazine, respectively. The obtained compound was identified by MS/FAB and $^1$H NMR.

$C_{47}H_{29}N_3$ cal. 635.24. found 635.25.

Synthesis Example 14: Synthesis of Compound 45B

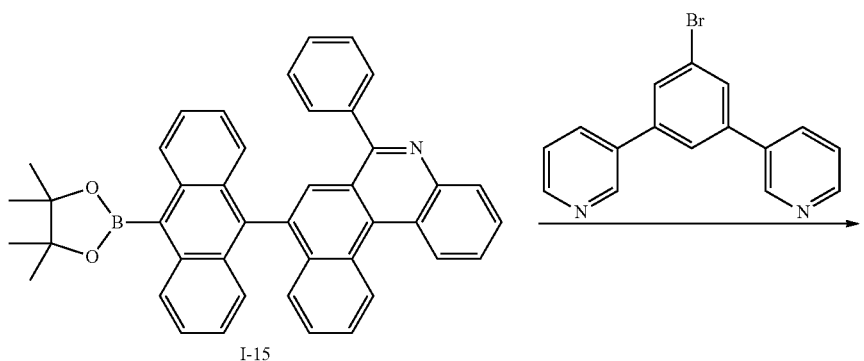

I-15

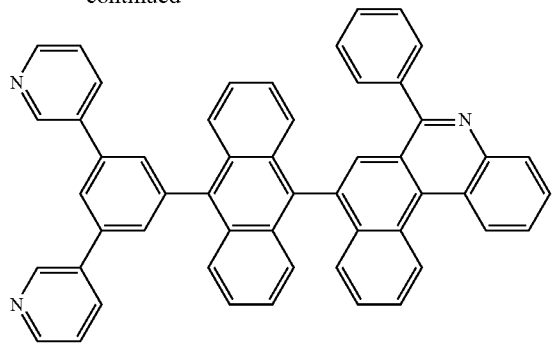

45B 4.48 g (yield: 63%) of Compound 45B was obtained in the same manner as in synthesizing Compound 2A of Synthesis Example 1, except that Intermediate I-15 and 3,3'-(5-bromo-1,3-phenylene)dipyridine were used instead of Intermediate I-5 and 2-chloro-4,6-diphenyl-1,3,5-triazine, respectively. The obtained compound was identified by MS/FAB and $^1$H NMR.

$C_{53}H_{33}N_3$ cal. 711.27. found 711.26.

Synthesis Example 15: Synthesis of Compound 61B

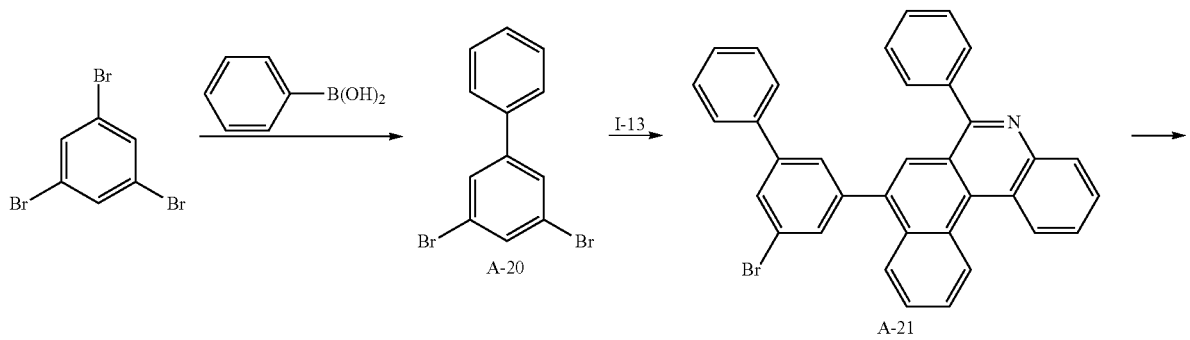

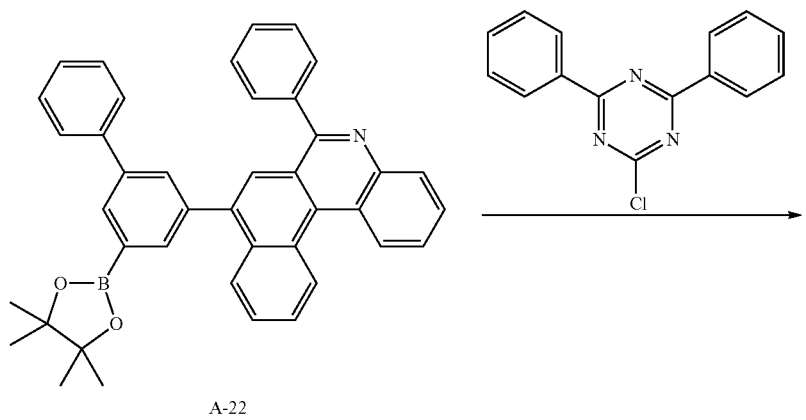

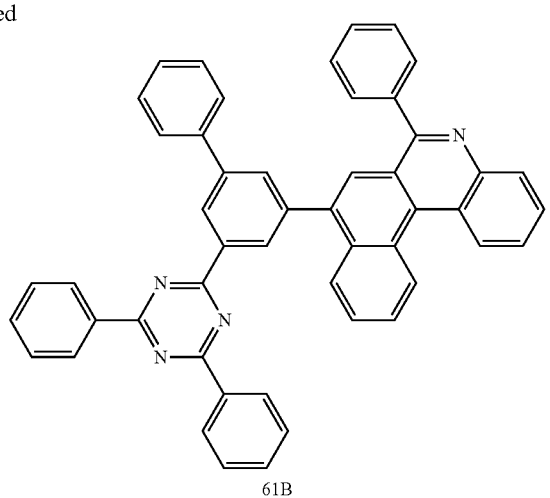
61B

Synthesis of Intermediate A-20

1.97 g (yield: 63%) of Intermediate A-20 was obtained in the same manner as in synthesizing Compound 2A of Synthesis Example 1, except that phenylboronic acid and 1,3,5-tribromobenzene were used instead of Intermediate I-5 and 2-chloro-4,6-diphenyl-1,3,5-triazine, respectively. The obtained compound was identified by LC-MS.

$C_{12}H_8Br_2$: M+1 310.9

Synthesis of Intermediate A-21

3.27 g (yield: 61%) of Intermediate A-21 was obtained in the same manner as in synthesizing Compound 2A of Synthesis Example 1, except that Intermediate I-13 and Intermediate A-20 were used instead of Intermediate I-5 and 2-chloro-4,6-diphenyl-1,3,5-triazine, respectively. The obtained compound was identified by LC-MS.

$C_{35}H_{22}BrN$: M+1 536.1

Synthesis of Intermediate A-22

4.38 g (yield: 75%) of Intermediate A-22 was obtained in the same manner as in synthesizing Intermediate I-1 of Synthesis Example 1, except that Intermediate A-21 was used instead of 1-bromonaphthalene. The obtained compound was identified by LC-MS.

$C_{41}H_{34}BNO_2$: M+1 584.3

Synthesis of Compound 61B 5.443 g (yield: 79%) of Compound 61B was obtained in the same manner as in synthesizing Compound 2A of Synthesis Example 1, except that Intermediate A-22 was used instead of Intermediate I-5. The obtained compound was identified by MS/FAB and $^1$H NMR.

$C_{50}H_{32}N_4$ cal. 688.26. found 688.25.

Synthesis Example 16: Synthesis of Compound 62B

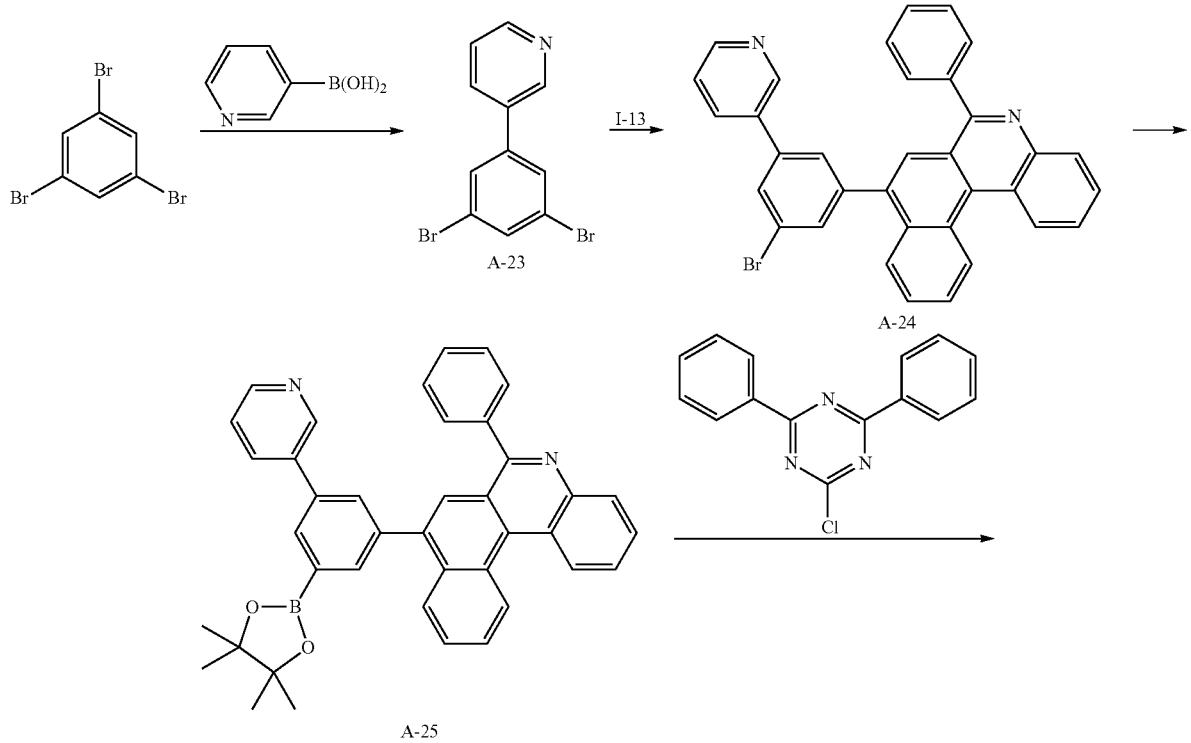

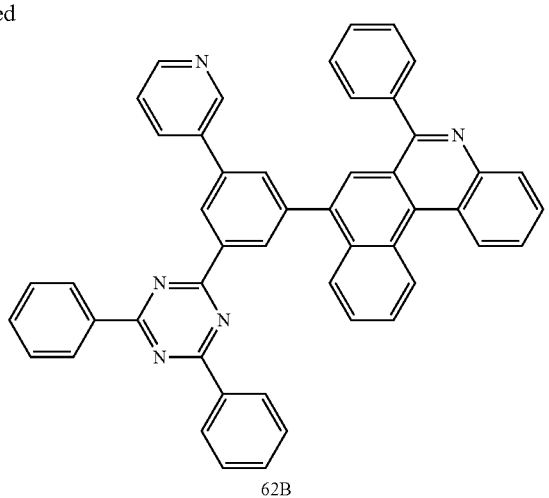

62B

Synthesis of Intermediate A-23

1.97 g (yield: 60%) of Intermediate A-23 was obtained in the same manner as in synthesizing Compound 2A of Synthesis Example 1, except that 3-pyridineboronic acid and 1,3,5-tribromobenzene were used instead of Intermediate I-5 and 2-chloro-4,6-diphenyl-1,3,5-triazine, respectively. The obtained compound was identified by LC-MS.

$C_{11}H_7Br_2N$: M+1 311.9

Synthesis of Intermediate A-24

3.33 g (yield: 62%) of Intermediate A-24 was obtained in the same manner as in synthesizing Compound 2A of Synthesis Example 1, except that Intermediate I-13 and Intermediate A-23 were used instead of Intermediate I-5 and 2-chloro-4,6-diphenyl-1,3,5-triazine, respectively. The obtained compound was identified by LC-MS.

$C_{34}H_{21}BrN_2$: M+1 537.1

Synthesis of Intermediate A-25

4.27 g (yield: 73%) of Intermediate A-25 was obtained in the same manner as in synthesizing Intermediate I-1 of Synthesis Example 1, except that Intermediate A-24 was used instead of 1-bromonaphthalene. The obtained compound was identified by LC-MS.

$C_{40}H_{33}BN_2O_2$: M+1 585.3

Synthesis of Compound 62B 5.31 g (yield: 77%) of Compound 62B was obtained in the same manner as in synthesizing Compound 2A of Synthesis Example 1, except that Intermediate A-25 was used instead of Intermediate I-5. The obtained compound was identified by MS/FAB and $^1$H NMR.

$C_{49}H_{31}N_5$ cal. 689.26. found 689.27.

Synthesis Example 17: Synthesis of Compound 3C

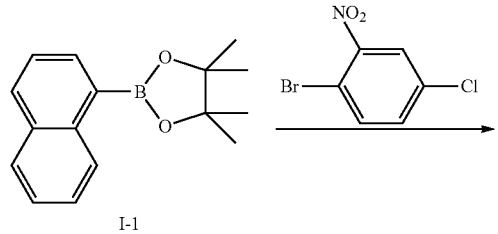

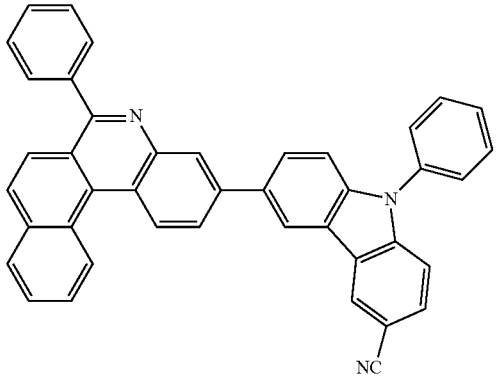

Synthesis of Intermediate I-16

2.30 g (yield: 81%) of Intermediate I-16 was obtained in the same manner as in synthesizing Intermediate I-2 of Synthesis Example 1, except that 2-bromo-5-chloronitrobenzene was used instead of 1-bromo-2-nitrobenzene. The obtained compound was identified by LC-MS.

$C_{16}H_{10}ClNO_2$: M+1 284.0

Synthesis of Intermediate I-17

2.28 g (yield: 90%) of Intermediate I-17 was obtained in the same manner as in synthesizing Intermediate I-3 of Synthesis Example 1, except that Intermediate I-16 was used instead of Intermediate I-2. The obtained compound was identified by LC-MS.

$C_{16}H_{12}ClN$: M+1 254.1

Synthesis of Intermediate I-18

1.67 g (yield: 49%) of Intermediate I-18 was obtained in the same manner as in synthesizing Intermediate I-4 of Synthesis Example 1, except that benzaldehyde was used instead of benzaldehyde. The obtained compound was identified by LC-MS.

$C_{23}H_{14}ClN$: M+1 340.1

Synthesis of Compound 3C 3.77 g (yield: 66%) of Compound 3C was obtained in the same manner as in synthesizing Compound 2A of Synthesis Example 1, except that Intermediate I-18 and Intermediate A-2 were used instead of Intermediate I-5 and 2-chloro-4,6-diphenyl-1,3,5-triazine, respectively. The obtained compound was identified by MS/FAB and $^1$H NMR.

$C_{42}H_{25}N_3$ cal. 571.20. found 571.19.

Synthesis Example 18: Synthesis of Compound 11C

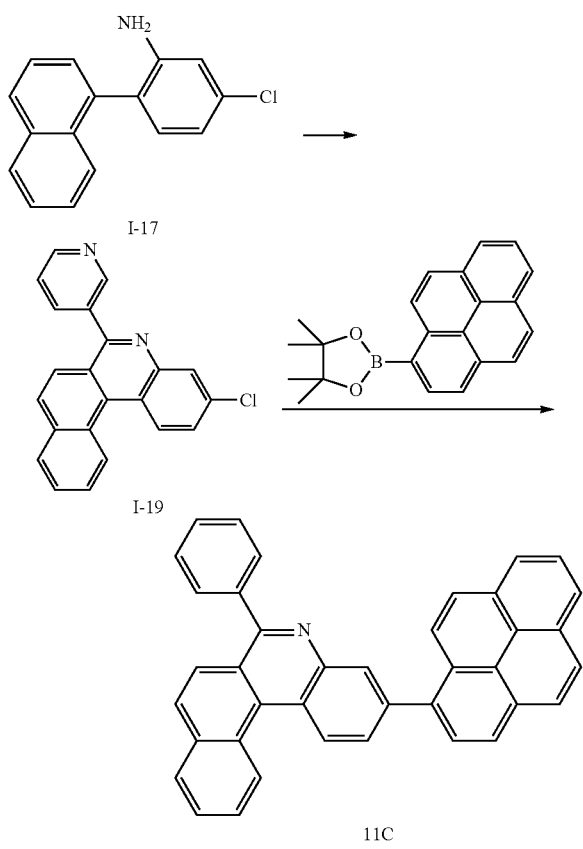

Synthesis of Intermediate I-19

1.60 g (yield: 47%) of Intermediate I-19 was obtained in the same manner as in synthesizing Intermediate I-4 of Synthesis Example 1, except that 3-pyridine carboaldehyde and Intermediate I-17 were used instead of 4-bromobenzaldehyde and Intermediate I-3. The obtained compound was identified by LC-MS.

$C_{22}H_{13}ClN_2$: M+1 341.1

Synthesis of Compound 11C 3.60 g (yield: 71%) of Compound 11C was obtained in the same manner as in synthesizing Compound 2A of Synthesis Example 1, except that Intermediate I-19 and pyrenyl-1-boronic acid pinacol ester were used instead of Intermediate I-5 and 2-chloro-4,6-diphenyl-1,3,5-triazine, respectively. The obtained compound was identified by MS/FAB and $^1$H NMR.

$C_{38}H_{22}N_2$ cal. 506.18. found 506.19.

Synthesis Example 19: Synthesis of Compound 27C

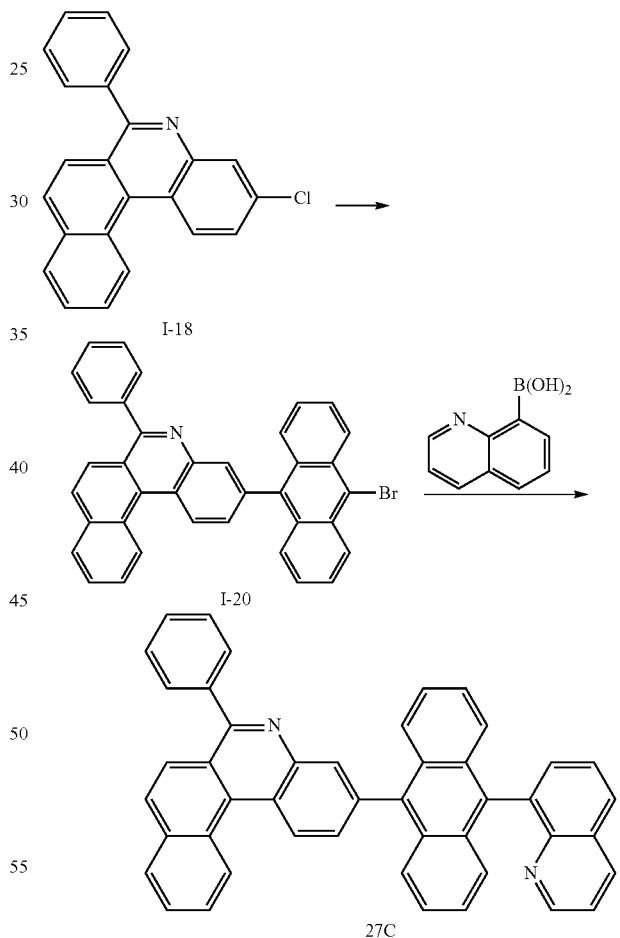

Synthesis of Intermediate I-20

3.25 g (yield: 58%) of Intermediate I-20 was obtained in the same manner as in synthesizing Compound 2A of Synthesis Example 1, except that 10-bromoanthracene-9-boronic acid and Intermediate I-18 were used instead of Intermediate I-5 and 2-chloro-4,6-diphenyl-1,3,5-triazine, respectively. The obtained compound was identified by LC-MS.

$C_{37}H_{22}BrN$: M+1 560.1

Synthesis of Compound 27C 3.96 g (yield: 65%) of Compound 27C was obtained in the same manner as in synthesizing Compound 2A of Synthesis Example 1, except that quinoline-8-boronic acid and Intermediate I-20 were used instead of Intermediate I-5 and 2-chloro-4,6-diphenyl-1,3,5-triazine, respectively. The obtained compound was identified by MS/FAB and NMR.

$C_{46}H_{28}N_2$ cal. 608.23. found 608.25.

Synthesis Example 20: Synthesis of Compound 47C

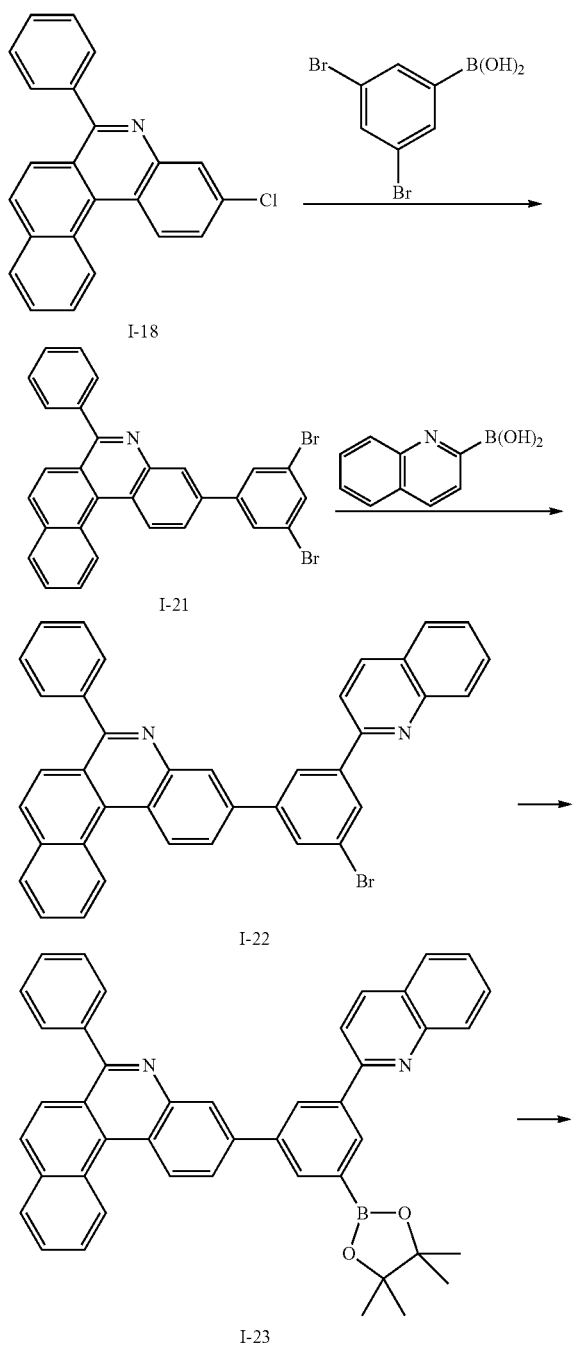

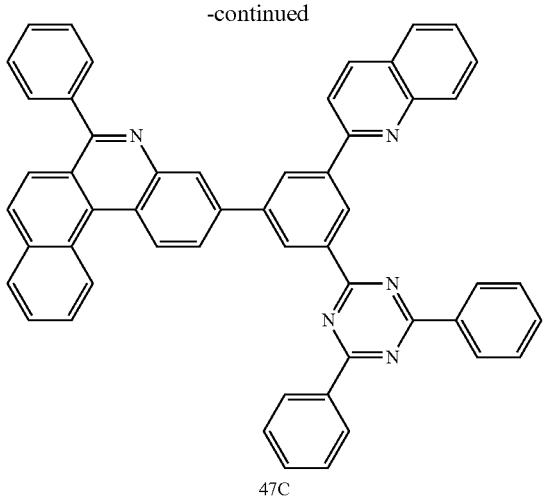

47C

Synthesis of Intermediate I-21

3.07 g (yield: 57%) of Intermediate I-21 was obtained in the same manner as in synthesizing Compound 2A of Synthesis Example 1, except that 3,5-dibromophenyl boronic acid and Intermediate I-18 were used instead of Intermediate I-5 and 2-chloro-4,6-diphenyl-1,3,5-triazine, respectively. The obtained compound was identified by LC-MS.

$C_{29}H_{17}Br_2N$: M+1 538.0

Synthesis of Intermediate I-22

3.29 g (yield: 56%) of Intermediate I-22 was obtained in the same manner as in synthesizing Compound 2A of Synthesis Example 1, except that quinoline-2-boronic acid and Intermediate I-21 were used instead of Intermediate I-5 and 2-chloro-4,6-diphenyl-1,3,5-triazine, respectively. The obtained compound was identified by LC-MS.

$C_{38}H_{23}BrN_2$: M+1 587.1

Synthesis of Intermediate I-23

4.44 g (yield: 70%) of Intermediate I-23 was obtained in the same manner as in synthesizing Intermediate I-1 of Synthesis Example 1, except that Intermediate I-22 was used instead of 1-bromonaphthalene. The obtained compound was identified by LC-MS.

$C_{44}H_{35}BN_2O_2$: M+1 635.3

Synthesis of Compound 47C 5.55 g (yield: 75%) of Compound 47C was obtained in the same manner as in synthesizing Compound 2A of Synthesis Example 1, except that Intermediate I-23 was used instead of Intermediate I-5. The obtained compound was identified by MS/FAB and $^1$H NMR.

$C_{53}H_{33}N_5$ cal. 739.27. found 739.26.

Synthesis Example 21: Synthesis of Compound 35A

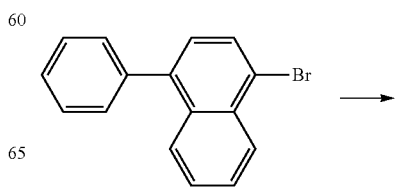

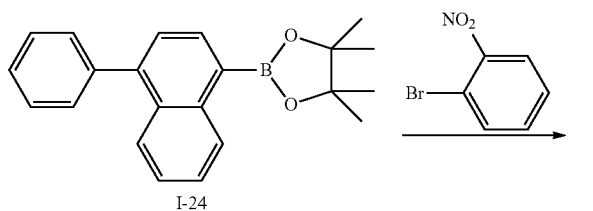

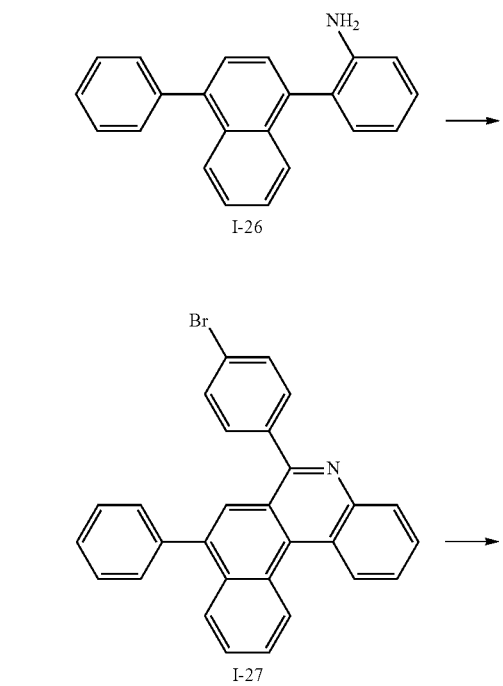

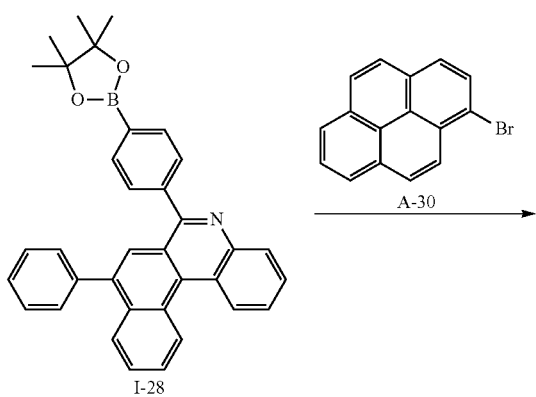

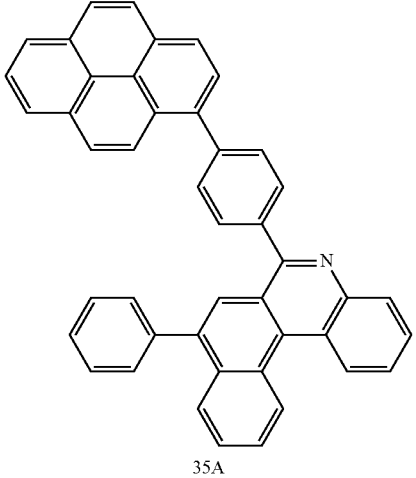

Synthesis of Intermediate I-24

Intermediate I-24 was synthesized in the same manner as in synthesizing Intermediate I-1 of Synthesis Example 1, except that 1-bromo-4-phenylnaphthalene was used instead of 1-bromonaphthalene.

Synthesis of Intermediate I-25

Intermediate I-25 was synthesized in the same manner as in synthesizing Intermediate I-2 of Synthesis Example 1, except that Intermediate I-24 was used instead of Intermediate I-1.

Synthesis of Intermediate I-26,

Intermediate I-26 was synthesized in the same manner as in synthesizing Intermediate I-3 of Synthesis Example 1, except that Intermediate I-25 was used instead of Intermediate I-2.

Synthesis of Intermediate I-27

Intermediate I-27 was synthesized in the same manner as in synthesizing Intermediate I-4 of Synthesis Example 1, except that Intermediate I-26 was used instead of Intermediate I-3.

Synthesis of Intermediate I-28

Intermediate I-28 was synthesized in the same manner as in synthesizing Intermediate I-5 of Synthesis Example 1, except that Intermediate I-27 was used instead of Intermediate I-4.

Synthesis of Compound 35A 4.12 g (yield: 71%) of Compound 35 Å was obtained in the same manner as in synthesizing Compound 2A of Synthesis Example 1, except that Intermediate I-28 and Intermediate A-30 were used instead of Intermediate I-5 and 2-chloro-4,6-diphenyl-1,3,5-triazine, respectively. The obtained compound was identified by MS/FAB and $^1$H NMR.

$C_{45}H_{27}N$ cal. 581.21. found 581.20.

Synthesis Example 22: Synthesis of Compound 61A

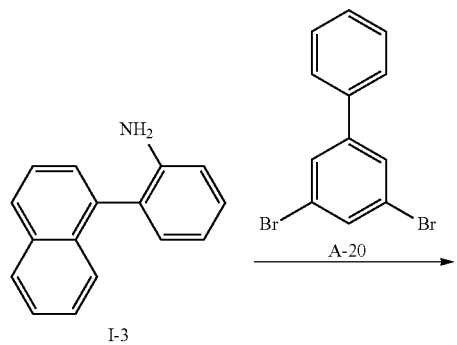

Synthesis of Intermediate I-29

Intermediate I-29 was synthesized in the same manner as in synthesizing Intermediate I-4 of Synthesis Example 1, except that Intermediate A-20 was used instead of 4-bromobenzaldehyde.

Synthesis of Intermediate I-30

Intermediate I-30 was synthesized in the same manner as in synthesizing Intermediate I-5 of Synthesis Example 1, except that Intermediate I-29 was used instead of Intermediate I-4.

Synthesis of Compound 61A 4.77 g (yield: 78%) of Compound 61A was obtained in the same manner as in synthesizing Compound 2A of Synthesis Example 1, except that Intermediate I-30 was used instead of Intermediate I-5. The obtained compound was identified by MS/FAB and $^1$H NMR.

$C_{44}H_{28}N_4$ cal. 612.22. found 612.23.

Synthesis Example 23: Synthesis of Compound 18B

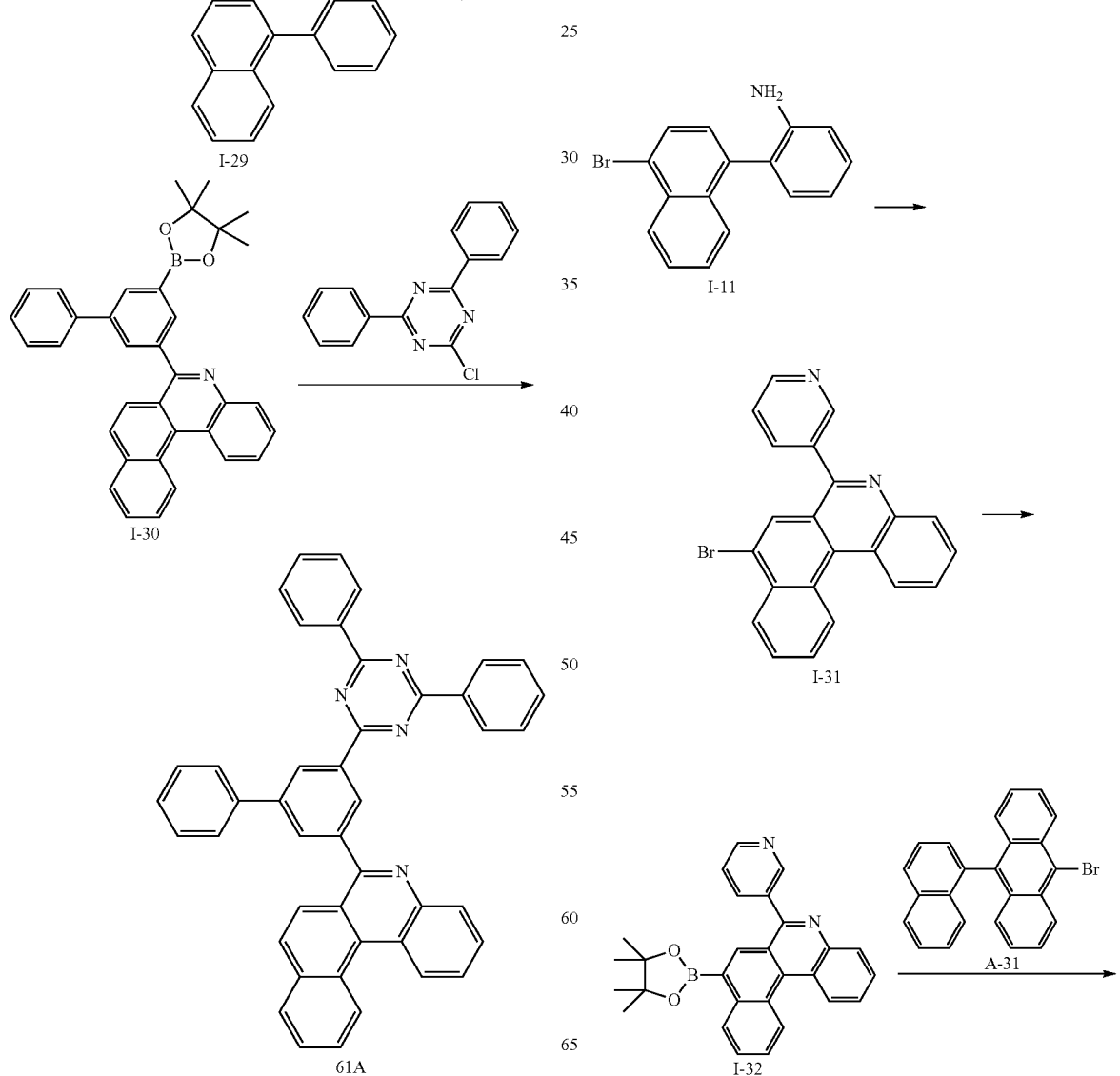

-continued

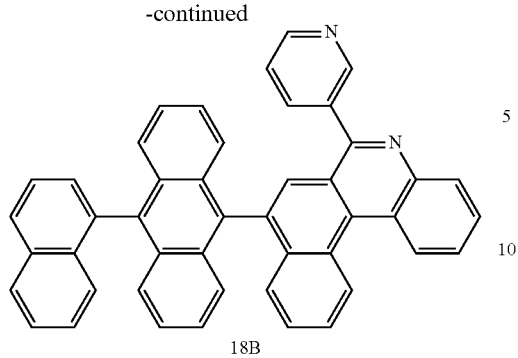

18B

Synthesis of Intermediate I-31

Intermediate I-31 was synthesized in the same manner as in synthesizing Intermediate I-12 of Synthesis Example 5, except that 3-pyridine carboaldehyde was used instead of benzaldehyde.

Synthesis of Intermediate I-32

Intermediate I-32 was synthesized in the same manner as in synthesizing Intermediate I-13 of Synthesis Example 5, except that Intermediate I-31 was used instead of Intermediate I-12.

Synthesis of Compound 18B 4.26 g (yield: 70%) of Compound 18B was obtained in the same manner as in synthesizing Compound 1B of Synthesis Example 5, except that Intermediate I-32 and Intermediate A-31 were used instead of Intermediate I-13 and Intermediate A-1, respectively. The obtained compound was identified by MS/FAB and $^1$H NMR.

$C_{46}H_{28}N_2$ cal. 608.23. found 608.24.

Synthesis Example 24: Synthesis of Compound 29B

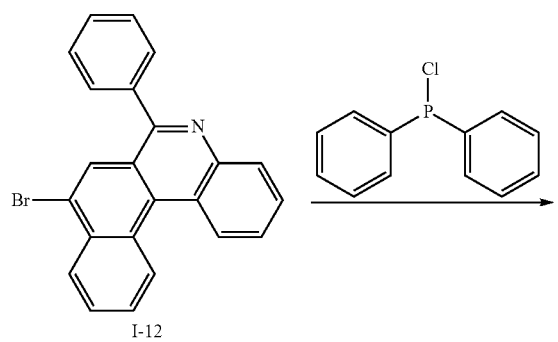

-continued

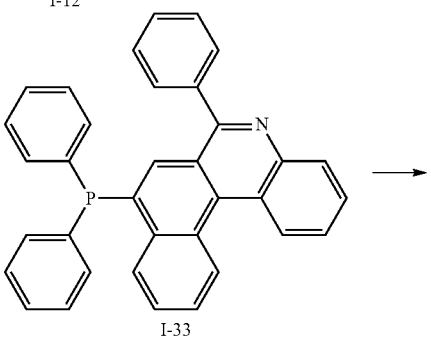

29B

Synthesis of Intermediate I-33

Intermediate I-33 was synthesized in the same manner as in synthesizing Intermediate I-8 of Synthesis Example 3, except that Intermediate I-12 was used instead of Intermediate I-4.

Synthesis of Compound 29B 3.38 g (yield: 67%) of Compound 29B was obtained in the same manner as in synthesizing Compound 2A of Synthesis Example 3, except that Intermediate I-33 was used instead of Intermediate I-8. The obtained compound was identified by MS/FAB and $^1$H NMR.

$C_{35}H_{24}NOP$ cal. 505.16 found 505.17.

Synthesis Example 25: Synthesis of Compound 18C

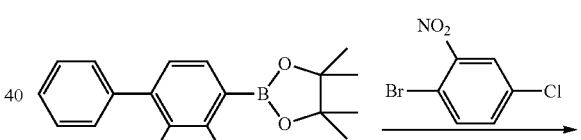

I-34

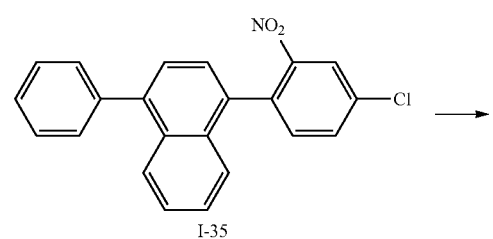

I-35

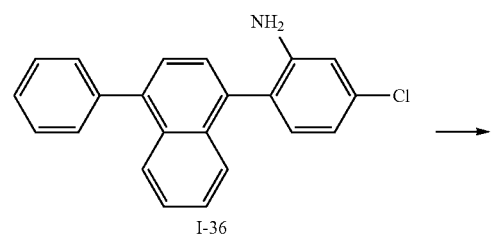

I-36

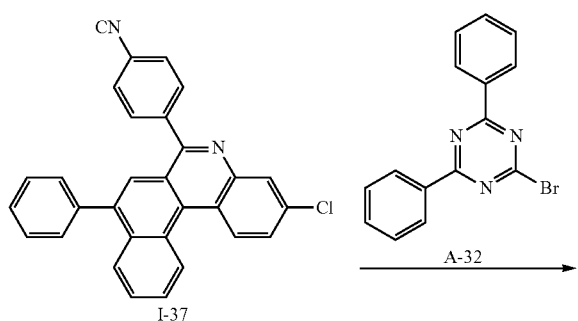

Synthesis of Intermediate I-35

Intermediate I-35 was synthesized in the same manner as in synthesizing Intermediate I-16 of Synthesis Example 17, except that Intermediate I-34 was used instead of Intermediate I-1.

Synthesis of Intermediate I-36

Intermediate I-36 was synthesized in the same manner as in synthesizing Intermediate I-17 of Synthesis Example 17, except that Intermediate I-35 was used instead of Intermediate I-16.

Synthesis of Intermediate I-37

Intermediate I-37 was synthesized in the same manner as in synthesizing Intermediate I-18 of Synthesis Example 17, except that Intermediate I-36 and 4-cyanobenzaldehyde were used instead of Intermediate I-17 and benzaldehyde, respectively.

Synthesis of Compound 18C 4.65 g (yield: 73%) of Compound 18C was obtained in the same manner as in synthesizing Compound 3C of Synthesis Example 17, except that Intermediate I-37 and Intermediate A-32 were used instead of Intermediate I-18 and Intermediate A-2, respectively. The obtained compound was identified by MS/FAB and $^1$H NMR.

$C_{45}H_{27}N_5$ cal. 637.23. found 637.24.

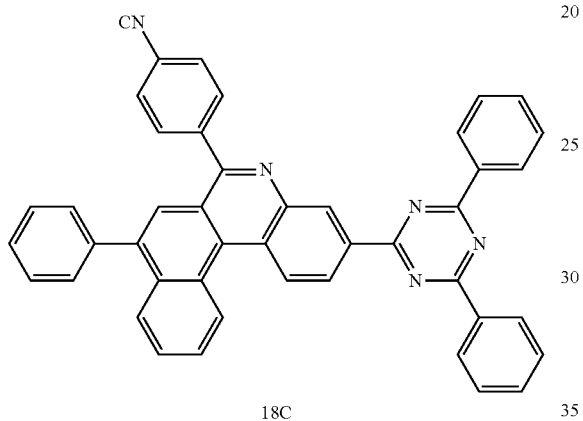

Synthesis Example 26: Synthesis of Compound 8D

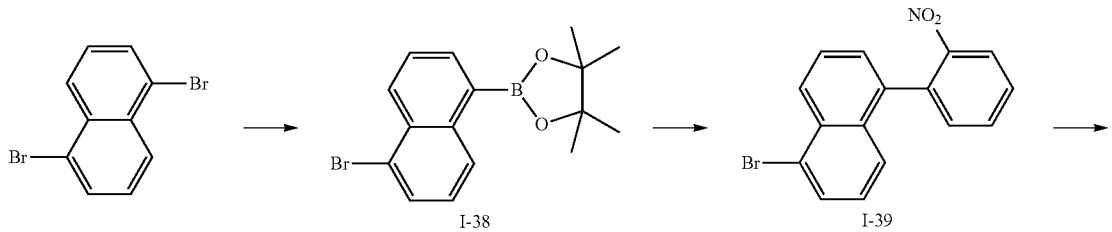

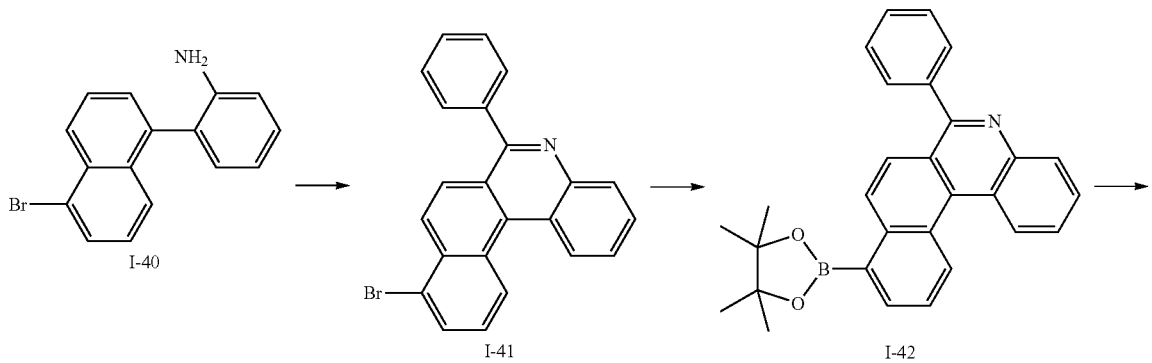

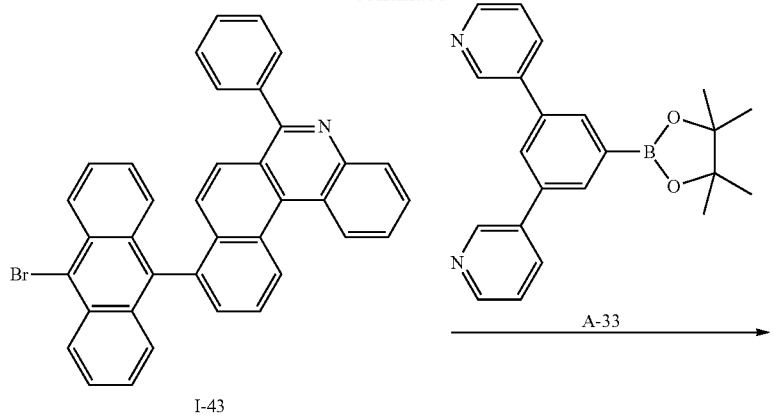

Synthesis of Intermediate I-38

2.46 g (yield: 74%) of Intermediate I-38 was obtained in the same manner as in synthesizing Intermediate I-1 of Synthesis Example 1, except that 1,5-dibromonaphthalene was used instead of 1-bromonaphthalene. The obtained compound was identified by LC-MS.

$C_{16}H_{18}BBrO_2$: M+1 333.1

Synthesis of Intermediate I-39

2.63 g (yield: 80%) of Intermediate I-39 was obtained in the same manner as in synthesizing Intermediate I-2 of Synthesis Example 1, except that Intermediate I-38 was used instead of Intermediate I-1. The obtained compound was identified by LC-MS.

$C_{16}H_{10}BrNO_2$: M+1 328.0

Synthesis of Intermediate I-40

2.71 g (yield: 91%) of Intermediate I-40 was obtained in the same manner as in synthesizing Intermediate I-3 of Synthesis Example 1, except that Intermediate I-39 was used instead of Intermediate I-2. The obtained compound was identified by LC-MS.

$C_{16}H_{12}BrN$: M+1 298.0

Synthesis of Intermediate I-41

2.04 g (yield: 53%) of Intermediate I-41 was obtained in the same manner as in synthesizing Intermediate I-4 of Synthesis Example 1, except that benzaldehyde and Intermediate I-40 were used instead of 4-bromobenzaldehyde and Intermediate I-3. The obtained compound was identified by LC-MS.

$C_{23}H_{14}BrN$: M+1 384.0

Synthesis of Intermediate I-42

3.23 g (yield: 75%) of Intermediate I-42 was obtained in the same manner as in synthesizing Intermediate I-5 of Synthesis Example 1, except that Intermediate I-41 was used instead of Intermediate I-4. The obtained compound was identified by LC-MS.

$C_{29}H_{26}BNO_2$: M+1 432.2

Synthesis of Intermediate I-43

4.26 g (yield: 76%) of Intermediate I-43 was obtained in the same manner as in synthesizing Compound 2A of Synthesis Example 1, except that Intermediate I-42 and 9,10-dibromoanthracene were used instead of Intermediate I-5 and 2-chloro-4,6-diphenyl-1,3,5-triazine, respectively. The obtained compound was identified by LC-MS.

$C_{37}H_{22}BrN$: M+1 560.1

Synthesis of Compound 8D 3.79 g (yield: 70%) of Compound 8D was obtained in the same manner as in synthesizing Compound 2A of Synthesis Example 1, except that Intermediate I-43 and Intermediate A-33 were used instead of Intermediate I-5 and 2-chloro-4,6-diphenyl-1,3,5-triazine, respectively. The obtained compound was identified by MS/FAB and $^1$H NMR.

$C_{53}H_{33}N_3$ cal. 711.27. found 711.26.

Additional compounds were synthesized by using appropriate intermediate compounds according to the same synthesis method as described above. Table 1 below shows data of $^1$H NMR and MS/FAB with respect to the synthesized compounds.

Other compounds, in addition to the synthesized compounds as shown in Table 1 below, may be obtained by referring to methods and raw materials described above.

TABLE 1

| Compound | ¹H NMR (CDCl₃, 400 MHz) | MS/FAB found | MS/FAB calc. |
|---|---|---|---|
| 2A | δ = 8.74-8.72 (m, 1H), 8.71-8.70 (m, 2H), 8.69-8.67 (m, 2H), 8.56-8.55 (m, 1H), 8.54-8.53 (m, 1H), 8.48-8.46 (m, 1H), 8.42-8.41 (m, 1H), 8.40-8.36 (m, 2H), 8.28-8.26 (m, 1H), 7.95-7.91 (m, 1H), 7.86-7.82 (m, 1H), 7.72-7.68 (m, 1H), 7.55-7.54 (m, 1H), 7.53-7.52 (m, 2H), 7.51-7.50 (m, 1H), 7.47-7.41 (m, 5H) | 536.19 | 536.20 |
| 4A | δ = 8.81-8.80 (m, 2H), 8.72-8.69 (m, 1H), 8.58-8.56 (m, 2H), 8.54-8.52 (m, 1H), 8.48-8.45 (m, 1H), 8.28-8.21 (m, 3H), 8.03 (t, 1H), 7.99 (t, 1H), 7.94-7.91 (m, 1H), 7.87-7.81 (m, 6H), 7.72-7.68 (m, 1H), 7.48-7.42 (m, 5H) | 535.21 | 535.20 |
| 10A | δ = 8.69-8.67 (m, 1H), 8.47-8.45 (m, 1H), 8.41-8.38 (m, 1H), 8.26-8.22 (m, 3H), 8.01-8.00 (m, 2H), 7.95-7.91 (m, 1H), 7.86-7.82 (m, 1H), 7.72-7.68 (m, 1H), 7.49-7.44 (m, 3H) | 330.13 | 330.12 |
| 14A | δ = 8.71-8.69 (m, 1H), 8.48-8.46 (m, 2H), 8.40-8.36 (m, 2H), 8.25-8.22 (m, 2H), 7.95-7.91 (m, 2H), 7.88-7.80 (m, 3H), 7.72-7.68 (m, 3H), 7.52-7.41 (m, 8H), 7.32-7.24 (m, 2H) | 571.21 | 571.20 |
| 21A | δ = 8.72-8.70 (m, 1H), 8.49-8.47 (m, 1H), 8.42-8.38 (m, 1H), 8.27-8.25 (m, 1H), 8.03-8.00 (m, 2H), 7.95-7.92 (m, 1H), 7.86-7.82 (m, 1H), 7.79-7.74 (m, 2H), 7.72-7.65 (m, 5H), 7.52-7.47 (m, 2H), 7.45-7.39 (m, 7H) | 505.17 | 505.16 |
| 26A | δ = 9.10-9.07 (m, 1H), 8.86-8.84 (m, 1H), 8.78-8.75 (m, 1H), 8.72-8.70 (m, 1H), 8.49-8.45 (m, 1H), 8.33-8.31 (m, 1H), 7.95-7.91 (m, 2H), 7.85-7.78 (m, 5H), 7.72-7.68 (m, 1H), 7.63-7.60 (m, 1H), 7.53-7.38 (m, 8H) | 506.14 | 506.15 |
| 30A | δ = 9.03-9.01 (m, 1H), 8.65-8.63 (m, 1H), 8.55-8.53 (m, 1H), 8.51-8.49 (m, 1H), 8.41-8.40 (m, 1H), 8.34-8.33 (m, 1H), 8.25-8.21 (m, 3H), 8.18-8.17 (m, 1H), 8.14-8.12 (m, 1H), 8.00-7.94 (m, 3H), 7.86-7.82 (m, 2H), 7.75-7.67 (m, 3H), 7.64-7.61 (m, 1H), 7.52-7.44 (m, 6H), 7.35-7.26 (m, 2H) | 648.25 | 648.23 |
| 35A | δ = 8.68-8.66 (m, 1H), 8.41-8.40 (m, 1H), 8.30-8.25 (m, 5H), 8.20-8.11 (m, 7H), 8.09-8.05 (m, 1H), 7.88-7.81 (m, 5H), 7.75-7.67 (m, 3H), 7.48-7.44 (m, 2H), 7.40-7.36 (m, 2H) | 581.20 | 581.21 |
| 40A | δ = 8.87-8.86 (m, 1H), 8.70-8.63 (m, 6H), 8.59-8.56 (m, 3H), 8.45-8.42 (m, 2H), 8.35-8.31 (m, 2H), 8.26-8.22 (m, 2H), 7.86-7.82 (m, 1H), 7.77-7.70 (m, 3H), 7.63-7.59 (m, 1H), 7.54-7.51 (m, 4H), 7.49-7.41 (m, 4H) | 663.25 | 663.24 |
| 45A | δ = 8.75-8.72 (m, 1H), 8.50-8.47 (m, 1H), 8.32-8.30 (m, 1H), 8.25-8.23 (m, 2H), 8.14-8.12 (m, 1H), 8.04-7.97 (m, 4H), 7.95-7.87 (m, 2H), 7.82-7.78 (m, 1H), 7.72-7.68 (m, 1H), 7.65 (d, 1H), 7.63-7.59 (m, 2H), 7.47-7.40 (m, 3H), 7.35-7.31 (m, 2H), 7.28-7.24 (m, 2H) | 532.20 | 532.19 |
| 48A | δ = 8.77-8.73 (m, 3H), 8.51-8.47 (m, 3H), 8.28-8.25 (m, 1H), 8.12-8.10 (dd, 2H), 8.06-8.02 (m, 3H), 7.97 (d, 2H), 7.93-7.87 (m, 5H), 7.72-7.68 (m, 1H), 7.61-7.57 (m, 2H), 7.47-7.41 (m, 5H), 7.30-7.26 (m, 2H) | 635.25 | 635.24 |
| 55A | δ = 8.67-8.65 (m, 1H), 8.50-8.45 (m, 2H), 8.39-8.35 (m, 1H), 8.26-8.24 (m, 1H), 7.95-7.89 (m, 2H), 7.86-7.83 (m, 3H), 7.73-7.65 (m, 4H), 7.59-7.42 (m, 5H), 7.34-7.30 (m, 1H), 7.25-7.21 (m, 2H) | 471.17 | 471.16 |
| 58A | δ = 8.80-8.76 (m, 2H), 8.74-8.72 (m, 1H), 8.53-8.49 (m, 1H), 8.35-8.34 (m, 1H), 8.26-8.24 (m, 1H), 8.09-8.02 (m, 2H), 7.97-7.87 (m, 6H), 7.84-7.68 (m, 4H), 7.61-7.57 (m, 2H), 7.49-7.40 (m, 7H), 7.30-7.25 (m, 2H) | 671.20 | 671.22 |
| 59A | δ = 8.79-8.77 (m, 1H), 8.60-8.58 (m, 2H), 8.56-8.53 (m, 1H), 8.28-8.26 (m, 1H), 8.04-8.02 (m, 3H), 7.99-7.97 (dd, 2H), 7.94-7.88 (m, 4H), 7.79-7.77 (m, 1H), 7.72-7.68 (m, 1H), 7.65-7.63 (dd, 2H), 7.47-7.40 (m, 3H), 7.35-7.26 (m, 4H) | 559.19 | 559.20 |
| 61A | δ = 9.04 (t, 1H), 8.79-8.75 (m, 6H), 8.56 (t, 1H), 8.48-8.45 (m, 1H), 8.28-8.26 (m, 1H), 8.21-8.18 (m, 1H), 7.95-7.91 (m, 1H), 7.86-7.82 (m, 1H), 7.79-7.77 (m, 2H), 7.72-7.68 (m, 1H), 7.57-7.51 (m, 5H), 7.46-7.38 (m, 7H) | 612.22 | 612.23 |
| 67A | δ = 9.09 (t, 1H), 9.03-9.01 (m, 1H), 8.91-8.90 (m, 2H), 8.81-8.79 (m, 1H), 8.76 (t, 1H), 8.74-8.73 (dd, 2H), 8.61-8.58 (m, 2H), 8.49-8.45 (m, 1H), 8.29-8.26 (m, 2H), 8.21-8.12 (m, 5H), 8.04-8.01 (m, 2H), 7.95-7.91 (m, 1H), 7.86-7.83 (m, 1H), 7.72-7.65 (m, 3H), 7.60-7.55 (m, 3H), 7.47-7.41 (m, 3H) | 713.28 | 713.26 |
| 72A | δ = 9.06 (t, 1H), 8.80-8.78 (m, 1H), 8.77 (t, 1H), 8.69-8.67 (m, 2H), 8.50-8.45 (m, 2H), 8.28-8.26 (m, 1H), 8.21-8.18 (m, 3H), 8.12-8.08 (m, 3H), 8.00-7.98 (m, 2H), 7.94-7.90 (m, 2H), 7.86-7.82 (m, 1H), 7.79-7.63 (m, 7H), 7.57-7.42 (m, 6H), 7.27-7.18 (m, 2H) | 762.30 | 762.28 |
| 78A | δ = 9.11-9.09 (m, 1H), 8.78-8.75 (m, 4H), 8.70-8.67 (m, 1H), 8.58-8.55 (m, 2H), 8.49-8.45 (m, 2H), 8.20-8.17 (m, 1H), 8.11-8.08 (m, 1H), 7.95-7.91 (m, 1H), 7.81-7.78 (m, 2H), 7.72-7.68 (m, 3H), 7.55-7.49 (m, 5H), 7.46-7.41 (m, 4H) | 637.22 | 637.23 |
| 83A | δ = 8.81-8.79 (m, 2H), 8.51-8.47 (m, 4H), 8.44-8.42 (m, 1H), 8.40-8.37 (m, 1H), 8.34-8.33 (m, 1H), 8.08-8.06 (m, 1H), 8.01 (t, 1H), 7.99 (t, 1H), 7.96-7.92 (m, 2H), 7.83-7.76 (m, 6H), 7.54-7.43 (m, 8H), 7.38-7.34 (m, 1H) | 611.25 | 611.24 |

TABLE 1-continued

| Compound | ¹H NMR (CDCl₃, 400 MHz) | MS/FAB found | MS/FAB calc. |
|---|---|---|---|
| 1B | δ = 8.70-8.68 (m, 1H), 8.51-8.50 (m, 1H), 8.42-8.41 (m, 1H), 8.38-8.37 (m, 1H), 8.26-8.23 (m, 2H), 8.09-8.06 (m, 1H), 7.95-7.92 (m, 2H), 7.87-7.82 (m, 2H), 7.75-7.58 (m, 7H), 7.53-7.46 (m, 4H), 7.43-7.39 (m, 1H), 7.34-7.24 (m, 2H) | 571.22 | 571.20 |
| 7B | δ = 9.09-9.08 (m, 1H), 8.94-8.92 (m, 1H), 8.69-8.65 (m, 1H), 8.53-8.51 (m, 1H), 8.31-8.29 (m, 4H), 8.27-8.26 (m, 1H), 8.00 (s, 1H), 7.96-7.93 (m, 2H), 7.88-7.82 (m, 2H), 7.75-7.71 (m, 1H), 7.68-7.59 (m, 4H), 7.53-7.48 (m, 4H), 7.31-7.27 (m, 2H) | 535.21 | 535.20 |
| 15B | δ = 8.78-8.77 (m, 1H), 8.69-8.67 (m, 1H), 8.53-8.51 (m, 1H), 8.46-8.45 (m, 1H), 8.34-8.31 (m, 2H), 8.26-8.24 (m, 1H), 8.14-8.12 (m, 1H), 8.04-8.01 (m, 2H), 7.93-7.90 (m, 2H), 7.86-7.81 (m, 3H), 7.79-7.77 (m, 1H), 7.75-7.68 (m, 3H), 7.47-7.38 (m, 2H) | 483.16 | 483.17 |
| 18B | δ = 9.01-9.00 (m, 1H), 8.71-8.69 (m, 1H), 8.68-8.66 (m, 1H), 8.63-8.62 (m, 1H), 8.42-8.40 (m, 1H), 8.28-8.25 (m, 2H), 7.87-7.81 (m, 6H), 7.80-7.70 (m, 5H), 7.66-7.64 (m, 1H), 7.42-7.30 (m, 8H), 7.08-7.04 (m, 1H) | 608.24 | 608.23 |
| 21B | δ = 8.67-8.65 (m, 1H), 8.49-8.48 (m, 1H), 8.44-8.43 (m, 1H), 8.39-8.38 (m, 1H), 8.30-8.26 (m, 2H), 7.94-7.92 (m, 2H), 7.88-7.79 (m, 7H), 7.75-7.59 (m, 7H), 7.53-7.47 (m, 4H), 7.42-7.24 (m, 7H) | 747.28 | 747.27 |
| 22B | δ = 8.58-8.55 (m, 1H), 8.40-8.39 (m, 1H), 8.32-8.30 (m, 2H), 8.28-8.27 (m, 1H), 8.25-8.22 (m, 2H), 8.15-8.14 (m, 1H), 8.04-8.00 (m, 3H), 7.97-7.91 (m, 4H), 7.86-7.80 (m, 2H), 7.75-7.58 (m, 7H), 7.53-7.46 (m, 4H), 7.43-7.39 (m, 1H), 7.34-7.28 (m, 2H) | 697.24 | 697.25 |
| 23B | δ = 8.57-8.55 (m, 1H), 8.47-8.46 (m, 1H), 8.40-8.38 (m, 1H), 8.26-8.23 (m, 3H), 8.09-8.07 (m, 1H), 7.96-7.94 (m, 2H), 7.86-7.82 (m, 1H), 7.75-7.58 (m, 11H), 7.53-7.39 (m, 13H), 7.36-7.30 (m, 1H) | 746.26 | 746.25 |
| 25B | δ = 8.57-8.55 (m, 1H), 8.46-8.45 (m, 1H), 8.26-8.23 (m, 2H), 8.11-8.08 (m, 1H), 7.96-7.94 (m, 2H), 7.85-7.72 (m, 8H), 7.68-7.47 (m, 12H), 7.43-7.32 (m, 9H) | 757.24 | 757.25 |
| 26B | δ = 8.68-8.65 (m, 1H), 8.45-8.44 (m, 1H), 8.27-8.24 (m, 2H), 8.18-8.14 (m, 1H), 7.95-7.92 (m, 2H), 7.86-7.82 (m, 1H), 7.75-7.47 (m, 15H), 7.44-7.39 (m, 5H) | 581.20 | 581.19 |
| 31B | δ = 8.66-8.64 (m, 1H), 8.51-8.50 (m, 1H), 8.27-8.25 (m, 1H), 8.14-8.12 (m, 1H), 7.97-7.91 (m, 5H), 7.86-7.82 (m, 3H), 7.79-7.75 (m, 2H), 7.73-7.70 (m, 1H), 7.68-7.55 (m, 5H), 7.52-7.48 (m, 2H), 7.40-7.36 (m, 1H) | 521.15 | 521.14 |
| 32B | δ = 8.58-8.55 (m, 1H), 8.42-8.41 (m, 1H), 8.25-8.22 (m, 2H), 7.96-7.91 (m, 4H), 7.87-7.81 (m, 3H), 7.78-7.60 (m, 14H), 7.52-7.47 (m, 2H), 7.44-7.30 (m, 9H) | 757.25 | 757.25 |
| 33B | δ = 8.57-8.55 (m, 1H), 8.31-8.30 (m, 2H), 8.28 (d, 1H), 8.24-8.20 (m, 2H), 7.95-7.92 (m, 2H), 7.86-7.82 (m, 1H), 7.81-7.77 (m, 3H), 7.68-7.60 (m, 7H), 7.56-7.44 (m, 6H), 7.42-7.38 (m, 5H), 7.25-7.21 (m, 2H) | 618.23 | 618.22 |
| 35B | δ = 8.56-8.54 (m, 1H), 8.32-8.30 (m, 2H), 8.25-8.24 (m, 1H), 8.22-8.20 (m, 1H), 8.04-8.03 (m, 1H), 8.02-8.00 (m, 2H), 7.97-7.92 (m, 4H), 7.86-7.82 (m, 1H), 7.75-7.47 (m, 16H), 7.44-7.39 (m, 5H) | 707.25 | 707.24 |
| 37B | δ = 8.59-8.57 (m, 1H), 8.43-8.42 (m, 1H), 8.24-8.20 (m, 2H), 7.97-7.93 (m, 4H), 7.85-7.80 (m, 5H), 7.78-7.55 (m, 11H), 7.52-7.48 (m, 2H), 7.40-7.31 (m, 5H) | 697.20 | 697.21 |
| 40B | δ = 8.65-8.63 (m, 1H), 8.49-8.48 (m, 1H), 8.28-8.24 (m, 3H), 8.14-8.11 (m, 1H), 7.95-7.93 (m, 2H), 7.90-7.88 (m, 2H), 7.86-7.81 (m, 5H), 7.78-7.71 (m, 4H), 7.67-7.58 (m, 3H), 7.42-7.30 (m, 5H), 7.21-7.18 (m, 1H) | 632.24 | 632.23 |
| 44B | δ = 8.67-8.65 (m, 1H), 8.55-8.53 (m, 2H), 8.44-8.43 (m, 1H), 8.24-8.21 (m, 2H), 8.03-8.01 (m, 2H), 7.95-7.93 (m, 2H), 7.90-7.88 (m, 2H), 7.86-7.71 (m, 5H), 7.67-7.59 (m, 3H), 7.56-7.54 (m, 2H), 7.47-7.45 (m, 2H), 7.42-7.38 (m, 3H), 7.17-7.13 (m, 2H) | 635.25 | 635.24 |
| 45B | δ = 8.83-8.81 (m, 2H), 8.67-8.65 (m, 1H), 8.52-8.49 (m, 2H), 8.44-8.43 (m, 1H), 8.27-8.24 (m, 2H), 8.06-8.04 (m, 2H), 7.97-7.93 (m, 4H), 7.88-7.86 (m, 1H), 7.84-7.73 (m, 8H), 7.68-7.59 (m, 3H), 7.57-7.53 (m, 2H), 7.47-7.44 (m, 2H), 7.42-7.37 (m, 1H), 7.34-7.30 (m, 2H) | 711.26 | 711.27 |
| 54B | δ = 8.76-8.72 (m, 2H), 8.66-8.64 (m, 1H), 8.35-8.34 (m, 1H), 8.27-8.25 (m, 1H), 8.16-8.12 (m, 2H), 7.96-7.90 (m, 6H), 7.85-7.82 (m, 4H), 7.81-7.69 (m, 6H), 7.67-7.58 (m, 3H), 7.47-7.43 (m, 2H), 7.40-7.36 (m, 1H) | 647.20 | 647.22 |
| 61B | δ = 8.74-8.70 (m, 6H), 8.61 (t, 1H), 8.53-8.52 (m, 1H), 8.40-8.38 (m, 1H), 8.28-8.24 (m, 2H), 8.18-8.16 (m, 1H), 7.96-7.92 (m, 2H), 7.86-7.82 (m, 1H), 7.75-7.69 (m, 3H), 7.68-7.58 (m, 4H), 7.55-7.51 (m, 4H), 7.45-7.37 (m, 6H) | 688.25 | 688.26 |
| 62B | δ = 9.02-9.01 (m, 1H), 8.81-8.75 (m, 6H), 8.65 (t, 1H), 8.60-8.58 (m, 2H), 8.41-8.39 (m, 1H), 8.28-8.26 (m, 1H), 8.20-8.16 (m, 3H), 7.95-7.92 (m, 2H), 7.86-7.81 (m, 1H), 7.75-7.59 (m, 5H), 7.55-7.51 (m, 4H), 7.47-7.41 (m, 4H) | 689.27 | 689.26 |

TABLE 1-continued

| Compound | $^1$H NMR (CDCl$_3$, 400 MHz) | MS/FAB found | MS/FAB calc. |
|---|---|---|---|
| 71B | δ = 8.85-8.84 (m, 2H), 8.79 (t, 1H), 8.71-8.67 (m, 2H), 8.65-8.62 (m, 2H), 8.55-8.54 (m, 1H), 8.41-8.38 (m, 1H), 8.28-8.26 (m, 1H), 8.22 (t, 1H), 8.18-8.12 (m, 5H), 8.07-8.01 (m, 3H), 7.95-7.90 (m, 3H), 7.86-7.82 (m, 1H), 7.79-7.52 (m, 12H), 7.45-7.42 (m, 1H), 7.27-7.17 (m, 2H) | 838.33 | 838.31 |
| 77B | δ = 9.01-8.99 (m, 1H), 8.75-8.72 (m, 2H), 8.64 (t, 1H), 8.60-8.58 (m, 2H), 8.42-8.38 (m, 5H), 8.28-8.25 (m, 1H), 8.20-8.16 (m, 3H), 7.95-7.92 (m, 2H), 7.86-7.83 (m, 1H), 7.75-7.58 (m, 5H), 7.47-7.42 (m, 2H), 7.40-7.37 (m, 4H), 2.41 (s, 6H) | 717.30 | 717.29 |
| 3C | δ = 8.59-8.54 (m, 2H), 8.49-8.45 (m, 3H), 8.36-8.34 (m, 1H), 8.26-8.23 (m, 1H), 7.96-7.86 (m, 3H), 7.77-7.74 (dd, 1H), 7.71-7.69 (dd, 1H), 7.65-7.58 (m, 3H), 7.53-7.41 (m, 7H), 7.34-7.24 (m, 3H) | 571.19 | 571.20 |
| 5C | δ = 9.01-9.00 (m, 1H), 8.73-8.71 (m, 1H), 8.54-8.52 (m, 2H), 8.49-8.46 (m, 1H), 8.42-8.38 (m, 1H), 8.30-8.28 (m, 1H), 8.23-8.21 (dd, 2H), 8.07-8.05 (m, 1H), 8.00-7.97 (dd, 2H), 7.95-7.87 (m, 3H), 7.66-7.58 (m, 3H), 7.52-7.48 (m, 1H), 7.45-7.41 (m, 3H), 7.39-7.30 (m, 4H) | 558.22 | 558.21 |
| 6C | δ = 8.82-8.80 (m, 1H), 8.53-8.49 (m, 2H), 8.47-8.44 (m, 1H), 8.11-8.09 (m, 1H), 7.95-7.85 (m, 6H), 7.78-7.72 (m, 4H), 7.65-7.60 (m, 3H), 7.56-7.51 (m, 2H), 7.45-7.40 (m, 7H) | 582.20 | 582.19 |
| 11C | δ = 8.92-8.91 (m, 1H), 8.75-8.73 (m, 1H), 8.66-8.64 (m, 1H), 8.61-8.59 (m, 1H), 8.57-8.56 (m, 1H), 8.47-8.43 (m, 2H), 8.40-8.35 (m, 2H), 8.27-8.25 (m, 1H), 8.20-8.18 (m, 3H), 8.09-8.05 (m, 1H), 7.95-7.91 (m, 1H), 7.88-7.86 (m, 1H), 7.81-7.79 (m, 1H), 7.69-7.67 (m, 1H), 7.56-7.54 (m, 1H), 7.45-7.42 (m, 2H), 7.39-7.36 (m, 1H) | 506.19 | 506.18 |
| 16C | δ = 8.69-8.67 (m, 2H), 8.57-8.55 (m, 1H), 8.48-8.47 (m, 1H), 8.45-8.42 (m, 1H), 8.39-8.37 (m, 1H), 8.29 (t, 1H), 8.24-8.19 (m, 3H), 7.95-7.92 (m, 3H), 7.88-7.87 (m, 1H), 7.85 (d, 1H), 7.62-7.58 (m, 2H), 7.54-7.50 (m, 2H), 7.46-7.42 (m, 3H) | 522.15 | 522.14 |
| 18C | δ = 9.02-9.01 (m, 1H), 8.92-8.90 (m, 1H), 8.81-8.79 (m, 1H), 8.70-8.68 (m, 4H), 8.53-8.52 (m, 1H), 8.27-8.24 (m, 3H), 8.17-8.15 (m, 2H), 8.04-8.01 (m, 2H), 7.83-7.80 (dd, 1H), 7.72-7.68 (m, 1H), 7.54-7.51 (m, 4H), 7.48-7.36 (m, 6H) | 637.24 | 637.23 |
| 27C | δ = 9.01-8.99 (dd, 1H), 8.81-8.79 (m, 1H), 8.61-8.60 (m, 1H), 8.56-8.54 (m, 1H), 8.49-8.43 (m, 3H), 8.33-8.26 (m, 3H), 8.23-8.20 (m, 1H), 7.95-7.87 (m, 5H), 7.66-7.59 (m, 4H), 7.47-7.35 (m, 8H) | 608.25 | 608.23 |
| 32C | δ = 8.97-8.95 (dd, 1H), 8.80-8.78 (m, 1H), 8.62-8.60 (m, 1H), 8.57-8.54 (m, 1H), 8.49-8.45 (m, 1H), 8.38-8.36 (dd, 1H), 8.33-8.30 (m, 1H), 8.27 (t, 1H), 8.23-8.21 (dd, 1H), 8.13-8.11 (m, 1H), 7.95-7.85 (m, 6H), 7.68-7.55 (m, 8H), 7.47-7.41 (m, 4H), 7.37-7.33 (m, 4H) | 684.25 | 684.26 |
| 40C | δ = 8.81-8.78 (m, 1H), 8.61-8.60 (m, 1H), 8.57-8.54 (m, 1H), 8.49-8.46 (m, 1H), 8.32-8.30 (m, 1H), 8.14-8.10 (m, 1H), 7.95-7.87 (m, 5H), 7.79-7.75 (m, 2H), 7.69-7.60 (m, 8H), 7.57-7.54 (m, 2H), 7.52-7.39 (m, 9H), 7.37-7.33 (m, 4H) | 757.26 | 757.25 |
| 47C | δ = 9.00 (t, 1H), 8.85 (t, 1H), 8.81-8.78 (m, 4H), 8.66-8.62 (m, 2H), 8.59 (t, 1H), 8.56-8.54 (m, 1H), 8.49-8.45 (m, 1H), 8.33-8.28 (m, 2H), 8.20-8.15 (m, 2H), 7.95-7.84 (m, 4H), 7.77-7.73 (m, 1H), 7.66-7.59 (m, 4H), 7.55-7.51 (m, 2H), 7.45-7.41 (m, 5H) | 739.26 | 739.27 |
| 52C | δ = 8.72 (t, 1H), 8.69-8.67 (m, 2H), 8.64-8.60 (m, 1H), 8.60 (t, 1H), 8.58-8.54 (m, 2H), 8.48-8.45 (m, 1H), 8.26-8.23 (m, 1H), 8.21-8.19 (m, 1H), 8.18-8.17 (m, 2H), 8.10-8.08 (m, 2H), 8.00-7.97 (m, 2H), 7.95-7.87 (m, 3H), 7.74-7.70 (m, 2H), 7.68-7.59 (m, 7H), 7.51-7.47 (m, 2H), 7.45-7.38 (m, 6H) | 788.30 | 788.29 |
| 55C | δ = 9.02-8.99 (m, 1H), 8.73 (t, 1H), 8.63-8.54 (m, 5H), 8.49-8.45 (m, 1H), 8.27-8.24 (m, 2H), 8.18-8.11 (m, 5H), 7.95-7.87 (m, 3H), 7.66-7.60 (m, 3H), 7.52-7.49 (m, 4H), 7.45-7.41 (m, 4H), 1.31 (s, 18H) | 801.38 | 801.38 |
| 8D | δ = 8.83-8.81 (m, 2H), 8.68-8.65 (m, 2H), 8.59-8.57 (m, 3H), 8.26-8.23 (m, 2H), 8.06-8.02 (m, 3H), 7.97 (d, 2H), 7.88-7.81 (m, 6H), 7.75-7.69 (m, 1H), 7.67-7.61 (m, 6H), 7.57-7.53 (m, 2H), 7.47-7.44 (m, 2H), 7.31-7.28 (m, 2H) | 711.26 | 711.27 |
| 20D | δ = 8.80-8.74 (m, 6H), 8.71 (t, 1H), 8.68 (t, 1H), 8.61-8.59 (m, 1H), 8.27-8.25 (m, 1H), 8.20 (t, 1H), 7.90-7.82 (m, 4H), 7.75-7.70 (m, 3H), 7.65-7.60 (m, 5H), 7.55-7.51 (m, 4H), 7.45-7.39 (m, 5H) | 688.27 | 688.26 |

Example 1

A 15 Ω/cm² (1,200 Å) ITO glass substrate (manufactured by Corning) was cut into a size of 50 mm×50 mm×0.7 mm and ultrasonically washed out with isopropyl alcohol and pure water, each for 5 minutes. Afterwards, the ITO glass substrate was irradiated by UV for 30 minutes, cleaned by exposing to ozone, and then, transported to a vacuum evaporator.

ADN as a host and 4,4'-bis[2-(4-(N,N-diphenylamino)phenyl)vinyl]biphenyl (hereinafter, referred to as DPAVBi) as a dopant were co-deposited on the HTL at a weight ratio of 98:2 to form an emission layer having a thickness of 300 Å.

Compound 2A was vacuum deposited on the emission layer to form an ETL having a thickness of 300 Å, and LiF was vacuum deposited on the ETL to form an EIL having a thickness of 10 Å. Then, Al was vacuum deposited on the EIL to form a cathode having a thickness of 3,000 Å, thereby manufacturing an organic light-emitting device.

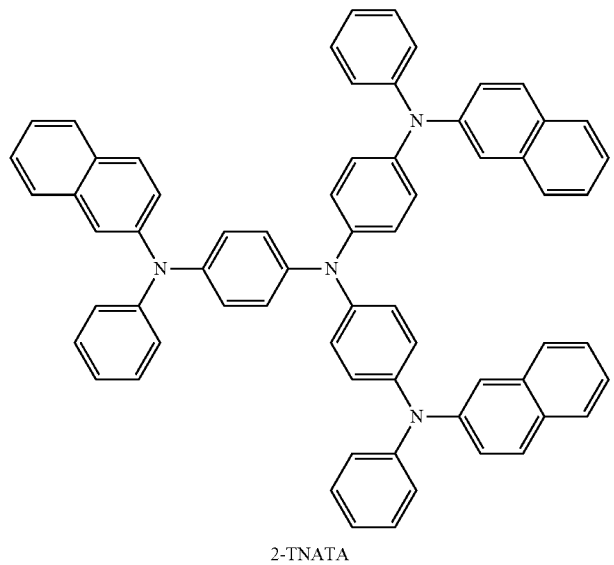

2-TNATA

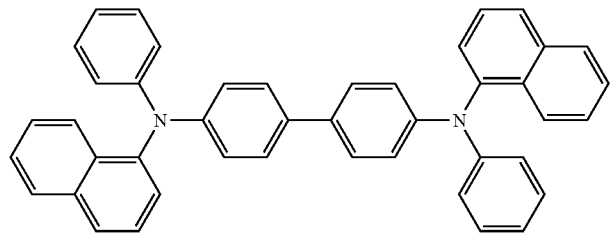

NPB

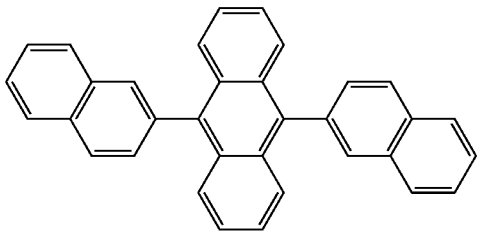

ADN

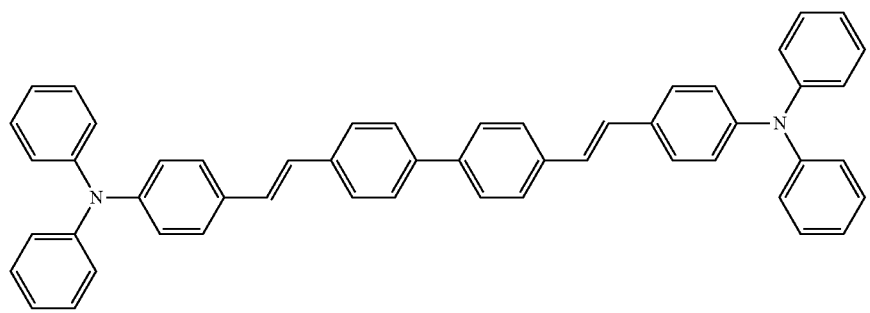

DPAVBi

2-TNATA was vacuum deposited on the ITO anode to form an HIL having a thickness of 600 Å. 4,4'-bis[N-(1-naphthyl)-N-phenylamino]biphenyl (hereinafter, referred to as NPB) was vacuum deposited on the HIL to form an HTL having a thickness of 300 Å.

Examples 2 to 21 and Comparative Examples 1 to 3

Organic light-emitting devices were manufactured in the same manner as in Example 1, except that in forming the ETL, the compounds shown in Table 2 below were used, respectively, instead of Compound 2A.

Evaluation Example 1

The organic light-emitting devices of Examples 1 to 21 and Comparative Examples 1 to 3 were evaluated in terms of driving voltage, current density, brightness, emission color, efficiency, and half-lifespan (@100 mA/cm$^2$) by using PR650 Spectroscan Source Measurement Unit. (manufactured by PhotoResearch Company). The results are shown in Table 2 below.

TABLE 2

|  | Electron transport layer | Driving voltage (V) | Current density (mA/cm$^2$) | Brightness (cd/m$^2$) | Efficiency (cd/A) | Emission color | Half-lifespan (hr @ 100 mA/cm$^2$) |
|---|---|---|---|---|---|---|---|
| Example 1 | Compound 2A | 5.53 | 50 | 3,185 | 6.37 | Blue | 268 hr |
| Example 2 | Compound 14A | 5.95 | 50 | 3,005 | 6.01 | Blue | 302 hr |
| Example 3 | Compound 21A | 6.04 | 50 | 3,075 | 6.15 | Blue | 342 hr |
| Example 4 | Compound 35A | 6.01 | 50 | 3,160 | 6.32 | Blue | 277 hr |
| Example 5 | Compound 61A | 5.45 | 50 | 3,210 | 6.42 | Blue | 271 hr |
| Example 6 | Compound 1B | 5.84 | 50 | 3,175 | 6.35 | Blue | 289 hr |
| Example 7 | Compound 18B | 6.08 | 50 | 3,035 | 6.07 | Blue | 298 hr |
| Example 8 | Compound 21B | 5.48 | 50 | 3,485 | 6.97 | Blue | 280 hr |
| Example 9 | Compound 25B | 5.95 | 50 | 3,090 | 6.18 | Blue | 341 hr |
| Example 10 | Compound 26B | 5.88 | 50 | 3,110 | 6.22 | Blue | 326 hr |
| Example 11 | Compound 29B | 5.76 | 50 | 3,155 | 6.31 | Blue | 346 hr |
| Example 12 | Compound 32B | 5.93 | 50 | 3,145 | 6.29 | Blue | 395 hr |
| Example 13 | Compound 37B | 5.95 | 50 | 3,095 | 6.19 | Blue | 312 hr |
| Example 14 | Compound 44B | 5.47 | 50 | 3,125 | 6.25 | Blue | 281 hr |
| Example 15 | Compound 45B | 5.42 | 50 | 3,085 | 6.17 | Blue | 294 hr |
| Example 16 | Compound 62B | 5.52 | 50 | 3,310 | 6.62 | Blue | 279 hr |
| Example 17 | Compound 11C | 5.91 | 50 | 3,155 | 6.31 | Blue | 299 hr |
| Example 18 | Compound 18C | 5.76 | 50 | 3,110 | 6.22 | Blue | 303 hr |
| Example 19 | Compound 27C | 5.72 | 50 | 3,040 | 6.08 | Blue | 266 hr |
| Example 20 | Compound 47C | 5.68 | 50 | 3,090 | 6.18 | Blue | 270 hr |
| Example 21 | Compound 8D | 5.60 | 50 | 3,250 | 6.46 | Blue | 305 hr |
| Comparative Example 1 | Alq$_3$ | 7.35 | 50 | 2,065 | 4.13 | Blue | 145 hr |
| Comparative Example 2 | Compound D | 6.65 | 50 | 2,825 | 5.65 | Blue | 218 hr |
| Comparative Example 3 | Compound F | 6.54 | 50 | 2,730 | 5.46 | Blue | 264 hr |

-continued
2A
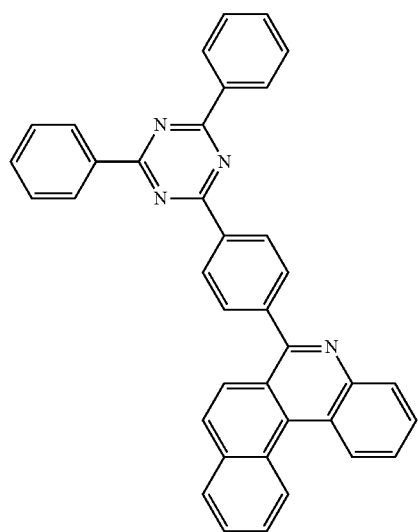
35A
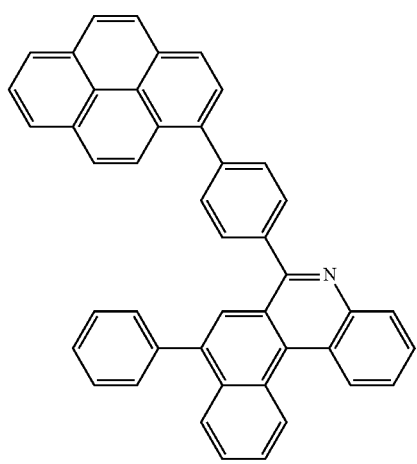
14A
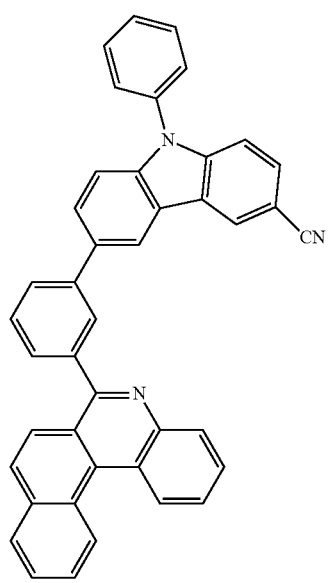
61A
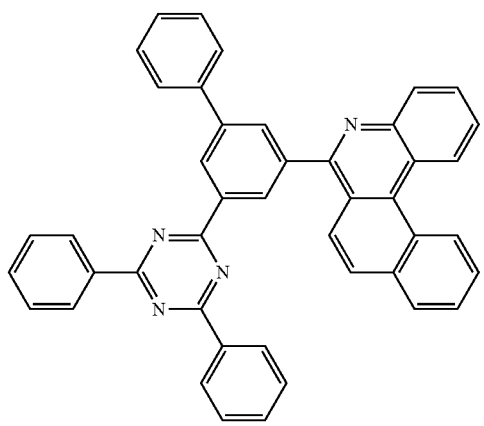
21A
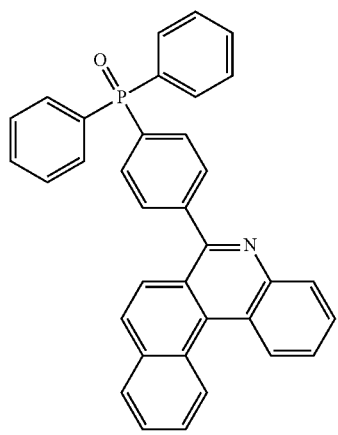
1B
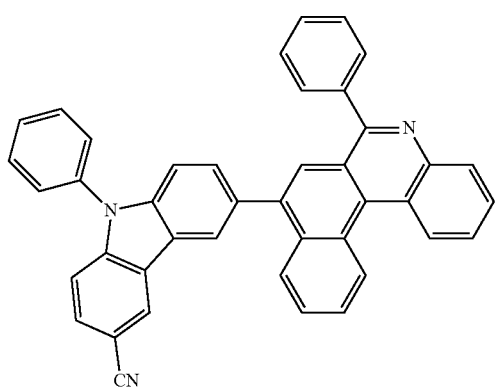

-continued
18B
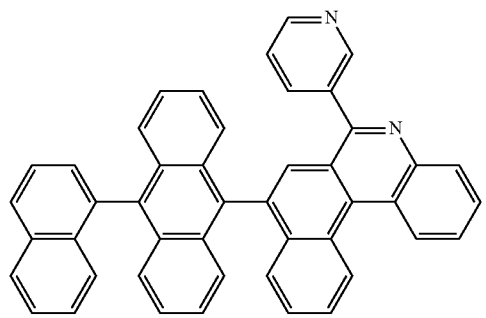
21B
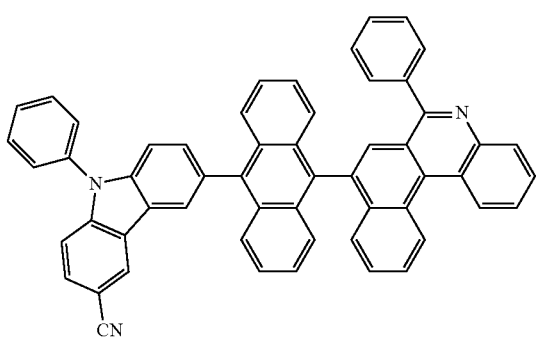
25B
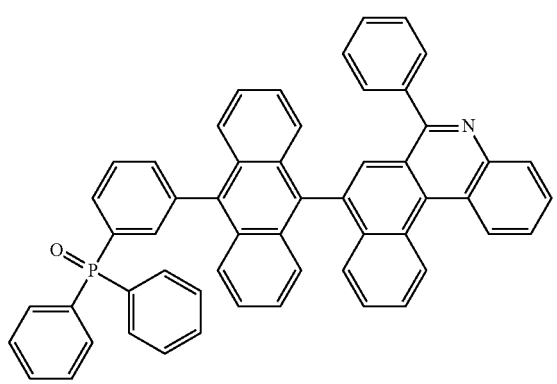
26B
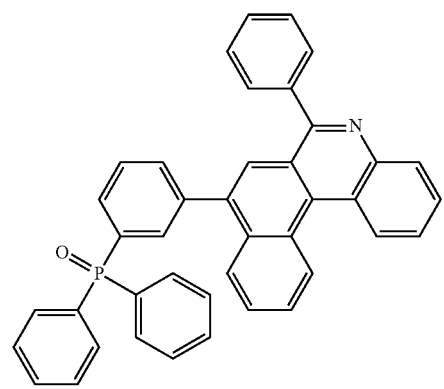
-continued
29B
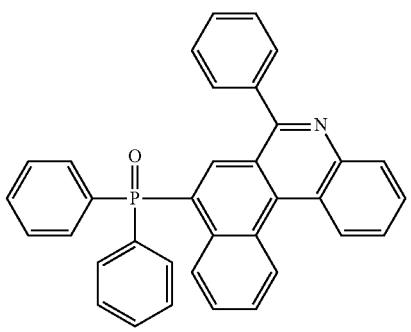
32B
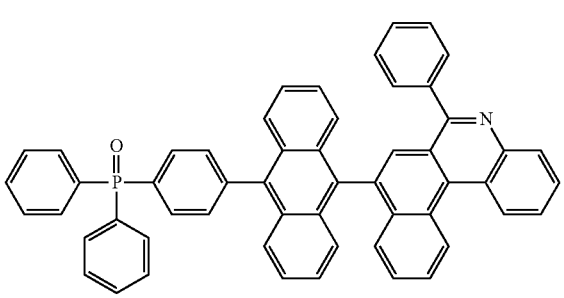
37B
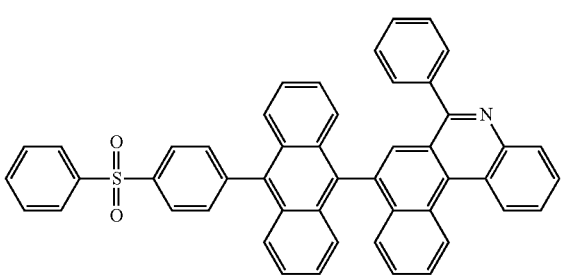
44B
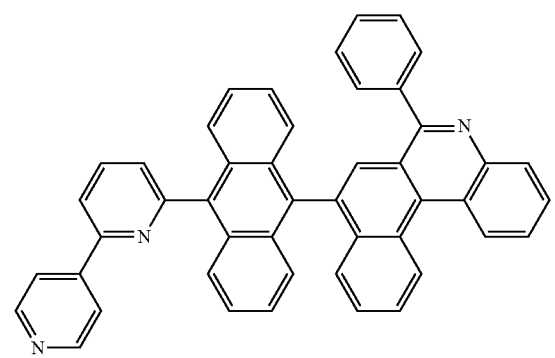

45B
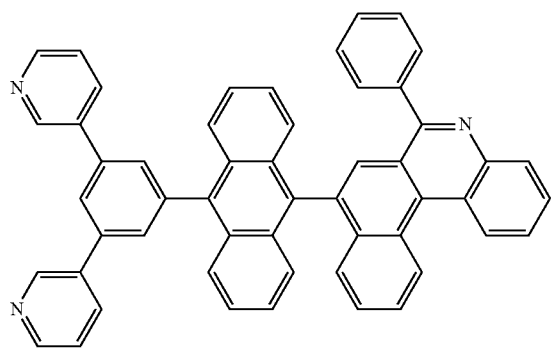
62B
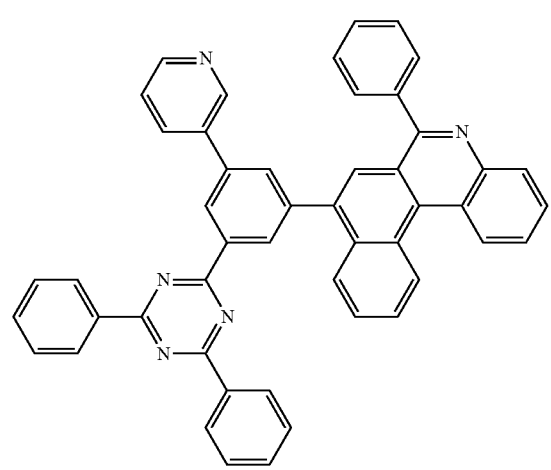
11C
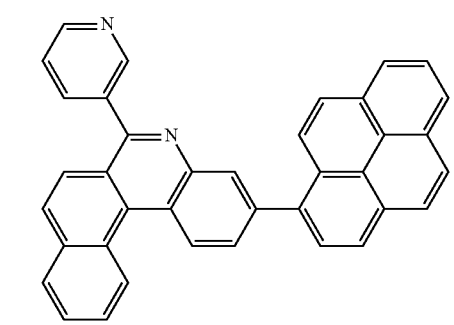
18C
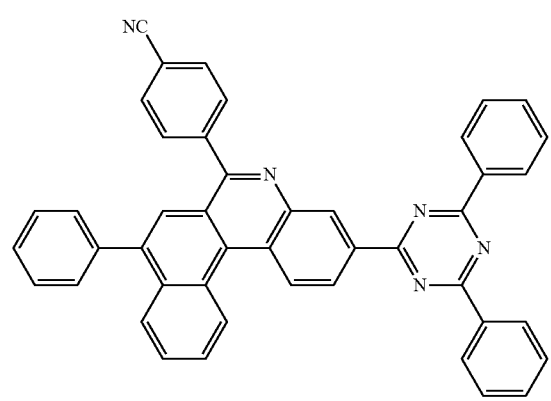
27C
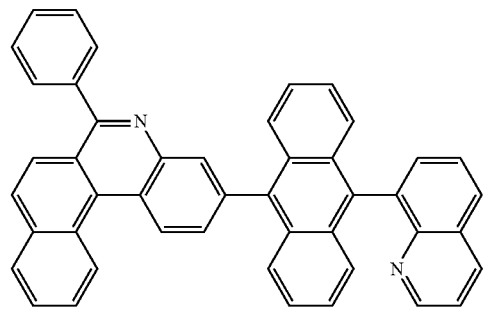
47C
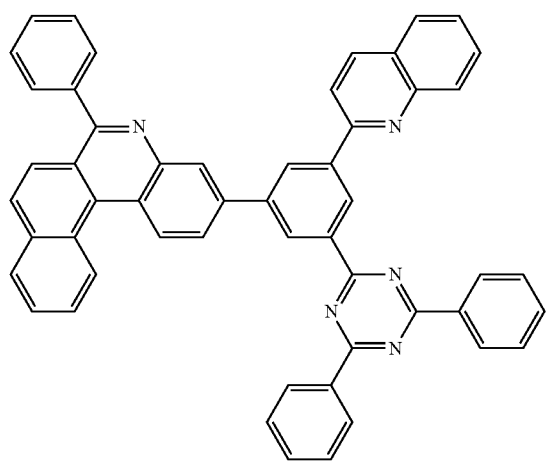
8D
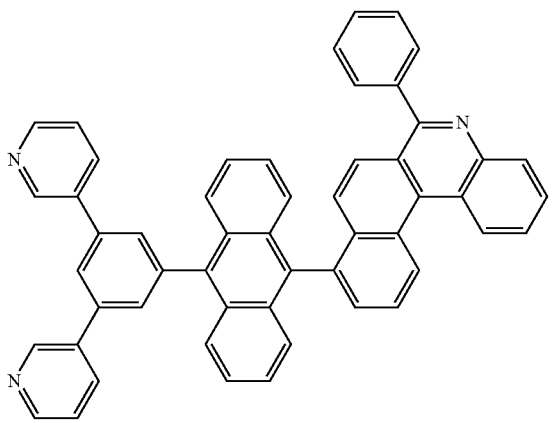
<Compound D>
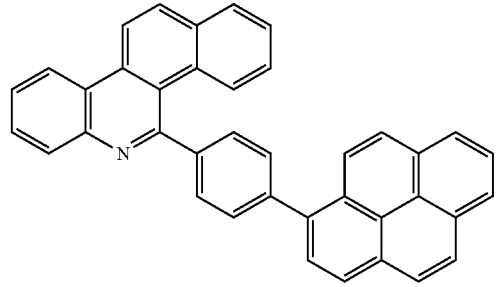

<Compound F>

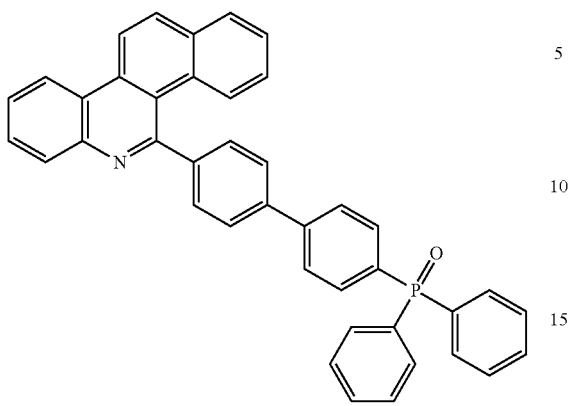

Referring to Table 2, above, it may be seen that the organic light-emitting devices of Examples 1 to 21 had excellent characteristics, such as low driving voltage, high brightness, high efficiency, and long lifespan, as compared with those of the organic light-emitting devices of Comparative Examples 1 to 3.

As described above, according to the embodiments, an organic light-emitting device including a condensed cyclic compound represented by one of the disclosed Formulae may have low driving voltage, high efficiency, high brightness, and long lifespan.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A condensed cyclic compound represented by one of Formulae 1-1 to 1-8, below:

<Formula 1-1>

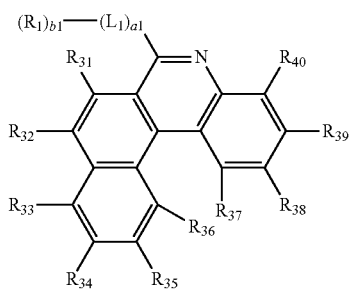

<Formula 1-2>

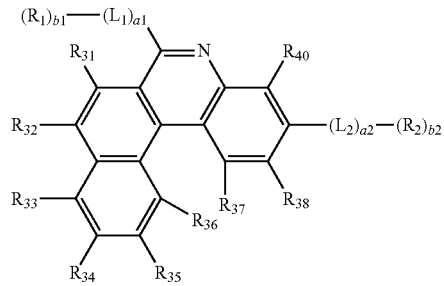

<Formula 1-3>

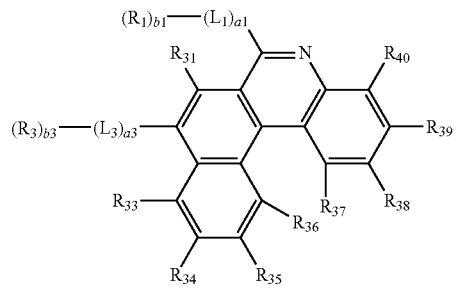

<Formula 1-4>

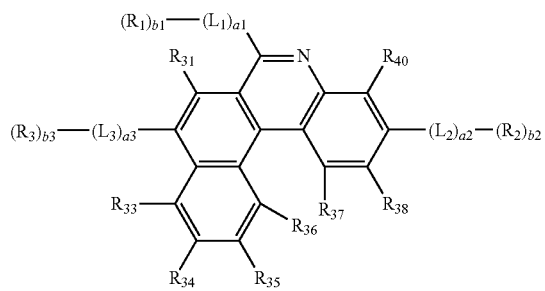

<Formula 1-5>

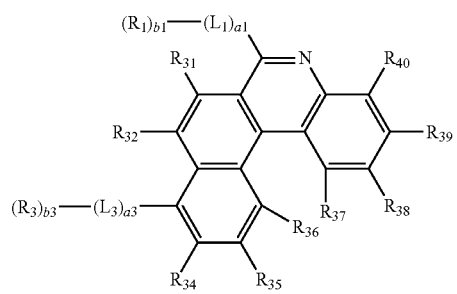

<Formula 1-6>

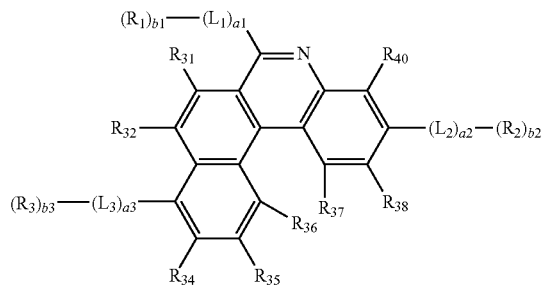

-continued

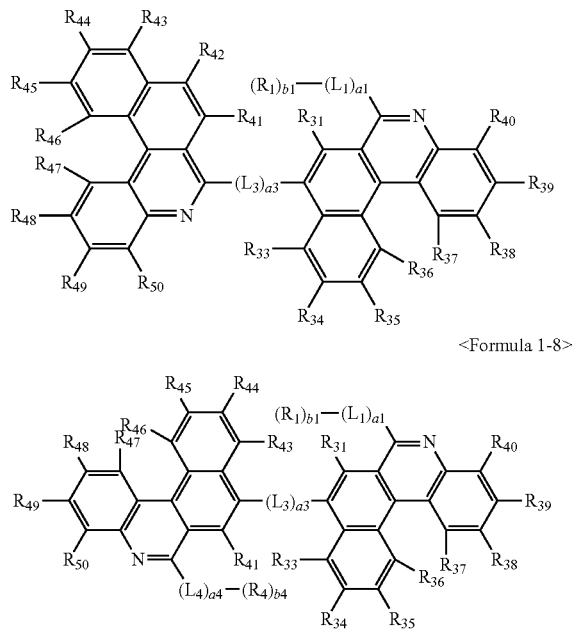

<Formula 1-7>

<Formula 1-8> wherein, in Formulae 1-2 to 1-8, $L_1$ to $L_4$ are each independently selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, a substituted or unsubstituted $C_6$-$C_{60}$ arylene group, a substituted or unsubstituted $C_1$-$C_{60}$ heteroarylene group, a substituted or unsubstituted divalent non-aromatic condensed polycyclic group, a substituted or unsubstituted divalent non-aromatic condensed heteropolycyclic group, *—P(=O)$R_{10}$—*', *—P(=S)$R_{11}$—*', *—S(=O)—*', and *—S(=O)$_2$—*', a1 to a4 are each independently an integer selected from 1 to 5, $R_1$ to $R_4$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, *—P(=O)($R_{12}$)($R_5$), *—P(=S)($R_6$)($R_7$), *—S(=O)($R_8$), and *—S(=O)$_2$($R_9$), b1 to b4 are each independently an integer selected from 0 to 5, $R_5$ to $R_{12}$ are each independently selected from a hydrogen, a deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_{31}$ to $R_{50}$ are each independently selected from:
a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; and
a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof,

* and *' indicate binding sites to neighboring atoms, wherein, in Formula 1-1, $L_1$ is selected from a substituted or unsubstituted $C_3$-$C_{10}$ cycloalkylene group, a substituted or unsubstituted $C_1$-$C_{10}$ heterocycloalkylene group, a substituted or unsubstituted $C_3$-$C_{10}$ cycloalkenylene group, a substituted or unsubstituted $C_1$-$C_{10}$ heterocycloalkenylene group, an unsubstituted $C_6$-$C_{60}$ arylene group, a substituted or unsubstituted $C_1$-$C_{60}$ heteroarylene group, a substituted or unsubstituted divalent non-aromatic condensed polycyclic group, a substituted or unsubstituted divalent non-aromatic condensed heteropolycyclic group, *—P(=O)$R_{10}$—*', *—P(=S)$R_{11}$—*', *—S(=O)—*', and *—S(=O)$_2$—*', a1 is an integer selected from 1 to 5, $R_1$ is a hydrogen, a deuterium, —F, —Cl, —Br, —I, a cyano group, a nitro group, an amino group, an amidino group, a hydrazine group, a hydrazone group, a carboxylic acid or a salt thereof, a sulfonic acid or a salt thereof, a phosphoric acid or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_6$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, a substituted or unsubstituted monovalent non-aromatic condensed heteropolycyclic group, *—P(=O)($R_{12}$)($R_5$), *—P(=S)($R_6$) ($R_7$), *—S(=O)($R_8$), and *—S(=O)$_2$($R_9$), b1 is an integer selected from 0 to 5, $R_5$ to $R_{12}$ are each independently selected from a hydrogen, a deuterium, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{10}$ cycloalkyl group, a substituted or unsubstituted $C_1$-$C_{10}$ heterocycloalkyl group, a substituted or unsubstituted $C_3$-$C_{10}$ cycloalkenyl group, a substituted or unsubstituted $C_1$-$C_{10}$ heterocycloalkenyl group, a substituted or unsubstituted $C_6$-$C_{60}$ aryl group, a substituted or unsubstituted $C_0$-$C_{60}$ aryloxy group, a substituted or unsubstituted $C_6$-$C_{60}$ arylthio group, a substituted or unsubstituted $C_1$-$C_{60}$ heteroaryl group, a substituted or unsubstituted monovalent non-aromatic condensed polycyclic group, and a substituted or unsubstituted monovalent non-aromatic condensed heteropolycyclic group, $R_{31}$ to $R_{40}$ are each independently selected from:
  a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{60}$ alkyl group, a $C_2$-$C_{60}$ alkenyl group, a $C_2$-$C_{60}$ alkynyl group, and a $C_1$-$C_{60}$ alkoxy group; and
  a $C_1$-$C_{60}$ alkyl group, a $C_2$-$C_{60}$ alkenyl group, a $C_2$-$C_{60}$ alkynyl group, and a $C_1$-$C_{60}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof,

* and *' indicate binding sites to neighboring atoms, and wherein the condensed cyclic compound represented by Formula 1-1 above excludes compounds shown below:

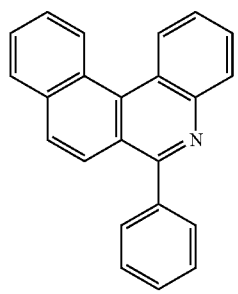

-continued

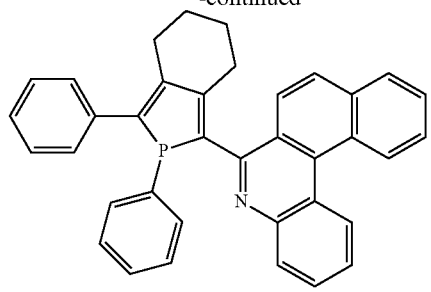

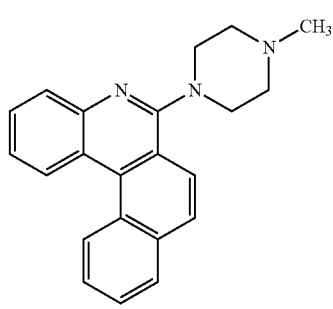

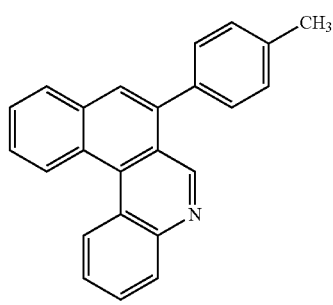

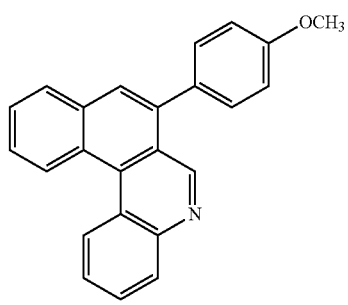

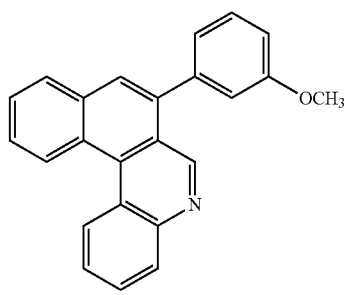

-continued

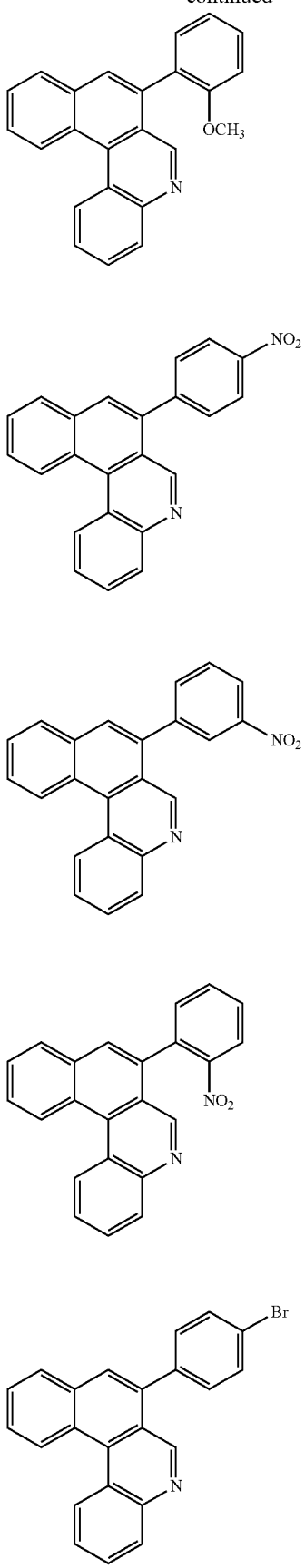

-continued

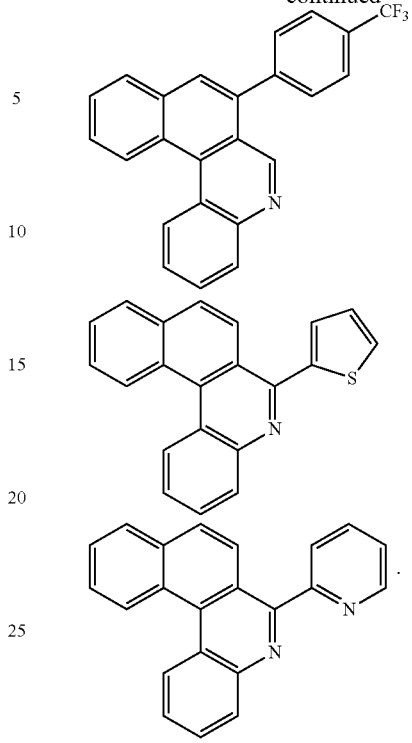

2. The condensed cyclic compound as claimed in claim 1, wherein $L_1$ to $L_4$ in Formulae 1-2 to 1-8 are each independently selected from:

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, an imidazopyrimidinylene group, a benzoxanthenylene group, a benzonaphthofuranylene group, and a dinaphthofuranylene group;

a phenylene group, a pentalenylene group, an indenylene group, a naphthylene group, an azulenylene group, a heptalenylene group, an indacenylene group, an acenaphthylene group, a fluorenylene group, a spiro-fluorenylene group, a benzofluorenylene group, a dibenzofluorenylene group, a phenalenylene group, a phenanthrenylene group, an anthracenylene group, a fluoranthenylene group, a triphenylenylene group, a pyrenylene group, a chrysenylene group, a naphthacenylene group, a picenylene group, a perylenylene group, a pentaphenylene group, a hexacenylene group, a pentacenylene group, a rubicenylene group, a coronenylene group, an ovalenylene group, a pyrrolylene group, a thiophenylene group, a furanylene group, an imidazolylene group, a pyrazolylene group, a thiazolylene group, an isothiazolylene group, an oxazolylene group, an isooxazolylene group, a pyridinylene group, a pyrazinylene group, a pyrimidinylene group, a pyridazinylene group, an isoindolylene group, an indolylene group, an indazolylene group, a purinylene group, a quinolinylene group, an isoquinolinylene group, a benzoquinolinylene group, a phthalazinylene group, a naphthyridinylene group, a quinoxalinylene group, a quinazolinylene group, a cinnolinylene group, a carbazolylene group, a phenanthridinylene group, an acridinylene group, a phenanthrolinylene group, a phenazinylene group, a benzoimidazolylene group, a benzofuranylene group, a benzothiophenylene group, an isobenzothiazolylene group, a benzooxazolylene group, an isobenzooxazolylene group, a triazolylene group, a tetrazolylene group, an oxadiazolylene group, a triazinylene group, a dibenzofuranylene group, a dibenzothiophenylene group, a benzocarbazolylene group, a dibenzocarbazolylene group, a thiadiazolylene group, an imidazopyridinylene group, an imidazopyrimidinylene group, a benzoxanthenylene group, a benzonaphthofuranylene group, and a dinaphthofuranylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a biphenyl group, a terphenyl group, a phenyl group substituted with a $C_1$-$C_{20}$ alkyl group, and —Si($Q_{31}$)($Q_{32}$)($Q_{33}$); and

*—P(=O)$R_{10}$—*', *—P(=S)$R_{11}$—*', *—S(=O)—*', and *—S(=O)$_2$—*', wherein $Q_{31}$ to $Q_{33}$, $R_{10}$, and $R_{11}$ are each independently selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, an imidazopyrimidinyl group, a biphenyl group, a terphenyl group, and a phenyl group substituted with a $C_1$-$C_{20}$ alkyl group, and * and *' indicate binding sites to neighboring atoms.

3. The condensed cyclic compound as claimed in claim 1, wherein $L_1$ to $L_4$ in Formulae 1-2 to 1-8 are each independently selected from:

a phenylene group, a naphthylene group, a fluorenylene group, a phenalenylene group, a phenanthrenylene group, an anthracenylene group, a triphenylenylene group, a pyrenylene group, a chrysenylene group, a pyridinylene group, a pyrazinylene group, a pyrimidinylene group, a quinolinylene group, an isoquinolinylene group, a quinoxalinylene group, a quinazolinylene group, a carbazolylene group, a triazinylene group, a dibenzofuranylene group, a dibenzothiophenylene group, a benzoxanthenylene group, and a dinaphthofuranylene group;

a phenylene group, a naphthylene group, a fluorenylene group, a phenalenylene group, a phenanthrenylene group, an anthracenylene group, a triphenylenylene group, a pyrenylene group, a chrysenylene group, a pyridinylene group, a pyrazinylene group, a pyrimidinylene group, a quinolinylene group, an isoquinolinylene group, a quinoxalinylene group, a quinazolinylene group, a carbazolylene group, a triazinylene group, a dibenzofuranylene group, a dibenzothiophenylene group, a benzoxanthenylene group, and a dinaphthofuranylene group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzoxanthenyl group, a dinaphthofuranyl group, a biphenyl group, a terphenyl group, a phenyl group substituted with a $C_1$-$C_{20}$ alkyl group, and —Si($Q_{31}$)($Q_{32}$)($Q_{33}$); and

*—P(=O)$R_{10}$—*', *—P(=S)$R_{11}$—*', *—S(=O)—*', and *—S(=O)$_2$—*', wherein $Q_{31}$ to $Q_{33}$ are each independently selected from a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and a phenyl group substituted with a $C_1$-$C_{20}$ alkyl group, $R_{10}$ and $R_{11}$ are each independently selected from a phenyl group, a naphthyl group, a fluorenyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzoxanthenyl group, a dinaphthofuranyl group, a biphenyl group, a terphenyl group, and a phenyl group substituted with a $C_1$-$C_{20}$ alkyl group, * and *' indicate binding sites to neighboring atoms.

4. The condensed cyclic compound as claimed in claim 1, wherein $L_1$ to $L_4$ in Formulae 1-2 to 1-8 are each independently selected from a group represented by Formulae 3-1 to 3-49 below, *—P(=O)$R_{10}$—*', *—P(=S)$R_{11}$—*', *—S(=O)—*', and *—S(=O)$_2$—*':

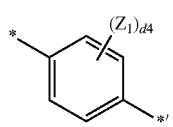

Formula 3-1

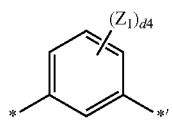

Formula 3-2

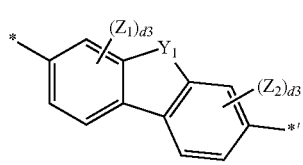

Formula 3-3

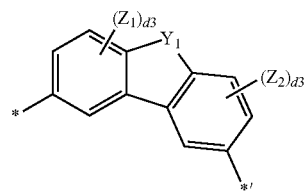

Formula 3-4

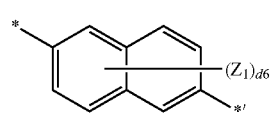

Formula 3-5

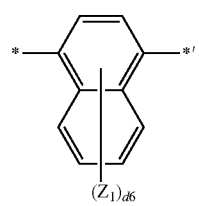

Formula 3-6

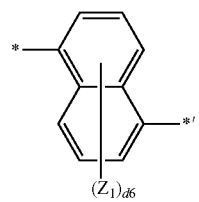

Formula 3-7

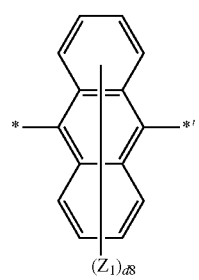

Formula 3-8

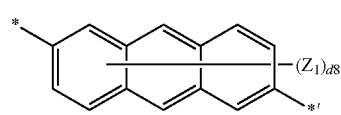

Formula 3-9

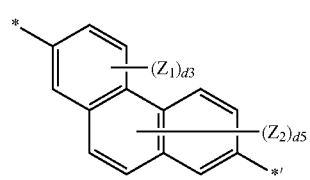

Formula 3-10

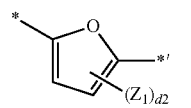

Formula 3-11

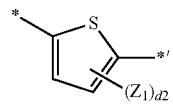

Formula 3-12

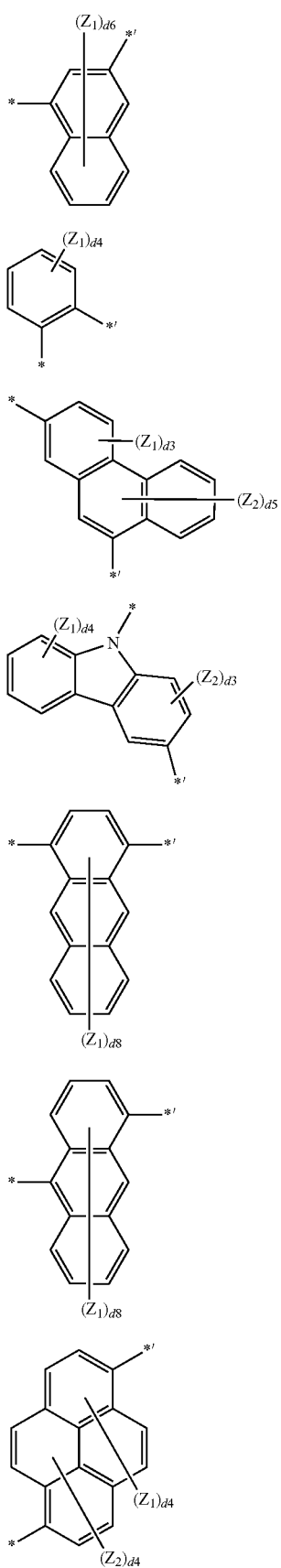
Formula 3-13
Formula 3-14
Formula 3-15
Formula 3-16
Formula 3-17
Formula 3-18
Formula 3-19
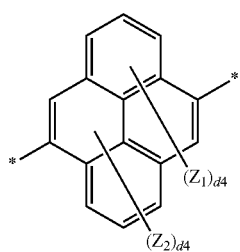
Formula 3-20
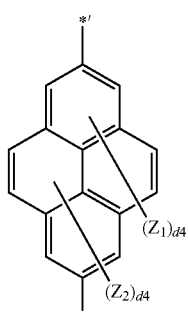
Formula 3-21
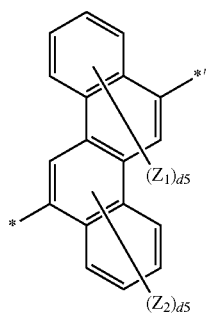
Formula 3-22
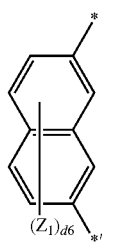
Formula 3-23
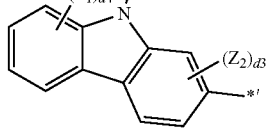
Formula 3-24
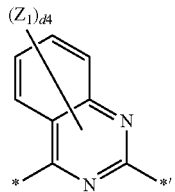
Formula 3-25

Formula 3-26
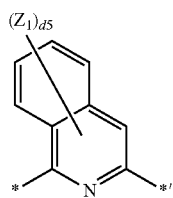
Formula 3-27
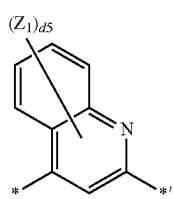
Formula 3-28
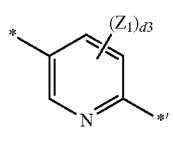
Formula 3-29
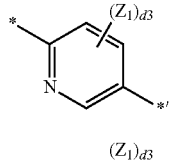
Formula 3-30
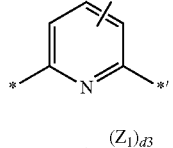
Formula 3-31
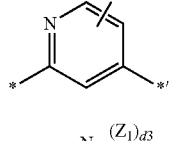
Formula 3-32
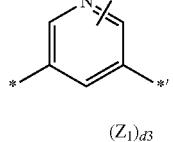
Formula 3-33
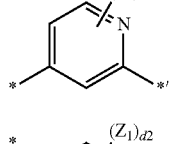
Formula 3-34
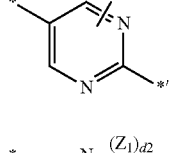
Formula 3-35
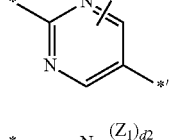
Formula 3-36
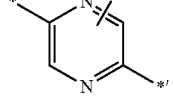
Formula 3-37
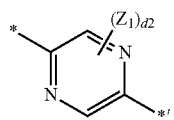
Formula 3-38
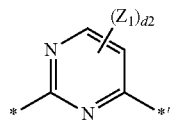
Formula 3-39
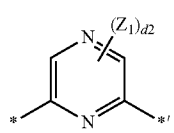
Formula 3-40
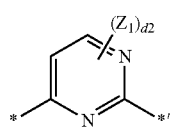
Formula 3-41
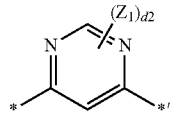
Formula 3-42
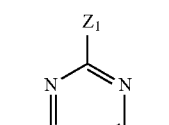
Formula 3-43
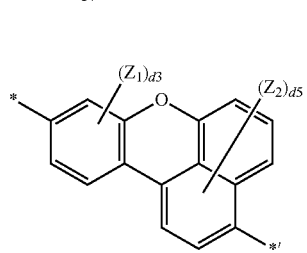
Formula 3-44
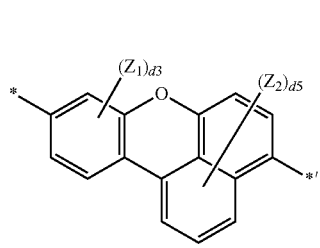
Formula 3-45
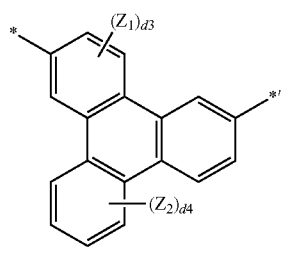

Formula 3-46

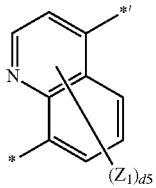

Formula 3-47

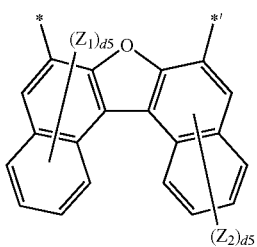

Formula 3-48

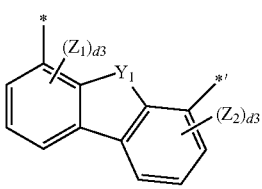

Formula 3-49

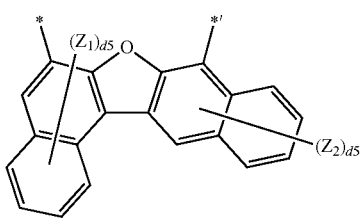

wherein, in Formulae 3-1 to 3-49, $Y_1$ is O, S, $C(Z_3)(Z_4)$, $N(Z_5)$, or $Si(Z_6)(Z_7)$;

$Z_1$ to $Z_7$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, a phenyl group substituted with a $C_1$-$C_{20}$ alkyl group, and —$Si(Q_{31})(Q_{32})(Q_{33})$, $Q_{31}$ to $Q_{33}$ are each independently selected from a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and a phenyl group substituted with a $C_1$-$C_{20}$ alkyl group, $R_{10}$ and $R_{11}$ are each independently selected from a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, an imidazopyrimidinyl group, a biphenyl group, a terphenyl group, and a phenyl group substituted with a $C_1$-$C_{20}$ alkyl group, d2 is 1 or 2,
d3 is an integer selected from 1 to 3,
d4 is an integer selected from 1 to 4,
d5 is an integer selected from 1 to 5,
d6 is an integer selected from 1 to 6,
d8 is an integer selected from 1 to 8, and
* and *' indicate binding sites to neighboring atoms.

5. The condensed cyclic compound as claimed in claim 1, wherein a1 to a4 are each independently 1 or 2.

6. The condensed cyclic compound as claimed in claim 1, wherein $R_1$ to $R_4$ in Formulae 1-2 to 1-8 and $R_1$ in Formula 1-1 are each independently selected from:

a hydrogen, a deuterium, —F, —Cl, —Br, —I, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a benzoxanthenyl group, a benzonaphthofuranyl group, and a dinaphthofuranyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a benzoxanthenyl group, a benzonaphthofuranyl group, and a dinaphthofuranyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a biphenyl group, a terphenyl group, a phenyl group substituted with a $C_1$-$C_{20}$ alkyl group, and —Si($Q_{31}$)($Q_{32}$)($Q_{33}$); and

*—P(=O)($R_{12}$)($R_5$), *—P(=S)($R_6$)($R_7$), *—S(=O)($R_8$), and *—S(=O)$_2$($R_9$), and wherein $Q_{31}$ to $Q_{33}$, $R_5$ to $R_9$ and $R_{12}$ are each independently selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, an imidazopyrimidinyl group, a biphenyl group, a terphenyl group, and a phenyl group substituted with a $C_1$-$C_{20}$ alkyl group, and * and *' indicate binding sites to neighboring atoms.

7. The condensed cyclic compound as claimed in claim 1, wherein $R_1$ to $R_4$ in Formulae 1-2 to 1-8 and $R_1$ in Formula 1-1 are each independently selected from:

a hydrogen, a deuterium, —F, —Cl, —Br, —I, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a phenyl group, a naphthyl group, a fluorenyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzoxanthenyl group, and a dinaphthofuranyl group;

a phenyl group, a naphthyl group, a fluorenyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzoxanthenyl group, and a dinaphthofuranyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzoxanthenyl group, a dinaphthofuranyl group, a biphenyl group, a terphenyl group, a phenyl group substituted with a $C_1$-$C_{20}$ alkyl group, and —Si($Q_{31}$)($Q_{32}$)($Q_{33}$); and

*—P(=O)($R_{12}$)($R_5$), *—P(=S)($R_6$)($R_7$), *—S(=O)($R_8$), and *—S(=O)$_2$($R_9$), wherein $Q_{31}$ to $Q_{33}$ are each independently selected from a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and a phenyl group substituted with a $C_1$-$C_{20}$ alkyl group, $R_5$ to $R_9$ and $R_{12}$ are each independently selected from a phenyl group, a naphthyl group, a fluorenyl group, a phenalenyl group, a phenanthrenyl group, an anthracenyl group, a triphenylenyl group, a pyrenyl group, a chrysenyl group, a pyridinyl group, a pyrazinyl group, a pyrimidinyl group, a quinolinyl group, an isoquinolinyl group, a quinoxalinyl group, a quinazolinyl group, a carbazolyl group, a triazinyl group, a dibenzofuranyl group, a dibenzothiophenyl group, a benzoxanthenyl group, a dinaphthofuranyl group, a biphenyl group, a terphenyl group, and a phenyl group substituted with a $C_1$-$C_{20}$ alkyl group, and * indicates a binding site to a neighboring atom.

8. The condensed cyclic compound as claimed in claim 1, wherein $R_1$ to $R_4$ in Formulae 1-2 to 1-8 and $R_1$ in Formula 1-1 are each independently selected from:

a hydrogen, a deuterium, —F, —Cl, —Br, —I, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, and a $C_1$-$C_{20}$ alkoxy group;

a $C_1$-$C_{20}$ alkyl group and a $C_1$-$C_{20}$ alkoxy group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, and a phosphoric acid or a salt thereof;

a group represented by one of Formulae 5-1 to 5-90 and 5-92 to 5-96 below; and

*—P(=O)($R_{12}$)($R_5$), *—P(=S)($R_6$)($R_7$), *—S(=O)($R_8$), and *—S(=O)$_2$($R_9$):

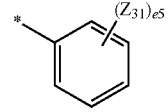

Formula 5-1

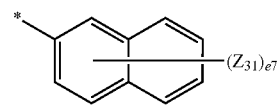

Formula 5-2

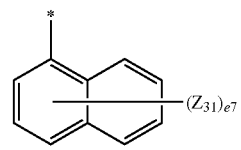

Formula 5-3

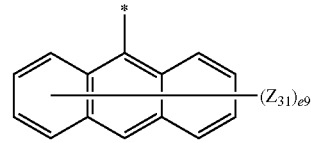

Formula 5-4

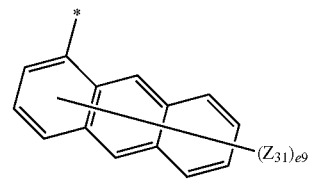

Formula 5-5

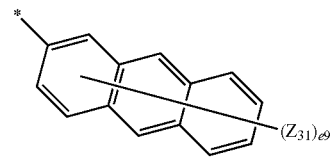

Formula 5-6

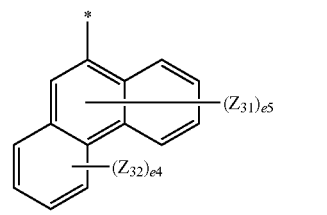

Formula 5-7

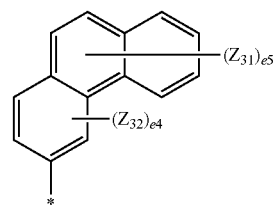

Formula 5-8

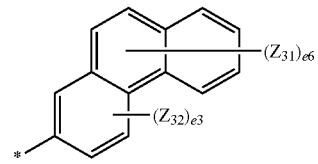

Formula 5-9

Formula 5-10
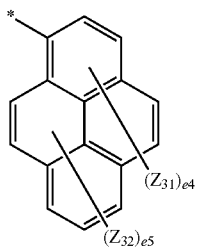
Formula 5-11
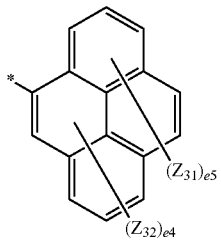
Formula 5-12
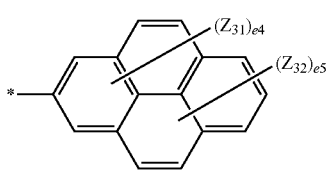
Formula 5-13
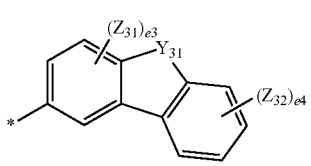
Formula 5-14
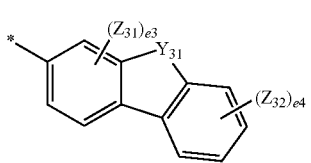
Formula 5-15
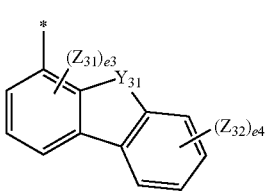
Formula 5-16
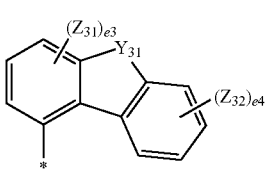
Formula 5-17
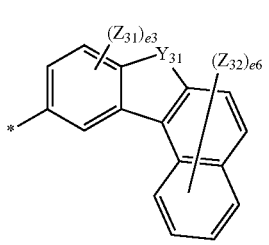
Formula 5-18
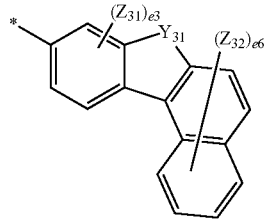
Formula 5-19
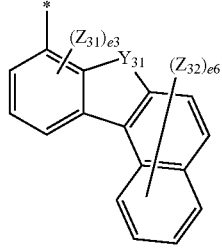
Formula 5-20
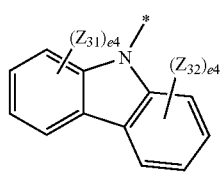
Formula 5-21
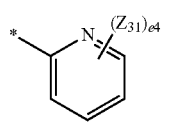
Formula 5-22
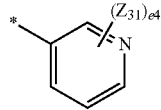
Formula 5-23
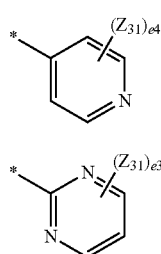
Formula 5-24
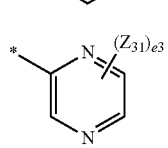
Formula 5-25
Formula 5-26
Formula 5-27
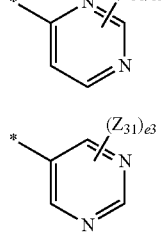

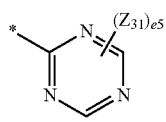
Formula 5-28
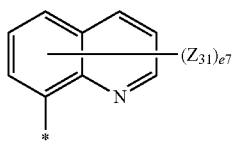
Formula 5-29
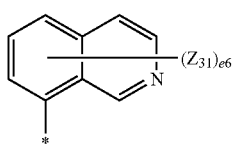
Formula 5-30
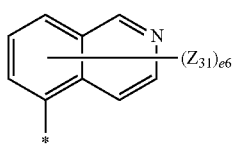
Formula 5-31
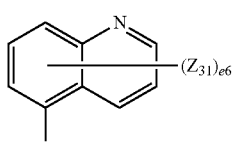
Formula 5-32
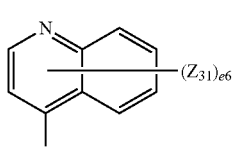
Formula 5-33
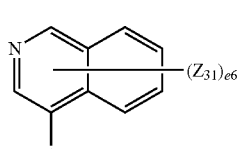
Formula 5-34
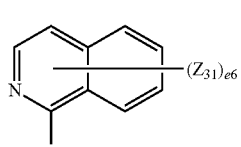
Formula 5-35
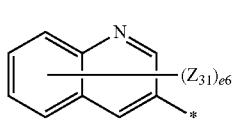
Formula 5-36
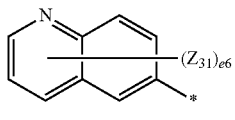
Formula 5-37
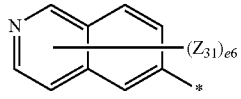
Formula 5-38
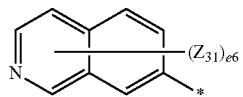
Formula 5-39
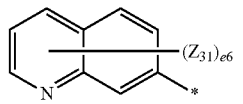
Formula 5-40
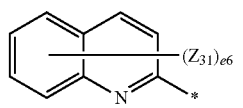
Formula 5-41
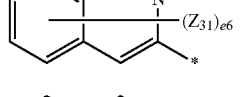
Formula 5-42
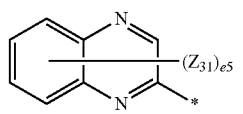
Formula 5-43
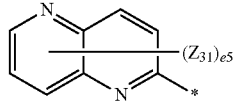
Formula 5-44
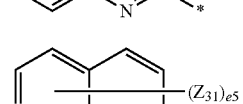
Formula 5-45
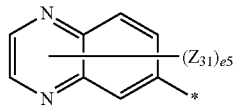
Formula 5-46
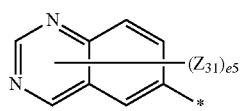
Formula 5-47
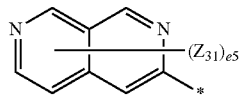
Formula 5-48
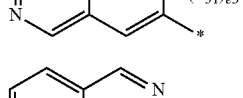
Formula 5-49
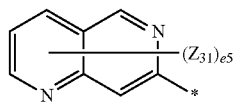
Formula 5-50
Formula 5-51
Formula 5-52

Formula 5-53
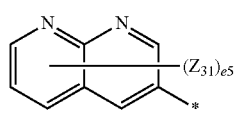
Formula 5-54
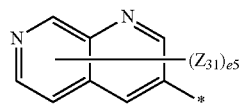
Formula 5-55
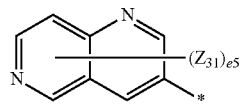
Formula 5-56
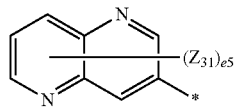
Formula 5-57
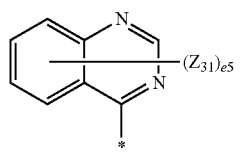
Formula 5-58
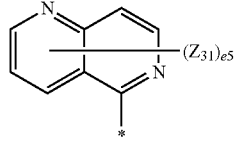
Formula 5-59
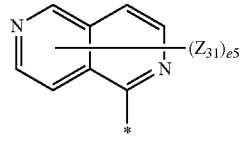
Formula 5-60
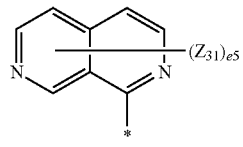
Formula 5-61
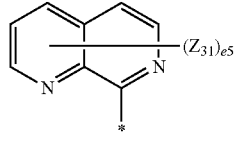
Formula 5-62
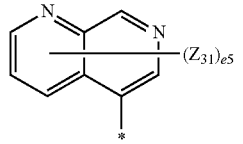
Formula 5-63
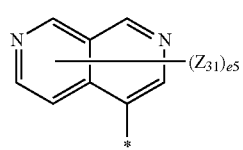
Formula 5-64
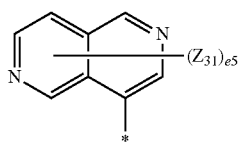
Formula 5-65
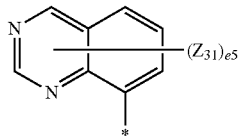
Formula 5-66
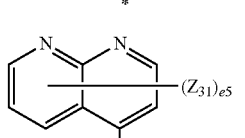
Formula 5-67
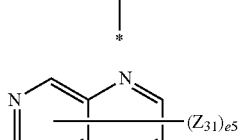
Formula 5-68
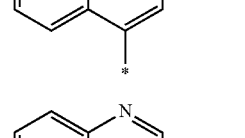
Formula 5-69
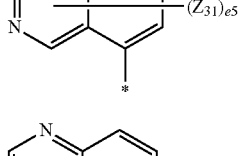
Formula 5-70
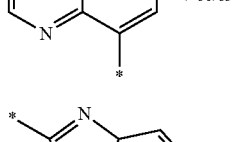
Formula 5-71
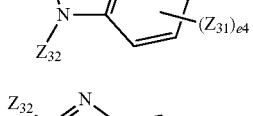
Formula 5-72
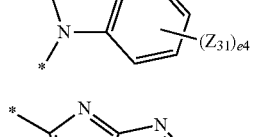
Formula 5-73
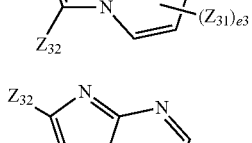
Formula 5-74
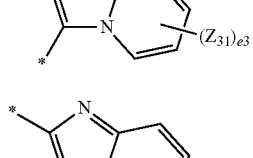

Formula 5-75

Formula 5-76

Formula 5-77

Formula 5-78

Formula 5-79

Formula 5-80

Formula 5-81

Formula 5-82

Formula 5-83

Formula 5-84

Formula 5-85

Formula 5-86

Formula 5-87

Formula 5-88

Formula 5-89

Formula 5-90

Formula 5-92

-continued

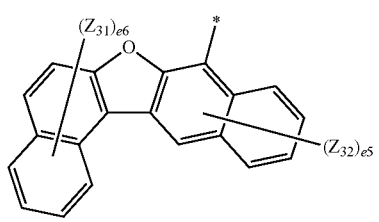

Formula 5-93

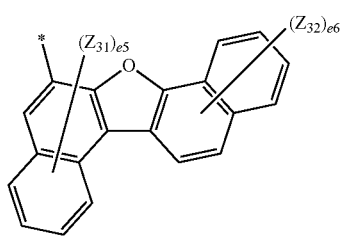

Formula 5-94

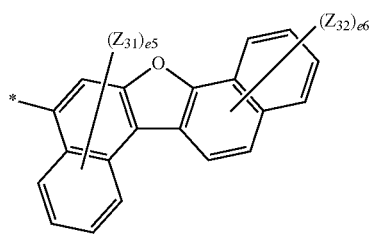

Formula 5-95

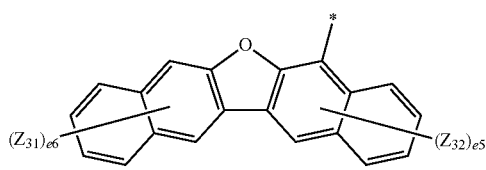

Formula 5-96 wherein in Formulae 5-1 to 5-90 and 5-92 to 5-96, $Y_{31}$ is O, S, $C(Z_{33})(Z_{34})$, $N(Z_{35})$, or $Si(Z_{36})(Z_{37})$, $Z_{31}$ to $Z_{37}$, $Z_{32a}$, and $Z_{32b}$ are each independently selected from a hydrogen, a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, a triazinyl group, a biphenyl group, a terphenyl group, a phenyl group substituted with a $C_1$-$C_{20}$ alkyl group, and —Si($Q_{31}$)($Q_{32}$)($Q_{33}$), wherein, $Q_{31}$ to $Q_{33}$ are each independently selected from a $C_1$-$C_{10}$ alkyl group, a $C_1$-$C_{10}$ alkoxy group, a phenyl group, a naphthyl group, a pyridinyl group, a pyrimidinyl group, a triazinyl group, a biphenyl group, a terphenyl group, and a phenyl group substituted with a $C_1$-$C_{20}$ alkyl group, $R_5$ to $R_9$ and $R_{12}$ are each independently selected from a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, an imidazopyrimidinyl group, a biphenyl group, a terphenyl group, and a phenyl group substituted with a $C_1$-$C_{20}$ alkyl group, e3 is an integer selected from 1 to 3,
e4 is an integer selected from 1 to 4,
e5 is an integer selected from 1 to 5,
e6 is an integer selected from 1 to 6,
e7 is an integer selected from 1 to 7,
e8 is an integer selected from 1 to 8,
e9 is an integer selected from 1 to 9, and
* indicates a binding site to a neighboring atom.

9. The condensed cyclic compound as claimed in claim 1, wherein b1 to b4 are each independently 0, 1, or 2.

10. The condensed cyclic compound as claimed in claim 1, wherein $R_{31}$ to $R_{50}$ are hydrogen.

11. The condensed cyclic compound as claimed in claim 1, wherein the condensed cyclic compound is represented by one of Formulae 1-3 to 1-8.

12. The condensed cyclic compound as claimed in claim 1, wherein:

the condensed cyclic compound is represented by Formula 1-1, and in Formula 1-1, $R_1$ is selected from:

a cyano group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a benzoxanthenyl group, a benzonaphthofuranyl group, and a dinaphthofuranyl group;

a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a benzoxanthenyl group, a benzonaphthofuranyl group, and a dinaphthofuranyl group, each substituted with at least one of a deuterium, —F, —Cl, —Br, —I, a hydroxyl group, a cyano group, a nitro group, an amino group, an amidino group, a hydrazine group, a hydrazone group, a carboxylic acid or a salt thereof, a sulfonic acid or a salt thereof, a phosphoric acid or a salt thereof, a $C_1$-$C_{20}$ alkyl group, a $C_1$-$C_{20}$ alkoxy group, a cyclopentyl group, a cyclohexyl group, a cycloheptyl group, a cyclopentenyl group, a cyclohexenyl group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, a picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, a dibenzocarbazolyl group, a thiadiazolyl group, an imidazopyridinyl group, an imidazopyrimidinyl group, a biphenyl group, a terphenyl group, a phenyl group substituted with a $C_1$-$C_{20}$ alkyl group, and —Si($Q_{31}$)($Q_{32}$)($Q_{33}$); and

*—P(=O)($R_{12}$)($R_5$), *—P(=S)($R_6$)($R_7$), *—S(=O)($R_8$), and *—S(=O)$_2$($R_9$), wherein $Q_{31}$ to $Q_{33}$, $R_5$ to $R_9$ and $R_{12}$ are each independently selected from a $C_1$-$C_{10}$ alkyl group, a $C_1$-$C_{10}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a triphenylenyl group, a pyrenyl group, a chrysenyl group, a pyrrolyl group, a thiophenyl group, a furanyl group, an imidazolyl group, a pyrazolyl group, a thiazolyl group, an isothiazolyl group, an oxazolyl group, an isooxazolyl group, a pyridinyl group, a pyrazinyl group, a pyrimidinyl group, a pyridazinyl group, a quinolinyl group, an isoquinolinyl group, a benzoquinolinyl group, a quinoxalinyl group, a quinazolinyl group, a carbazolyl group, a phenanthrolinyl group, a benzoimidazolyl group, a benzofuranyl group, a benzothiophenyl group, an isobenzothiazolyl group, a benzooxazolyl group, an isobenzooxazolyl group, a triazolyl group, an oxadiazolyl group, a triazinyl group, a dibenzofuranyl group, a dibenzothiophenyl group, a benzocarbazolyl group, a dibenzocarbazolyl group, a dibenzosilolyl group, a thiadiazolyl group, an imidazopyridinyl group, an imidazopyrimidinyl group, a biphenyl group, a terphenyl group, and a phenyl group substituted with a $C_1$-$C_{20}$ alkyl group, b1 is 1, 2, or 3, and * indicates a binding site to a neighboring atom.

13. The condensed cyclic compound as claimed in claim 1, wherein the condensed cyclic compound is one of the following compounds:

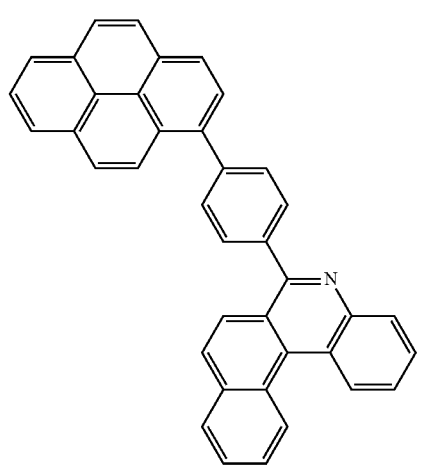

1A

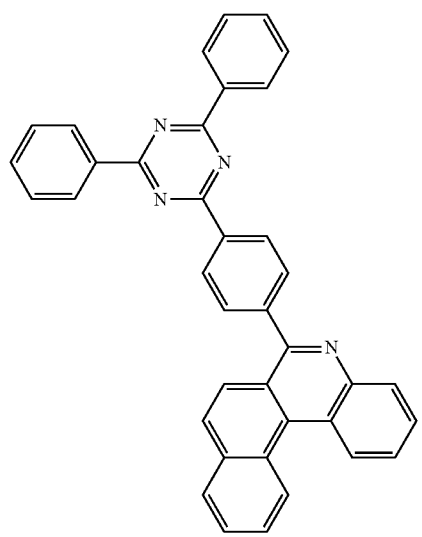
2A
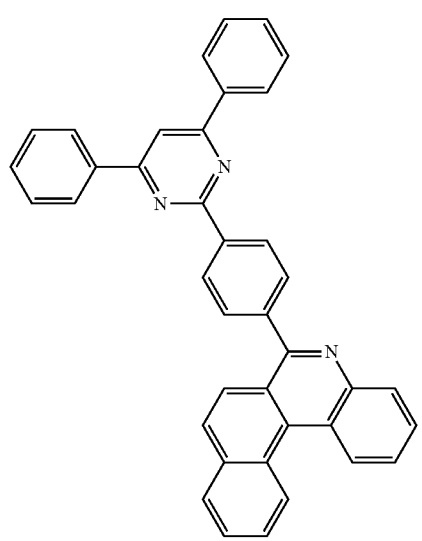
3A
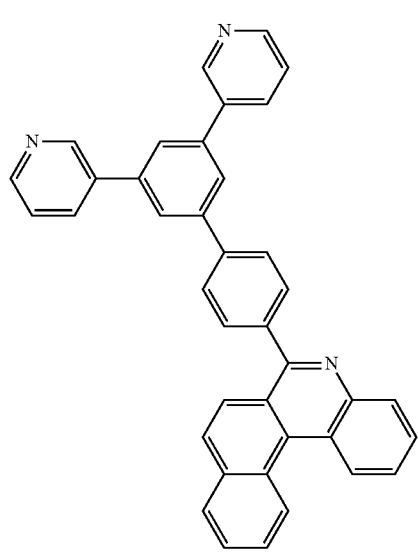
4A
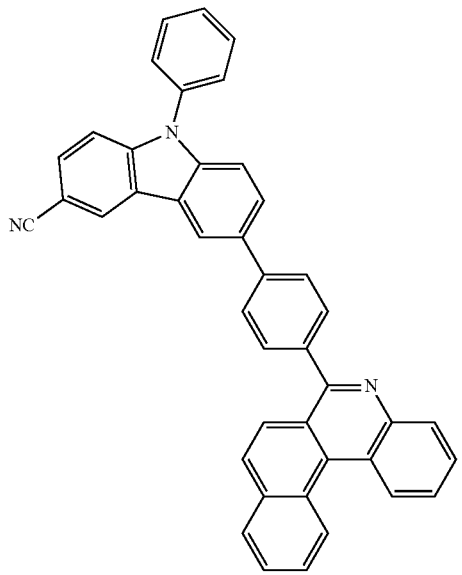
5A
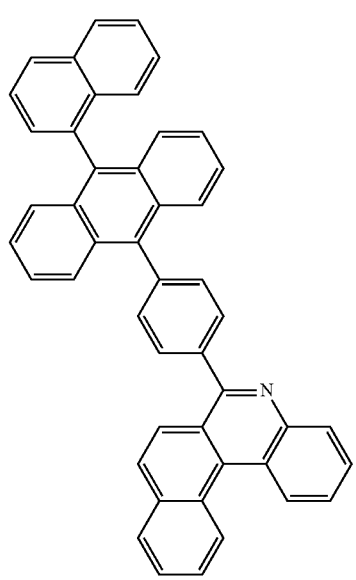
6A
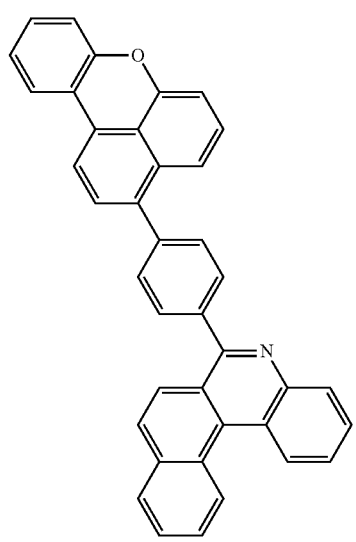
7A -continued
267
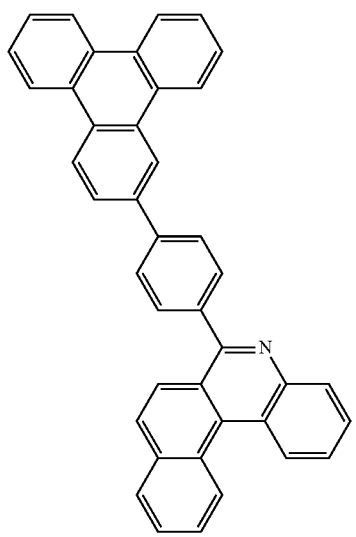
8A
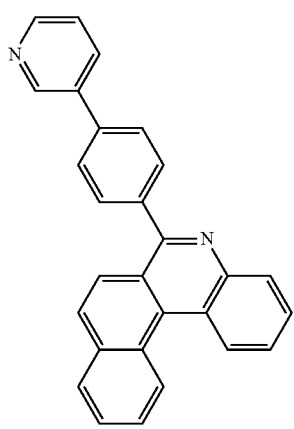
9A
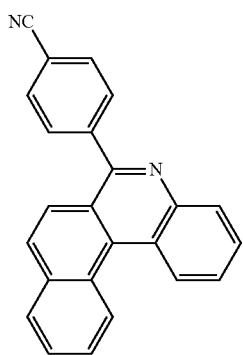
10A
268
-continued
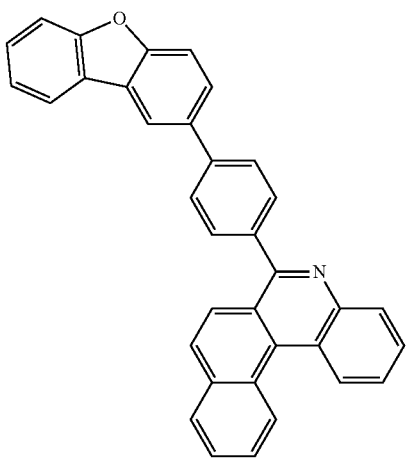
11A
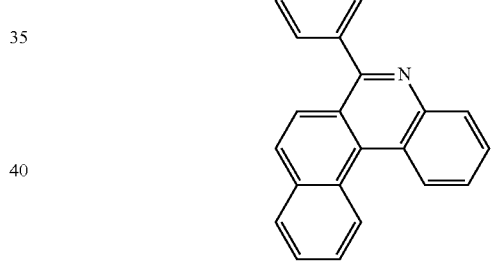
12A
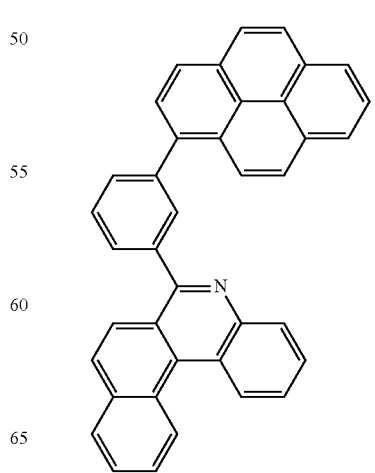
13A 269
-continued
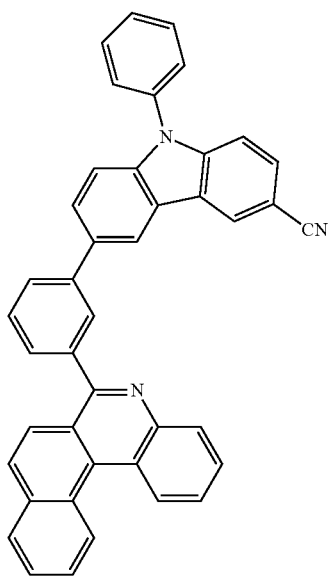
14A
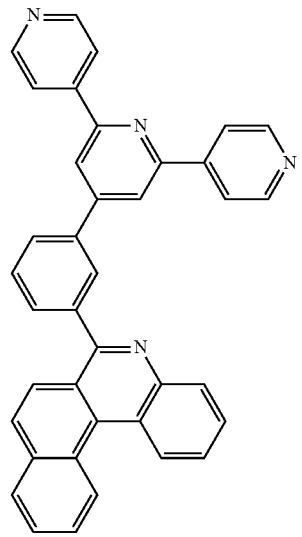
15A
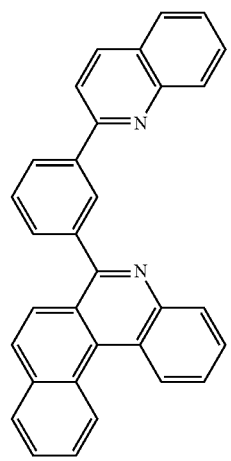
16A
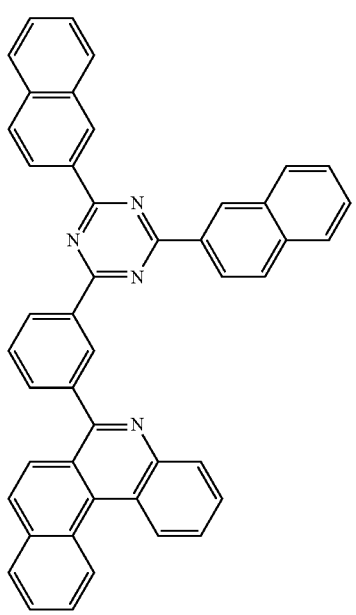
270
-continued
17A
18A
19A 271
-continued
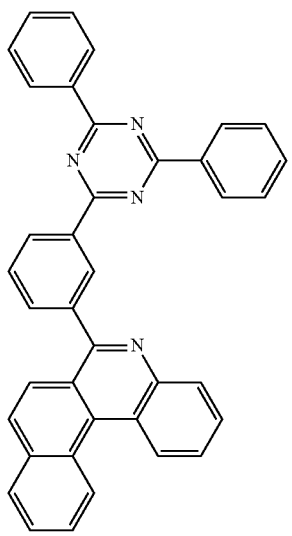
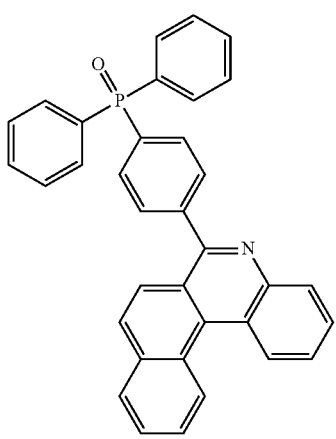
21A
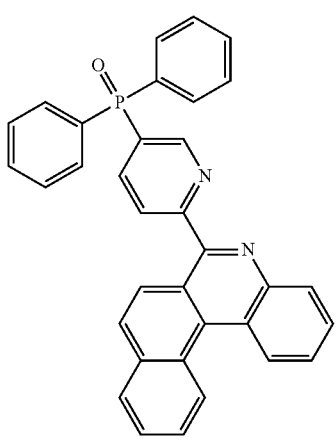
22A
272
-continued
20A
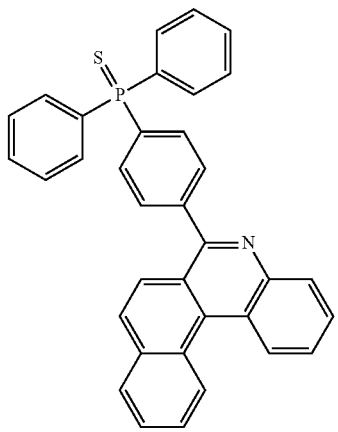
23A
24A
25A
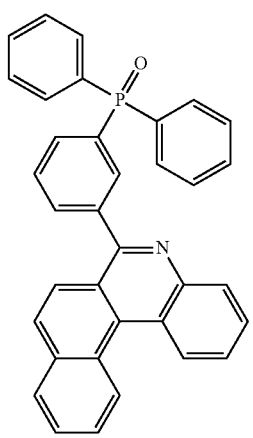

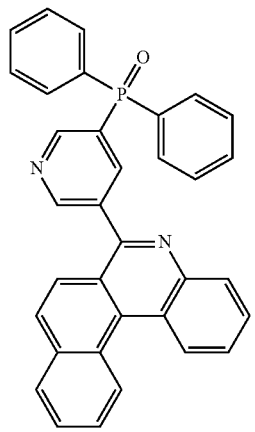
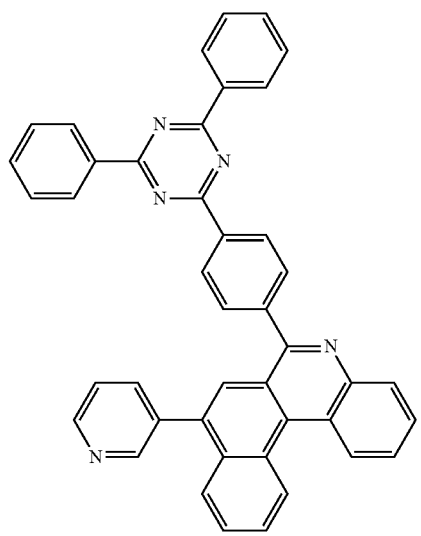
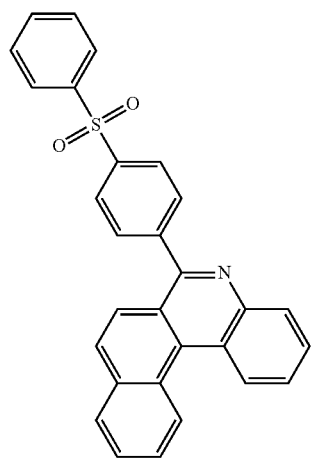
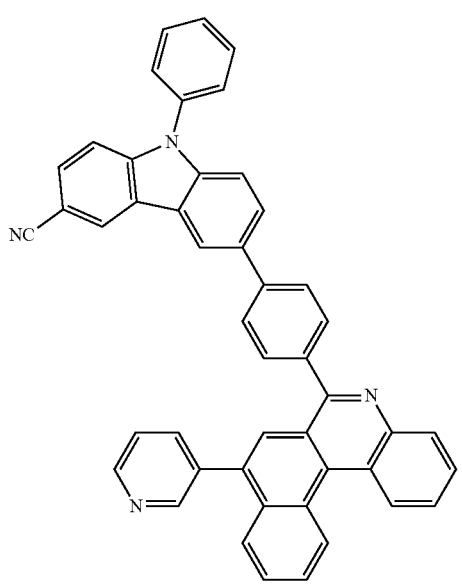
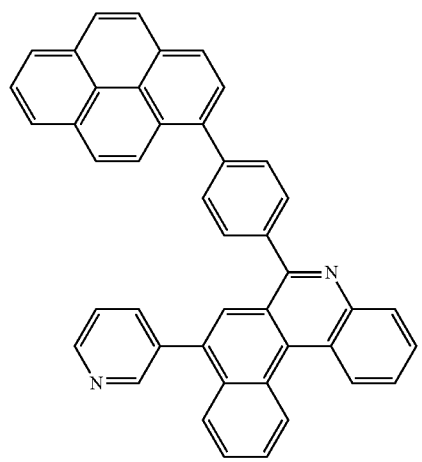
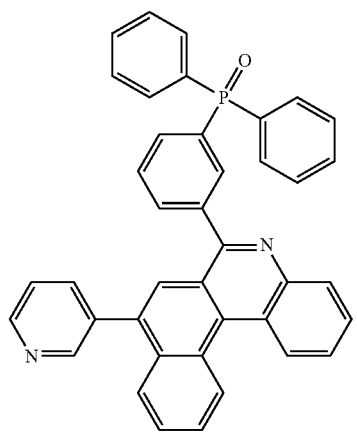

32A
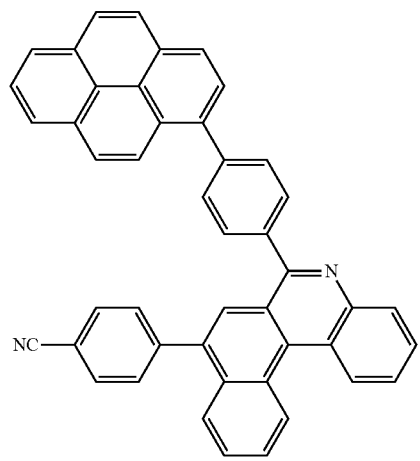
33A
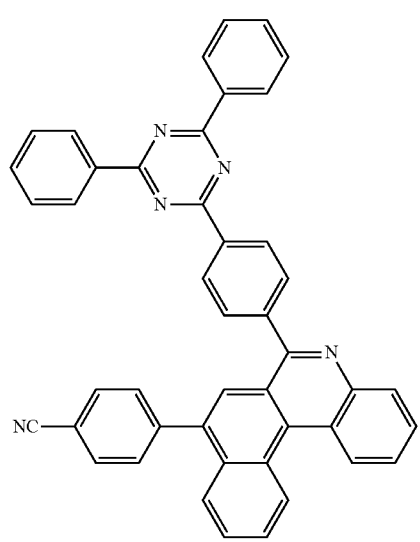
34A
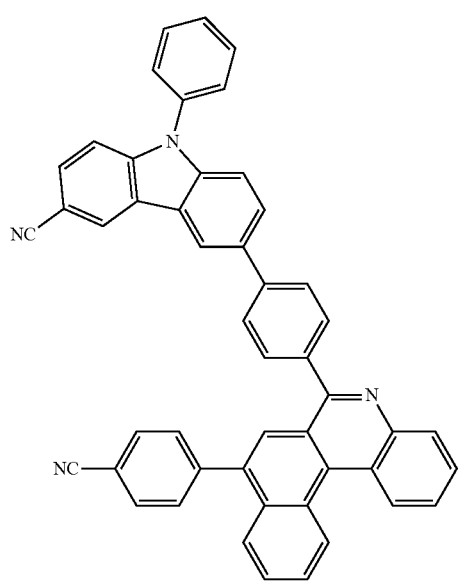
35A
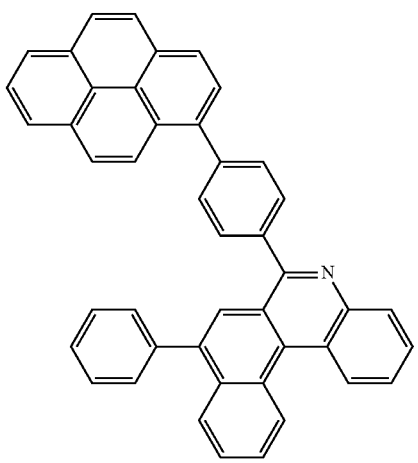
36A
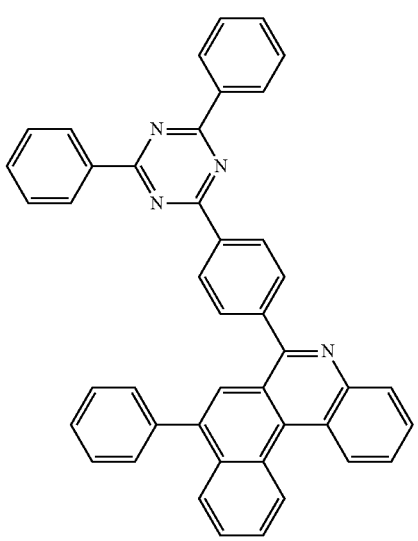
37A
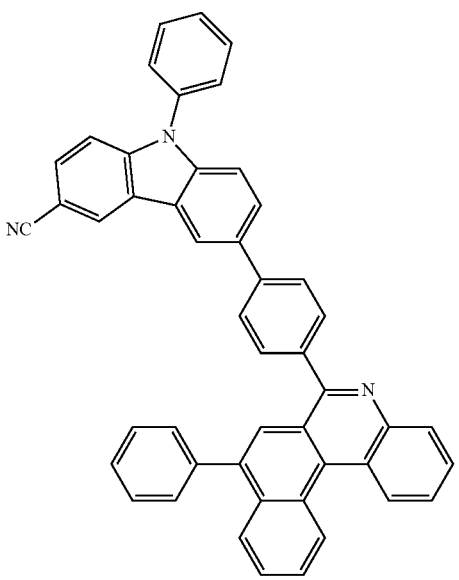

-continued
38A
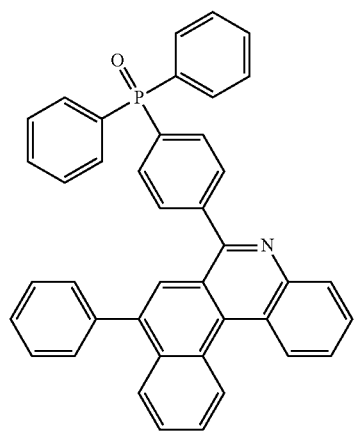
39A
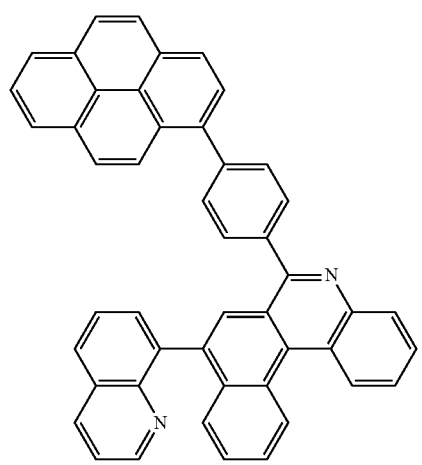
40A
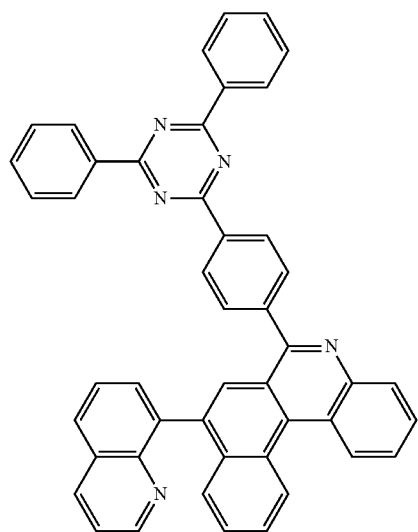
-continued
41A
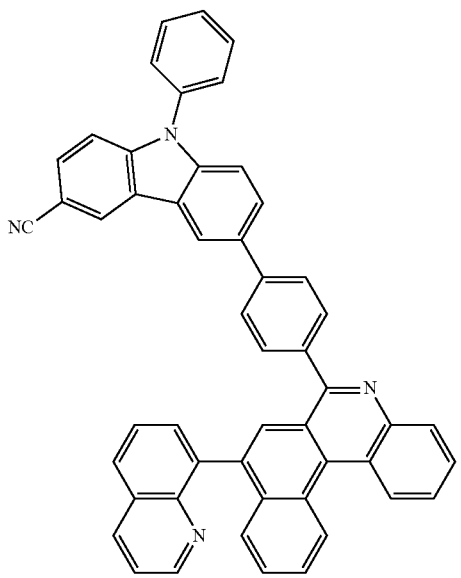
42A
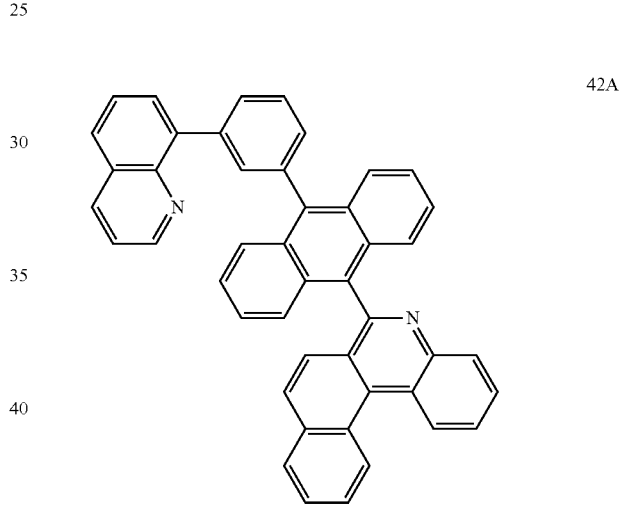
43A
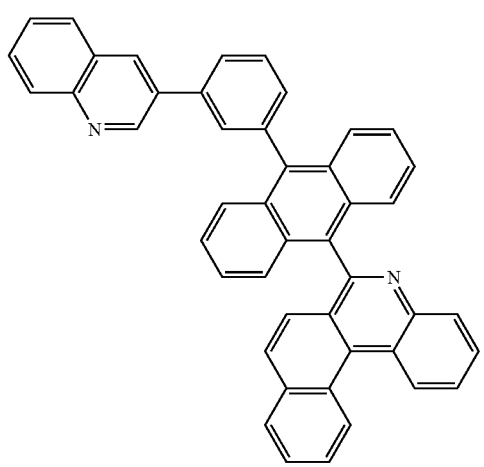

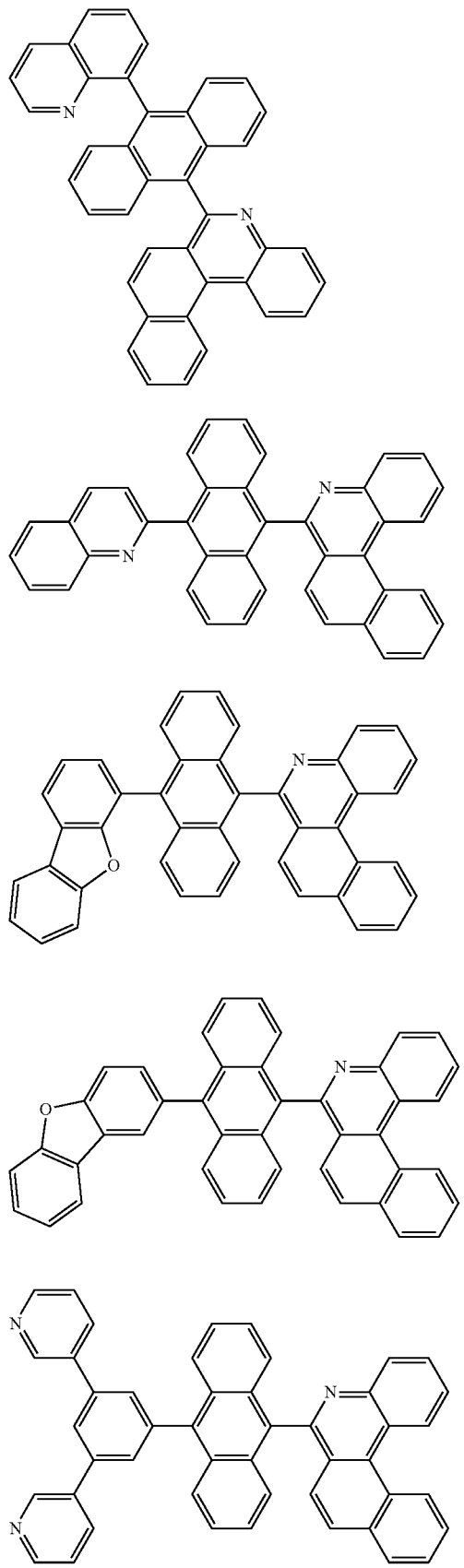
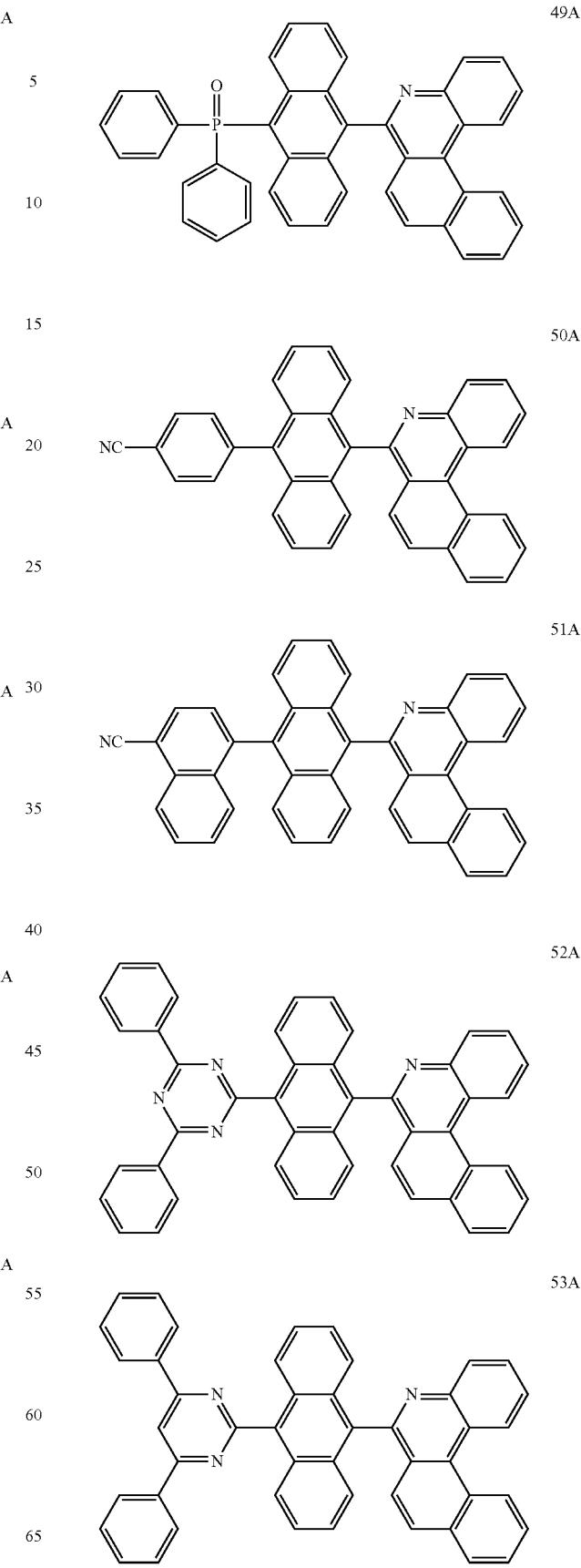

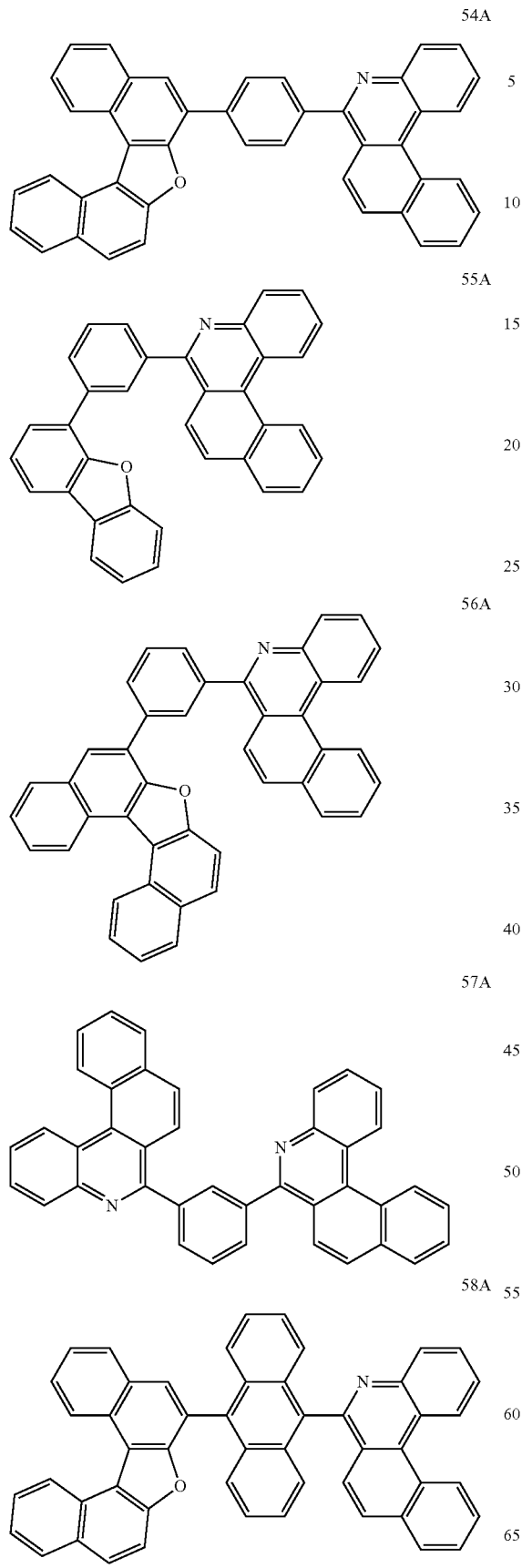
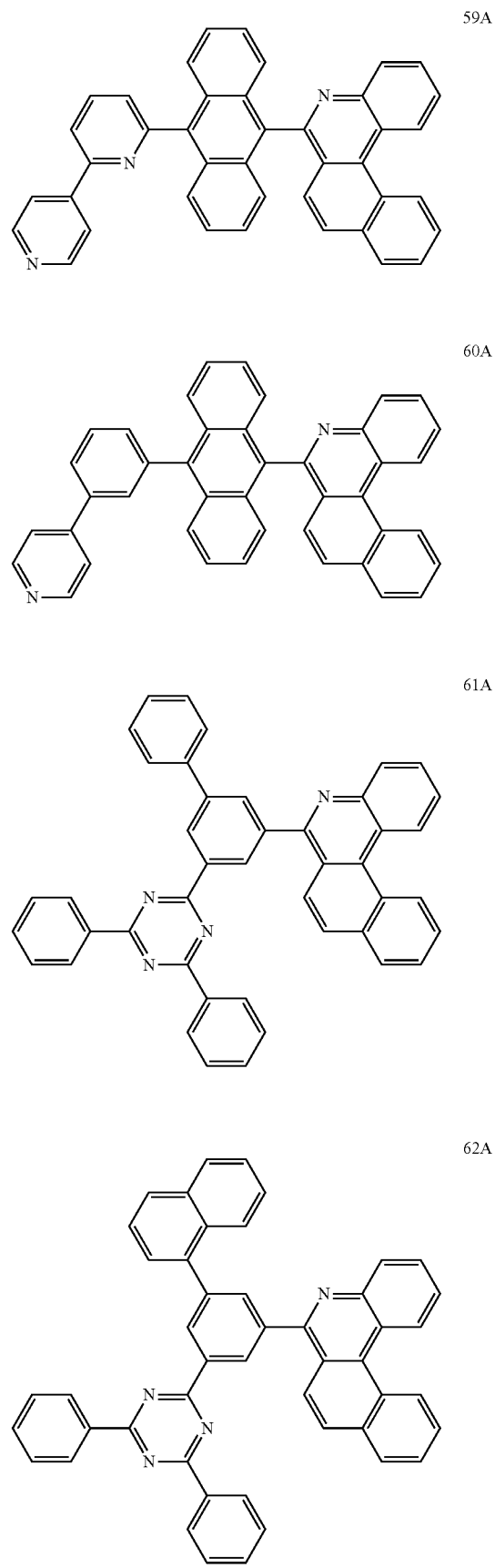

283
-continued
63A
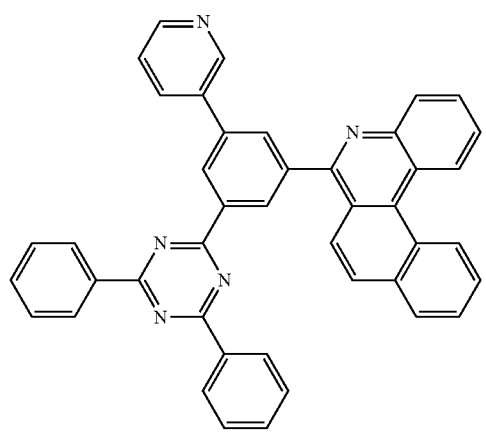
64A
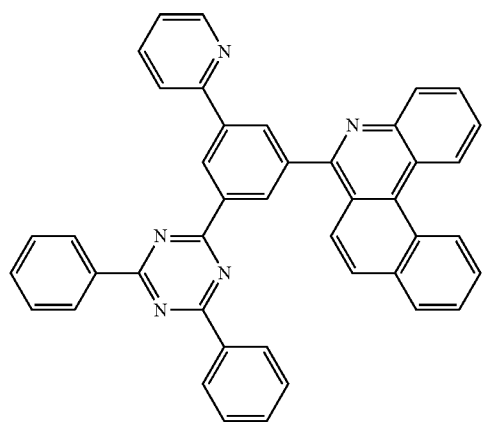
65A
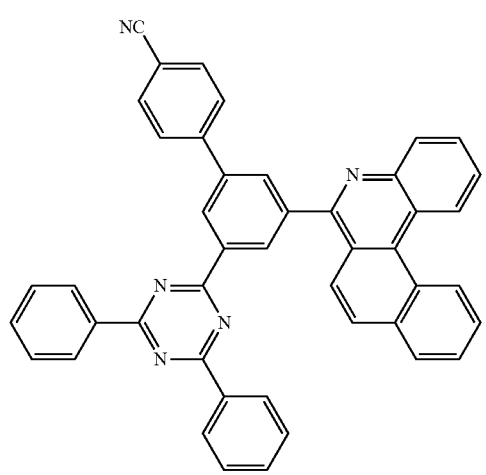
284
-continued
66A
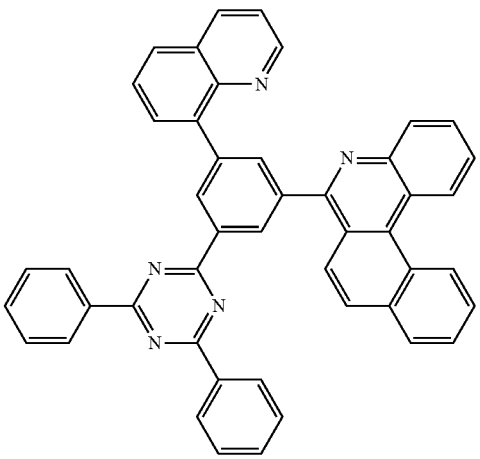
67A
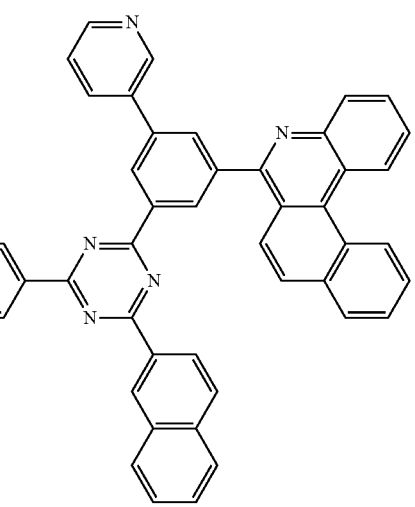
68A
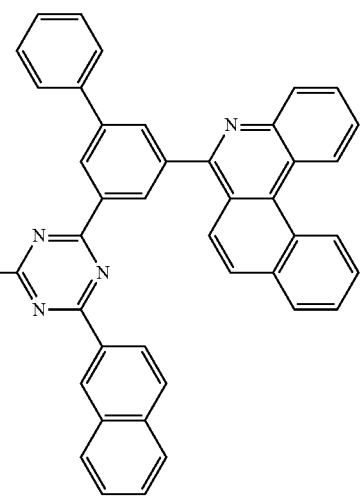

285
-continued
69A
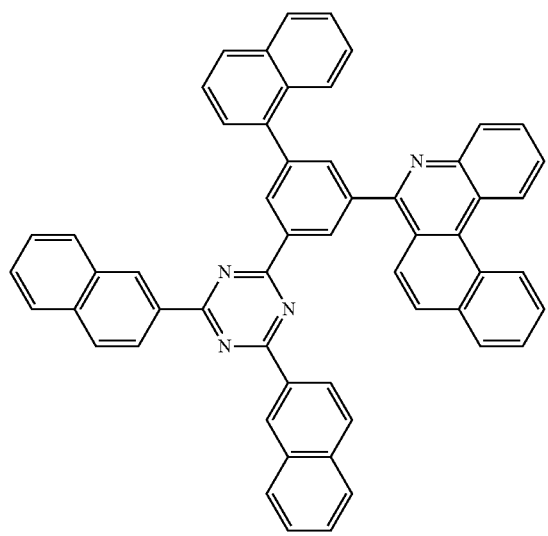
70A
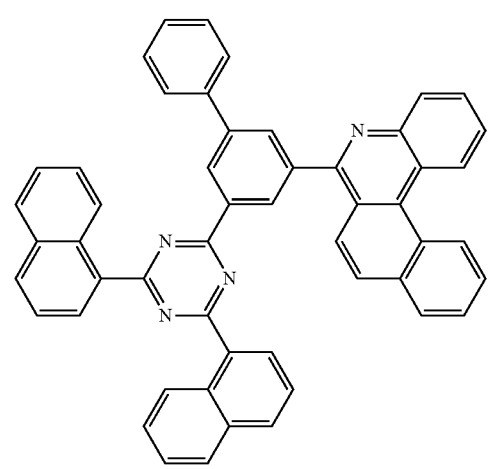
71A
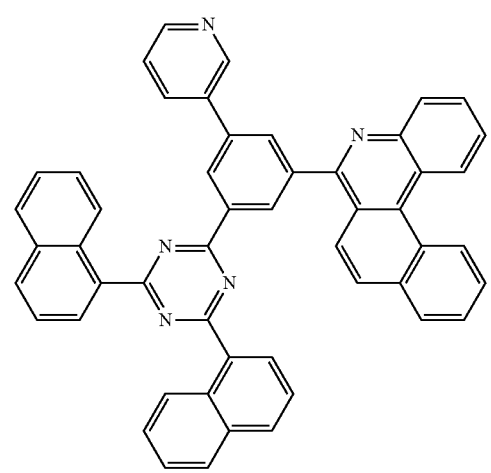
286
-continued
72A
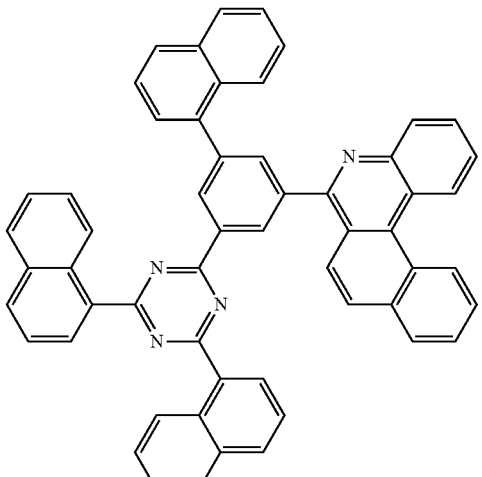
73A
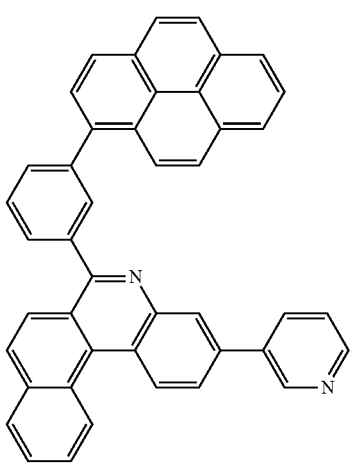
74A
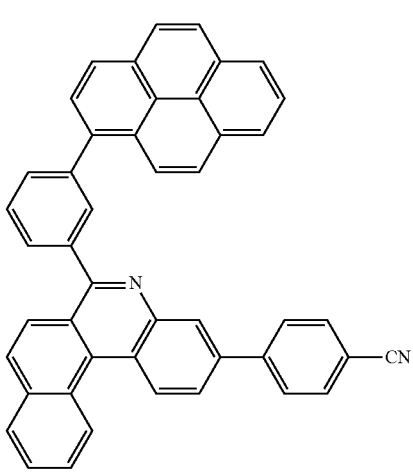

287 288
-continued -continued
75A
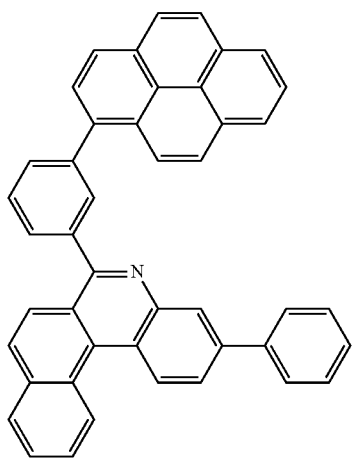 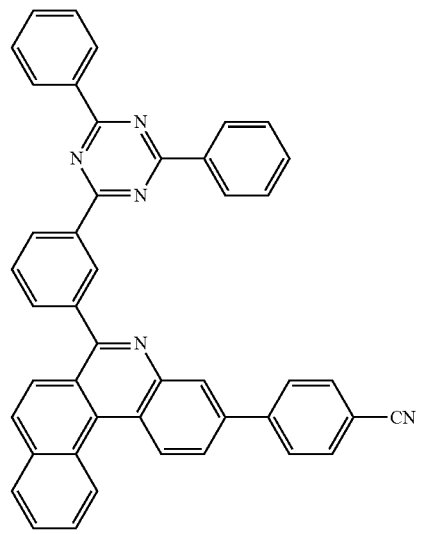
76A
78A
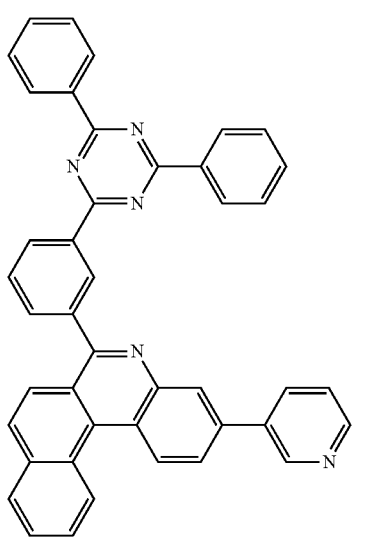 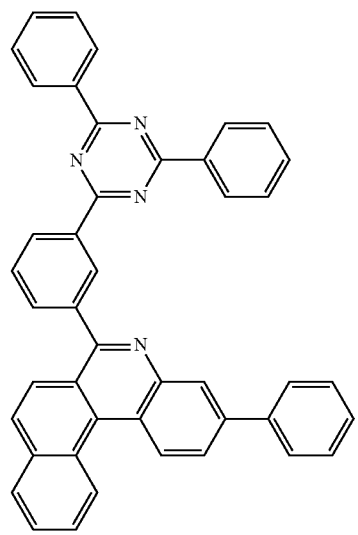
77A
79A
80A
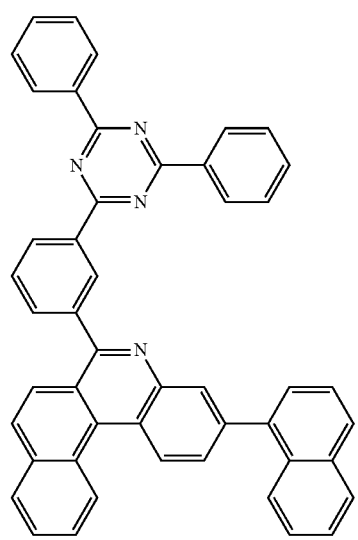

289
-continued
81A
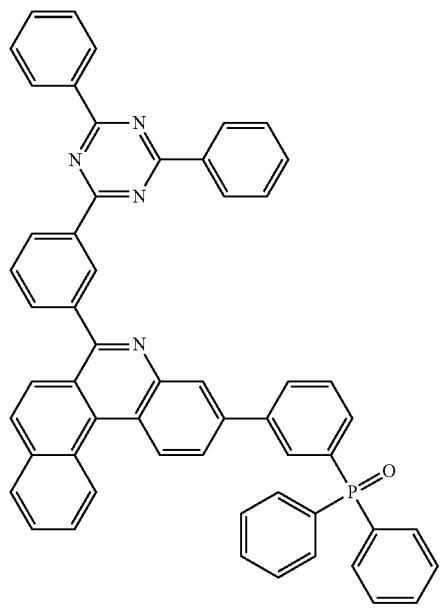
82A
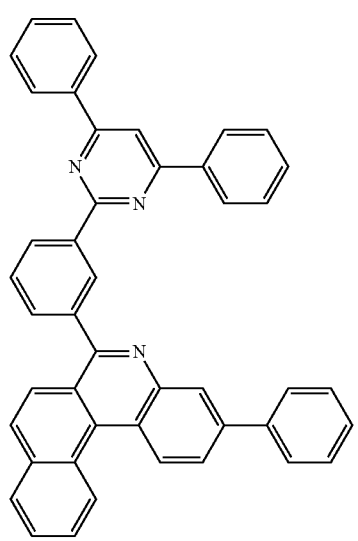
83A
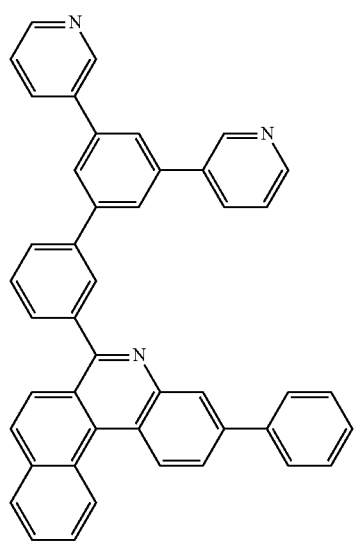
290
-continued
84A
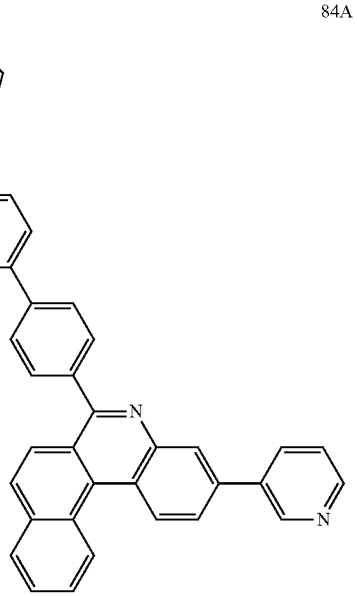
85A
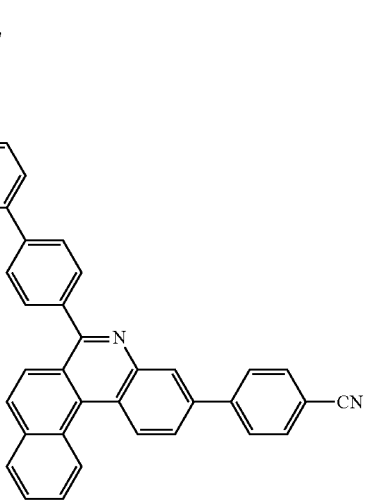

-continued
86A
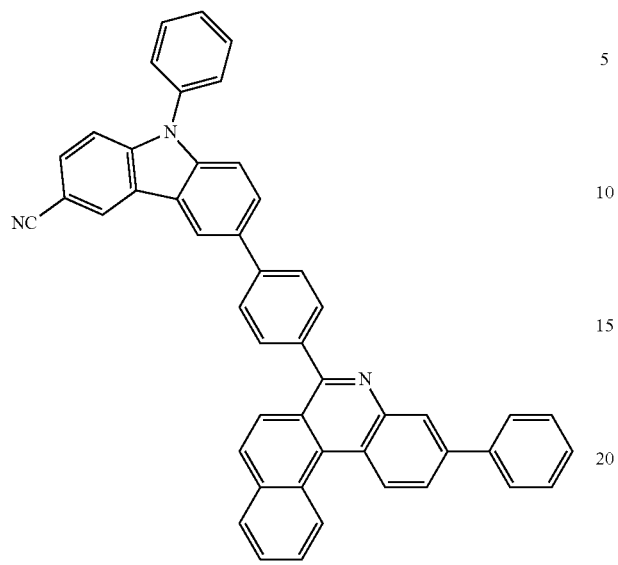
87A
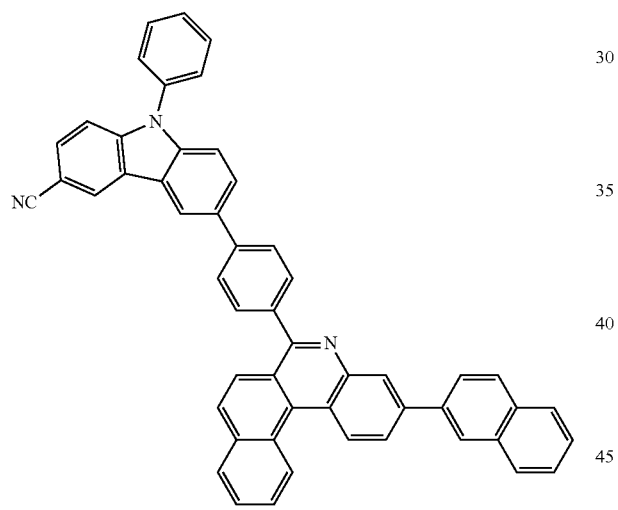
1B
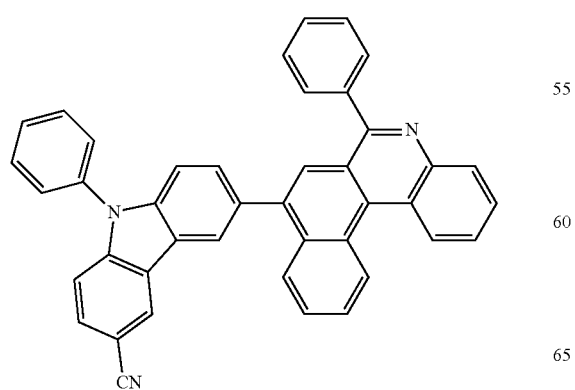
-continued
2B
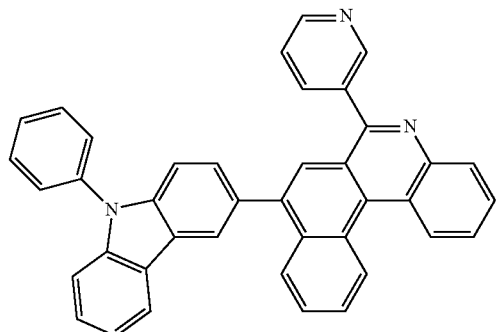
3B
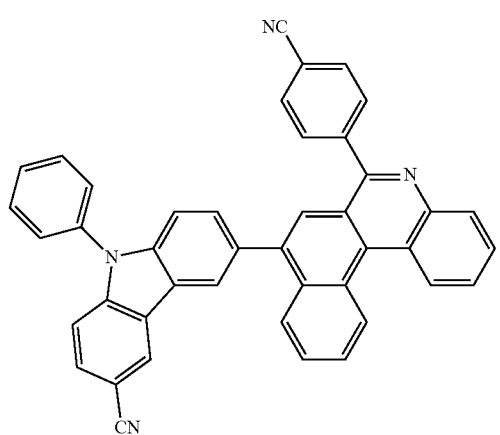
4B
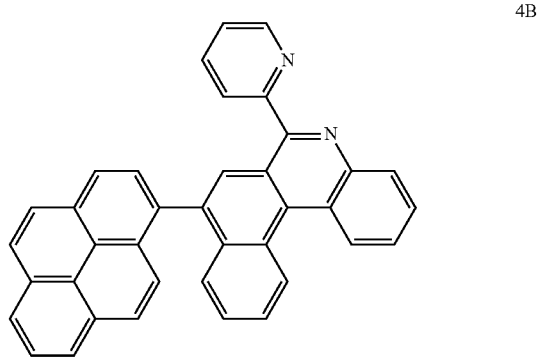
5B
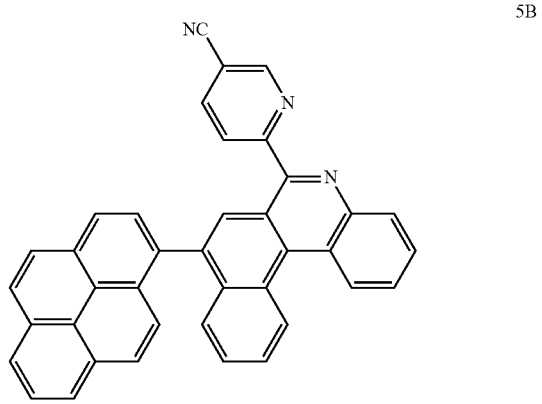

-continued
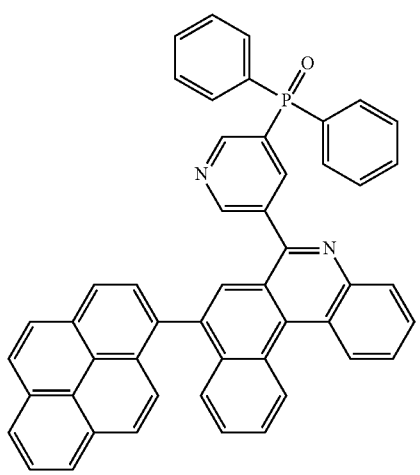
6B
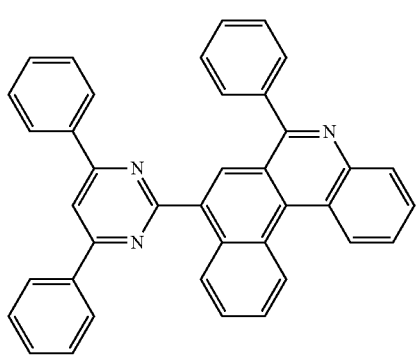
7B
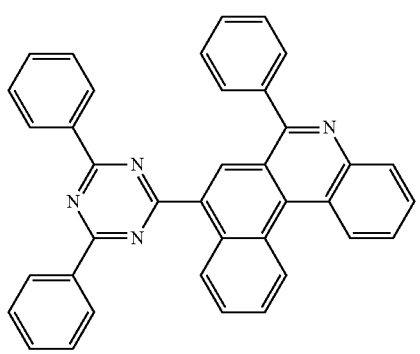
8B
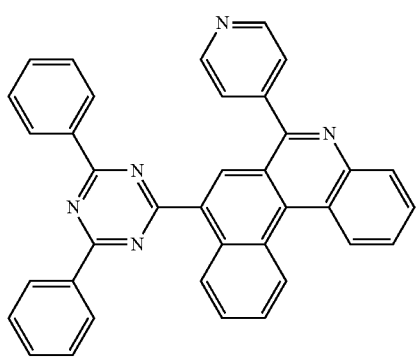
9B
-continued
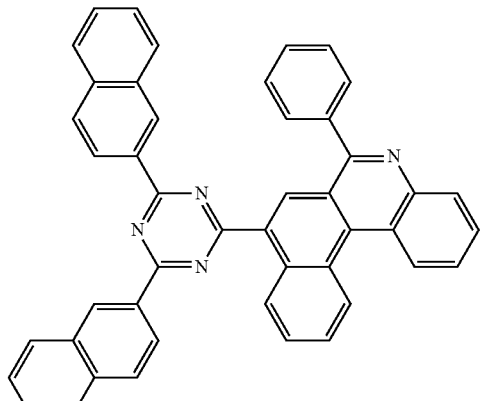
10B
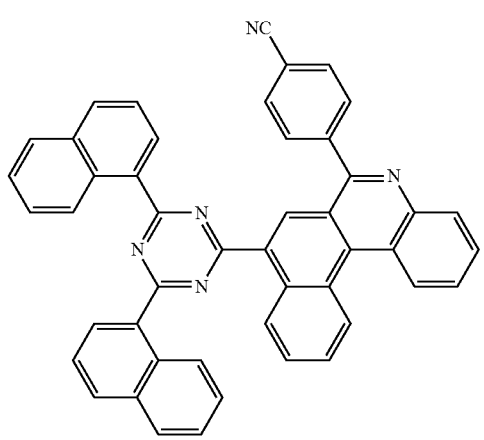
11B
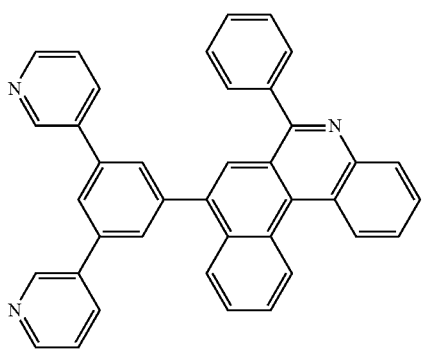
12B
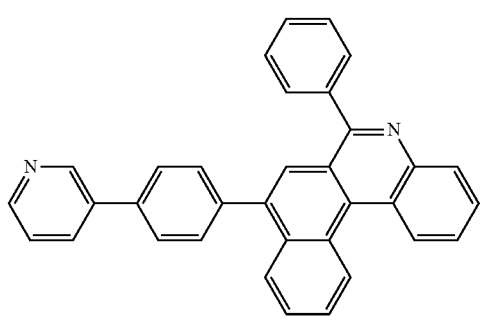
13B 14B 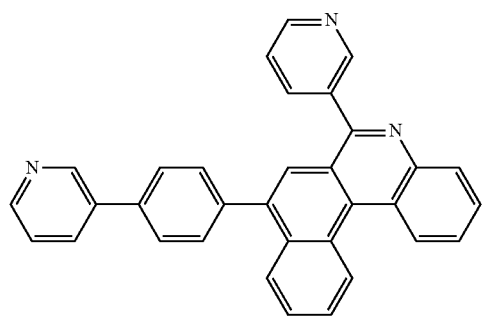
15B 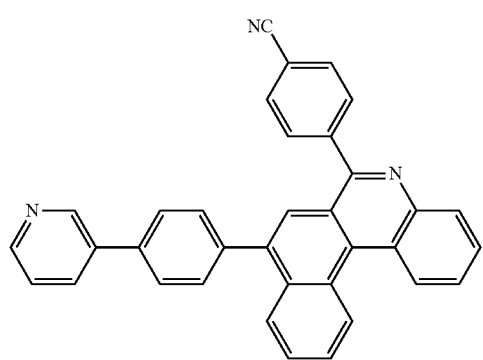
16B 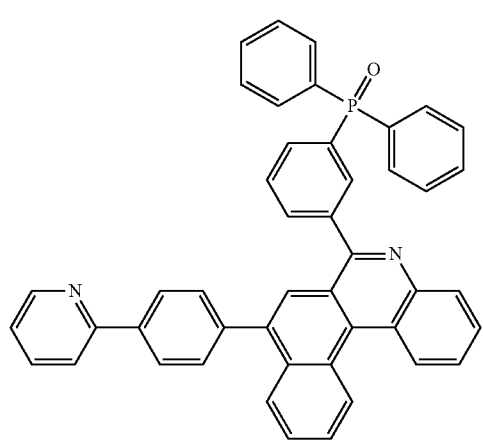
17B 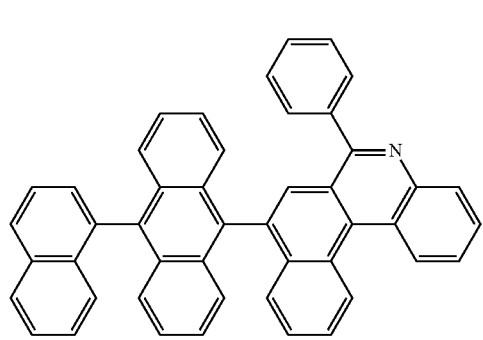
18B 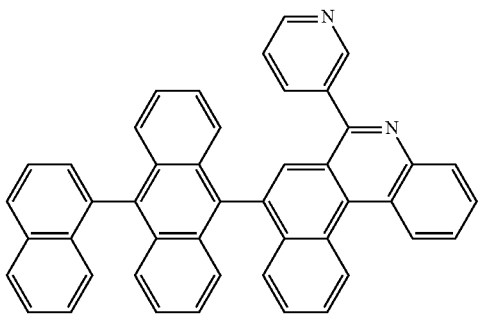
19B 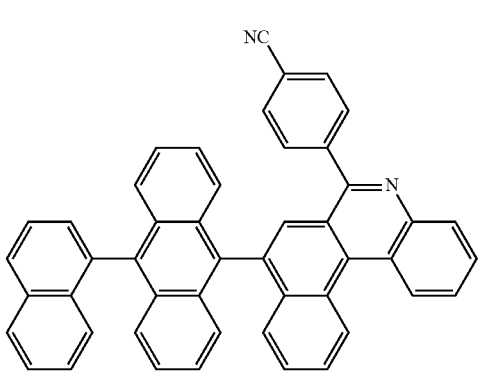
20B
21B 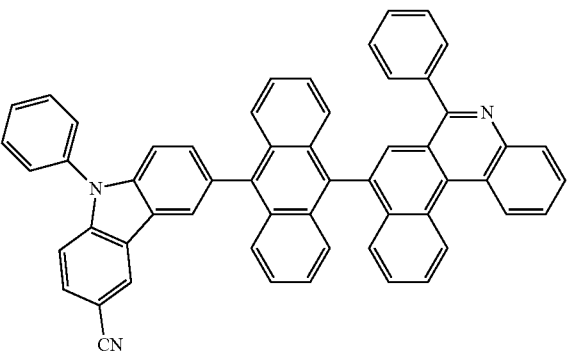

-continued
22B
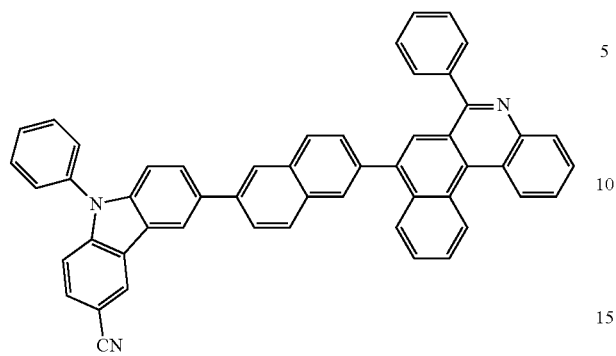
23B
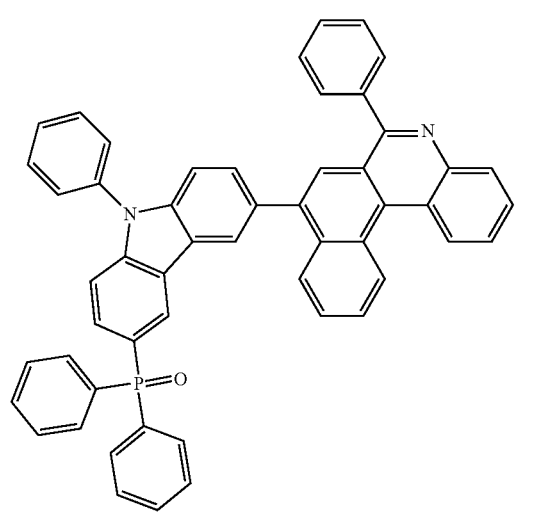
24B
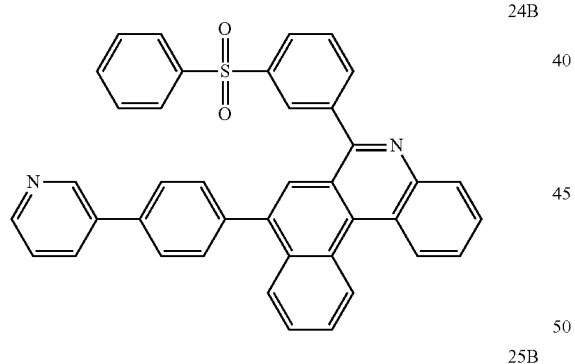
25B
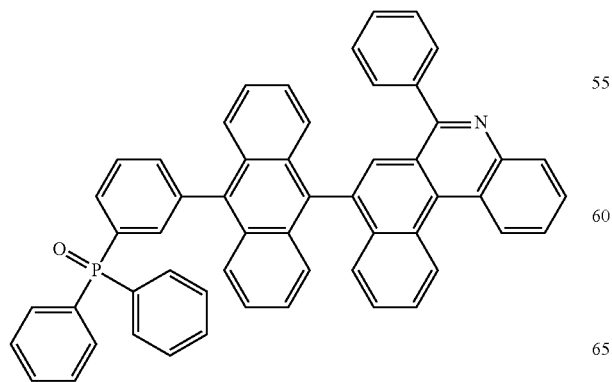
-continued
26B
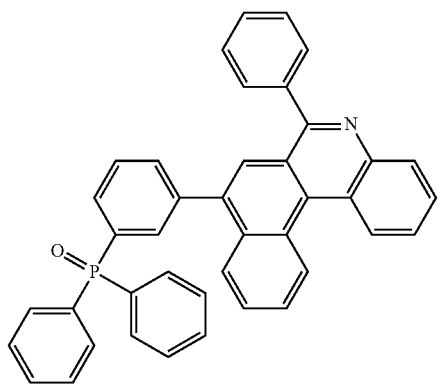
27B
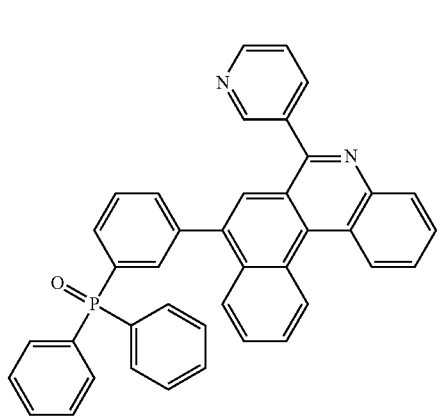
28B
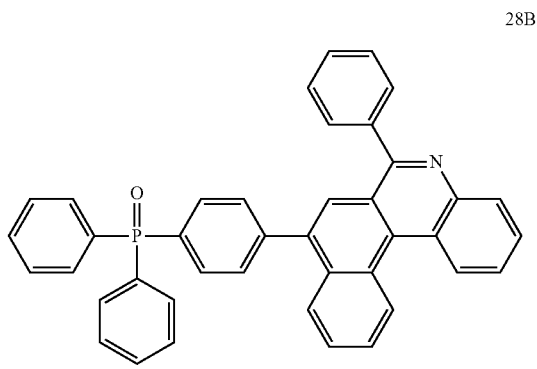
29B
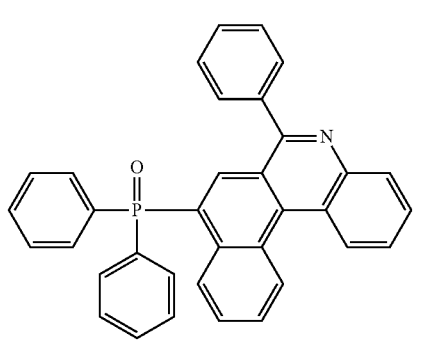

30B 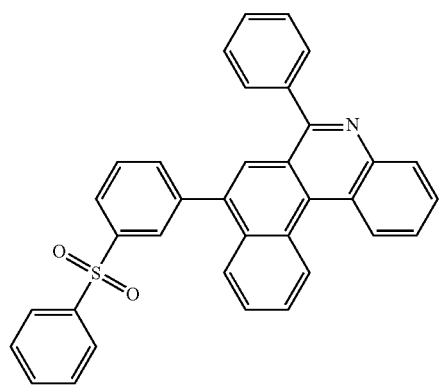
31B 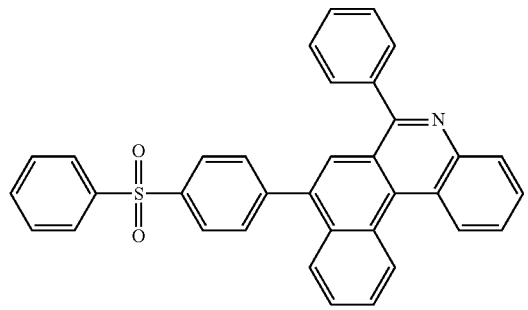
32B 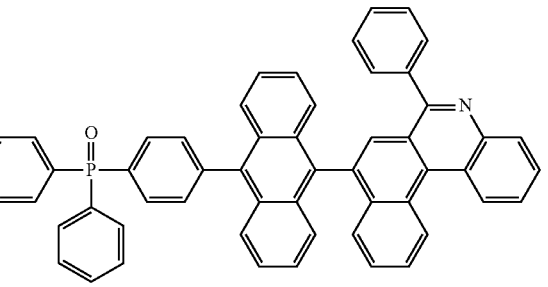
33B 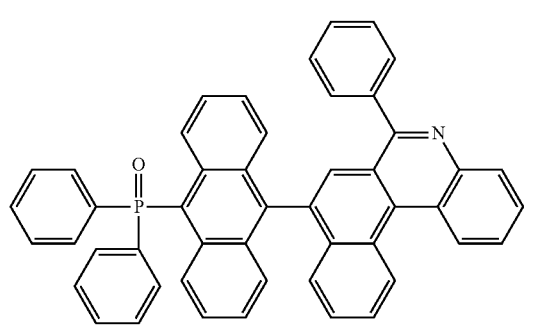
34B 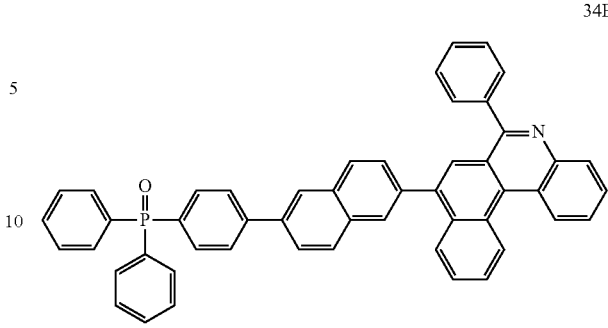
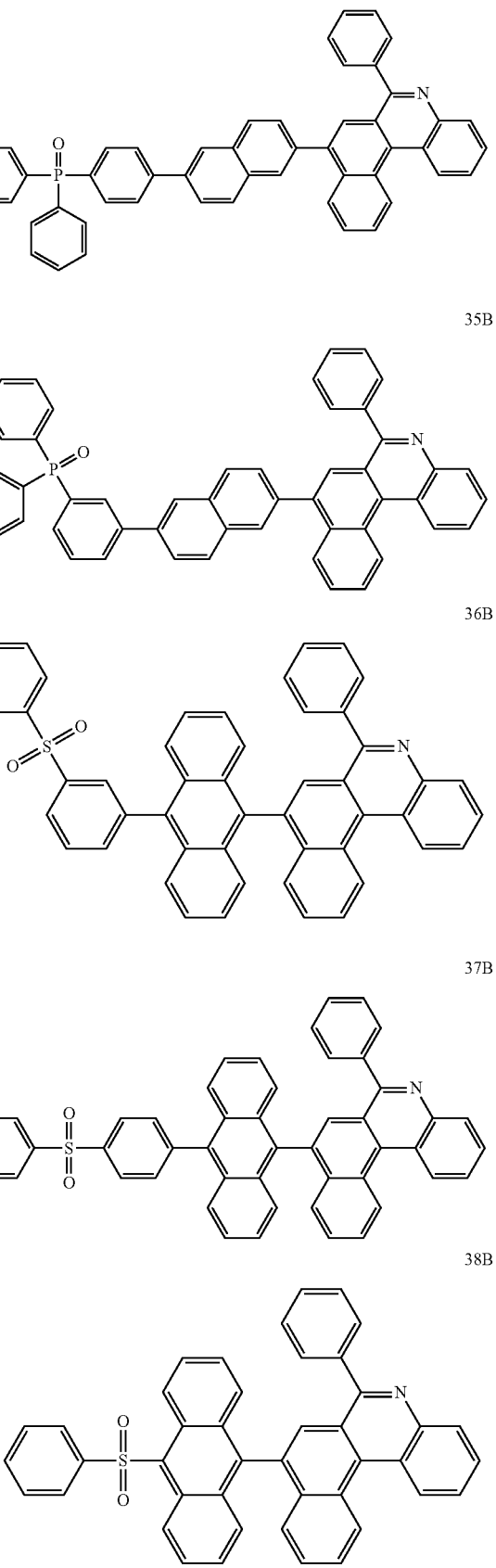

-continued
39B
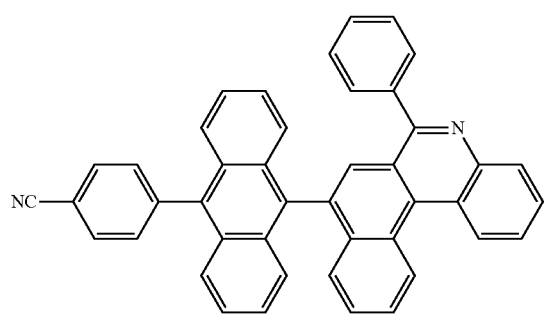
40B
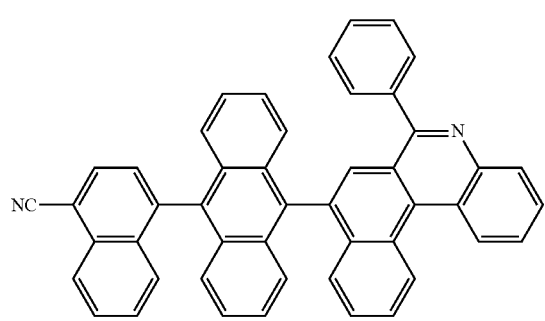
41B
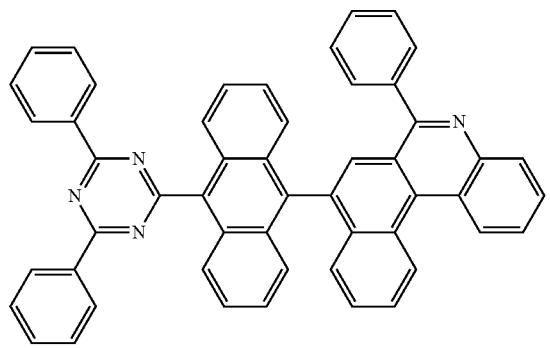
42B
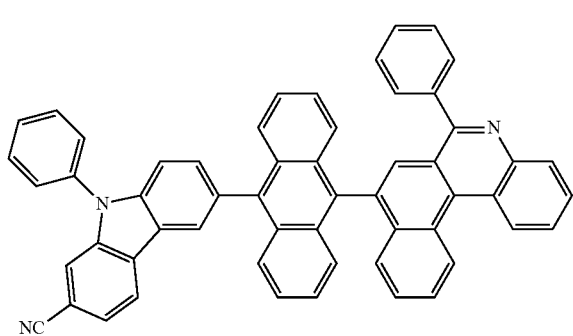
-continued
43B
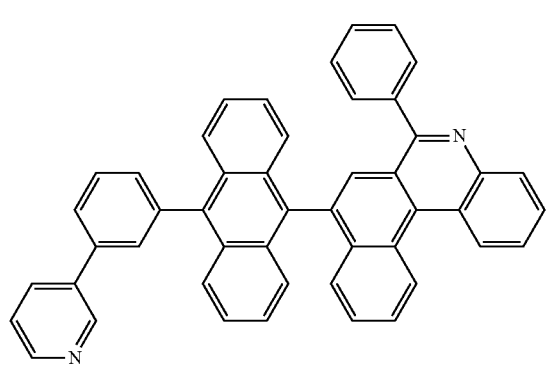
44B
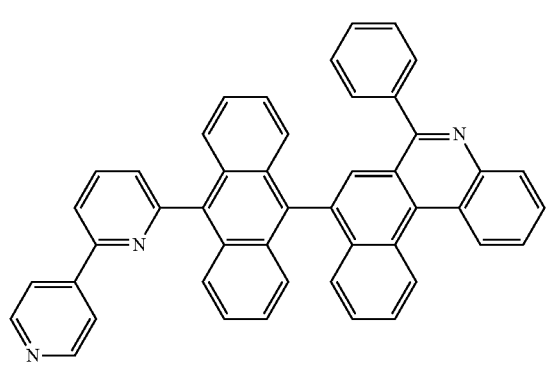
45B
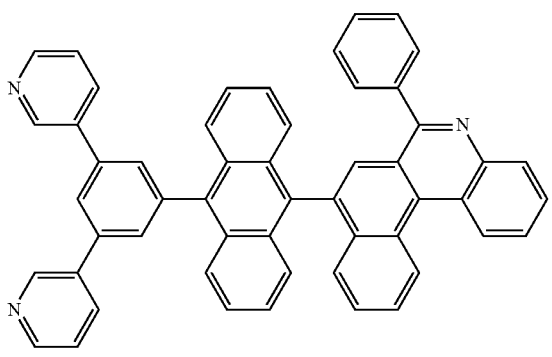
46B
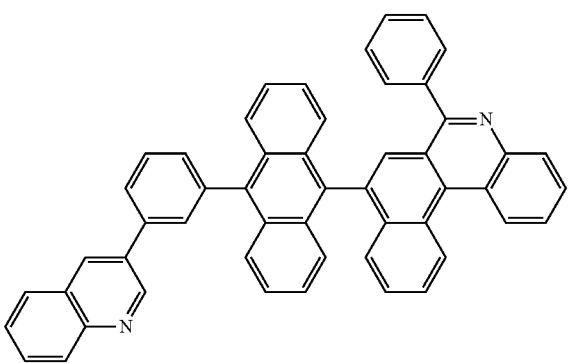

303
-continued

47B

48B

49B

50B

304
-continued

51B

52B

53B

54B

305
-continued
55B
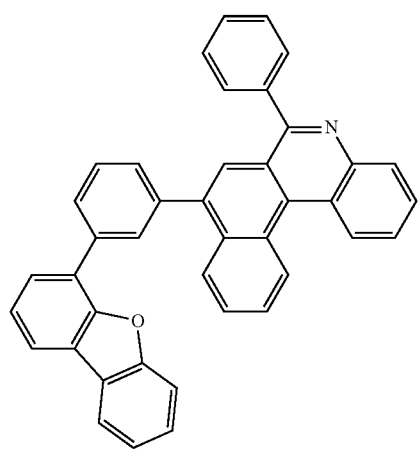
56B
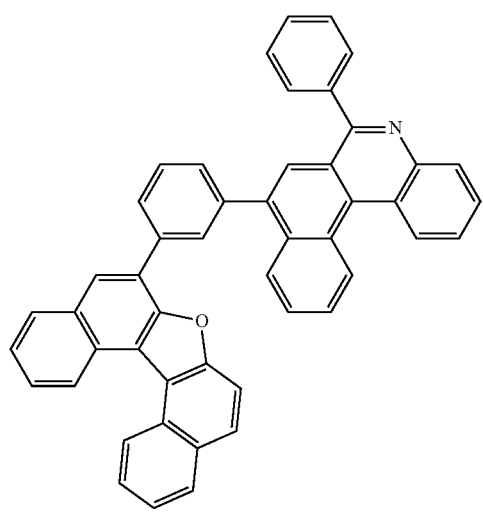
57B
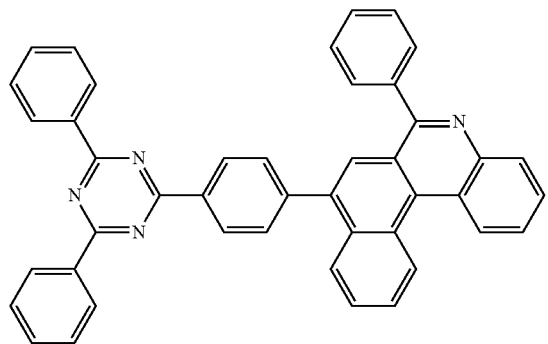
306
-continued
58B
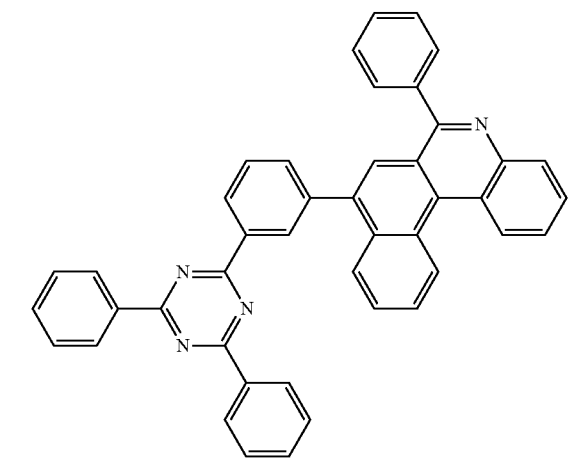
59B
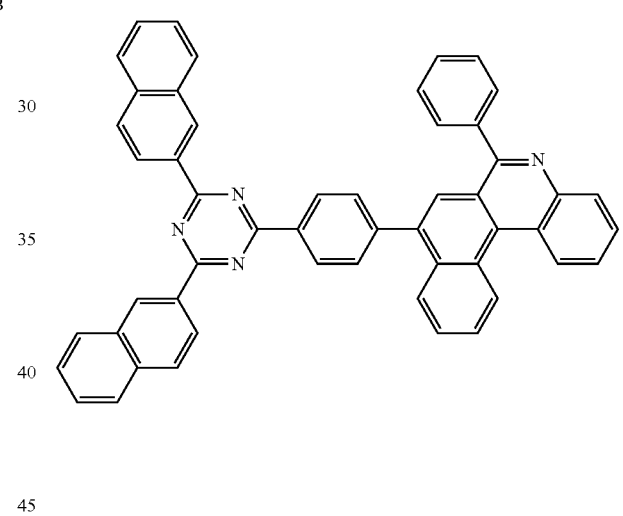
60B
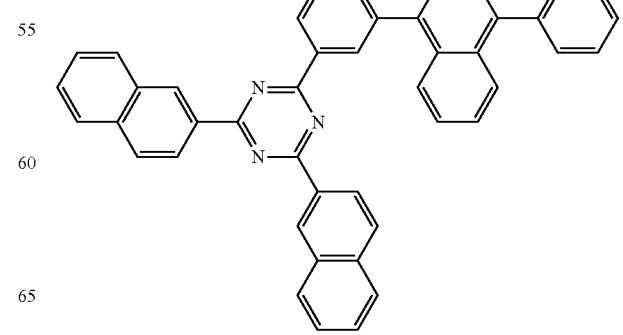

61B
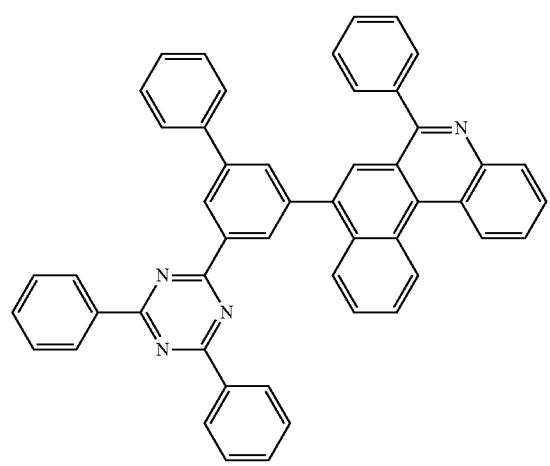
62B
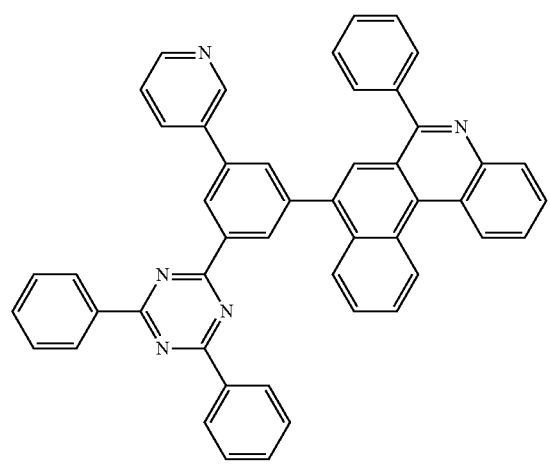
63B
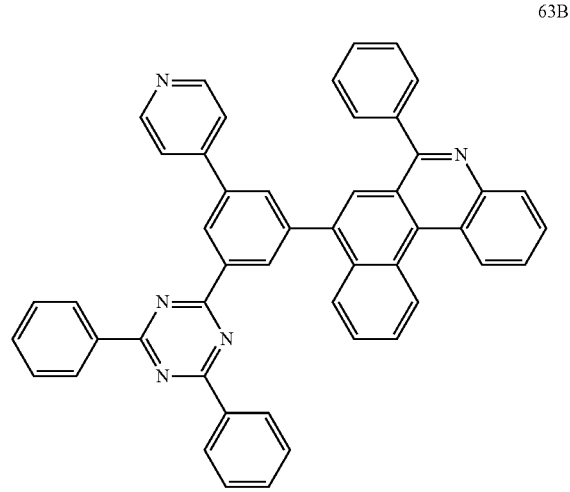
64B
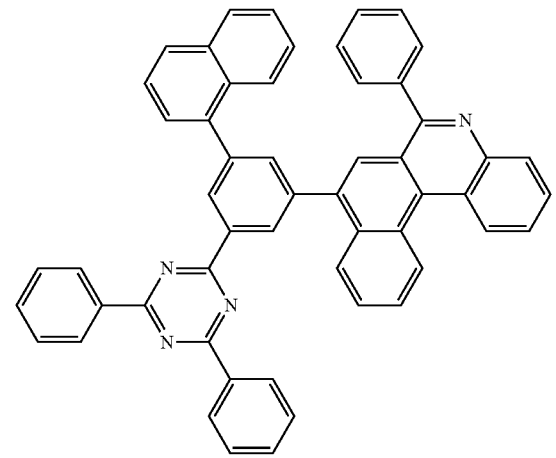
65B
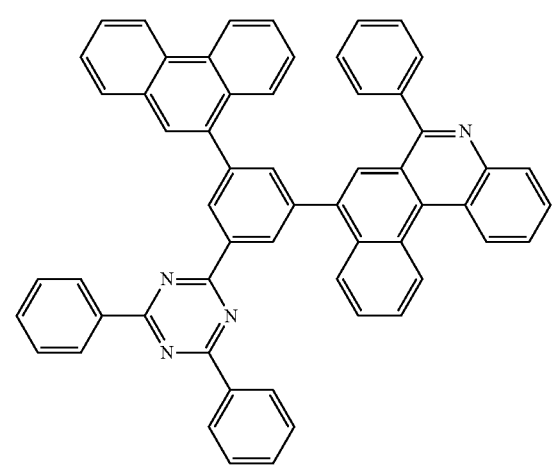
66B
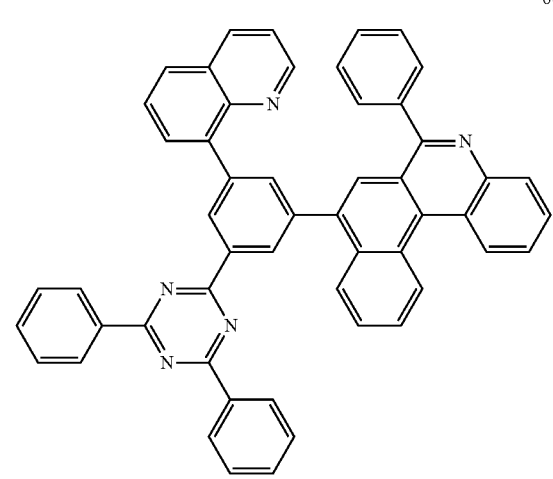

67B
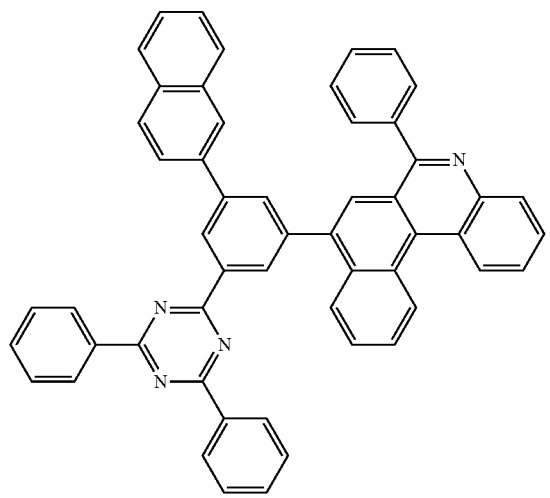
68B
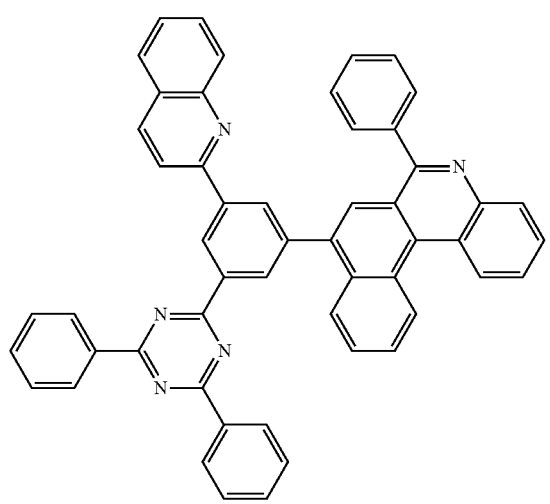
69B
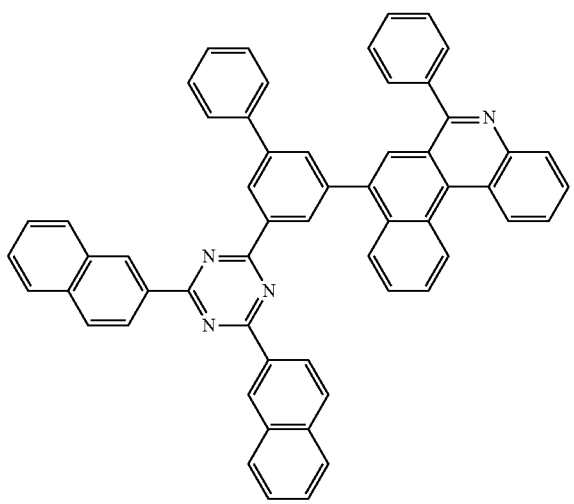
70B
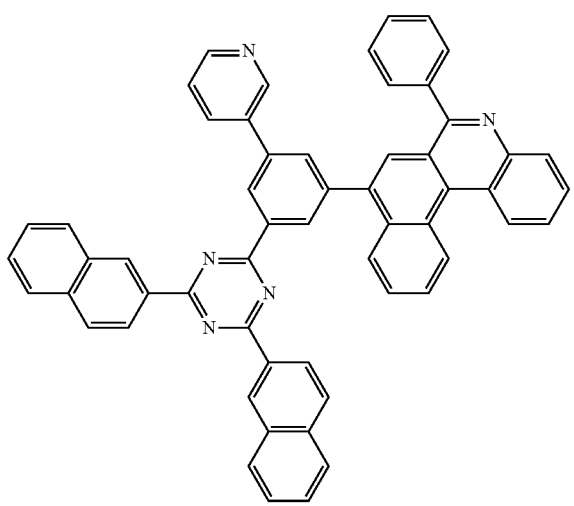
71B
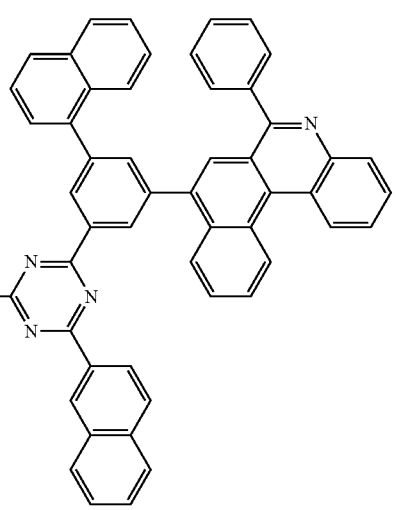
72B
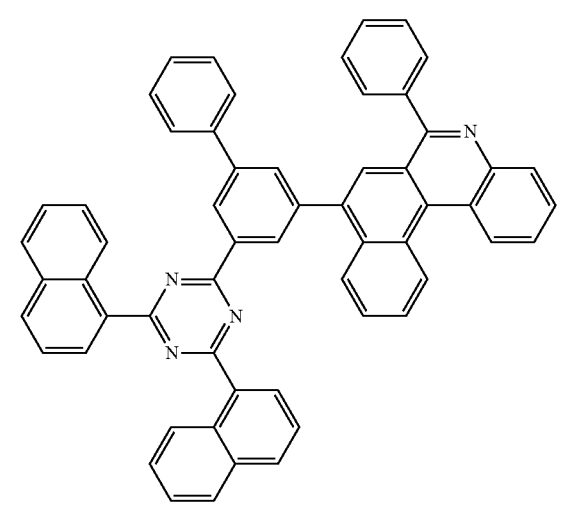

311
-continued
73B
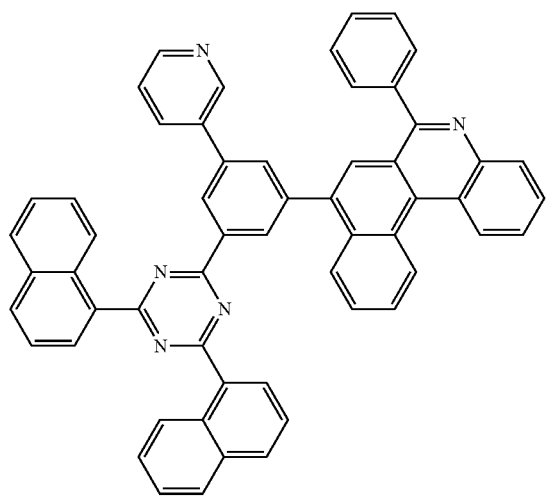
74B
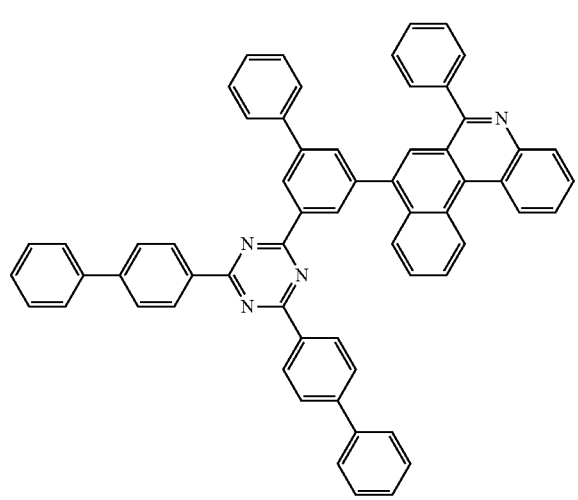
75B
312
-continued
76B
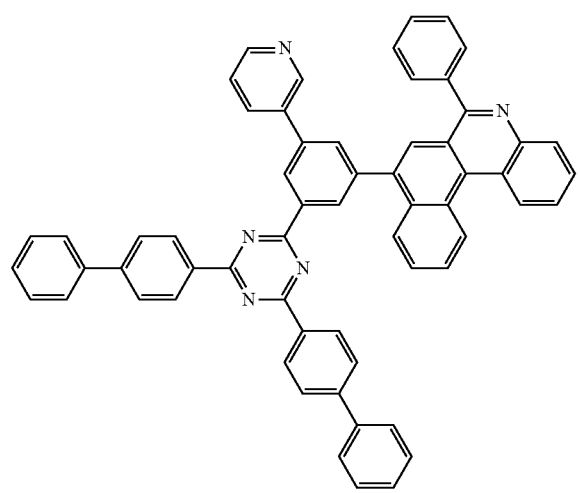
77B
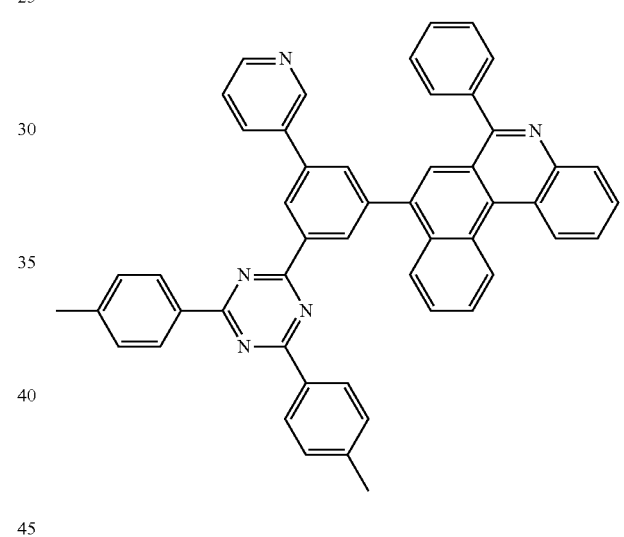
78B
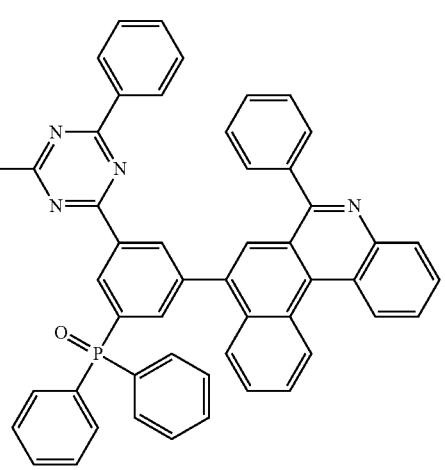

79B
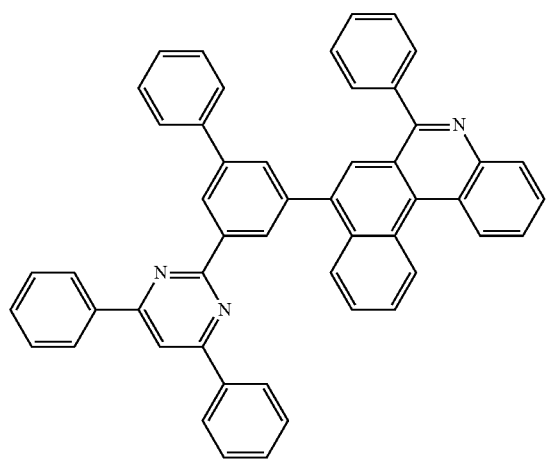
82B
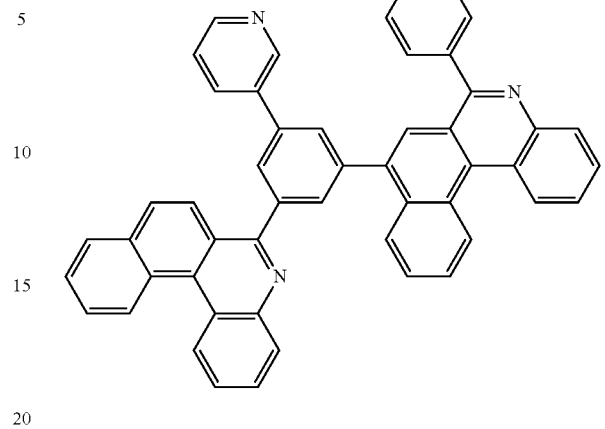
80B
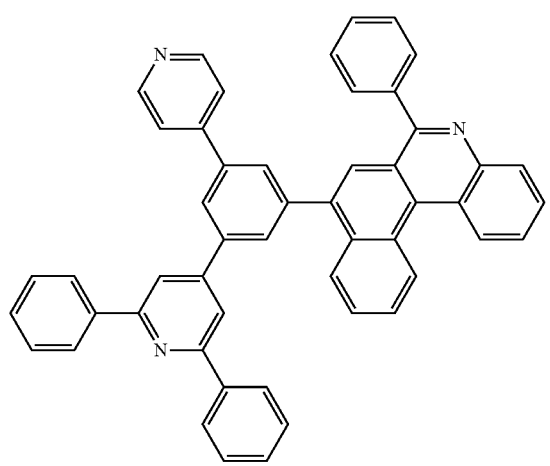
83B
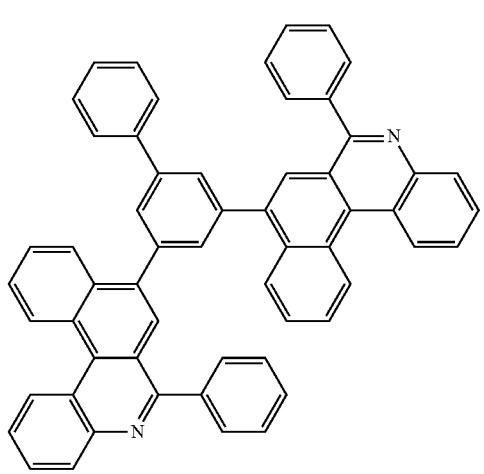
81B
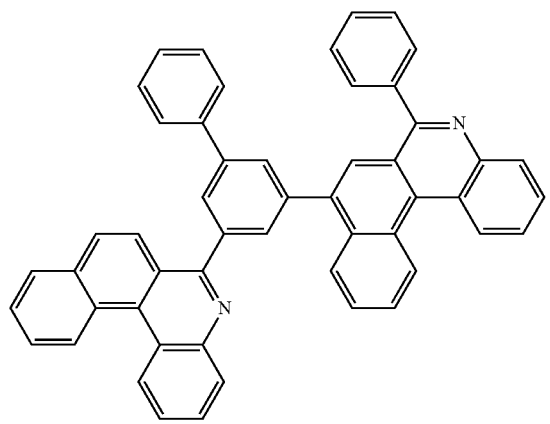
84B
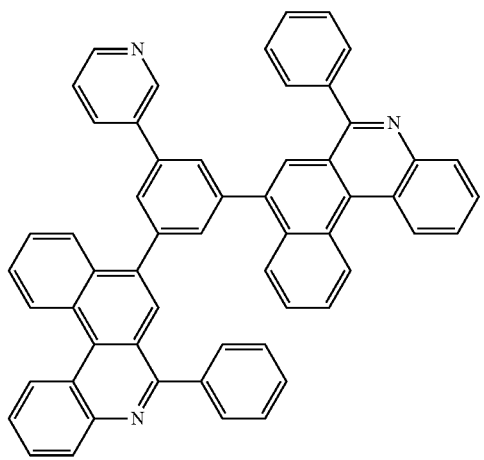

| 315 -continued | 316 -continued |
|---|---|
| 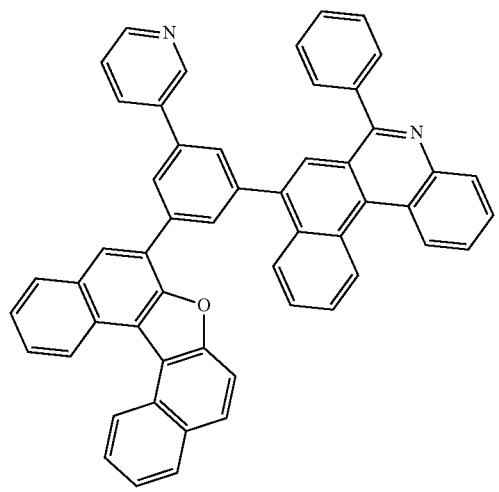 85B | 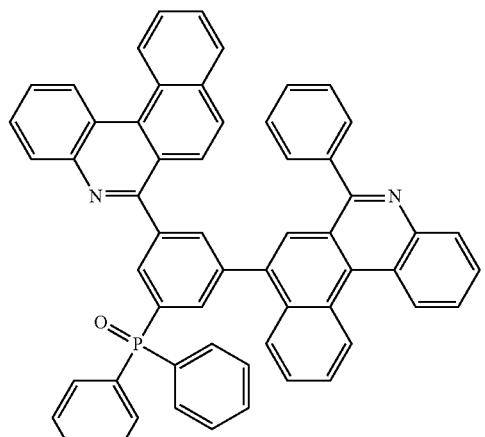 88B |
| 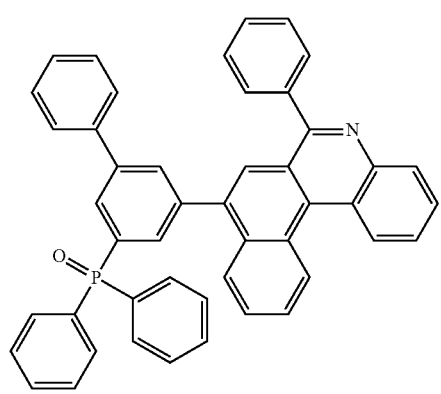 86B | 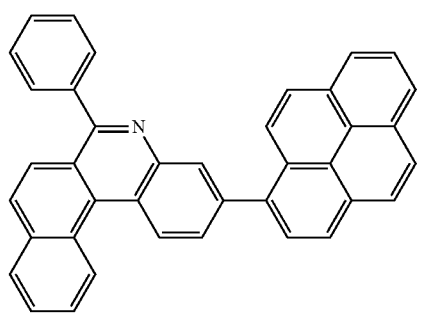 1C |
| | 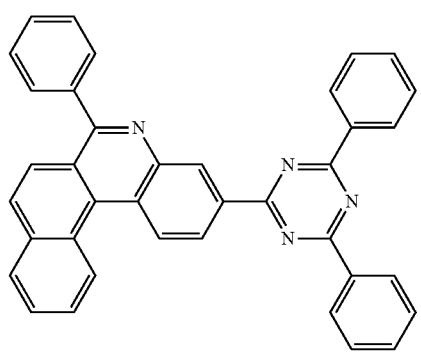 2C |
| 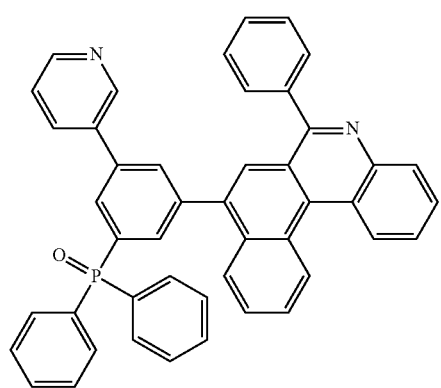 87B | 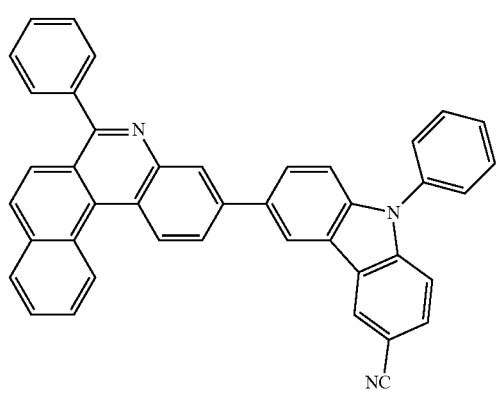 3C |

317
-continued
4C
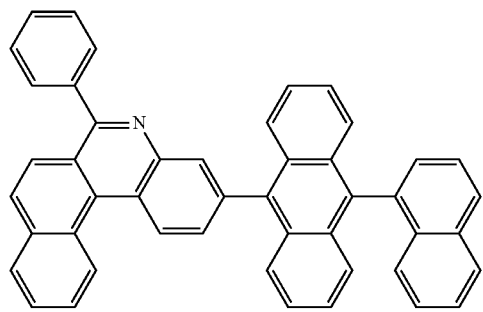
5C
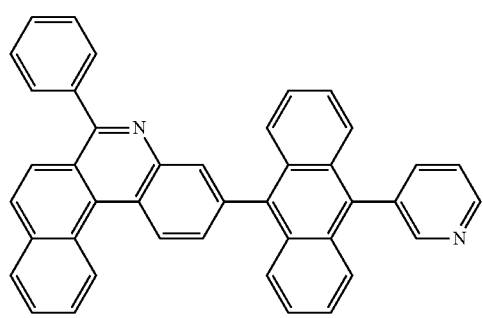
6C
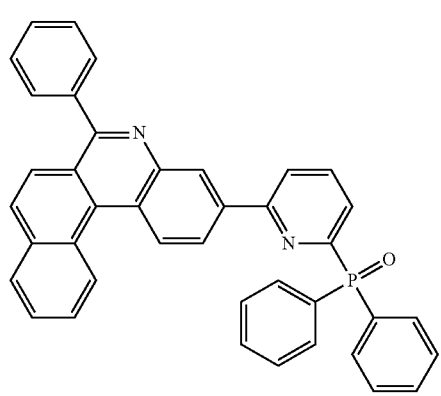
7C
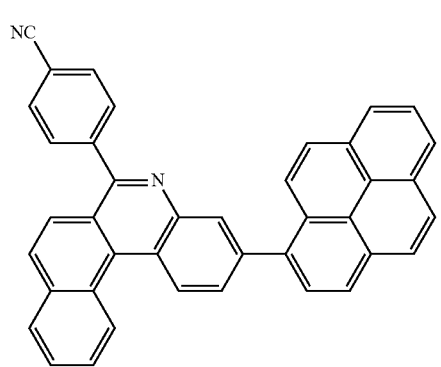
318
-continued
8C
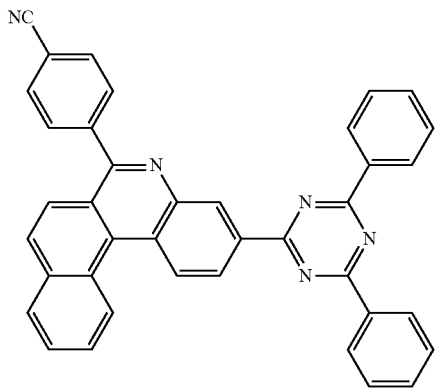
9C
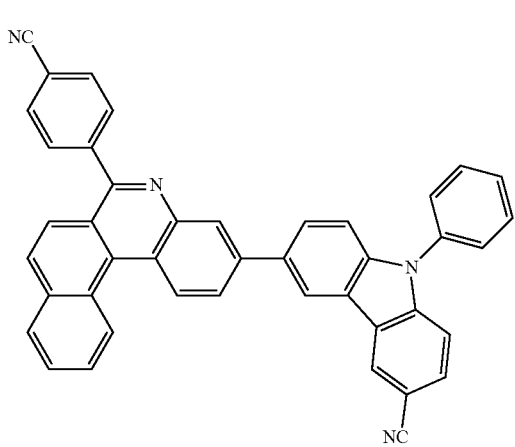
10C
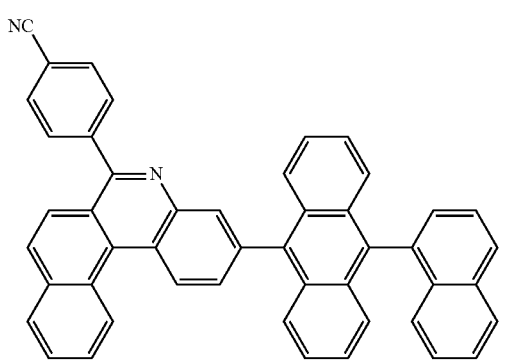
11C
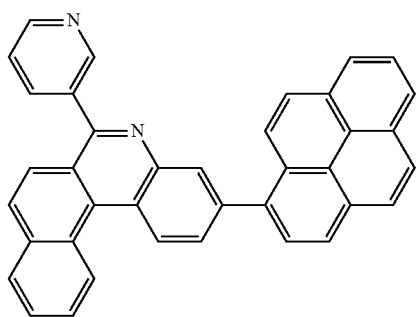

319
-continued
320
-continued
12C
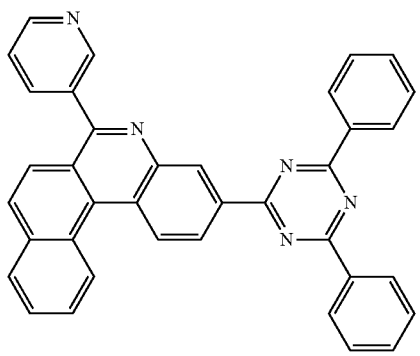
13C
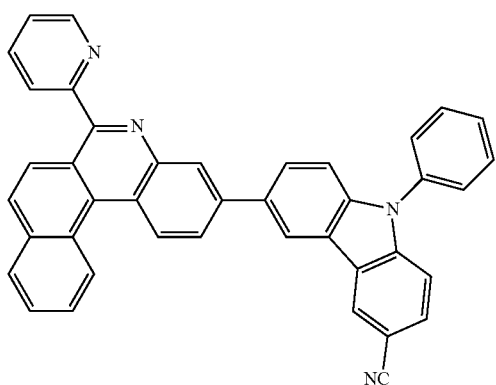
14C
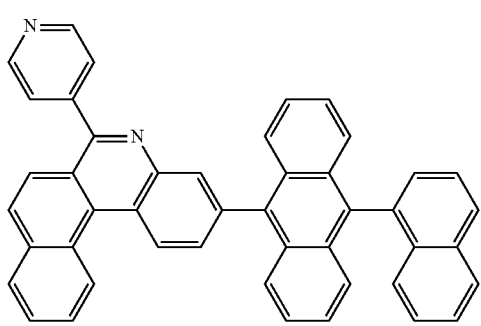
15C
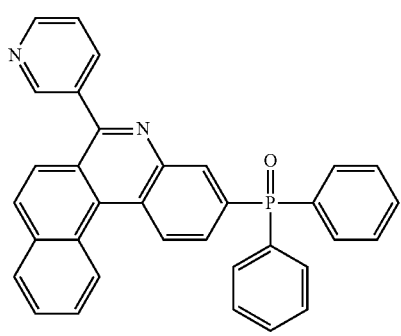
16C
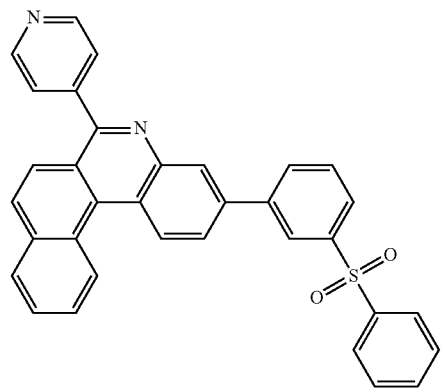
17C
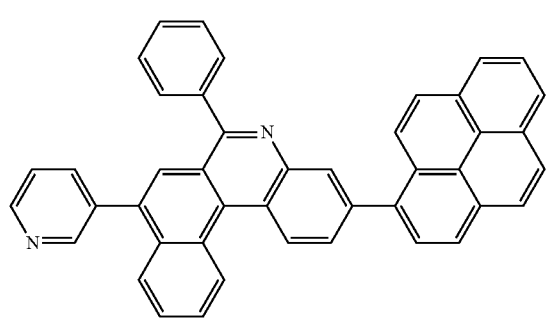
18C
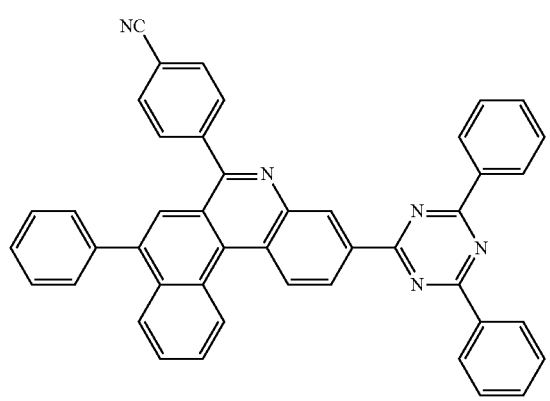
19C
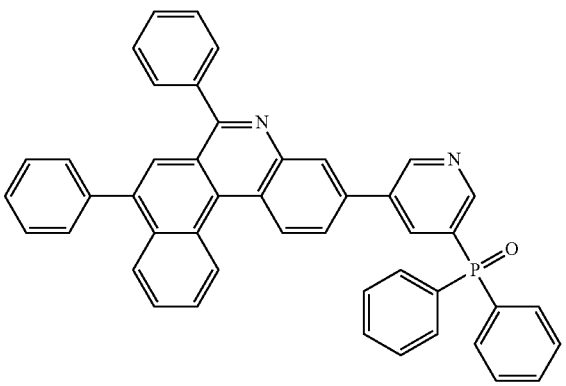

321
-continued
20C
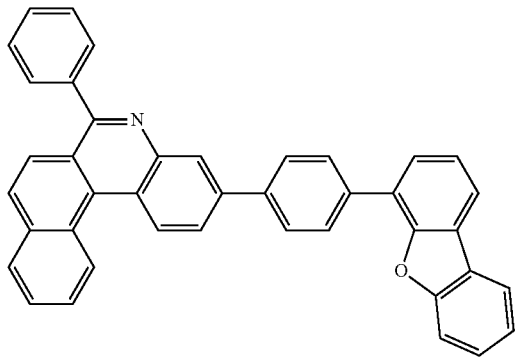
21C
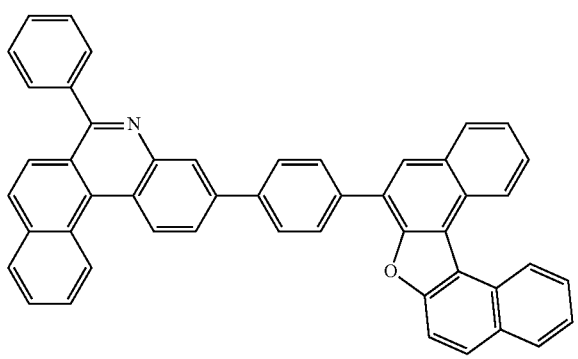
22C
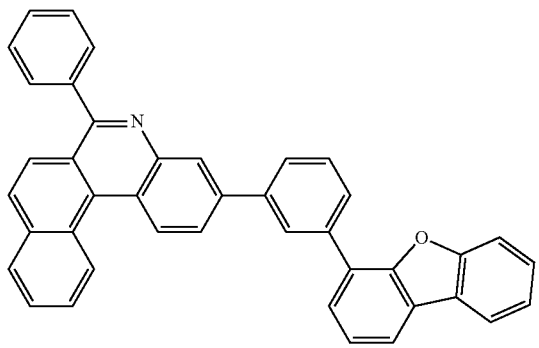
23C
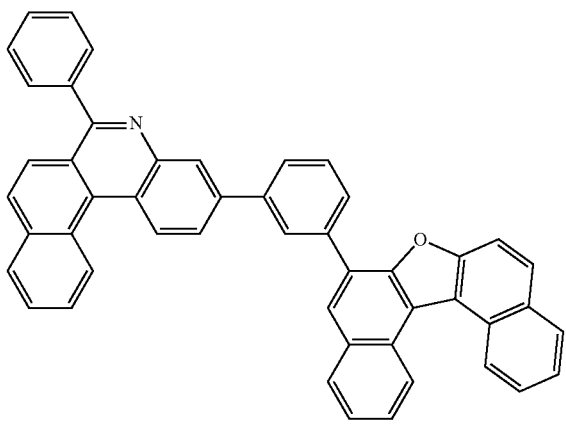
322
-continued
24C
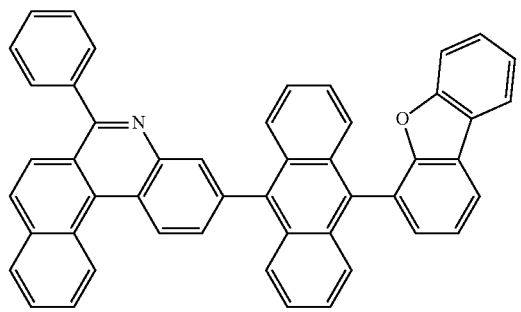
25C
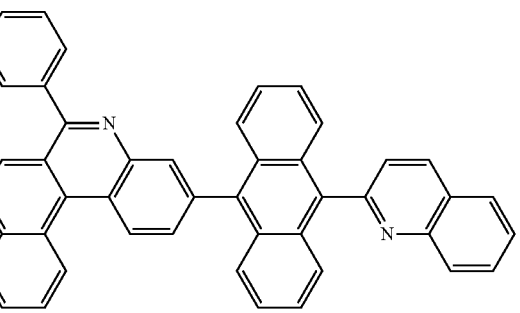
26C
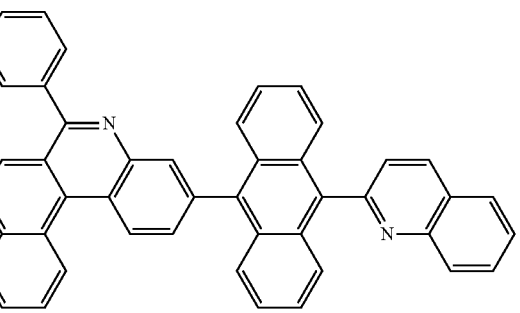
27C
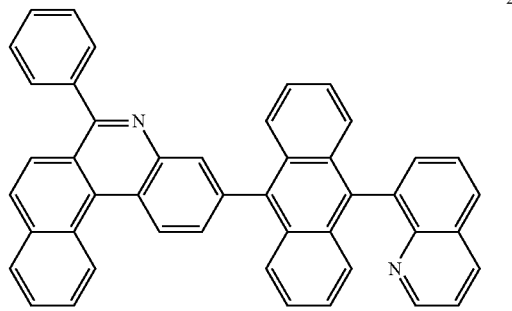

-continued
28C
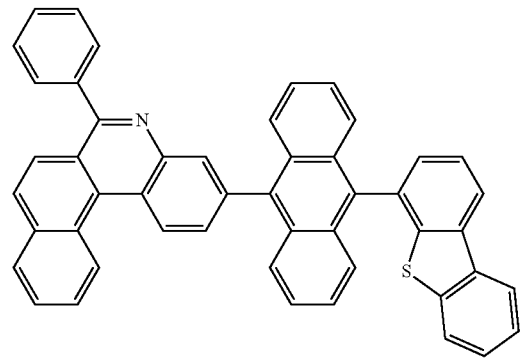
29C
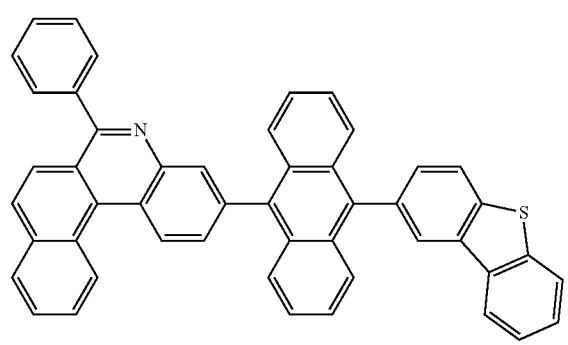
30C
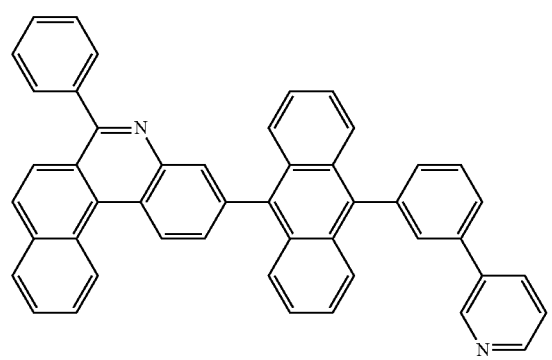
31C
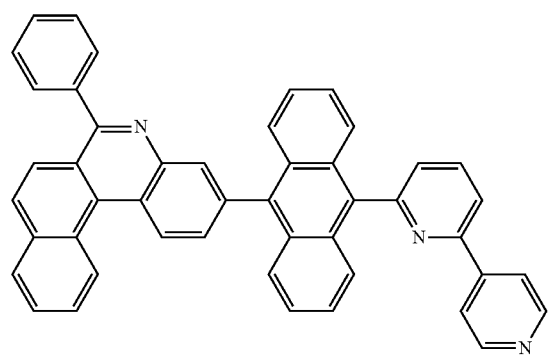
-continued
32C
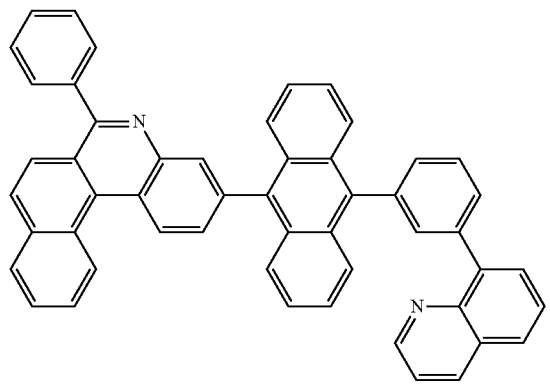
33C
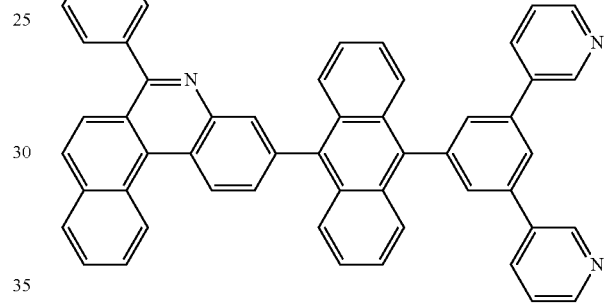
34C
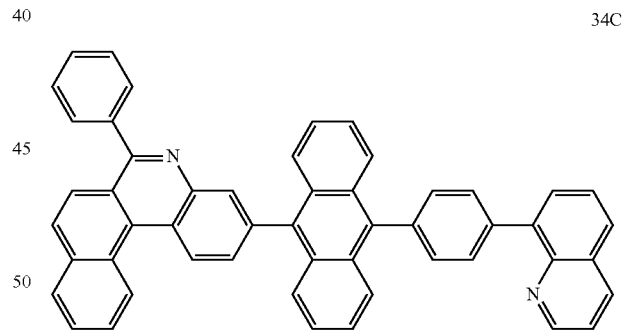
35C
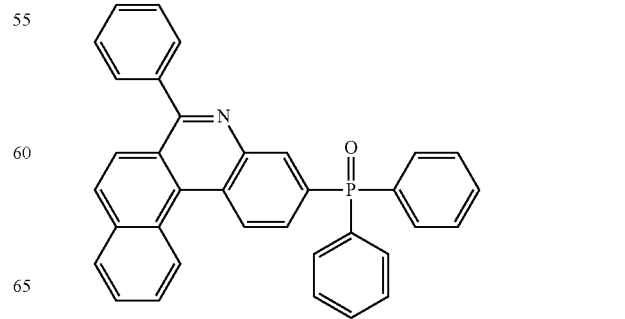

-continued
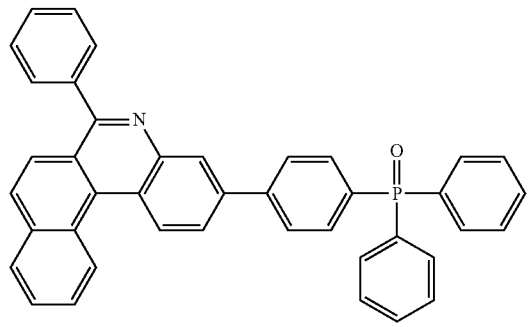
36C
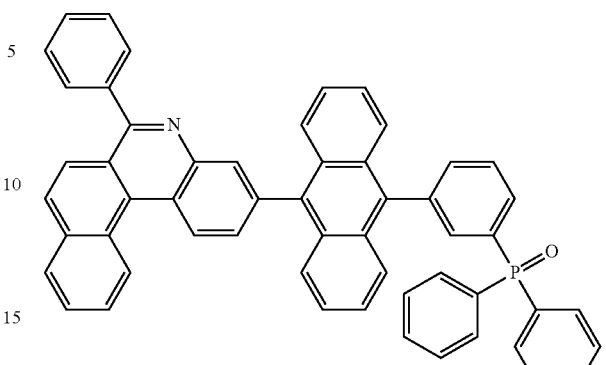
40C
37C
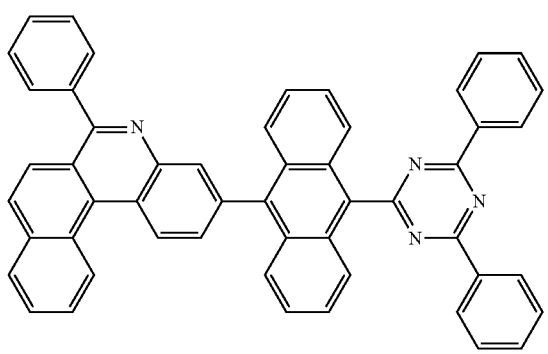
41C
38C
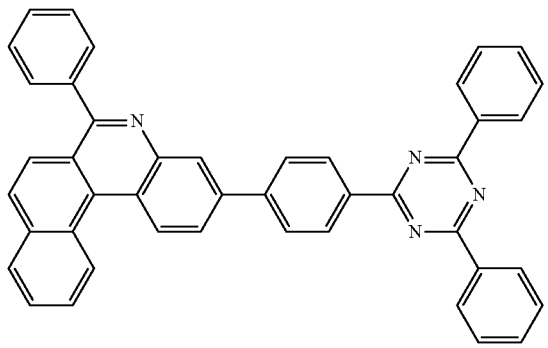
42C
39C
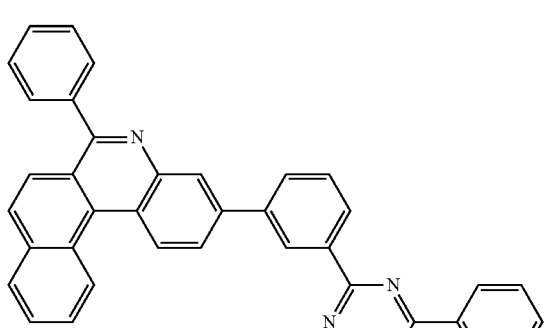
43C
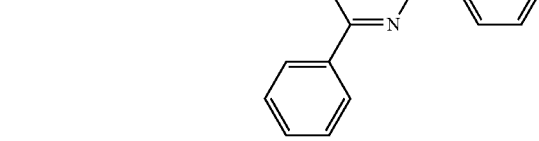

327
-continued
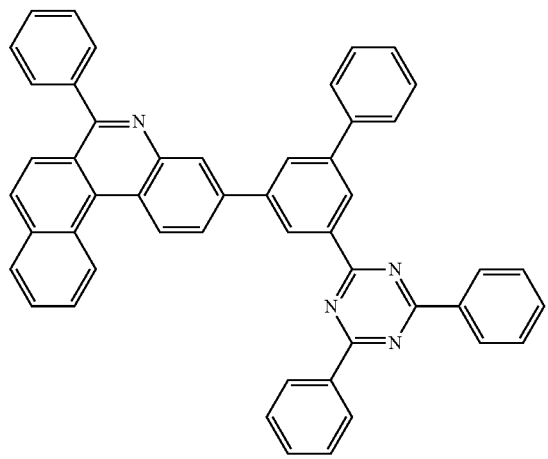
44C
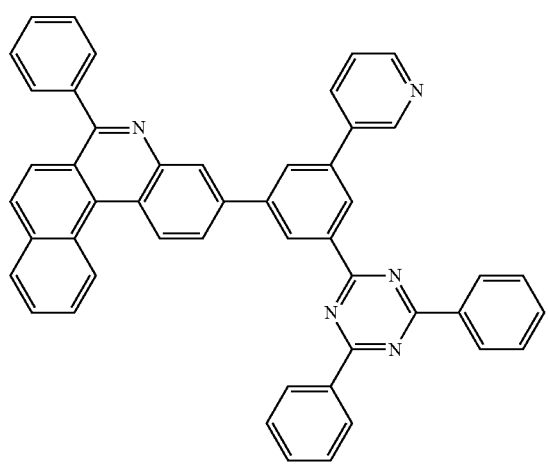
45C
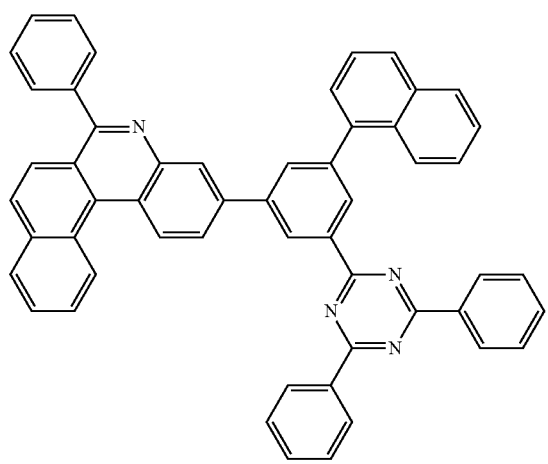
46C
328
-continued
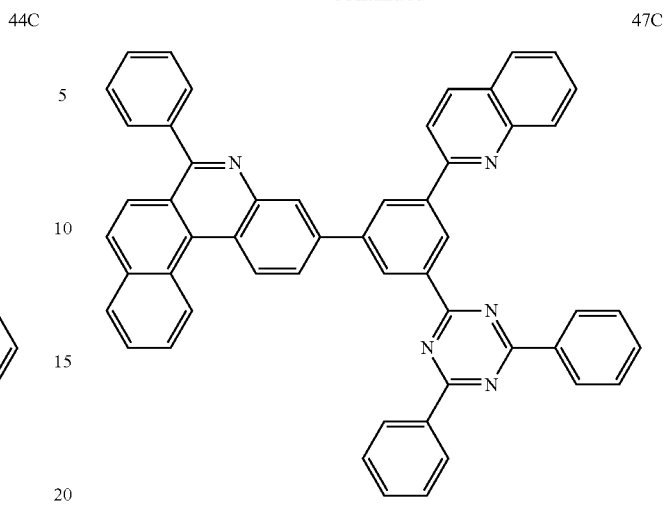
47C
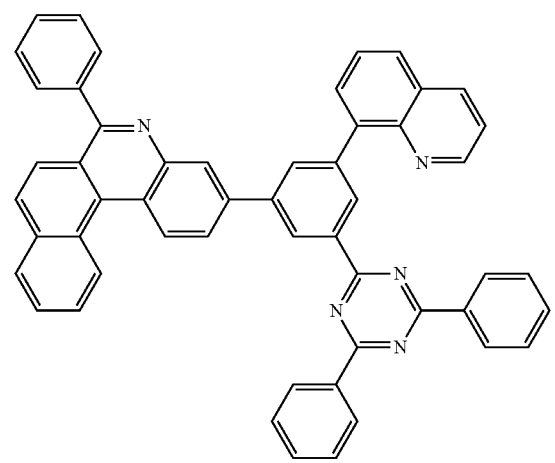
48C
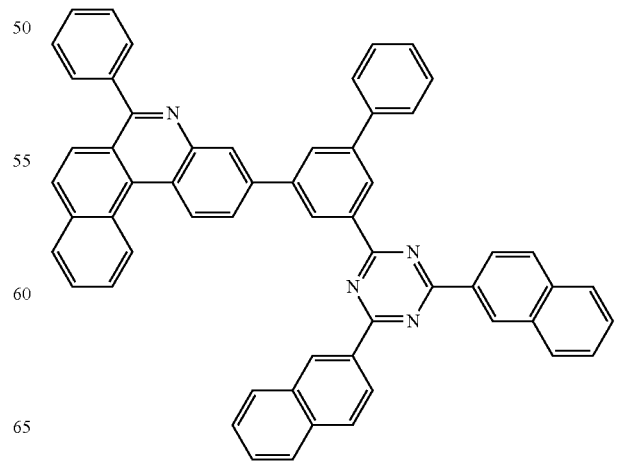
49C 329
-continued
50C
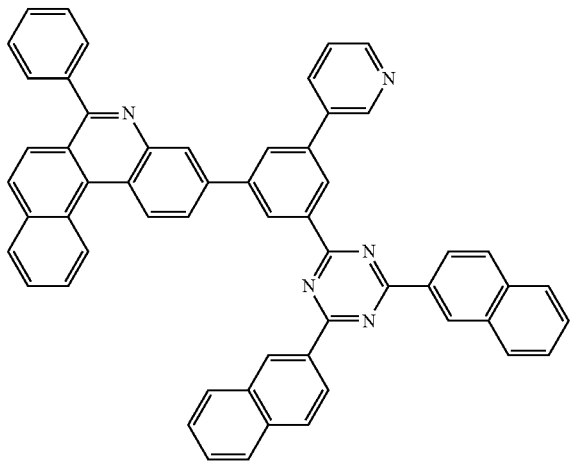
51C
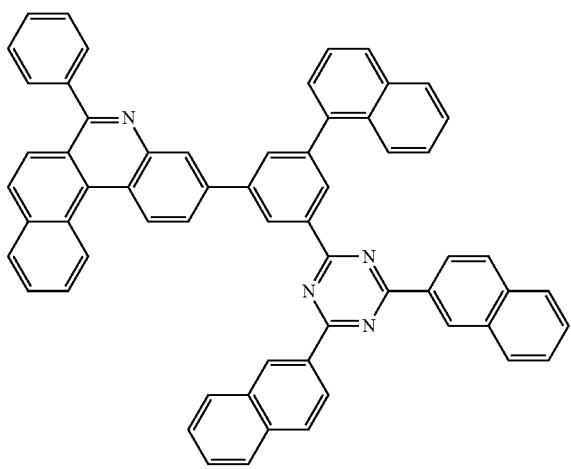
52C
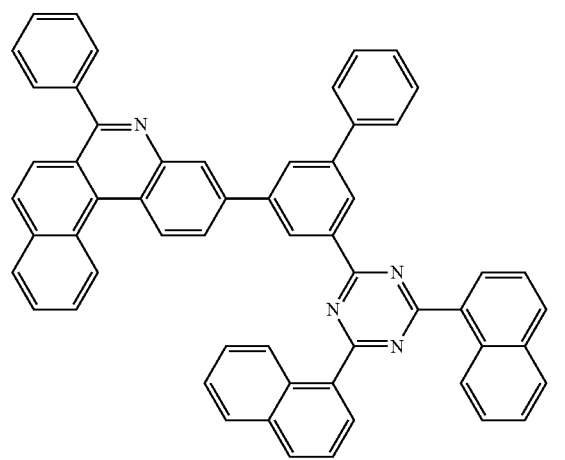
330
-continued
53C
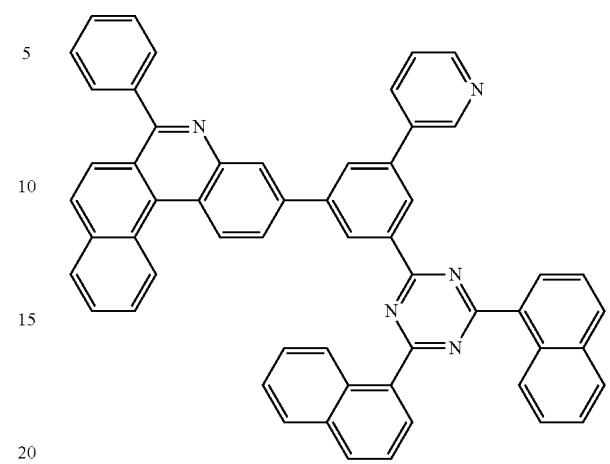
54C
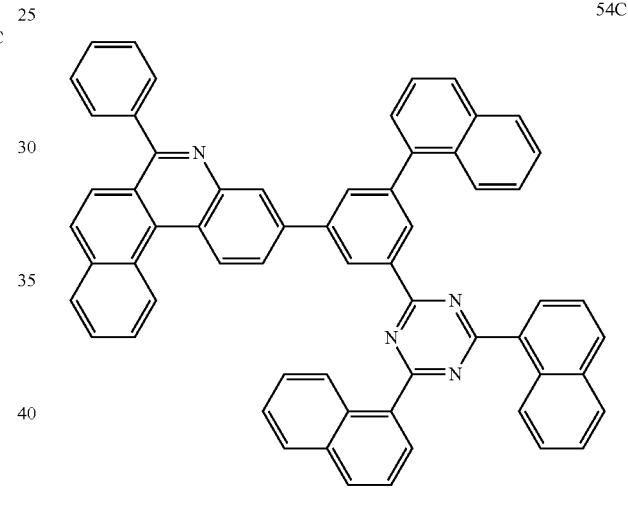
55C
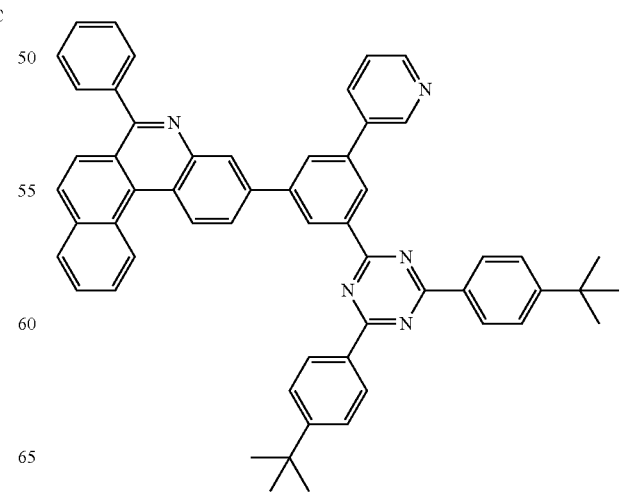

331
-continued
56C
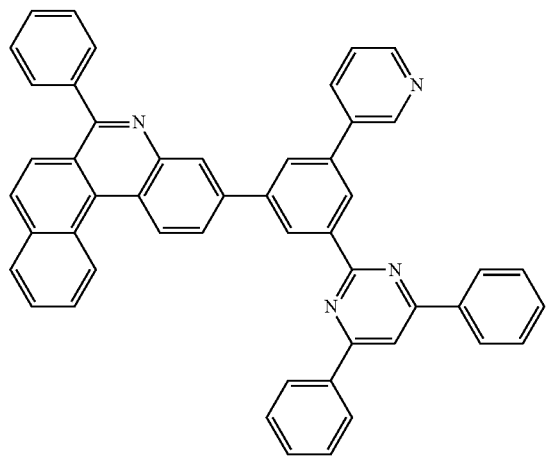
1D
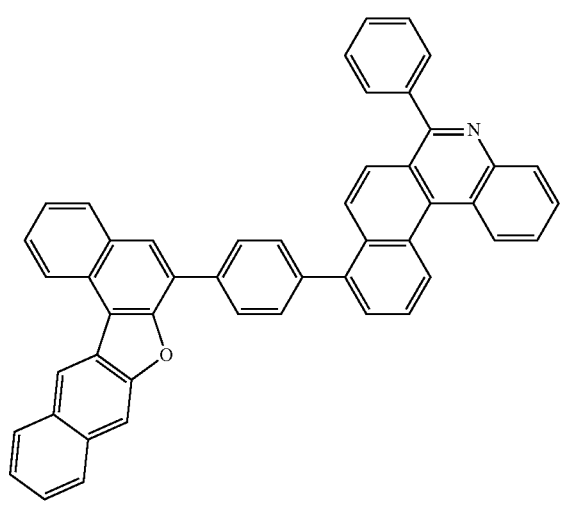
2D
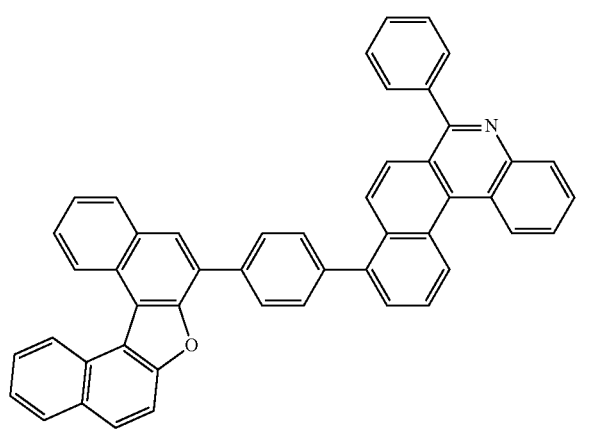
332
-continued
3D
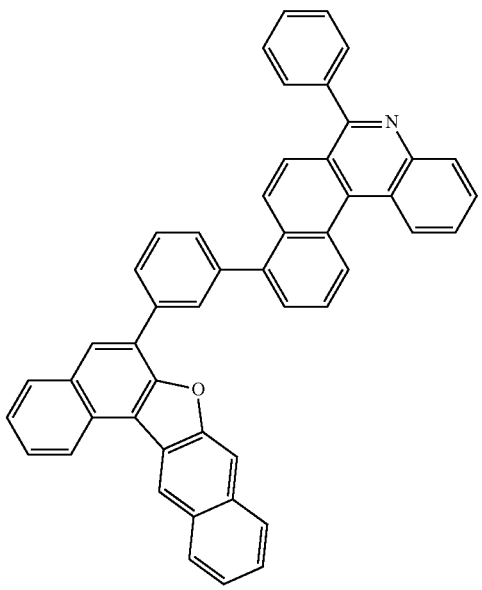
4D
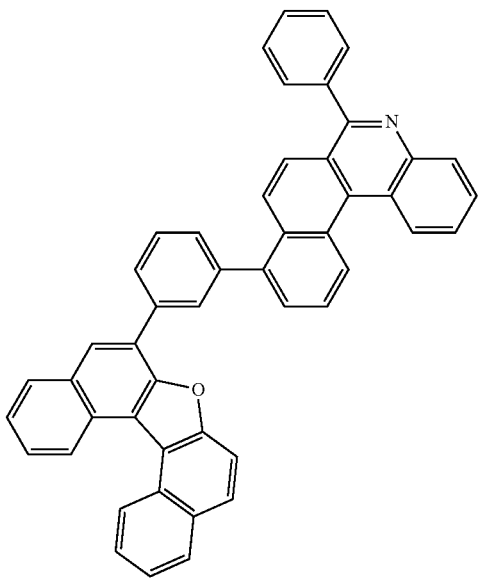
5D
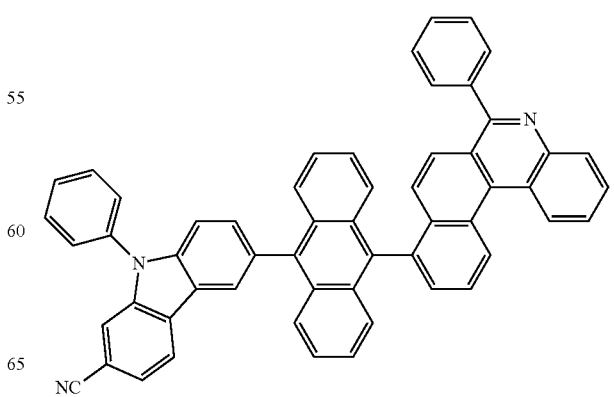

-continued
6D
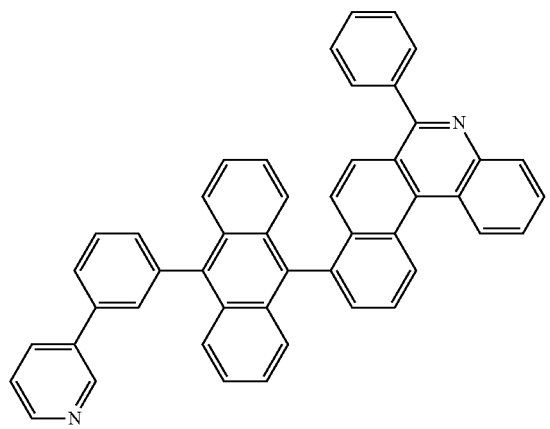
7D
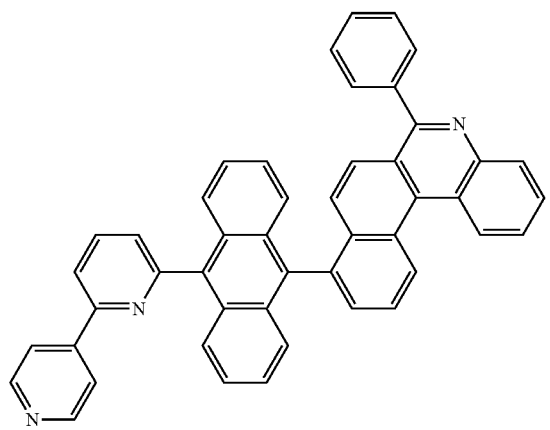
8D
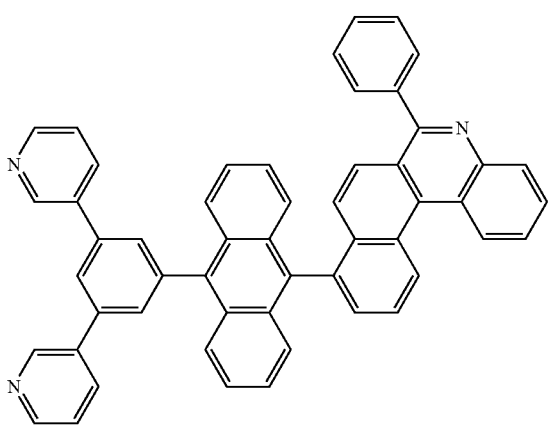
-continued
9D
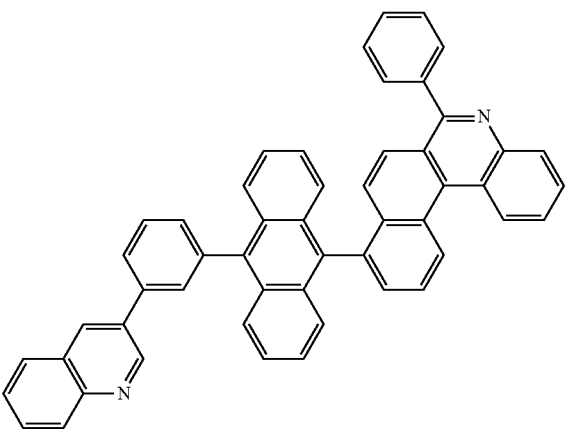
10D
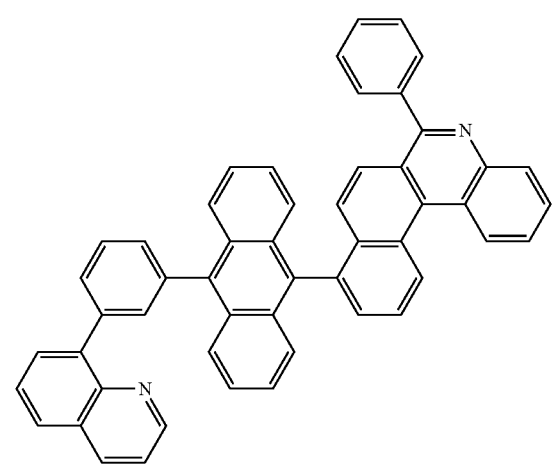
11D
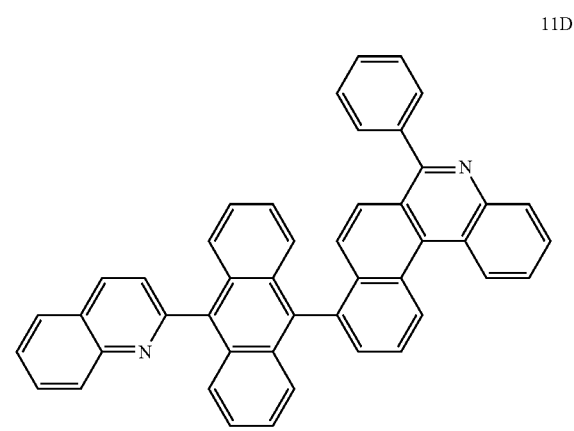

335
-continued
12D
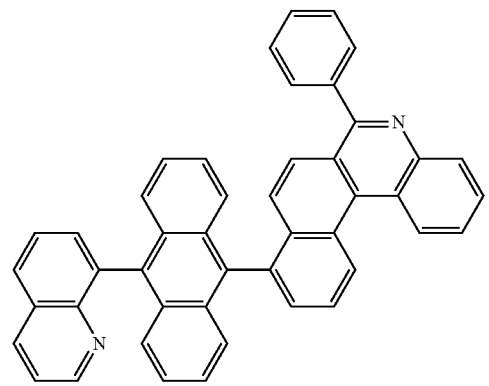
13D
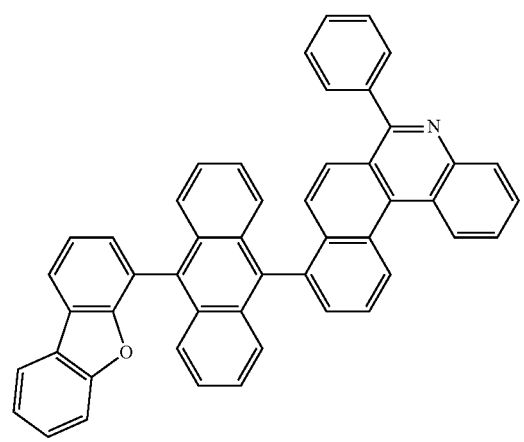
14D
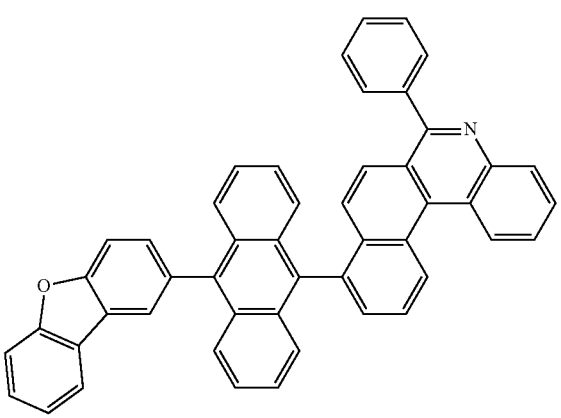
15D
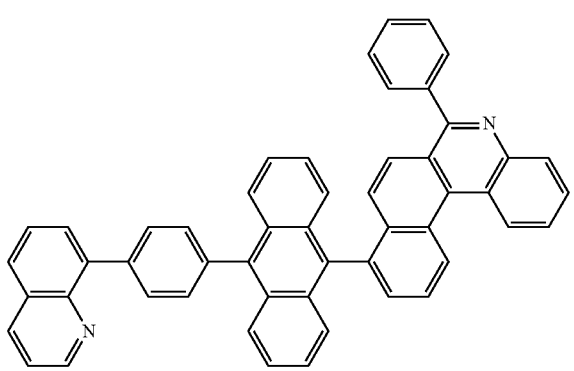
336
-continued
16D
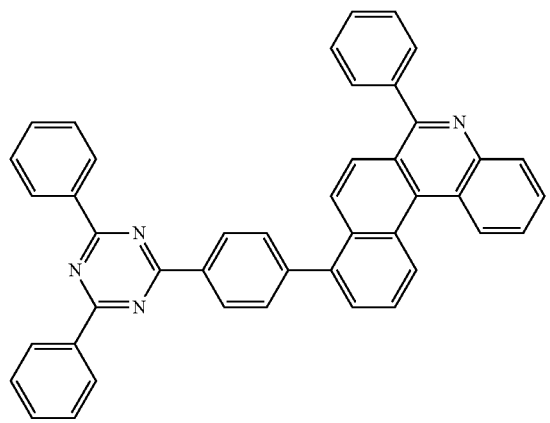
17D
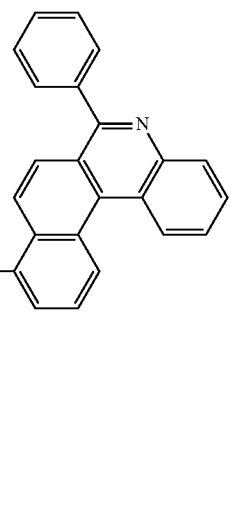
18D
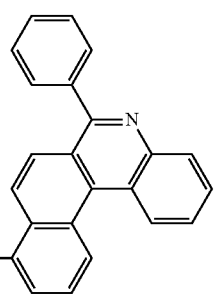

19D
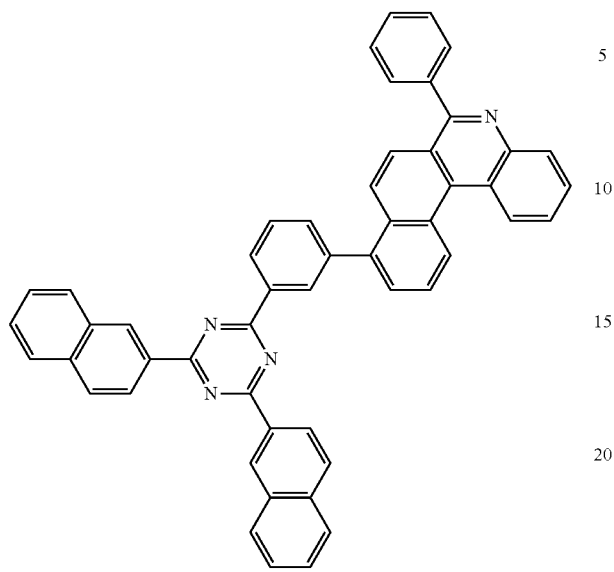
20D
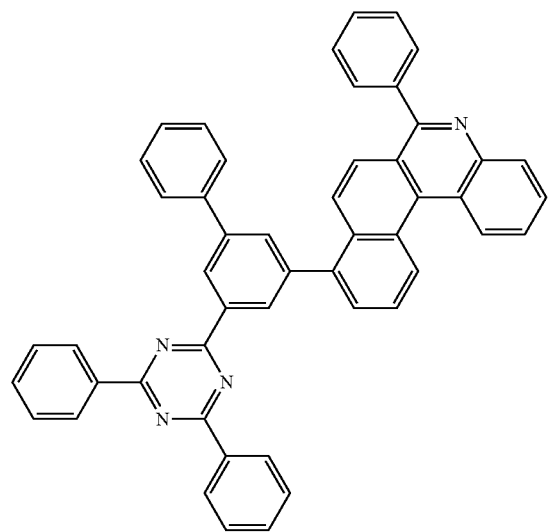
21D
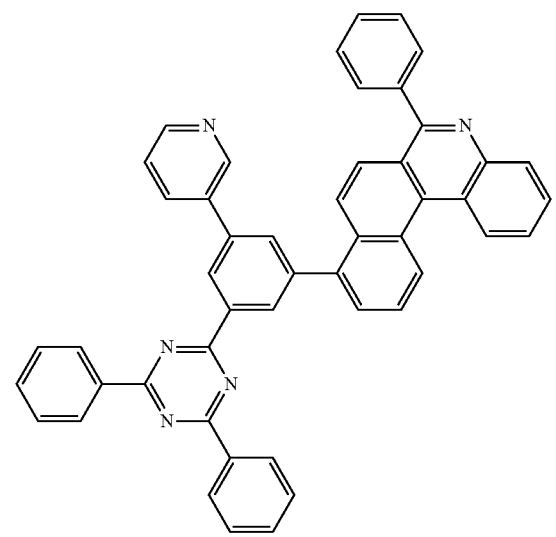
22D
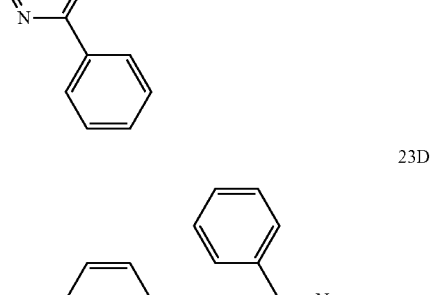
23D
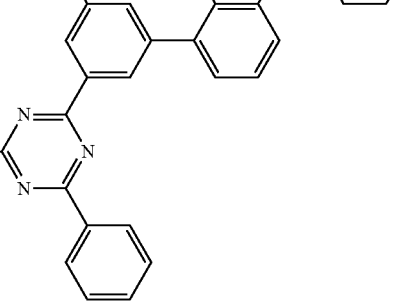

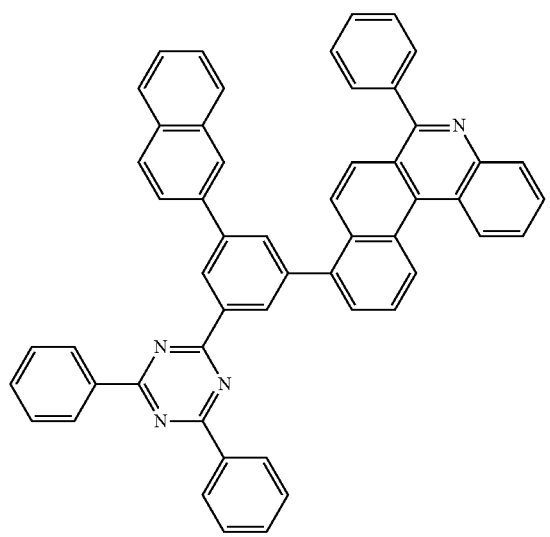
24D
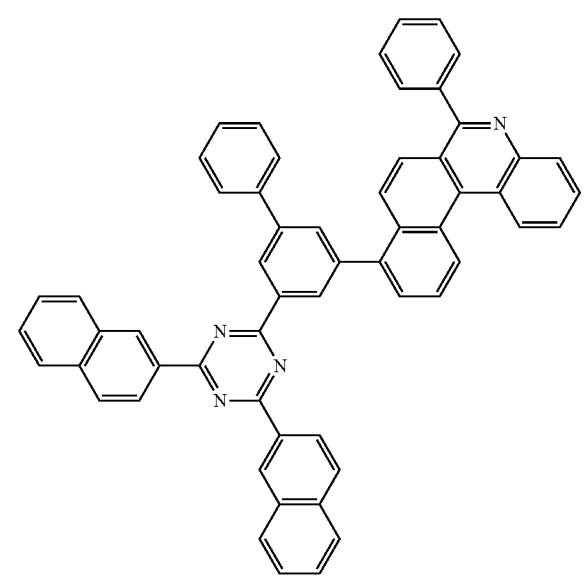
26D
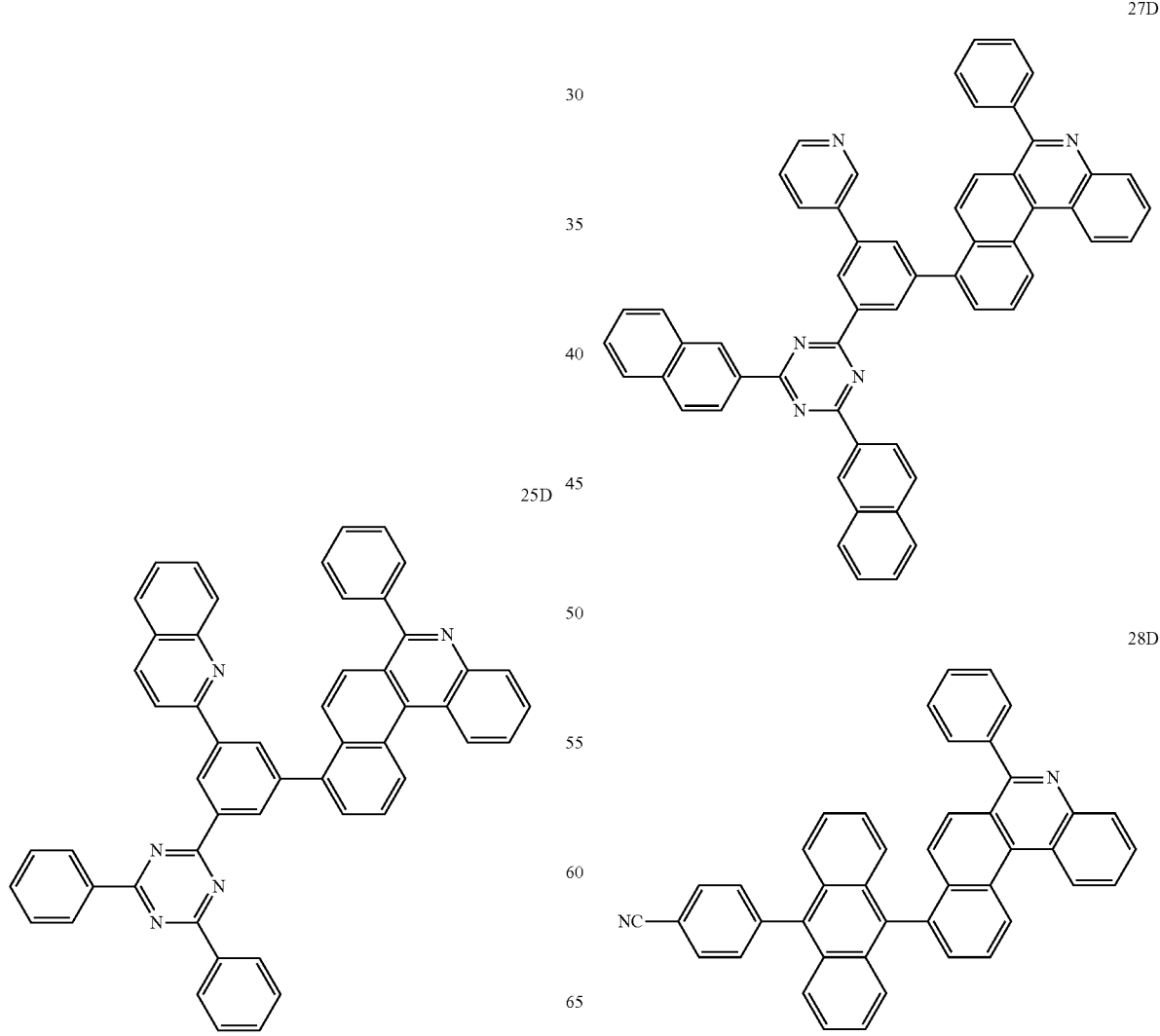
25D
27D
28D

-continued

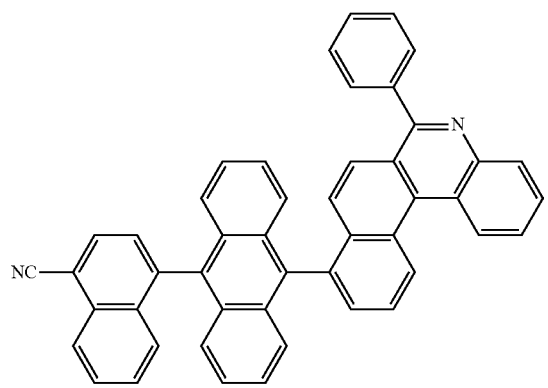

29D

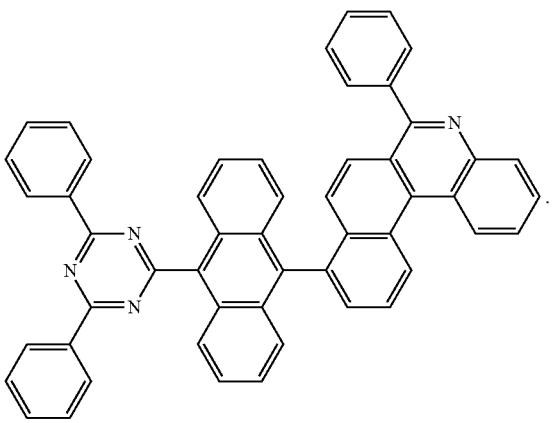

30D

14. An organic light-emitting device, comprising:
a first electrode;
a second electrode; and
an organic layer between the first electrode and the second electrode, the organic layer including an emission layer,
wherein the organic layer includes the condensed cyclic compound as claimed in claim 1.

15. The organic light-emitting device as claimed in claim 14, wherein:
the first electrode is an anode,
the second electrode is a cathode,
the organic layer includes:
a hole transport region between the first electrode and the emission layer, the hole transport region including at least one of a hole injection layer, a hole transport layer, a buffer layer, and electron blocking layer; and
an electron transport region between the emission layer and the second electrode, the electron transport region including at least one of a hole blocking layer, an electron transport layer, and an electron injection layer.

16. The organic light-emitting device as claimed in claim 15, wherein the electron transport region includes the condensed cyclic compound.

17. The organic light-emitting device as claimed in claim 15, wherein:
the electron transport region includes the electron transport layer, and
the electron transport layer includes the condensed cyclic compound.

18. The organic light-emitting device as claimed in claim 15 wherein the hole transport region includes a charge-generation material.

19. The organic light-emitting device as claimed in claim 14 wherein the emission layer includes at least one of an anthracene-containing compound, an arylamine-containing compound, and a styryl-containing compound.

20. The organic light-emitting device as claimed in claim 14, further comprising at least one of a first capping layer and a second capping layer, wherein:
the first capping layer is on a path where light generated in the emission layer is extracted through the first electrode,
the second capping layer is on a path where light generated in the emission layer is extracted through the second electrode, and
at least one of the first capping layer and the second capping layer includes the condensed cyclic compound.

* * * * *